US011103140B2

(12) United States Patent
Frank et al.

(10) Patent No.: US 11,103,140 B2
(45) Date of Patent: Aug. 31, 2021

(54) MONITORING BLOOD SUGAR LEVEL WITH A COMFORTABLE HEAD-MOUNTED DEVICE

(71) Applicant: Facense Ltd., Kiryat Tivon (IL)

(72) Inventors: Ari M Frank, Haifa (IL); Arie Tzvieli, Berkeley, CA (US); Ori Tzvieli, Berkeley, CA (US); Gil Thieberger, Kiryat Tivon (IL)

(73) Assignee: Facense Ltd., Kiryat Tivon (IL)

( * ) Notice: Subject to any disclaimer, the term of this patent is extended or adjusted under 35 U.S.C. 154(b) by 0 days.

(21) Appl. No.: 17/027,677

(22) Filed: Sep. 21, 2020

(65) Prior Publication Data

US 2021/0007607 A1    Jan. 14, 2021

Related U.S. Application Data

(63) Continuation-in-part of application No. 17/005,259, filed on Aug. 27, 2020, which is a
(Continued)

(51) Int. Cl.
*A61B 5/00* (2006.01)
*A61B 5/01* (2006.01)
(Continued)

(52) U.S. Cl.
CPC .......... *A61B 5/015* (2013.01); *A61B 5/0075* (2013.01); *A61B 5/14532* (2013.01);
(Continued)

(58) Field of Classification Search
CPC . A61B 5/02438; A61B 5/0205; A61B 5/0006; A61B 5/6898; A61B 5/0008;
(Continued)

(56) References Cited

U.S. PATENT DOCUMENTS 5,757,002 A  5/1998 Yamasaki et al.
6,513,379 B2 * 2/2003 Meyers .............. A47G 19/2227
215/11.2
(Continued)

FOREIGN PATENT DOCUMENTS

WO    WO2019181150 A1    9/2019

OTHER PUBLICATIONS

Ahn, J. M. (2017). New aging index using signal features of both photoplethysmograms and acceleration plethysmograms. Healthcare informatics research, 23(1), 53-59.
(Continued)

*Primary Examiner* — Gail Kaplan Verbitsky
(74) *Attorney, Agent, or Firm* — Active Knowledge Ltd.

(57) ABSTRACT

Described herein are embodiments of systems and methods for calculating glucose in a non-invasive manner using head-mounted sensors. In one embodiment, a system that calculates blood glucose levels includes a head-mounted contact photoplethysmography device that measures a signal indicative of a photoplethysmogram signal (PPG signal) at a first region comprising skin on a user's head, and a head-mounted camera configured to capture images of a second region comprising skin on the user's head. The system also includes a computer that identifies, based on the PPG signal, times of systolic notches and times of systolic peaks, and calculates the blood glucose level based on differences between a first subset of the images taken during the times of systolic notches and a second subset of the images taken during the times of systolic peaks. Optionally, the photoplethysmography device and the camera are couple to smartglasses worn on the user's head.

20 Claims, 22 Drawing Sheets

Related U.S. Application Data continuation-in-part of application No. 16/854,883, filed on Apr. 21, 2020, now Pat. No. 10,813,559, and a continuation-in-part of application No. 16/689,929, filed on Nov. 20, 2019, and a continuation-in-part of application No. 16/689,959, filed on Nov. 20, 2019, now Pat. No. 10,799,122, said application No. 16/854,883 is a continuation-in-part of application No. 16/453,993, filed on Jun. 26, 2019, now Pat. No. 10,667,697, said application No. 17/005,259 is a continuation-in-part of application No. 16/831,413, filed on Mar. 26, 2020, now Pat. No. 10,791,938, which is a continuation-in-part of application No. 16/551,654, filed on Aug. 26, 2019, now Pat. No. 10,638,938, which is a continuation-in-part of application No. 16/453,993, filed on Jun. 26, 2019, now Pat. No. 10,667,697, which is a continuation-in-part of application No. 16/375,841, filed on Apr. 4, 2019, now Pat. No. 10,376,163, which is a continuation-in-part of application No. 16/156,493, filed on Oct. 10, 2018, now Pat. No. 10,524,667, which is a continuation-in-part of application No. 15/635,178, filed on Jun. 27, 2017, now Pat. No. 10,136,856, and a continuation-in-part of application No. 15/231,276, filed on Aug. 8, 2016, now abandoned, and a continuation-in-part of application No. 15/832,855, filed on Dec. 6, 2017, now Pat. No. 10,130,308, which is a continuation-in-part of application No. 15/182,592, filed on Jun. 14, 2016, now Pat. No. 10,165,949, and a continuation-in-part of application No. 15/231,276, filed on Aug. 8, 2016, now abandoned, and a continuation-in-part of application No. 15/284,528, filed on Oct. 3, 2016, now Pat. No. 10,113,913, and a continuation-in-part of application No. 15/635,178, filed on Jun. 27, 2017, now Pat. No. 10,136,856, and a continuation-in-part of application No. 15/722,434, filed on Oct. 2, 2017, now Pat. No. 10,523,852, and a continuation-in-part of application No. 15/182,566, filed on Jun. 14, 2016, now Pat. No. 9,867,546, said application No. 16/156,493 is a continuation-in-part of application No. 15/833,115, filed on Dec. 6, 2017, now Pat. No. 10,130,261, which is a continuation-in-part of application No. 15/182,592, filed on Jun. 14, 2016, now Pat. No. 10,165,949, and a continuation-in-part of application No. 15/231,276, filed on Aug. 8, 2016, now abandoned, and a continuation-in-part of application No. 15/284,528, filed on Oct. 3, 2016, now Pat. No. 10,113,913, and a continuation-in-part of application No. 15/635,178, filed on Jun. 27, 2017, now Pat. No. 10,136,856, and a continuation-in-part of application No. 15/722,434, filed on Oct. 2, 2017, now Pat. No. 10,523,852, said application No. 16/453,993 is a continuation-in-part of application No. 16/147,695, filed on Sep. 29, 2018, now Pat. No. 10,376,153, which is a continuation of application No. 15/182,592, filed on Jun. 14, 2016, now Pat. No. 10,165,949, said application No. 16/689,929 is a continuation-in-part of application No. 16/156,586, filed on Oct. 10, 2018, now Pat. No. 10,524,696, which is a continuation-in-part of application No. 15/832,815, filed on Dec. 6, 2017, now Pat. No. 10,136,852, and a continuation-in-part of application No. 15/859,772, filed on Jan. 2, 2018, now Pat. No. 10,159,411.

(60) Provisional application No. 63/048,638, filed on Jul. 6, 2020, provisional application No. 63/024,471, filed on May 13, 2020, provisional application No. 63/006,827, filed on Apr. 8, 2020, provisional application No. 62/960,913, filed on Jan. 14, 2020, provisional application No. 62/945,141, filed on Dec. 7, 2019, provisional application No. 62/928,726, filed on Oct. 31, 2019, provisional application No. 62/722,655, filed on Aug. 24, 2018, provisional application No. 62/354,833, filed on Jun. 27, 2016, provisional application No. 62/372,063, filed on Aug. 8, 2016, provisional application No. 62/652,348, filed on Apr. 4, 2018, provisional application No. 62/667,453, filed on May 5, 2018, provisional application No. 62/456,105, filed on Feb. 7, 2017, provisional application No. 62/480,496, filed on Apr. 2, 2017, provisional application No. 62/566,572, filed on Oct. 2, 2017, provisional application No. 62/175,319, filed on Jun. 14, 2015, provisional application No. 62/202,808, filed on Aug. 8, 2015, provisional application No. 62/236,868, filed on Oct. 3, 2015.

(51) Int. Cl.

| | | |
|---|---|---|
| *G01J 5/12* | (2006.01) | |
| *G01J 5/02* | (2006.01) | |
| *A61B 5/16* | (2006.01) | |
| *A61B 5/145* | (2006.01) | |
| *G01J 5/00* | (2006.01) | |
| *A61B 5/1477* | (2006.01) | |
| *A61B 5/024* | (2006.01) | |

(52) U.S. Cl.
CPC ............ *A61B 5/165* (2013.01); *A61B 5/6803* (2013.01); *A61B 5/6814* (2013.01); *A61B 5/7282* (2013.01); *A61B 5/748* (2013.01); *G01J 5/0265* (2013.01); *G01J 5/12* (2013.01); *A61B 5/0077* (2013.01); *A61B 5/02438* (2013.01); *A61B 5/1477* (2013.01); *A61B 2562/0271* (2013.01); *A61B 2562/0276* (2013.01); *A61B 2576/00* (2013.01); *G01J 2005/0077* (2013.01); *G01J 2005/0085* (2013.01)

(58) Field of Classification Search
CPC ... A61B 5/02433; A61B 5/443; A61B 5/6801; A61B 5/6803; A61B 5/14551; A61B 5/029; A61B 5/0245; A61B 2562/0271; A61B 2562/0276; A61B 5/015; A61B 5/02055; A61B 5/02416; A61B 5/14532; A61B 5/00; G01J 2005/0077; G01J 2005/0085; G01J 5/0265; G01J 5/0025
See application file for complete search history.

(56) References Cited

U.S. PATENT DOCUMENTS

| | | | |
|---|---|---|---|
| 6,819,950 B2 | 11/2004 | Mills | |
| 7,111,980 B2* | 9/2006 | Pavlidis | ................. A61B 5/015 374/45 |
| 7,384,395 B2 | 6/2008 | Hatlestsad et al. | |
| 8,175,670 B2 | 5/2012 | Baker, Jr. et al. | |
| 8,251,903 B2 | 8/2012 | LeBoeuf et al. | |
| 8,512,253 B2 | 8/2013 | Reichman et al. | |
| 8,617,081 B2 | 12/2013 | Mestha et al. | |
| 8,700,111 B2* | 4/2014 | LeBoeuf | .............. A61B 5/4875 600/310 |
| 8,768,438 B2 | 7/2014 | Mestha et al. | |
| 8,855,384 B2 | 10/2014 | Kyal et al. | |
| 8,977,347 B2 | 3/2015 | Mestha et al. | |
| 9,020,185 B2 | 4/2015 | Mestha et al. | |

(56) References Cited

U.S. PATENT DOCUMENTS

| | | |
|---|---|---|
| 9,044,180 B2 | 6/2015 | LeBoeuf et al. |
| 9,220,856 B2 | 12/2015 | Martin et al. |
| 9,402,546 B2 | 8/2016 | Segman |
| 9,414,769 B2 | 8/2016 | Karst et al. |
| 9,489,817 B2 | 11/2016 | Gui |
| 9,610,035 B2 | 4/2017 | Aarts et al. |
| 9,805,475 B2 | 10/2017 | Rubinstein et al. |
| 9,808,204 B2 | 11/2017 | LeBoeuf et al. |
| 9,844,345 B2 | 12/2017 | Segman |
| 9,848,780 B1 | 12/2017 | DeBusschere et al. |
| 9,940,710 B2 | 4/2018 | Watanabe |
| 10,152,869 B2 | 12/2018 | Peyrard |
| 10,317,672 B2 | 6/2019 | Sarkar |
| 10,368,758 B2* | 8/2019 | Melker ............... A61B 5/6838 |
| 2005/0001728 A1* | 1/2005 | Appelt ................ G08B 21/182 |
| | | 340/573.1 |
| 2007/0276632 A1 | 11/2007 | Banet et al. |
| 2009/0182688 A1 | 7/2009 | van der Zwan et al. |
| 2010/0241011 A1 | 9/2010 | McCombie et al. |
| 2012/0022349 A1 | 1/2012 | Poupko et al. |
| 2012/0029320 A1 | 2/2012 | Watson et al. |
| 2013/0215244 A1 | 8/2013 | Mestha et al. |
| 2014/0213917 A1 | 7/2014 | Hobeika et al. |
| 2015/0005646 A1 | 1/2015 | Balakrishnan et al. |
| 2015/0112606 A1 | 4/2015 | He et al. |
| 2015/0297126 A1 | 10/2015 | Atsumori et al. |
| 2015/0305632 A1* | 10/2015 | Najarian .............. A61B 5/7207 |
| | | 600/301 |
| 2016/0007935 A1 | 1/2016 | Hernandez et al. |
| 2016/0022157 A1 | 1/2016 | Melker et al. |
| 2016/0070122 A1 | 3/2016 | Sales et al. |
| 2016/0098592 A1 | 4/2016 | Lee et al. |
| 2016/0106322 A1* | 4/2016 | Addison ............ A61B 5/02427 |
| | | 600/479 |
| 2016/0120411 A1 | 5/2016 | Hadley et al. |
| 2016/0167672 A1 | 6/2016 | Krueger |
| 2016/0224803 A1* | 8/2016 | Frank ................ G06F 16/24578 |
| 2016/0296124 A1 | 10/2016 | Wegerich et al. |
| 2016/0302677 A1 | 10/2016 | He |
| 2017/0007167 A1 | 1/2017 | Kostic et al. |
| 2017/0011210 A1 | 1/2017 | Cheong et al. |
| 2017/0095157 A1 | 4/2017 | Tzvieli et al. |
| 2017/0112376 A1 | 4/2017 | Gill et al. |
| 2017/0202505 A1 | 7/2017 | Kirenko et al. |
| 2017/0231490 A1 | 8/2017 | Toth et al. |
| 2017/0360312 A1* | 12/2017 | Joseph ............... A61B 5/14551 |
| 2017/0367590 A1 | 12/2017 | Sebe et al. |
| 2017/0367651 A1 | 12/2017 | Tzvieli et al. |
| 2018/0020991 A1* | 1/2018 | Aung ................ A61B 5/02416 |
| | | 600/480 |
| 2018/0031372 A1 | 2/2018 | Gill |
| 2018/0042486 A1 | 2/2018 | Yoshizawa et al. |
| 2018/0146870 A1 | 5/2018 | Shemesh et al. |
| 2018/0177416 A1 | 6/2018 | Church et al. |
| 2018/0192950 A1 | 7/2018 | LeBoeuf et al. |
| 2018/0199870 A1 | 7/2018 | Lee et al. |
| 2018/0206733 A1 | 7/2018 | Kasan et al. |
| 2018/0206735 A1 | 7/2018 | Holz et al. |
| 2018/0210547 A1 | 7/2018 | Sarkar |
| 2018/0214079 A1 | 8/2018 | Banet et al. |
| 2018/0289297 A1 | 10/2018 | Zalevsky et al. |
| 2018/0314879 A1 | 11/2018 | Khwaja et al. |
| 2019/0021615 A1 | 1/2019 | Rundo et al. |
| 2019/0117096 A1 | 4/2019 | Rundo et al. |
| 2019/0159735 A1 | 5/2019 | Rundo et al. |
| 2019/0174039 A1 | 6/2019 | Jung et al. |
| 2019/0196179 A1 | 6/2019 | Sarkar et al. |
| 2019/0204912 A1 | 7/2019 | Yang et al. |
| 2019/0216340 A1 | 7/2019 | Holz et al. |
| 2019/0313915 A1 | 10/2019 | Tzvieli et al. |
| 2020/0043606 A1 | 2/2020 | Segman |
| 2020/0237317 A1* | 7/2020 | Newberry ............ A61B 5/1455 |
| 2021/0038133 A1* | 2/2021 | Ajima ................. A61B 5/024 |

OTHER PUBLICATIONS

Alghoul, K., Alharthi, S., Al Osman, H., & El Saddik, A. (2017). Heart rate variability extraction from videos signals: ICA vs. EVM comparison. IEEE Access, 5, 4711-4719.

Allen, J. (2007). Photoplethysmography and its application in clinical physiological measurement. Physiological measurement, 28(3), R1.

Al-Naji, A., Gibson, K., Lee, S. H., & Chahl, J. (2017). Monitoring of cardiorespiratory signal: Principles of remote measurements and review of methods. IEEE Access, 5, 15776-15790.

Alzahrani, A., Hu, S., Azorin-Peris, V., Barrett, L., Esliger, D., Hayes, M., . . . & Kuoch, S. (2015). A multi-channel opto-electronic sensor to accurately monitor heart rate against motion artefact during exercise. Sensors, 15(10), 25681-25702.

Avolio, A. P., Butlin, M., & Walsh, A. (2009). Arterial blood pressure measurement and pulse wave analysis—their role in enhancing cardiovascular assessment. Physiological measurement, 31(1), R1.

Ballinger, B., Hsieh, J., Singh, A., Sohoni, N., Wang, J., Tison, G. H., . . . & Pletcher, M. J. (Apr. 2018). DeepHeart: semi-supervised sequence learning for cardiovascular risk prediction. In Thirty-Second AAAI Conference on Artificial Intelligence.

Birrenkott, D. A., Pimentel, M. A., Watkinson, P. J., & Clifton, D. A. (Aug. 2016). Robust estimation of respiratory rate via ECG-and PPG-derived respiratory quality indices. In 2016 38th Annual International Conference of the IEEE Engineering in Medicine and Biology Society (EMBC) (pp. 676-679). IEEE.

Buxi, D., Redoute, J. M., & Yuce, M. R. (2015). A survey on signals and systems in ambulatory blood pressure monitoring using pulse transit time. Physiological measurement, 36(3), R1.

Callego, E. C., & de Haan, G. (Mar. 2015). Automatic ROI for remote photoplethysmography using PPG and color features. In 10th International Conference on Computer Vision Theory and Applications VISAPP-2015.

Castaneda, D., Esparza, A., Ghamari, M., Soltanpur, C., & Nazeran, H. (2018). A review on wearable photoplethysmography sensors and their potential future applications in health care. International journal of biosensors & bioelectronics, 4(4), 195.

Charlton, P. H., Celka, P., Farukh, B., Chowienczyk, P., & Alastruey, J. (2018). Assessing mental stress from the photoplethysmogram: a numerical study. Physiological measurement, 39(5), 054001.

Constant, N., Douglas-Prawl, O., Johnson, S., & Mankodiya, K. (Jun. 2015). Pulse-Glasses: An unobtrusive, wearable HR monitor with Internet-of-Things functionality. In 2015 IEEE 12th International Conference on Wearable and Implantable Body Sensor Networks (BSN) (pp. 1-5). IEEE.

Corral, F., Paez, G., & Strojnik, M. (2014). A photoplethysmographic imaging system with supplementary capabilities. Optica Applicata, 44(2).

Ding, X. R., Zhao, N., Yang, G. Z., Pettigrew, R. I., Lo, B., Miao, F., . . . & Zhang, Y. T. (2016). Continuous blood pressure measurement from invasive to unobtrusive: celebration of 200th birth anniversary of Carl Ludwig. IEEE journal of biomedical and health informatics, 20(6), 1455-1465.

Elgendi, M. (2012). On the analysis of fingertip photoplethysmogram signals. Current cardiology reviews, 8(1), 14-25.

Escobar Restrepo, B., Torres Villa, R., & Kyriacou, P. (2018). Evaluation of the Linear Relationship Between Pulse Arrival Time and Blood Pressure in ICU Patients: Potential and Limitations. Frontiers in physiology, 9, 1848.

Fallet, S., Schoenenberger, Y., Martin, L., Braun, F., Moser, V., & Vesin, J. M. (Sep. 2017). Imaging photoplethysmography: A real-time signal quality index. In 2017 Computing in Cardiology (CinC) (pp. 1-4). IEEE.

Feng, L., Po, L. M., Xu, X., Li, Y., Cheung, C. H., Cheung, K. W., & Yuan, F. (Apr. 2015). Dynamic ROI based on K-means for remote photoplethysmography. In 2015 IEEE International Conference on Acoustics, Speech and Signal Processing (ICASSP) (pp. 1310-1314). IEEE.

(56) References Cited

OTHER PUBLICATIONS

Flament, F., Francois, G., Qiu, H., Ye, C., Hanaya, T., Batisse, D., . . . & Bazin, R. (2015). Facial skin pores: a multiethnic study. Clinical, cosmetic and investigational dermatology, 8, 85.

Fung, P., Dumont, G., Ries, C., Mott, C., & Ansermino, M. (Sep. 2004). Continuous noninvasive blood pressure measurement by pulse transit time. In the 26th annual international conference of the IEEE engineering in medicine and biology society (vol. 1, pp. 738-741). IEEE.

Holton, B. D., Mannapperuma, K., Lesniewski, P. J., & Thomas, J. C. (2013). Signal recovery in imaging photoplethysmography. Physiological measurement, 34(11), 1499.

Holz, C., & Wang, E. J. (2017). Glabella: Continuously sensing blood pressure behavior using an unobtrusive wearable device. Proceedings of the ACM on Interactive, Mobile, Wearable and Ubiquitous Technologies, 1(3), 58.

Huang, P. W., Lin, C. H., Chung, M. L., Lin, T. M., & Wu, B. F. (Nov. 2017). Image based contactless blood pressure assessment using Pulse Transit Time. In 2017 International Automatic Control Conference (CACS) (pp. 1-6). IEEE.

Huang, S. C., Hung, P. H., Hong, C. H., & Wang, H. M. (2014). A new image blood pressure sensor based on PPG, RRT, BPTT, and harmonic balancing. IEEE sensors Journal, 14(10), 3685-3692.

Ishikawa, T., Hyodo, Y., Miyashita, K., Yoshifuji, K., Komoriya, Y., & Imai, Y. (Feb. 2017). Wearable Motion Tolerant PPG Sensor for Instant Heart Rate in Daily Activity. In Biosignals (pp. 126-133).

Jain, M., Deb, S., & Subramanyam, A. V. (Sep. 2016). Face video based touchless blood pressure and heart rate estimation. In 2016 IEEE 18th International Workshop on Multimedia Signal Processing (MMSP) (pp. 1-5). IEEE.

Jarchi, D., & Casson, A. J. (2017). Towards photoplethysmography-based estimation of instantaneous heart rate during physical activity. IEEE Transactions on Biomedical Engineering, 64(9), 2042-2053.

Jarchi, D., Salvi, D., Tarassenko, L., & Clifton, D. (2018). Validation of Instantaneous Respiratory Rate Using Reflectance PPG from Different Body Positions. Sensors, 18(11), 3705.

Kachuee, M., Kiani, M. M., Mohammadzade, H., & Shabany, M. (2016). Cuffless blood pressure estimation algorithms for continuous health-care monitoring. IEEE Transactions on Biomedical Engineering, 64(4), 859-869.

Kamshilin, A. A., Miridonov, S., Teplov, V., Saarenheimo, R., & Nippolainen, E. (2011). Photoplethysmographic imaging of high spatial resolution. Biomedical optics express, 2(4), 996-1006.

Kamshilin, A. A., Sidorov, I. S., Bahayan, L., Volynsky, M. A., Giniatullin, R., & Mamontov, O. V. (2016). Accurate measurement of the pulse wave delay with imaging photoplethysmography. Biomedical optics express, 7(12), 5138-5147.

Kamshilin, A. A., Teplov, V., Nippolainen, E., Miridonov, S., & Giniatullin, R. (2013). Variability of microcirculation detected by blood pulsation imaging. PloS one, 8(2), e57117.

Kong, L., Zhao, Y., Dong, L., Jian, Y., Jin, X., Li, B., . . . & Wu, H. (2013). Non-contact detection of oxygen saturation based on visible light imaging device using ambient light. Optics express, 21(15), 17464-17471.

Kumar, M., Veeraraghavan, A., & Sabharwal, A. (2015). DistancePPG: Robust non-contact vital signs monitoring using a camera. Biomedical optics express, 6(5), 1565-1588.

Li, T., & Zhou, X. (Oct. 2018). Battery-free eye tracker on glasses. In Proceedings of the 24th Annual International Conference on Mobile Computing and Networking (pp. 67-82). ACM.

Lin, S. T., Chen, W. H., & Lin, Y. H. (2017). A pulse rate detection method for mouse application based on multi-PPG sensors. Sensors, 17(7), 1628.

Liu, J., Yan, B. P. Y., Dai, W. X., Ding, X. R., Zhang, Y. T., & Zhao, N. (2016). Multi-wavelength photoplethysmography method for skin arterial pulse extraction. Biomedical optics express, 7(10), 4313-4326.

McDuff, D. J., Estepp, J. R., Piasecki, A. M., & Blackford, E. B. (Aug. 2015). A survey of remote optical photoplethysmographic imaging methods. In 2015 37th annual international conference of the IEEE engineering in medicine and biology society (EMBC) (pp. 6398-6404). IEEE.

McDuff, D., Gontarek, S., & Picard, R. W. (2014). Improvements in remote cardiopulmonary measurement using a five band digital camera. IEEE Transactions on Biomedical Engineering, 61(10), 2593-2601.

McDuff, D., Gontarek, S., & Picard, R. W. (2014). Remote detection of photoplethysmographic systolic and diastolic peaks using a digital camera. IEEE Transactions on Biomedical Engineering, 61(12), 2948-2954.

Mcduff, D., Hurter, C., & Gonzalez-Franco, M. (Nov. 2017). Pulse and vital sign measurement in mixed reality using a HoloLens. In Proceedings of the 23rd ACM Symposium on Virtual Reality Software and Technology (p. 34). ACM.

Meredith, D. J., Clifton, D., Charlton, P., Brooks, J., Pugh, C. W., & Tarassenko, L. (2012). Phomplethysmographic derivation of respiratory rate: a review of relevant physiology. Journal of medical engineering & technology, 36(1), 1-7.

Moco, A. V., Stuijk, S., & De Haan, G. (2016). Ballistocardiographic artifacts in PPG imaging. IEEE Transactions on Biomedical Engineering, 63(9), 1804-1811.

Moço, A., Stuijk, S., & de Haan, G. (2019). Posture effects on the calibratability of remote pulse oximetry in visible light. Physiological measurement, 40(3), 035005.

Moço, A., Stuijk, S., van Gastel, M., & de Haan, G. (2018). Impairing Factors in Remote-PPG Pulse Transit Time Measurements on the Face. In Proceedings of the IEEE Conference on Computer Vision and Pattern Recognition Workshops (pp. 1358-1366).

Po, L. M., Feng, L., Li, Y., Xu, X., Cheung, T. C. H., & Cheung, K. W. (2018). Block-based adaptive ROI for remote photoplethysmography. Multimedia Tools and Applications, 77(6), 6503-6529.

Poh, M. Z., McDuff, D. J., & Picard, R. W. (2010). Non-contact, automated cardiac pulse measurements using video imaging and blind source separation. Optics express, 18(10), 10762-10774.

Proença, J., Muehlsteff, J., Aubert, X., & Carvalho, P. (Aug. 2010). Is pulse transit time a good indicator of blood pressure changes during short physical exercise in a young population?. In 2010 Annual International Conference of the IEEE Engineering in Medicine and Biology (pp. 598-601). IEEE.

Ramirez, G. A., Fuentes, O., Crites Jr, S. L., Jimenez, M., & Ordonez, J. (2014). Color analysis of facial skin: Detection of emotional state. In Proceedings of the IEEE Conference on Computer Vision and Pattern Recognition Workshops (pp. 468-473).

Rouast, P. V., Adam, M. T., Chiong, R., Cornforth, D., & Lux, E. (2018). Remote heart rate measurement using low-cost RGB face video: a technical literature review. Frontiers of Computer Science, 12(5), 858-872.

Rundo, F., Conoci, S., Ortis, A., & Battiato, S. (2018). An advanced bio-inspired photoplethysmography (PPG) and ECG pattern recognition system for medical assessment. Sensors, 18(2), 405.

Saadatzi, M. N., Tafazzoli, F., Welch, K. C., & Graham, J. H. (Aug. 2016). Emotigo: Bluetooth-enabled eyewear for unobtrusive physiology-based emotion recognition. In 2016 IEEE International Conference on Automation Science and Engineering (CASE) (pp. 903-909). IEEE.

Samria, R., Jain, R., Jha, A., Saini, S., & Chowdhury, S. R. (Apr. 2014). Noninvasive cuffless estimation of blood pressure using Photoplethysmography without electrocardiograph measurement. In 2014 IEEE Region 10 Symposium (pp. 254-257). IEEE.

Shao, D., Tsow, F., Liu, C., Yang, Y., & Tao, N. (2017). Simultaneous monitoring of ballistocardiogram and photoplethysmogram using a camera. IEEE Transactions on Biomedical Engineering, 64(5), 1003-1010.

Sharma, M., Barbosa, K., Ho, V., Griggs, D., Ghirmai, T., Krishnan, S., . . . & Cao, H. (2017). Cuff-less and continuous blood pressure monitoring: A methodological review. Technologies, 5(2), 21.

Shirbani, F., Blackmore, C., Kazzi, C., Tan, I., Butlin, M., & Avolio, A. P. (Jul. 2018). Sensitivity of Video-Based Pulse Arrival Time to Dynamic Blood Pressure Changes. In 2018 40th Annual International Conference of the IEEE Engineering in Medicine and Biology Society (EMBC) (pp. 3639-3641). IEEE.

(56) References Cited

OTHER PUBLICATIONS

Solà, J., Proença, M., Braun, F., Pierrel, N., Degiorgis, Y., Verjus, C., . . . & Schoettker, P. (2016). Continuous non-invasive monitoring of blood pressure in the operating room: a cuffless optical technology at the fingertip. Current Directions in Biomedical Engineering, 2(1), 267-271.
Song, S. H., Cho, J. S., Oh, H. S., Lee, J. S., & Kim, I. Y. (Sep. 2009). Estimation of blood pressure using photoplethysmography on the wrist. In 2009 36th Annual Computers in Cardiology Conference (CinC) (pp. 741-744). IEEE.
Sun, Y., & Thakor, N. (2016). Photoplethysmography revisited: from contact to noncontact, from point to imaging. IEEE Transactions on Biomedical Engineering, 63(3), 463-477.
Trumpp, A., Rasche, S., Wedekind, D., Rudolf, M., Malberg, H., Matschke, K., & Zaunseder, S. (2017). Relation between pulse pressure and the pulsation strength in camera-based photoplethysmograms. Current Directions in Biomedical Engineering, 3(2), 489-492.
Vuksanović, V., Sheppard, L. W., & Stefanovska, A. (2008). Nonlinear relationship between level of blood flow and skin temperature for different dynamics of temperature change. Biophysical journal, 94(10), L78-L80.
Wang, W., den Brinker, A. C., Stuijk, S., & de Haan, G. (2016). Algorithmic principles of remote PPG. IEEE Transactions on Biomedical Engineering, 64(7), 1479-1491.
Warren, K., Harvey, J., Chon, K., & Mendelson, Y. (2016). Improving pulse rate measurements during random motion using a wearable multichannel reflectance photoplethysmograph. Sensors, 16(3), 342.
Wu, B. F., Huang, P. W., Lin, C. H., Chung, M. L., Tsou, T. Y., & Wu, Y. L. (2018). Motion resistant image-photoplethysmography based on spectral peak tracking algorithm. IEEE Access, 6, 21621-21634.
Zaunseder, S., Trumpp, A., Wedekind, D., & Malberg, H. (2018). Cardiovascular assessment by imaging photoplethysmography—a review. Biomedical Engineering/Biomedizinische Technik, 63(5), 617-634.
Zhang, G., Shan, C., Kirenko, I., Long, X., & Aarts, R. (2017). Hybrid optical unobtrusive blood pressure measurements. Sensors, 17(7), 1541.
U.S. Appl. No. 10/216,981, filed Feb. 26, 2019, Tzvieli et al.
U.S. Appl. No. 10/349,887, filed Jul. 16, 2019, Tzvieli et al.
U.S. Appl. No. 10/376,163, filed Aug. 13, 2019, Tzvieli et al.
U.S. Appl. No. 10/638,938, filed May 5, 2020, Tzvieli et al.
U.S. Appl. No. 10/687,739, filed Jun. 23, 2020, Segman.
U.S. Appl. No. 10/791,938, filed Oct. 6, 2020, Tzvieli et al.
U.S. Appl. No. 10/799,122, filed Oct. 13, 2020, Tzvieli et al.
Rosen, J., & Yosipovitch, G. (2018). Skin manifestations of diabetes mellitus. In Endotext [Internet]. MDText. com, Inc.
Kamel, M. I., Elhenawy, Y. I., & Saudi, W. M. (2018). Relation between cutaneous and extracutaneous complications in pediatric patients with type 1 diabetes. Dermato-endocrinology, 10(1), e1467717.
Azizian, Z., Behrangi, E., Hasheminasabzavareh, R., Kazemlo, H., Esmaeeli, R., & Hassani, P. (2019). Prevalence Study of Dermatologic Manifestations among Diabetic Patients. Advances in preventive medicine, 2019.
Pandey, S., Mishra, P., Sharma, N., & Shyam, B. K. (2015). Dermatological Manifestations in Diabetes Mellitus at NGMCTH Kohalpur. Journal of Nepalgunj Medical College, 13(2), 31-34.
Blanes-Vidal, V., Majtner, T., Avendaño-Valencia, L. D., Yderstraede, K. B., & Nadimi, E. S. (2019). Invisible Color Variations of Facial Erythema: A Novel Early Marker for Diabetic Complications?. Journal of diabetes research, 2019.
Bruen, D., Delaney, C., Florea, L., & Diamond, D. (2017). Glucose sensing for diabetes monitoring: recent developments. Sensors, 17(8), 1866.
Sempionatto, J. R., Nakagawa, T., Pavinatto, A., Mensah, S. T., Imani, S., Mercier, P., & Wang, J. (2017). Eyeglasses based wireless electrolyte and metabolite sensor platform. Lab on a Chip, 17(10), 1834-1842.
Kim, J., Campbell, A. S., & Wang, J. (2018). Wearable non-invasive epidermal glucose sensors: A review. Talanta, 177, 163-170.
Gu, W. (Apr. 2017). Non-intrusive blood glucose monitor by multi-task deep learning: PhD forum abstract. In Proceedings of the 16th ACM/IEEE International Conference on Information Processing in Sensor Networks (pp. 249-250).
Habbu, S., Dale, M., & Ghongade, R. (2019). Estimation of blood glucose by non-invasive method using photoplethysmography. Sādhanā, 44(6), 135.
Pfützner, A., Strobl, S., Demircik, F., Redert, L., Pfützner, J., Pfützner, A. H., & Lier, A. (2018). Evaluation of a new noninvasive glucose monitoring device by means of standardized meal experiments. Journal of diabetes science and technology, 12(6), 1178-1183.
Segman, Y. (2018). Device and method for noninvasive glucose assessment. Journal of diabetes science and technology, 12(6), 1159-1168.
International search report, PCT/M2020/060196, dated Feb. 7, 2021.
Written opinion of the international searching authority, PCT/IB2020/060196, dated Feb. 7, 2021.

* cited by examiner

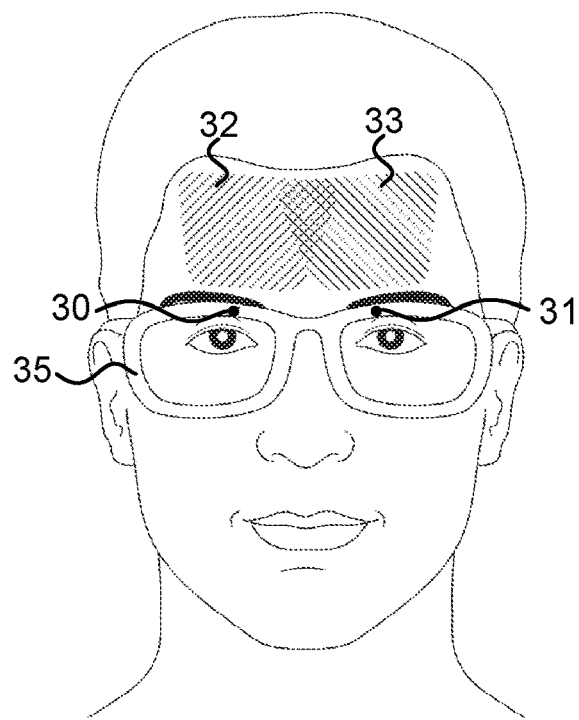
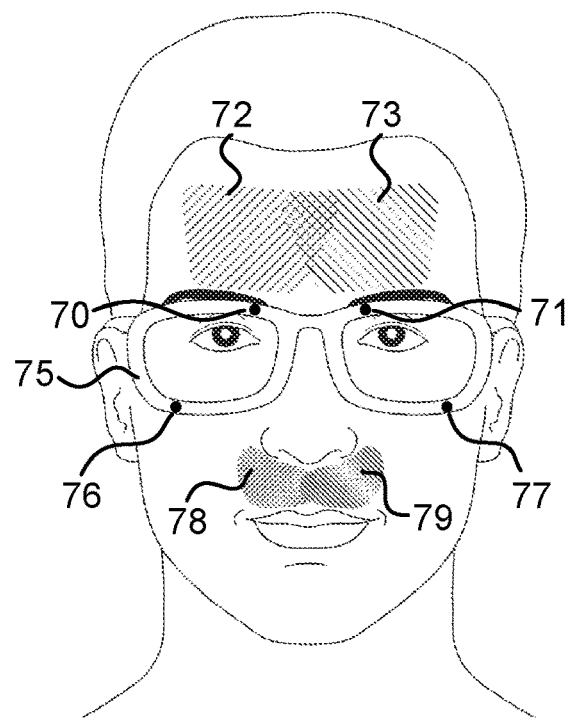
FIG. 12
FIG. 13
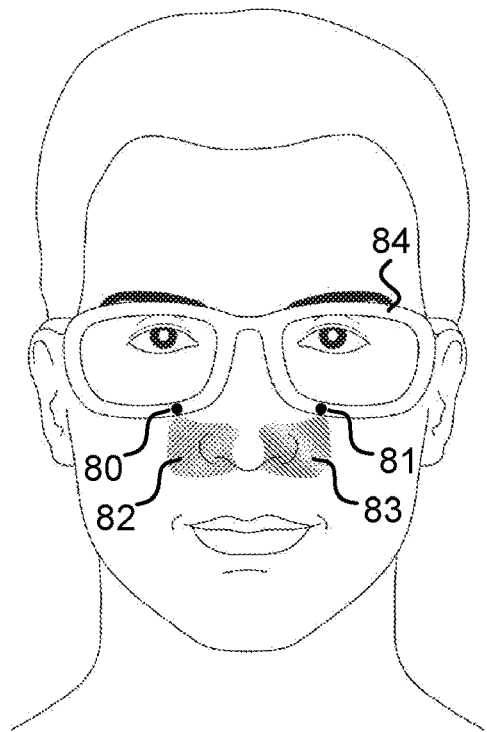
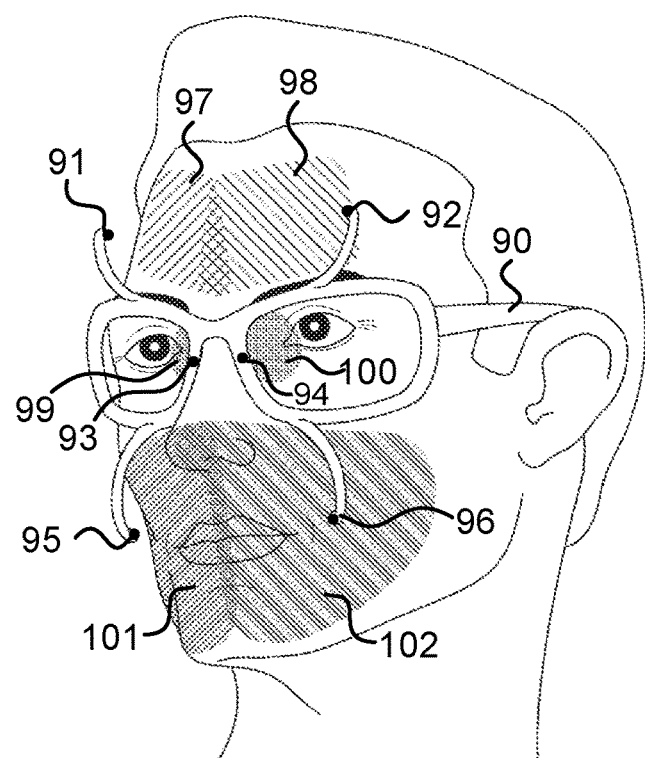
FIG. 14
FIG. 15

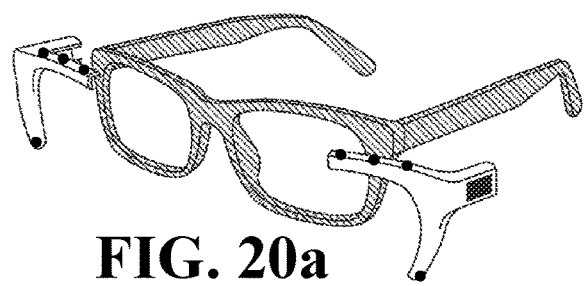
FIG. 20a
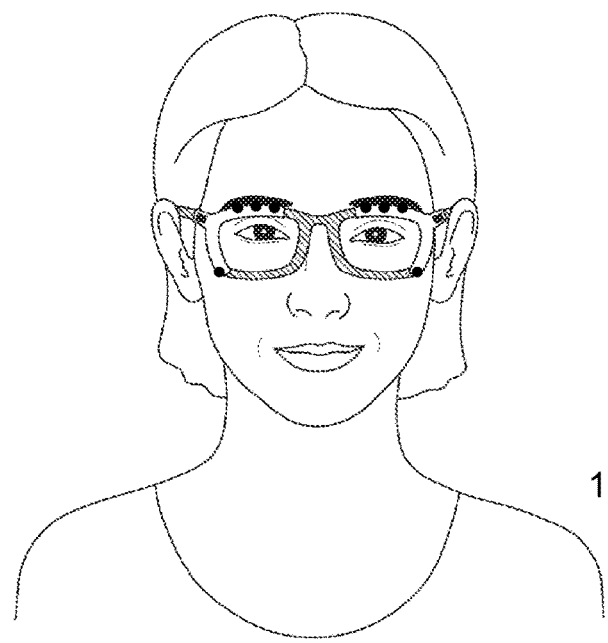
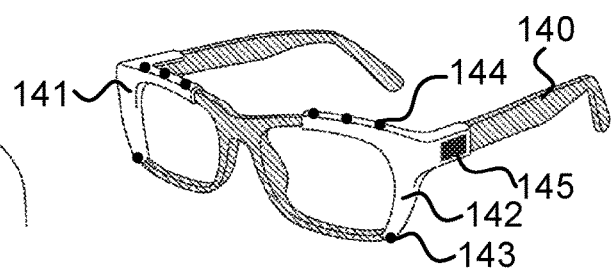
FIG. 20c  FIG. 20b
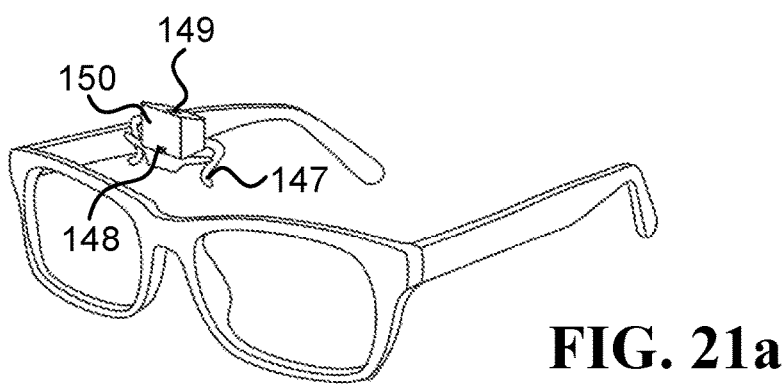
FIG. 21a
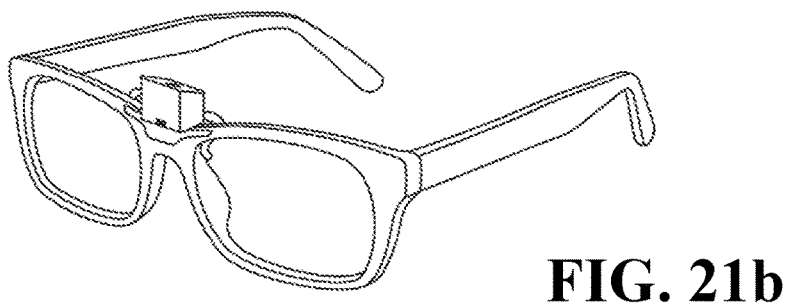
FIG. 21b

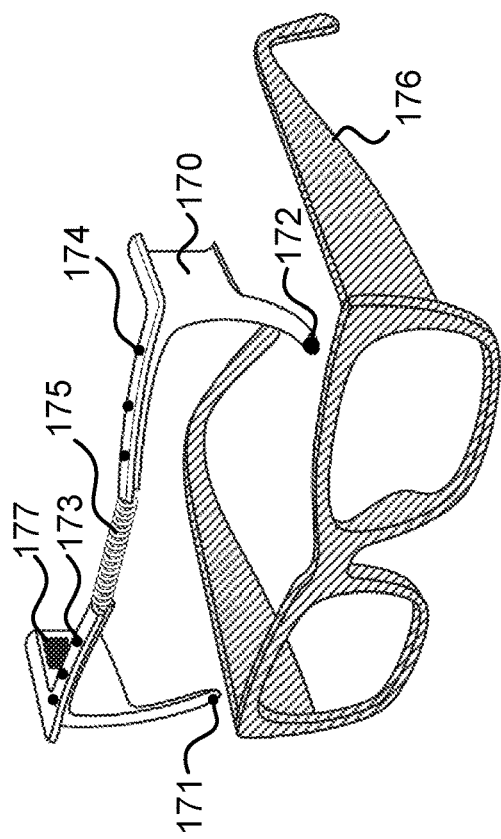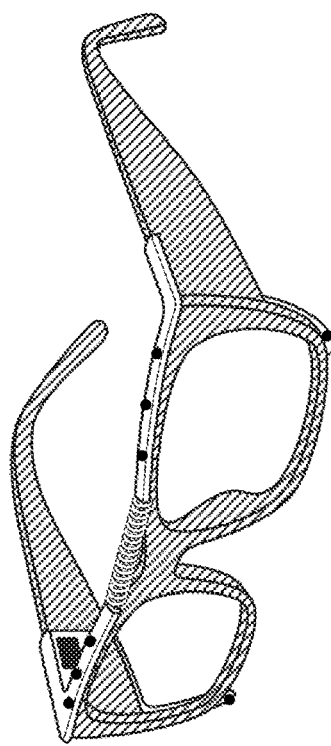
FIG. 23a
FIG. 23b
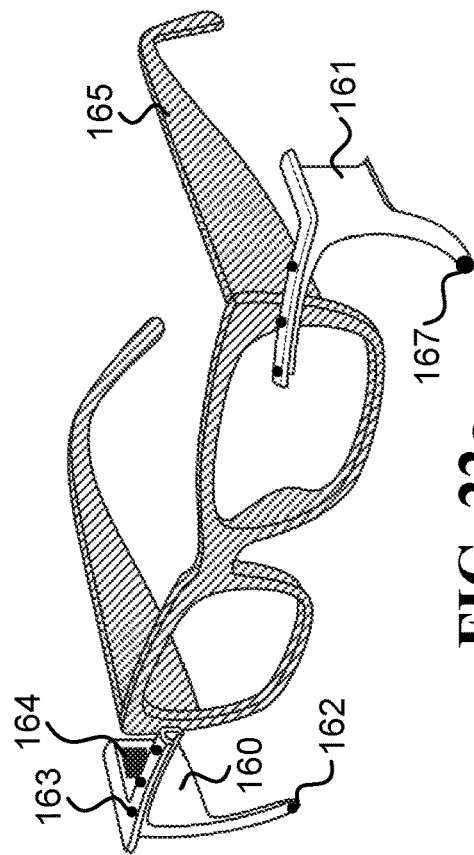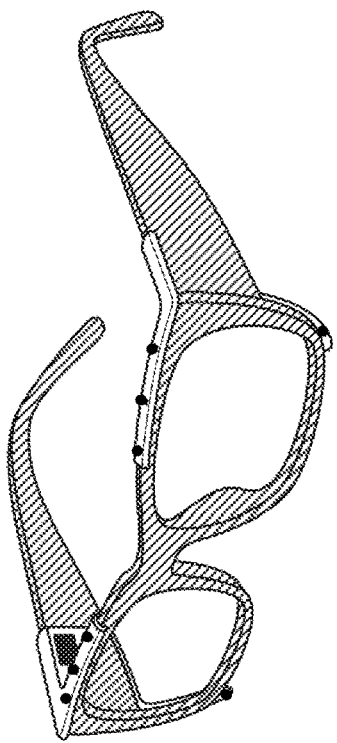
FIG. 22a
FIG. 22b

MONITORING BLOOD SUGAR LEVEL WITH A COMFORTABLE HEAD-MOUNTED DEVICE

CROSS-REFERENCE TO RELATED APPLICATIONS

This application claims priority to U.S. Provisional Patent Application No. 62/928,726, filed Oct. 31, 2019, U.S. Provisional Patent Application No. 62/945,141, filed Dec. 7, 2019, U.S. Provisional Patent Application No. 62/960,913, filed Jan. 14, 2020, U.S. Provisional Patent Application No. 63/006,827, filed Apr. 8, 2020, U.S. Provisional Patent Application No. 63/024,471, filed May 13, 2020, and U.S. Provisional Patent Application No. 63/048,638, filed Jul. 6, 2020.

This application is a Continuation-In-Part of U.S. application Ser. No. 16/854,883, filed Apr. 21, 2020, which is herein incorporated by reference in its entirety. This application is a Continuation-In-Part of U.S. application Ser. No. 17/005,259, filed Aug. 27, 2020, which is herein incorporated by reference in its entirety. U.S. Ser. No. 17/005,259 is a Continuation-In-Part of U.S. application Ser. No. 16/689,959, filed Nov. 20, 2019, which claims priority to U.S. Provisional Patent Application No. 62/874,430, filed Jul. 15, 2019. U.S. Ser. No. 17/005,259 is also a Continuation-In-Part of U.S. application Ser. No. 16/854,883, filed Apr. 21, 2020, which is a Continuation-In-Part of U.S. application Ser. No. 16/453,993, filed Jun. 26, 2019, now U.S. Pat. No. 10,667,697. U.S. Ser. No. 17/005,259 is also a Continuation-In-Part of U.S. application Ser. No. 16/831,413, filed Mar. 26, 2020, which is a Continuation-In-Part of U.S. application Ser. No. 16/551,654, filed Aug. 26, 2019, now U.S. Pat. No. 10,638,938. U.S. Ser. No. 16/551,654 is a Continuation-In-Part of U.S. application Ser. No. 16/453,993, filed Jun. 26, 2019. U.S. Ser. No. 16/453,993 is a Continuation-In-Part of U.S. application Ser. No. 16/375,841, filed Apr. 4, 2019. U.S. Ser. No. 16/375,841 is a Continuation-In-Part of U.S. application Ser. No. 16/156,493, now U.S. Pat. No. 10,524,667, filed Oct. 10, 2018. U.S. Ser. No. 16/156,493, is a Continuation-In-Part of U.S. application Ser. No. 15/635,178, filed Jun. 27, 2017, now U.S. Pat. No. 10,136,856, which claims priority to U.S. Provisional Patent Application No. 62/354,833, filed Jun. 27, 2016, and U.S. Provisional Patent Application No. 62/372,063, filed Aug. 8, 2016. U.S. Ser. No. 16/156,493 is also a Continuation-In-Part of U.S. application Ser. No. 15/231,276, filed Aug. 8, 2016, which claims priority to U.S. Provisional Patent Application No. 62/202,808, filed Aug. 8, 2015, and U.S. Provisional Patent Application No. 62/236,868, filed Oct. 3, 2015. U.S. Ser. No. 16/156,493 is also a Continuation-In-Part of U.S. application Ser. No. 15/832,855, filed Dec. 6, 2017, now U.S. Pat. No. 10,130,308, which claims priority to U.S. Provisional Patent Application No. 62/456,105, filed Feb. 7, 2017, and U.S. Provisional Patent Application No. 62/480,496, filed Apr. 2, 2017, and U.S. Provisional Patent Application No. 62/566,572, filed Oct. 2, 2017. U.S. Ser. No. 15/832,855 is a Continuation-In-Part of U.S. application Ser. No. 15/182,592, filed Jun. 14, 2016, now U.S. Pat. No. 10,165,949, a Continuation-In-Part of U.S. application Ser. No. 15/231,276, filed Aug. 8, 2016, a Continuation-In-Part of U.S. application Ser. No. 15/284,528, filed Oct. 3, 2016, now U.S. Pat. No. 10,113,913, a Continuation-In-Part of U.S. application Ser. No. 15/635,178, filed Jun. 27, 2017, now U.S. Pat. No. 10,136,856, and a Continuation-In-Part of U.S. application Ser. No. 15/722,434, filed Oct. 2, 2017. U.S. Ser. No. 15/832,855 is a Continuation-In-Part of U.S. application Ser. No. 15/182,566, filed Jun. 14, 2016, now U.S. Pat. No. 9,867,546, which claims priority to U.S. Provisional Patent Application No. 62/175,319, filed Jun. 14, 2015, and U.S. Provisional Patent Application No. 62/202,808, filed Aug. 8, 2015. U.S. Ser. No. 15/182,592 claims priority to U.S. Provisional Patent Application No. 62/175,319, filed Jun. 14, 2015, and U.S. Provisional Patent Application No. 62/202,808, filed Aug. 8, 2015. U.S. Ser. No. 15/284,528 claims priority to U.S. Provisional Patent Application No. 62/236,868, filed Oct. 3, 2015, and U.S. Provisional Patent Application No. 62/354,833, filed Jun. 27, 2016, and U.S. Provisional Patent Application No. 62/372,063, filed Aug. 8, 2016.

U.S. Ser. No. 16/156,493 is also a Continuation-In-Part of U.S. application Ser. No. 15/833,115, filed Dec. 6, 2017, now U.S. Pat. No. 10,130,261. U.S. Ser. No. 15/833,115 is a Continuation-In-Part of U.S. application Ser. No. 15/182,592, a Continuation-In-Part of U.S. application Ser. No. 15/231,276, filed Aug. 8, 2016, a Continuation-In-Part of U.S. application Ser. No. 15/284,528, a Continuation-In-Part of U.S. application Ser. No. 15/635,178, and a Continuation-In-Part of U.S. application Ser. No. 15/722,434, filed Oct. 2, 2017. U.S. Ser. No. 16/453,993 is also a Continuation-In-Part of U.S. application Ser. No. 16/147,695, filed Sep. 29, 2018. U.S. Ser. No. 16/147,695 is a Continuation of U.S. application Ser. No. 15/182,592, filed Jun. 14, 2016, which claims priority to U.S. Provisional Patent Application No. 62/175,319, filed Jun. 14, 2015, and U.S. Provisional Patent Application No. 62/202,808, filed Aug. 8, 2015.

U.S. Ser. No. 17/005,259 is also a Continuation-In-Part of U.S. Ser. No. 16/689,929, filed Nov. 20, 2019, that is a Continuation-In-Part of U.S. Ser. No. 16/156,586, filed Oct. 10, 2018, that is a Continuation-In-Part of U.S. application Ser. No. 15/832,815, filed Dec. 6, 2017, which claims priority to U.S. Provisional Patent Application No. 62/456,105, filed Feb. 7, 2017, and U.S. Provisional Patent Application No. 62/480,496, filed Apr. 2, 2017, and U.S. Provisional Patent Application No. 62/566,572, filed Oct. 2, 2017. U.S. Ser. No. 16/156,586 is also a Continuation-In-Part of U.S. application Ser. No. 15/859,772 Jan. 2, 2018, now U.S. Pat. No. 10,159,411.

ACKNOWLEDGMENTS

Gil Thieberger would like to thank his holy and beloved teacher, Lama Dvora-hla, for her extraordinary teachings and manifestation of wisdom, love, compassion and morality, and for her endless efforts, support, and skills in guiding him and others on their paths to freedom and ultimate happiness. Gil would also like to thank his beloved parents for raising him with love and care.

BACKGROUND

The blood glucose level is a very important value for diabetes patients to keep track of Blood glucose testing provides useful information for diabetes management, and physicians recommend diabetes patients monitor their blood glucose level several times a day. This is often quite inconvenient and painful, since most blood glucose monitoring techniques involve invasive drawing of blood samples. Thus, there is a need for a more convenient way to monitor blood glucose levels, without the need to draw blood samples multiple times a day on a continuous basis.

SUMMARY

Described herein are embodiments of systems and methods for calculating glucose in a non-invasive manner using head-mounted sensors. Noninvasive glucose monitoring devices are pain-free and enable taking multiple measurements of glucose levels per day. It is believed that, for some people, the variation of the facial skin color with the heartbeats changes as a function of their blood glucose level. Different facial skin regions show different variations of the facial skin color, and these different variations are also believed to change, for some people, as a function of their blood glucose level. However, these changes are small and cannot be extracted solely from images of skin on the face. Therefore, in some embodiments described herein, a contact photoplethysmography (PPG) device is used to detect times of systolic notches and times of systolic peaks. These times are used to identify which of the images were taken during the times of systolic notches and which of the images were taken during the times of systolic peaks, and based on that, the facial skin colors during the systolic notches and systolic peaks can be compared more accurately in order to calculate the blood glucose level.

Some embodiments described herein utilize head-mounted sensors to obtain PPG signals from one side or both sides of a user's head. A PPG signal is an optically obtained plethysmogram that is indicative of blood volume changes in the microvascular bed of tissue. A PPG signal is often obtained by using a pulse oximeter, which illuminates the skin and measures changes in light absorption. Another possibility for obtaining the PPG signal is using an imaging photoplethysmography (iPPG) device. As opposed to contact PPG devices, iPPG does not require contact with the skin and is obtained by a non-contact sensor, such as a video camera. Other names known in the art for iPPG include: remote photoplethysmography (rPPG), remote photoplethysmographic imaging, remote imaging photoplethysmography, remote-PPG, and multi-site photoplethysmography (MPPG).

Some aspects of this disclosure involve utilization of sensors that are physically coupled to smartglasses in order to conveniently, and optionally continuously, monitor users. Smartglasses are generally comfortable to wear, lightweight, and can have extended battery life. Thus, they are well suited as an instrument for long-term monitoring of patient's physiological signals and activity.

One aspect of this disclosure involves a system configured to calculate blood glucose level. In some embodiments, the system includes a head-mounted contact photoplethysmography device that measures a signal indicative of a photoplethysmogram signal (PPG signal) at a first region comprising skin on a user's head, and a head-mounted camera configured to capture images of a second region comprising skin on the user's head. The system also includes a computer that identifies, based on the PPG signal, times of systolic notches and times of systolic peaks, and calculates the blood glucose level based on differences between a first subset of the images taken during the times of systolic notches and a second subset of the images taken during the times of systolic peaks.

In one embodiment, the computer extracts imaging photoplethysmogram signals (iPPG signals) from the images, and calculates the blood glucose level based on differences between amplitudes of the iPPG signals during the times of systolic notches and the iPPG signals during the times of systolic peaks.

In another embodiment, the computer calculates a first hemoglobin concentration pattern based on the first subset of the images, calculates a second hemoglobin concentration pattern based on the second subset of the images, and calculates the blood glucose level based on differences between the first and second hemoglobin concentration patterns.

In yet another embodiment, the computer extracts a first set of facial flushing patterns based on the first subset of the images, extracts a second set of facial flushing patterns based on the second subset of the images, and calculates the blood glucose level based on differences between the first and second facial flushing patterns.

Another aspect of this disclosure is a method for calculating blood glucose level. In one embodiment, the method includes at least the following steps: In Step 1, receiving, from a head-mounted contact photoplethysmography device, a signal indicative of a photoplethysmogram signal (PPG signal) at a first region comprising skin on a user's head. In Step 2, receiving, from a head-mounted camera, images of a second region comprising skin on the user's head. In Step 3, identifying, based on the PPG signal, times of systolic notches and times of systolic peaks. And in Step 4, calculating the blood glucose level based on differences between a first subset of the images taken during the times of systolic notches and a second subset of the images taken during the times of systolic peaks.

Yet another aspect of this disclosure involves a system configured to calculate blood glucose levels. In one embodiment, the system includes a head-mounted contact photoplethysmography device configured to measure a signal indicative of a photoplethysmogram signal (PPG signal) at a first region comprising skin on a user's head, and a head-mounted camera configured to capture images of a second region comprising skin on the user's head. The system also includes a first head-mounted temperature sensor configured to measure skin temperature ($T_{skin}$) at a first region on a user's head, and a second head-mounted temperature sensor configured to measure temperature of the environment ($T_{env}$). The system includes a computer that: (i) generates feature values based on: the PPG signal, the images, $T_{skin}$, and $T_{env}$; and (ii) utilizes a machine learning-based model to calculate the blood glucose level based on the feature values.

BRIEF DESCRIPTION OF THE DRAWINGS

The embodiments are herein described by way of example only, with reference to the following drawings:

FIG. 12, FIG. 13, FIG. 14 and FIG. 15 illustrate head-mounted systems (HMSs) configured to measure various ROIs relevant to some of the embodiments describes herein;

FIG. 20a, FIG. 20b, and FIG. 20c illustrate embodiments of two right and left clip-on devices that are configured to attached/detached from an eyeglasses frame;

FIG. 21a and FIG. 21b illustrate an embodiment of a clip-on device that includes inward-facing head-mounted cameras pointed at the lower part of the face and the forehead;

FIG. 22a and FIG. 22b illustrate an embodiment of a single-unit clip-on device that is configured to be attached behind an eyeglasses frame;

FIG. 23a and FIG. 23b illustrate embodiments of right and left clip-on devices that are configured to be attached behind an eyeglasses frame;

DETAILED DESCRIPTION

Figure 1A:
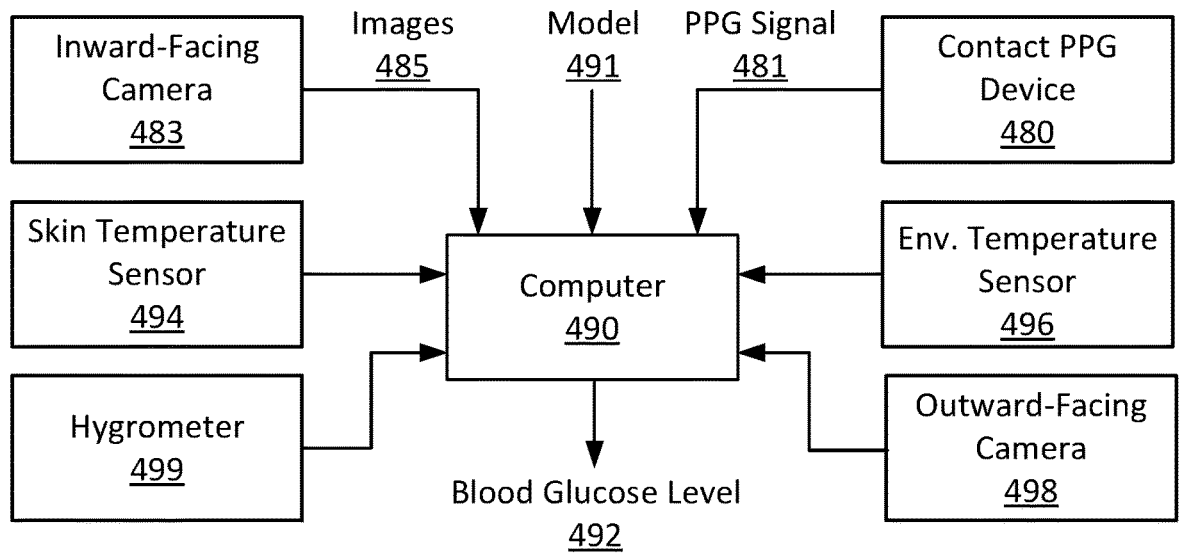
FIG. 1a illustrates an embodiment of a system that calculates blood glucose levels.

The following is a discussion of some aspects of various systems that include head-mounted elements (e.g., sensors on smartglasses) that may be utilized for various applications.

Sentences in the form of "a frame configured to be worn on a user's head" or "a frame worn on a user's head" refer to a mechanical structure that loads more than 50% of its weight on the user's head. For example, an eyeglasses frame may include two temples connected to two rims connected by a bridge; the frame in Oculus Rift™ includes the foam placed on the user's face and the straps; and the frame in Google Glass™ is similar to an eyeglasses frame. Additionally or alternatively, the frame may connect to, be affixed within, and/or be integrated with, a helmet (e.g., a safety helmet, a motorcycle helmet, a combat helmet, a sports helmet, a bicycle helmet, etc.), goggles, and/or a brainwave-measuring headset.

Sentences in the form of "a frame configured to be worn on a user's head in a consistent manner" refer to a frame that is located in the same position relative to the head when worn repeatedly, and thus sensors attached to that frame are most likely to be positioned each time at the same location relative to the head. For example, eyeglasses frames, goggles, and helmets are all included under the definition of a frame that is worn in a consistent manner. However, a flexible headband, or adhesive sensors that are placed manually one by one, are not worn in a consistent manner, because these sensors are most likely to be positioned each time in a different location relative to the head.

The term "smartglasses" refers to any type of a device that resembles eyeglasses, and includes a frame configured to be worn on a user's head in a consistent manner, and includes electronics to operate one or more sensors. The frame may be an integral part of the smartglasses, and/or an element that is connected to the smartglasses. Examples of smartglasses include: any type of eyeglasses with electronics (whether prescription or plano), sunglasses with electronics, safety goggles with electronics, sports goggle with electronics, augmented reality devices, virtual reality devices, and mixed reality devices. In addition, the term "eyeglasses frame" refers to one or more of the following devices, whether with or without electronics: smartglasses, prescription eyeglasses, plano eyeglasses, prescription sunglasses, plano sunglasses, safety goggles, sports goggle, an augmented reality device, virtual reality devices, and a mixed reality device.

The term "smart-helmet" refers to a helmet that includes a frame configured to be worn on a user's head in a consistent manner, and includes electronics to operate one or more sensors. The frame may be an integral part of the smart-helmet, and/or an element that is connected to the smart-helmet. Examples of smart-helmets include: a safety helmet with electronics, a motorcycle helmet with electronics, a combat helmet with electronics, a sports helmet with electronics, and a bicycle helmet with electronics.

Examples of electronics that may be included in smartglasses and/or a smart-helmet include one or more of the following electronic components: a computer, a microcontroller, a processor, a memory, and a communication interface. The electronics of the smartglasses and/or smart-helmets may be integrated in various ways. For example, the electronics may be integrated into the package of one of the sensors, such as a camera housing that is physically coupled to a helmet, where the housing includes the imaging sensor and its processor, memory, power supply and wireless communication unit. In another example, the electronics may be integrated into the frame, such as a microcontroller, power supply and wireless communication unit that are integrated into an eyeglasses frame, and configured to operate a PPG device and a microphone that are physically coupled to the frame.

The term "temperature sensor" refers to a device that measures temperature and/or temperature change. The temperature sensor may be a contact thermometer (such as a thermistor, a thermocouple), and/or a non-contact thermal cameras (such as a thermopile sensor, a microbolometer sensor, a pyroelectric sensor, or a ferroelectric sensor). Some examples of temperature sensors useful to measure skin temperature include: thermistors, thermocouples, thermoelectric effect, thermopiles, microbolometers, and pyroelectric sensors. Some examples of temperature sensors useful to measure environment temperature include: thermistors, resistance temperature detectors, thermocouples; thermopiles, and semiconductor-based sensors.

The term "movement sensor" refers to a sensor comprising one or more of the following components: a 3-axis gyroscope, a 3-axis accelerometer, and a magnetometer. The movement sensor may also include a sensor that measures barometric pressure.

The term "acoustic sensor" refers to a device that converts sound waves into an electrical signal. An acoustic sensor can be a microphone, such as a dynamic microphone that works via electromagnetic induction, a piezoelectric microphone that uses the phenomenon of piezoelectricity, a fiber-optic microphone that converts acoustic waves into electrical signals by sensing changes in light intensity, a Micro-Electrical-Mechanical System (MEMS) microphone (such as silicon MEMS and piezoelectric MEMS), and/or other sensors that measure sound waves, such as described in the following examples: (i) Han, Jae Hyun, et al. "Basilar membrane-inspired self-powered acoustic sensor enabled by highly sensitive multi tunable frequency band." Nano Energy 53 (2018): 198-205, describes a self-powered flexible piezoelectric acoustic sensor having high sensitivity, (ii) Rao, Jihong, et al. "Recent Progress in Self-Powered Skin Sensors." Sensors 19.12 (2019): 2763. describes various self-powered acoustic skin sensors, such as an integrated triboelectric nanogenerator (TENG) with a polymer tube that can pick up and recover human throat voice even in an extremely noisy or windy environment, and (iii) Scanlon, Michael V. Acoustic sensor for voice with embedded physiology. Army Research Lab Adelphi MD, 1999, describes a gel-coupled acoustic sensor able to collect information related to the function of the heart, lungs, and changes in voice patterns.

"Visible-light camera" refers to a non-contact device designed to detect at least some of the visible spectrum, such as a video camera with optical lenses and CMOS or CCD sensor. A "thermal camera" refers herein to a non-contact device that measures electromagnetic radiation having wavelengths longer than 2500 nanometer (nm) and does not touch its region of interest (ROI). A thermal camera may include one sensing element (pixel), or multiple sensing elements that are also referred to herein as "sensing pixels", "pixels", and/or focal-plane array (FPA). A thermal camera may be based on an uncooled thermal sensor, such as a thermopile sensor, a microbolometer sensor (where microbolometer refers to any type of a bolometer sensor and its equivalents), a pyroelectric sensor, or a ferroelectric sensor.

A reference to a "camera" herein may relate to various types of devices. In one example, a camera is a visible-light camera. In another example, a camera may capture light in the ultra-violet range. And in another example, a camera may capture near infrared radiation (e.g., wavelengths between 750 and 2000 nm).

Sentences in the form of "inward-facing head-mounted camera" refer to a camera configured to be worn on a user's head and to remain pointed at its ROI, which is on the user's face, also when the user's head makes angular and lateral movements (such as movements with an angular velocity above 0.1 rad/sec, above 0.5 rad/sec, and/or above 1 rad/sec). A head-mounted camera (which may be inward-facing and/or outward-facing) may be physically coupled to a frame worn on the user's head, may be physically coupled to eyeglasses using a clip-on mechanism (configured to be attached to and detached from the eyeglasses), may be physically coupled to a hat or a helmet, or may be mounted to the user's head using any other known device that keeps the camera in a fixed position relative to the user's head also when the head moves. Sentences in the form of "sensor physically coupled to the frame" mean that the sensor moves with the frame, such as when the sensor is fixed to (or integrated into) the frame, and/or when the sensor is fixed to (or integrated into) an element that is physically coupled to the frame, and/or when the sensor is connected to the frame with a clip-on mechanism.

Various embodiments described herein involve calculations based on machine learning approaches. Herein, the terms "machine learning approach" and/or "machine learning-based approaches" refer to learning from examples using one or more approaches. Examples of machine learning approaches include: decision tree learning, association rule learning, regression models, nearest neighbors classifiers, artificial neural networks, deep learning, inductive logic programming, support vector machines, clustering, Bayesian networks, reinforcement learning, representation learning, similarity and metric learning, sparse dictionary learning, genetic algorithms, rule-based machine learning, and/or learning classifier systems.

Herein, a "machine learning-based model" is a model trained using one or more machine learning approaches. For brevity's sake, at times, a "machine learning-based model" may simply be called a "model". Referring to a model as being "machine learning-based" is intended to indicate that the model is trained using one or more machine learning approaches (otherwise, "model" may also refer to a model generated by methods other than machine learning).

Herein, "feature values" (also known as feature vector, feature data, and numerical features) may be considered input to a computer that utilizes a model to perform the calculation of a value, such as a value indicative of one or more vital signs of a user. It is to be noted that the terms "feature" and "feature value" may be used interchangeably when the context of their use is clear. However, a "feature" typically refers to a certain type of value, and represents a property, while "feature value" is the value of the property with a certain instance (i.e., the value of the feature in a certain sample).

It is to be noted that when it is stated that feature values are generated based on data comprising multiple sources, it means that for each source, there is at least one feature value that is generated based on that source (and possibly other data). For example, stating that feature values are generated from an image capturing first and second regions ($IM_{ROI1}$ and $IM_{ROI2}$, respectively) means that the feature values include at least a first feature value generated based on $IM_{ROI1}$ and a second feature value generated based on $IM_{ROI2}$.

In addition to feature values generated based on measurements taken by sensors mentioned in a specific embodiment, at least some feature values utilized by a computer of the specific embodiment may be generated based on additional sources of data that were not specifically mentioned in the specific embodiment. Some examples of such additional sources of data include: (i) contextual information such as the time of day (e.g., to account for effects of the circadian rhythm), day of month (e.g., to account for effects of the lunar rhythm), day in the year (e.g., to account for seasonal effects), and/or stage in a menstrual cycle; (ii) information about the user being measured such as sex, age, weight, height, body build, genetics, medical records, and/or intake of substances; (iii) measurements of the environment, such as temperature, humidity level, noise level, elevation, air quality, a wind speed, precipitation, and infrared radiation; and/or (iv) values of physiological signals of the user obtained by sensors that are not mentioned in the specific embodiment, such as an electrocardiogram (ECG) sensor, an electroencephalography (EEG) sensor, a galvanic skin response (GSR) sensor, a movement sensor, an acoustic sensor, and/or a temperature sensor.

A machine learning-based model of a specific embodiment may be trained, in some embodiments, based on data collected in day-to-day, real world scenarios. As such, the data may be collected at different times of the day, while users perform various activities, and in various environmental conditions. Utilizing such diverse training data may enable a trained model to be more resilient to the various effects that different conditions can have on the measurements, and consequently, be able to achieve better detection of a required parameter in real world thy-to-day scenarios.

Herein the terms "photoplethysmogram signal", "photoplethysmographic signal", "photoplethysmography signal", and other similar variations are interchangeable and refer to the same type of signal. A photoplethysmogram signal may be referred to as a "PPG signal", or an "iPPG signal" when specifically referring to a PPG signal obtained from a camera. The terms "photoplethysmography device", "photoplethysmographic device", "photoplethysmogram device", and other similar variations are also interchangeable and refer to the same type of device that measures a signal from which it is possible to extract the photoplethysmogram signal. The photoplethysmography device may be referred to as "PPG device".

Sentences in the form of "a sensor configured to measure a signal indicative of a photoplethysmogram signal" refer to at least one of: (i) a contact PPG device, such as a pulse oximeter that illuminates the skin and measures changes in light absorption, where the changes in light absorption are indicative of the PPG signal, and (ii) a non-contact camera that captures images of the skin, where a computer extracts the PPG signal from the images using an imaging photoplethysmography (iPPG) technique. Other names known in the art for iPPG include: remote photoplethysmography (rPPG), remote photoplethysmographic imaging, remote imaging photoplethysmography, remote-PPG, and multi-site photoplethysmography (MPPG). Additional names known in the art for iPPG from the face include: facial hemoglobin concentration changes, dynamic hemoglobin concentration/ information extraction, facial blood flow changes, and transdermal optical imaging.

A PPG signal is often obtained by using a pulse oximeter, which illuminates the skin and measures changes in light absorption. Another possibility for obtaining the PPG signal is using an imaging photoplethysmography (iPPG) device. As opposed to contact PPG devices, iPPG does not require contact with the skin and is obtained by a non-contact sensor, such as a video camera.

A time series of values measured by a PPG device, which is indicative of blood flow changes due to pulse waves, is typically referred to as a waveform (or PPG waveform to indicate it is obtained with a PPG device). It is well known that PPG waveforms show significant gender-related differences, age-related differences, and health-related differences. As a result, the PPG waveforms of different people often display different characteristics (e.g., slightly different shapes and/or amplitudes). In addition, the PPG waveform depends on the site at which it is measured, skin temperature, skin tone, and other parameters.

The analysis of PPG signals usually includes the following steps: filtration of a PPG signal (such as applying bandpass filtering and/or heuristic filtering), extraction of feature values from fiducial points in the PPG signal (and in some cases may also include extraction of feature values from non-fiducial points in the PPG signal), and analysis of the feature values.

One type of features that is often used when performing calculations involving PPG signals involves fiducial points related to the waveforms of the PPG signal and/or to functions thereof (such as various derivatives of the PPG signal). There are many known techniques to identify the fiducial points in the PPG signal, and to extract the feature values. The following are some non-limiting examples of how to identify fiducial points.

FIG. 1$d$ is a schematic illustration of some of the various fiducial points often used in the art (and described below). These examples of fiducial points include fiducial points of the PPG signal, fiducial points in the first derivative of the PPG signal (velocity photoplethysmogram, VPG), and fiducial points in the second derivative of the PPG signal (acceleration photoplethysmogram, APG).

Fiducial points in the PPG signal may include: the systolic notch 920, which is the minimum at the PPG signal onset; the systolic peak 921, which is the maximum of the PPG signal; the dicrotic notch 922, which coincident with e 934 (see below at the second derivative of the PPG signal); and the diastolic peak 923, which is the first local maximum of the PPG signal after the dicrotic notch and before 0.8 of the duration of the cardiac cycle, or if there is no such local maximum, then the first local maximum of the second derivative after e and before 0.8 of the duration of the cardiac cycle.

Fiducial points in the first derivative of the PPG signal (velocity photoplethysmogram, VPG) may include: the maximum slope peak in systolic of VPG 925; the local minima slope in systolic of VPG 926; the global minima slope in systolic of VPG 927; and the maximum slope peak in diastolic of VPG 928.

Fiducial points in the second derivative of the PPG signal (acceleration photoplethysmogram, APG) may include: a 930, which is the maximum of APG prior to the maximum of VPG; b 931, which is the first local minimum of APG following a; c 932, which is the greatest maximum of APG between b and e 934, or if no maxima then the first of (i) the first maximum of VPG after e 934, and (ii) the first minimum of APG after e 934; d 933, which is the lowest minimum of APG after c 932 and before e 934, or if no minima then coincident with c 932; e 934, which is the second maximum of APG after maximum of VPG and before 0.6 of the duration of the cardiac cycle, unless the c wave is an inflection point, in which case take the first maximum; and f 935, which is the first local minimum of APG after e 934 and before 0.8 of the duration of the cardiac cycle.

Fiducial points in the third derivative of the PPG signal (PPG′″) may include: the first local maximum of PPG′″ after b 931; and the last local minimum of PPG′″ before d 933, unless c=d, in which case take the first local minimum of PPG′″ after d 933, and if there is a local maximum of the PPG signal between this point and the dicrotic notch then use it instead.

Feature values of the PPG signal may also be extracted from relationships in the PPG signal and/or its derivatives. The following are some non-limiting examples such possible feature values: pulse width, peak to peak time, ratio of areas before and after dicrotic notch in a complete cycle, baseline wander (BW), which is the mean of the amplitudes of a beat's peak and trough; amplitude modulation (AM), which is the difference between the amplitudes of each beat's peak and trough; and frequency modulation (FM), which is the time interval between consecutive peaks.

Examples of additional features that can be extracted from the PPG signal, together with schematic illustrations of the feature locations on the PPG signal, can be found in the following three publications: (i) Peltokangas, Mikko, et al. "Parameters extracted from arterial pulse waves as markers of atherosclerotic changes: performance and repeatability." IEEE journal of biomedical and health informatics 22.3 (2017): 750-757; (ii) Ahn, Jae Mok. "New aging index using signal features of both photoplethysmograms and acceleration plethysmograms." Healthcare informatics research 23.1 (2017): 53-59; (iii) Charlton, Peter H., et al. "Assessing mental stress from the photoplethysmogram: a numerical study." Physiological measurement 39.5 (2018): 054001, and (iv) Peralta, Elena, et al. "Optimal fiducial points for pulse rate variability analysis from forehead and finger photoplethysmographic signals." Physiological measurement 40.2 (2019): 025007.

Although the above mentioned references describe manual feature selection, the features may be selected using any appropriate feature engineering technique, including using automated feature engineering tools that help data scientists to reduce data exploration time, and enable non-experts, who may not be familiar with data science and/or PPG characteristics, to quickly extract value from their data with little effort.

Unless there is a specific reference to a specific derivative of the PPG signal, phrases of the form of "based on the PPG signal" refer to the PPG signal and any derivative thereof, including the first derivative of the PPG signal, the second derivative of the PPG signal, and the third derivative of the PPG signal. For example, a sentence in the form of "a computer configured to detect a physiological signal based on the PPG signal" is to be interpreted as "a computer configured to detect a physiological signal based on at least one of: the PPG signal, a first derivative of the PPG signal, a second derivative of the PPG signal, a third derivative of the PPG signal, and/or any other derivative of the PPG signal".

Algorithms for filtration of the PPG signal (and/or the images in the case of iPPG), extraction of feature values from fiducial points in the PPG signal, and analysis of the feature values extracted from the PPG signal are well known in the art, and can be found for example in the following references: (i) Allen, John. "Photoplethysmography and its application in clinical physiological measurement." Physiological measurement 28.3 (2007): R1, and also in the thousands of references citing this reference; (ii) Elgendi, Mohamed. "On the analysis of fingertip photoplethysmogram signals." Current cardiology reviews 8.1 (2012): 14-25, and also in the hundreds of references citing this reference; (iii) Holton, Benjamin D., et al. "Signal recovery in imaging photoplethysmography." Physiological measurement 34.11 (2013): 1499, and also in the dozens of references citing this reference, (iv) Sun, Yu, and Nitish Thakor. "Photoplethysmography revisited: from contact to noncontact, from point to imaging." IEEE Transactions on Biomedical Engineering 63.3 (2015): 463-477, and also in the dozens of references citing this reference, (v) Kumar, Mayank, Ashok Veeraraghavan, and Ashutosh Sabharwal. "DistancePPG: Robust non-contact vital signs monitoring using a camera." Biomedical optics express 6.5 (2015): 1565-1588, and also in the dozens of references citing this reference, (vi) Wang, Wenjin, et al. "Algorithmic principles of remote PPG." IEEE Transactions on Biomedical Engineering 64.7 (2016): 1479-1491, and also in the dozens of references citing this reference, and (vii) Rouast, Philipp V., et al. "Remote heart rate measurement using low-cost RGB face video: a technical literature review." Frontiers of Computer Science 12.5 (2018): 858-872, and also in the dozens of references citing this reference.

In the case of iPPG, the input comprises images having multiple pixels. The images from which the iPPG signal and/or the hemoglobin concentration patterns are extracted may undergo various preprocessing to improve the signal, such as color space transformation, blind source separation using algorithms such as independent component analysis (ICA) or principal component analysis (PCA), and various filtering techniques, such as detrending, bandpass filtering, and/or continuous wavelet transform (CWT). Various preprocessing techniques known in the art that may assist in extracting iPPG signals from images are discussed in Zaunseder et al. (2018), "Cardiovascular assessment by imaging photoplethysmography—a review", Biomedical Engineering 63(5), 617-634.

FIG. 1a illustrates an embodiment of a system that calculates blood glucose levels. Embodiments of the system may utilize different types of sensors, which may include a head-mounted contact photoplethysmography device 480 (also referred to herein as "PPG device 480"), an inward-facing head-mounted camera 483 (also referred to herein as "camera 483"), and a computer 490. Embodiments of the system may optionally include additional components, such as one or more of the following: a head-mounted skin temperature sensor 494 (also referred to herein as "skin temperature sensor 494"), a head-mounted environment temperature sensor 496 (also referred to herein as "environment temperature sensor 496"), a head-mounted outward-facing camera 498 (also referred to herein as "outward-facing camera 498"), and a head-mounted hygrometer 499.

In one embodiment, the PPG device 480 measures a signal indicative of a photoplethysmogram signal (PPG signal 481) at a first region comprising skin on a user's head. In one example, the first region may include a portion of skin on the user's nose. In another example, the first region may include a portion of skin on one of the user's temples. In yet another example, the first region may include a portion of skin on a mastoid process on one of the sides of the user's head. Optionally, the PPG device 480 includes one or more light sources configured to illuminate the first region. For example, the one or more light sources may include light emitting diodes (LEDs) that illuminate the first region. Optionally, the one or more LEDs include at least two LEDs, where each illuminates the first region with light at a different wavelength. In one example, the at least two LEDs include a first LED that illuminates the first region with green light and a second LED that illuminates the first regions with an infrared light. Optionally, the PPG device 480 includes one or more photodetectors configured to detect extents of reflections from the first region. In another example, the PPG device 480 includes four light sources, which may be monochromatic (such as 625 nm, 740 nm, 850 nm, and 940 nm), and a CMOS or CCD image sensor (without a near-infrared filter, at least until 945 nm). The PPG devices provides measurements of the light reflected from the skin, and the computer calculates the glucose levels based on associations between combinations of the reflected lights and the user's blood glucose levels.

The camera 483 captures images 485 of a second region on the user's head. In one example, the second region may include a portion of skin on one of the user's cheeks (e.g., the region 484 illustrated in FIG. 1b). In another example, the second region may include a portion of skin on the user's forehead. In yet another example, the second region may include a portion of skin on one of the user's temples.

In different embodiments, the camera 483 may be located at different distances from the head. Optionally, with respect to the camera 483, the distance of the camera 483 from the head may be considered the length (measured throughout the optical axis) from the camera's lens to point on the head that is in the center of the images 485. In one example, the camera 483 is located more than 5 mm away from the user's head. In another example, the camera 483 is located more than 10 mm away from the user's head.

Head-mounted inward-facing cameras, such as the camera 483, are typically small and lightweight. In some embodiments, the camera 483 weighs below 10 g and even below 2 g. In one example the camera 483 is a multi-pixel video camera having a CMOS or a CCD sensor. The camera 483 may capture images at various rates. In one example, the images 485 include images captured at a frame rate of at least 3 frames per second (fps). In another example, the images 485 include images captured at a frame rate of at least 30 fps. In still another example, the images 485 include images captured at a frame rate of at least 256 fps. Images taken by the cameras 483 may have various resolutions. In one example, the images 485 include images that have a resolution of at least 8×8 pixels. In another example, the images 485 include images that have a resolution of at least 32×32 pixels. In yet another example, the images 485 include images that have a resolution of at least 640×480 pixels.

In some embodiments, the camera 483 may capture light in the near-infrared spectrum (NIR). Optionally, such a camera may include optics and sensors that capture light rays in at least one of the following NIR spectrum intervals: 700-800 nm, 700-900 nm, and 700-1,050 nm. Optionally, the sensors may be CCD and/or CMOS sensors designed to be sensitive in the NIR spectrum.

In some embodiments, the system may include a light source configured to direct electromagnetic radiation at the second region. Optionally, the light source comprises one or more of the following: a laser diode (LD), a light-emitting diodes (LED), and an organic light-emitting diode (OLED). It is to be noted that when embodiments described in this disclosure utilize light sources directed at a region of interest (ROI), such as an area appearing in images 485, the light source may be positioned in various locations relative to the ROI. In some embodiments, the light source may be positioned essentially directly above the ROI, such that electromagnetic radiation is emitted at an angle that is perpendicular (or within 10 degrees from being perpendicular) relative to the ROI. Optionally, the camera 483 may be positioned near the light source in order to capture the reflection of electromagnetic radiation from the ROI. In other embodiments, the light source may be positioned such that it is not perpendicular to the ROI. Optionally, the light source does not occlude the ROI. In one example, the light source points downwards from a frame of a pair of eyeglasses, and the ROI may include a portion of one of the wearer's cheeks. In another example, the light source may be located on an arm of a frame of a pair of eyeglasses and the ROI may be located above the arm or below it. In still another example, the system includes four light sources, which may be monochromatic (such as 625 nm, 740 nm, 850 nm, and 940 nm), and the camera sensor does not include a near-infrared filter (at least until 945 nm). The camera captures images of lights emitted from the light sources and reflected from the second region of skin, and the computer calculates the glucose levels based on associations between combinations of the reflected lights and the user's blood glucose levels. Optionally, the system further includes an outward-facing camera 498 having a color filter similar to the inward-facing camera 483, such that the images captured by the outward-facing camera 498 are utilized by the computer 490 to compensate for interferences from the environment which reduce the signal to noise ratio of the reflected lights captured in images 485.

Due to the position of the camera 483 relative to the face, in some embodiments, there may be an acute angle between the optical axis of the camera 483 and the second region (e.g., when the camera 483 is fixed to an eyeglasses frame and the second region is on, and/or includes a portion of, the forehead or a cheek). In order to improve the sharpness of the images 485, the camera 483 may be configured to operate in a way that takes advantage of the Scheimpflug principle. In one embodiment, the camera 483 includes a sensor and a lens; the sensor plane is tilted by a fixed angle greater than 2° relative to the lens plane according to the Scheimpflug principle in order to capture a sharper image when the eyeglasses are worn by the user (where the lens plane refers to a plane that is perpendicular to the optical axis of the lens, which may include one or more lenses). In another embodiment, the camera 483 includes a sensor, a lens, and a motor; the motor tilts the lens relative to the sensor according to the Scheimpflug principle. The tilt improves the sharpness of images when the eyeglasses are worn by the user.

In some embodiments, references to the camera 483 involve more than one camera. Optionally, the camera 483 may refer to two or more inward-facing head-mounted cameras, the second region includes two or more regions on the user's head that are respectively captured by the two or more inward-facing head-mounted cameras, and the images 485 include images each captured by a camera from among the two or more inward-facing head-mounted cameras. Optionally, the two or more regions include regions on different sides of the user's head.

In some embodiments, the second region covers a larger area of skin than the first region. In one example, the area of the second region is at least ten times larger than the area of the first region. In one example, the PPG device 480 does not obstruct the field of view of the camera 483 to the second region. In another example, the first region and the second region do not overlap.

In some embodiments, various devices, such as the PPG device 480, the camera 483, the computer 490, and/or other components of the system illustrated in FIG. 1a may be physically coupled to a frame of smartglasses or to a smart-helmet, which is designed to measure the user in day-to-day activities, over a duration of weeks, months, and/or years.

Figure 1B:
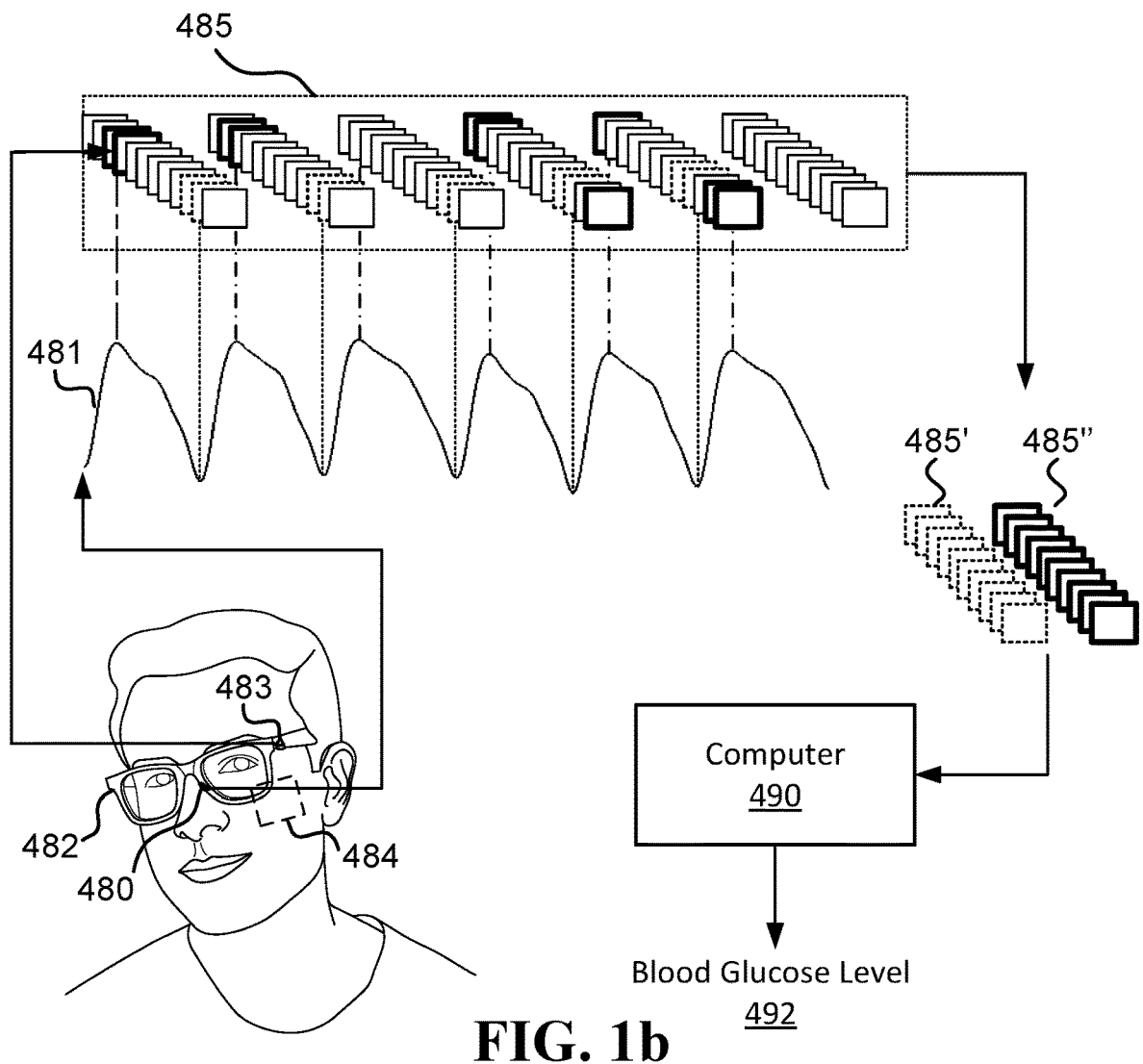
FIG. 1b illustrates selecting images based on times of systolic notches peaks.
Figure 1C:
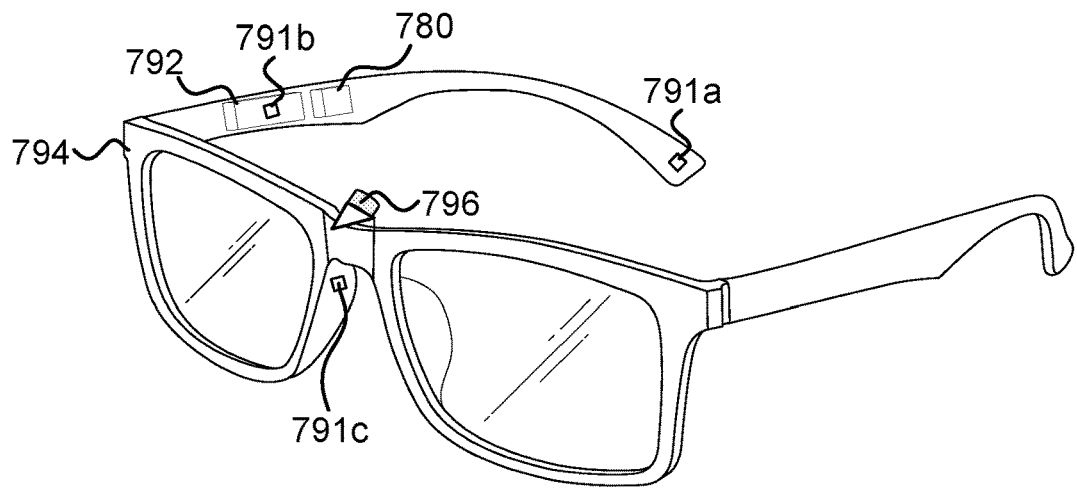
FIG. 1c illustrates smartglasses with a camera and several contact PPG devices.

FIG. 1c illustrates smartglasses that include camera 796 and several contact PPG devices, which may be utilized to collect the PPG signal 481 and the images 485, in some embodiments. The contact PPG devices correspond to the PPG device 480 and are used to measure the PPG signal 481. The contact PPG devices may be coupled at various locations on the frame 794, and thus may come in contact with various regions on the user's head. For example, contact PPG device 791a is located on the right temple tip, which brings it to contact with a region behind the user's ear (when the user wears the smartglasses). Contact PPG device 791b is located on the right temple of the frame 794, which puts it in contact with a region on the user's right temple (when wearing the smartglasses). It is to be noted that in some embodiments, in order to bring the contact PPG device close such that it touches the skin, various apparatuses may be utilized, such as spacers (e.g., made from rubber or plastic), and/or adjustable inserts that can help bridge a possible gap between the frame's temple and the user's face. Such an apparatus is spacer 792 which brings contact PPG device 791b in contact with the user's temple when the user wears the smartglasses. Another possible location for a contact PPG device is the nose bridge, as contact PPG device 791c is illustrated in the figure. It is to be noted the contact PPG device 791c may be embedded in the nose bridge (or one of its components), and/or physically coupled to a part of the nose bridge.

The computer 490 is configured, in some embodiments, to identify, based on the PPG signal 481, times of systolic notches and times of systolic peaks. The computer 490 then calculates a blood glucose level 492 based on differences between a first subset of the images 485 taken during the times of systolic notches and a second subset of the images 485 taken during the times of systolic peaks.

In different embodiments, a reference to "the computer 490" may refer to different components and/or a combination of components. In some embodiments, the computer 490 may include a processor located on a head-mounted device, such as the smartglasses 482 (illustrated in FIG. 1b). In other embodiments, at least some of the calculations attributed to the computer 490 may be performed on a remote processor, such as the user's smartphone and/or a cloud-based server. Thus, references to calculations being performed by the "computer 490" should be interpreted as calculations being performed utilizing one or more computers, with some of these one or more computers possibly being attached to a head-mounted device to which the PPG device 480 and the camera 483 are coupled. Examples of computers that may be utilized to perform the calculation of the blood glucose level 492 are computer 400 or computer 410, illustrated in FIG. 41a and FIG. 41b, respectively.

A systolic peak of a pulse wave is a fiducial point corresponding to a maximum value of a PPG signal of the pulse wave. Similarly, a systolic notch of the pulse wave is a fiducial point corresponding to a minimum value of the PPG signal of the pulse wave. Examples of these fiducial points are given in FIG. 1d (e.g., the systolic peak 921 and the systolic notch 920).

Herein, the alternative terms "blood glucose level", "blood sugar level", and "blood sugar concentration" may be used interchangeably and all refer to the concentration of glucose present in the blood, which may be measured in milligrams per deciliter (mg/dL).

Calculation of the blood glucose level 492 may involve the computer 490 utilizing an approach that may be characterized as involving machine learning. In some embodiments, this may involve the computer 490 generating feature values based on data that includes the first and second subsets of the images 485 and/or the PPG signal 481. Optionally, the computer 490 utilizes a model 491, which was previously trained, to calculate, based on the feature values, the blood glucose level 492. Optionally, the computer 490 forwards a value indicative of the blood glucose level 492 to a device of the user and/or to another computer system.

Generally, machine learning-based approaches utilized by embodiments described herein involve training a model on samples, with each sample including: feature values generated based on certain PPG signals measured by the PPG device 480, certain images taken by the cameras 483, and optionally other data, which were taken during a certain period, and a label indicative of the blood glucose level during the certain period, as determined by an external measurement device (e.g., from analysis of a blood sample). Optionally, a label indicative of the blood glucose level may be provided by the user, by a third party, and/or by a device used to measure the user's blood glucose level, such as a finger-stick blood test, a test strip, a portable meter, and/or a continuous glucose testing placed under the skin. Optionally, a label may be extracted based on analysis of electronic health records of the user, e.g., records generated while being monitored at a medical facility.

In some embodiments, the model 491 may be personalized for the user by training the model on samples that include: feature values generated based on measurements of the user, and corresponding labels indicative of the blood glucose level of the user while the measurements were taken (for example using finger-stick blood samples, test strips, portable meters, and/or a continuous glucose testing placed under the skin). In some embodiments, the model 491 may be generated based on measurements of multiple users, in which case, the model 491 may be considered a general model. Optionally, a model generated based on measurements of multiple users may be personalized for a certain user by being retrained on samples generated based on measurements of the certain user. Optionally, the data used to train the model 491 may include data obtained from a diverse set of users (e.g., users of different ages, weights, sexes, preexisting medical conditions, etc.). Optionally, the data used to train the model 491 includes data of other users with similar characteristics to the user (e.g., similar weight, age, sex, height, and/or preexisting conditions).

In order to achieve a robust model, in some embodiments, the samples used for the training of the model 491 may include samples based on data collected for different conditions. Optionally, the samples are generated based on data (that includes trusted blood glucose level readings) collected on different days, while indoors and outdoors, and while different environmental conditions persisted. In one example, the model 491 is trained on samples generated from a first set of training data taken during daytime, and is also trained on other samples generated from a second set of training data taken during nighttime. In a second example, the model 491 is trained on samples generated from a first set of training data taken while a user being measured was exercising and moving, and is also trained on other samples generated from a second set of data taken while the user being measured was sitting and not exercising.

In order to more accurately calculate blood glucose levels, in some embodiments, training data utilized to generate the model 491 may include samples with labels in various ranges, corresponding to different blood glucose levels. This data includes other subsets of the images 485, which were taken prior to when the first and second subsets of the images 485 were taken (which are used to calculate the blood glucose level 492).

In one example, training data used to generate the model 491 includes the following data: $3^{rd}$ and $4^{th}$ subsets of the images 485, taken during the times of systolic notches and systolic peaks, respectively, while the user had blood glucose level that was between 70 and 100; $5^{th}$ and $6^{th}$ subsets of the images 485, taken during the times of systolic notches and systolic peaks, respectively, while the user had blood glucose level that was between 100 and 125; $7^{th}$ and $8^{th}$ subsets of the images 485, taken during the times of systolic notches and systolic peaks, respectively, while the user had blood glucose level that was between 120 and 150; and $9^{th}$ and $10^{th}$ subsets of the images 485, taken during the times of systolic notches and systolic peaks, respectively, while the user had blood glucose level that was between 150 and 180. The images may include one or more colors. In one example, the images include three colors. In another example, the images include three colors in the visible range and one color in the NIR range. In still another example, the images include at least two colors in the visible range and at least two colors in the NIR range.

There are different ways in which the computer 490 may identify, based on the PPG signal 481, the times of systolic notches and the times of systolic peaks. In some embodiments, the identification of those times is done by providing the PPG signal 481, and/or feature values derived therefrom, as an input to a machine learning-based predictor that calculates the blood glucose level 492 (e.g., a neural network-based predictor). Thus, feature values generated based on images (as described in more detail below) may be correlated with the intensity of the PPG signal. Therefore, in such cases, the "identification" of the times of the systolic peaks and the times of the systolic notches may be a step that is implicitly performed by the neural network, and it need not be an explicit, separate step that precedes the calculation of the blood glucose level, rather it is a process that is an integral part of that calculation.

In some embodiments, the computer 490 identifies, based on the PPG signal 481, times of systolic notches and times of systolic peaks. The computer 490 may then utilize these identified times in different ways.

In some embodiments, the PPG device 480 touches and occludes the first region, while the camera 483 is not in direct contact with the second region. Therefore, the PPG signal 481 usually has a much better signal-to-noise (SNR) compared to iPPG signals extracted from the images 485. Furthermore, because both the first and the second regions are on the user's head, and because the PPG device 480 and the camera 483 measure the user essentially simultaneously, manifestation of the pulse arrival in the PPG signal 481 and iPPG signals extracted from the images 485 are typically highly correlated (e.g., the signals exhibit highly correlated pulse arrival times). This correlation enables the computer 490 to utilize pulse fiducial points identified in the PPG signal 481 (which is less noisy than the iPPG signals) to extract information from iPPG signals more efficiently and accurately. For example, the timings of fiducial points in the PPG signals 481 are used to select subsets of images, from among the images 485, which include corresponding occurrences of those fiducial points (e.g., systolic notches and systolic peaks).

In one embodiment, the same times corresponding to fiducial points, as determined based on the PPG signal 481, are also used for extracting fiducial points in the iPPG signals. Thus, the magnitudes of the fiducial points in the iPPG signals are taken essentially at the same times of the fiducial points in the PPG signal 481.

In another embodiment, times corresponding to fiducial points, as determined based on the PPG signal 481, may also be used to determine fiducial points in the iPPG signals, by applying a certain offset to the times. This certain offset may be used to account for the difference between the distances/route blood travels in order to reach the second region as opposed to the distance/route blood travels in order to reach the first region. In one example, an offset used between when a fiducial point (e.g., a systolic peak) occurs in the PPG signal 481, and when it manifests in a certain iPPG signal extracted from certain pixels in the images 485, may be a fixed offset (e.g., an offset that is a function of the relative distance of the second region from the first region). In another example, different sub-regions of the second region (e.g., corresponding to different pixels in the images 485) may have different offsets that are calculated empirically relative to the timings of fiducial points the PPG signal 481.

An offset used between when a fiducial point (e.g., a systolic peak) occurs in the PPG signal 481, and when it manifests in an iPPG signal recognizable in the images 485 may be adjusted to account for blood velocity. For example, the offset may be inversely proportional to the heart rate and/or blood pressure determined from the PPG signal 481. It is to be noted that offsets used between times of fiducial points identified in the PPG signal 481 and the iPPG signals may be user-specific and learned over time. For example, histograms of the offsets between the systolic peaks in the PPG signal 481 and systolic peaks of an iPPG signal, as observed over multiple pulses of the user, can be aggregated. Based on these histograms, the most frequent offset can be used to represent the difference between when systolic peaks occur in the PPG signal 481 and when it manifests the iPPG signal.

In yet another embodiment, times corresponding to fiducial points, as determined based on the PPG signal 481, may be used to set a range of times during which the same fiducial point is expected to manifest in an iPPG signal. For example, if a systolic peak is observed at time t in the PPG signal 481, a manifestation of a systolic peak will be extracted from a time that falls in [t+a, t+b], where a<b, and the values of a and b are set to correspond to the minimum and maximum offsets between manifestations of systolic peaks in the first region and a sub-region of the second region to which the iPPG signal corresponds. As discussed above, the values a and b may also be adjusted according to values such as the heart rate and/or blood pressure, and may also be learned for a specific user.

FIG. 1b illustrates a scenario in which certain images, from among the images 485, are selected based on times of systolic notches and systolic peaks identified in the PPG signal 481. The figure illustrates one embodiment of the system illustrated in FIG. 1a, in which a user is wearing glasses 482. The PPG device 480 is located, in this embodiment, in the nose piece of the glasses 482 (the first region in this embodiment is a region of skin in contact with the PPG device 480). The camera 483 is located on the front-end of a temple of the glasses 482 and is oriented downward, such that it captures images of the second region, which in this embodiment is a rectangular region 484 on the user's cheek (note that the second region need not be a perfect rectangle in practice—this shape is used for illustration purposes only). FIG. 1*b* shows an alignment between the PPG signal 481 and the images 485 (i.e., images taken appear above the value of the PPG signal measured when the images were taken). For each systolic peak and systolic notch in the PPG signal 481, a vertical line indicates one or more corresponding images from among the images 485. Images corresponding to systolic peaks are marked with a bold border, while images corresponding to systolic notches are marked with a dash border. In the figure, each systolic peak and notch has two corresponding images, but in various implementations, this number may vary (and need not be a fixed number). The computer 490 receives a first subset 485' of images corresponding to the systolic notches and a second subset 485" of images corresponding to the systolic peaks, and calculates the blood glucose level 492 based on a difference between these two subsets of images, using one or more of the techniques described herein.

In order to calculate the blood glucose level 492, the computer 490 may evaluate various types of differences between the first subset of the images 485 taken during the times of systolic notches and the second subset of the images taken during the times of systolic peaks. It is noted that the differences are not limited to the first and second subsets of the images, and may include additional subsets as well.

In some embodiments, at least some of the feature values utilized by the computer 490 to calculate the glucose blood level 492 include first and second sets of feature values generated from the first and second subsets of the images 485, respectively. Optionally, the differences between the first and second subsets of the images 485 determined from the differences between first and second sets of feature values. For example, the first set of feature values may include feature values indicative of one or more of the following: amplitudes of iPPG signals extracted from images in the first subset of the images 485, slopes of iPPG signals extracted from images in the first subset of the images 485, a first hemoglobin concentration pattern based on the first subset of the images 485, and a first set of facial flushing patterns based on the first subset of the images 485. Similarly, the second set of feature values may include feature values indicative of one or more of the following: amplitudes of iPPG signals extracted from images in the second subset of the images 485, slopes of iPPG signals extracted from images in the second subset of the images 485, a second hemoglobin concentration pattern based on the second subset of the images 485, and a second set of facial flushing patterns based on the second subset of the images 485.

In some embodiments, at least some of the feature values utilized by the computer 490 to calculate the glucose blood level 492 include a set of feature values generated by comparing the first and second subsets of the images 485 (and optionally other subsets as well), and calculating values representing differences between values extracted from the first and second subsets of the images 485 (and optionally the other subsets as well). For example, the set of feature values may include feature values indicative of one or more of the following: (i) a difference in amplitudes of iPPG signals extracted from images in the first subset of the images 485 and amplitudes of iPPG signals extracted from images in the second subset of the images 485; this difference may depend on the specific values of the different color channels in the images, (ii) a difference between a first hemoglobin concentration pattern based on the first subset of the images 485 and a second hemoglobin concentration pattern based on the second subset of the images 485; this difference may also depend on the specific values of the different color channels, and (iii) a difference between a first set of facial flushing patterns based on the first subset of the images 485 and a second set of facial flushing patterns based on the first subset of the images 485; this difference may also depend on the specific values of the different color channels.

The following are some examples of processing methods that may be applied to at least some of the images 485 in order to calculate various values (e.g., iPPG signals, hemoglobin concentration patterns, and/or facial flushing patterns) that may be utilized by the computer 490 to calculate the blood glucose level 492. In some embodiments, one or more of the processing methods may be applied by the computer 490 before the various values are used to calculate the blood glucose level 492 (e.g., the preprocessing methods are applied to generate feature values that are fed as input to a neural network). In some embodiments, one or more of the processing methods may be applied by the computer 490 as part of the calculations used to calculate the blood glucose level 492 directly. For example, some layers and/or portions of a deep learning network used by the computer 490 may implement processing operations of the images (e.g., which are involved in calculating the hemoglobin concentration patterns), while other portions of the deep learning network are used to perform calculations on values representing the hemoglobin concentration patterns (in order to calculate the blood glucose level 492).

Various preprocessing approaches may be utilized in order to assist in calculating the various values described above, which are calculated from the at least some of the images 485. Some non-limiting examples of the preprocessing approaches that may be used include: normalization of pixel intensities (e.g., to obtain a zero-mean unit variance time series signal), and conditioning a time series signal by constructing a square wave, a sine wave, or a user defined shape, such as that obtained from an ECG signal or a PPG signal as described in U.S. Pat. No. 8,617,081, titled "Estimating cardiac pulse recovery from multi-channel source data via constrained source separation". Additionally or alternatively, images may undergo various preprocessing to improve the signal, such as color space transformation (e.g., transforming RGB images into a monochromatic color or images in a different color space), blind source separation using algorithms such as independent component analysis (ICA) or principal component analysis (PCA), and various filtering techniques, such as detrending, bandpass filtering, and/or continuous wavelet transform (CWT). Various preprocessing techniques known in the art that may assist in extracting an iPPG signal from the images are discussed in Zaunseder et al. (2018), "Cardiovascular assessment by imaging photoplethysmography—a review", Biomedical Engineering 63(5), 617-634. An example of preprocessing that may be used in some embodiments is given in U.S. Pat. No. 9,020,185, titled "Systems and methods for non-contact heart rate sensing", which describes how times-series signals obtained from video of a user can be filtered and processed to separate an underlying pulsing signal by, for example, using an ICA algorithm.

Another approach that may be utilized in order to assist in calculating the various values described above, which are calculated from the at least some of the images 485, involves Eulerian video magnification, as described in Wu, Hao-Yu, et al. "Eulerian video magnification for revealing subtle changes in the world." ACM transactions on graphics (TOG) 31.4 (2012): 1-8, and also in the hundreds of references citing this reference. The goal of Eulerian video magnification is to reveal temporal variations in videos that are difficult or impossible to see with the naked eye and display them in an indicative manner. This method takes a standard video sequence as input, and applies spatial decomposition, followed by temporal filtering to the frames. The resulting signal is then amplified to reveal hidden information. This method is successfully applied in many applications in order to visualize the flow of blood as it fills the face and also to amplify and reveal small motions.

Yet another approach that may be utilized in order to assist in calculating the various values described above, which are calculated from the at least some of the images 485, involves accentuating the color of facial flushing in the images. In one example, facial flushing values are calculated based on applying decorrelation stretching to the images (such as using a three color space), then applying K-means clustering (such as three clusters corresponding to the three color space), and optionally repeating the decorrelation stretching using a different color space. In another example, facial flushing values are calculated based on applying decorrelation stretching to the images (such as using a three color space), and then applying a linear contrast stretch to further expand the color range.

Figure 1D:
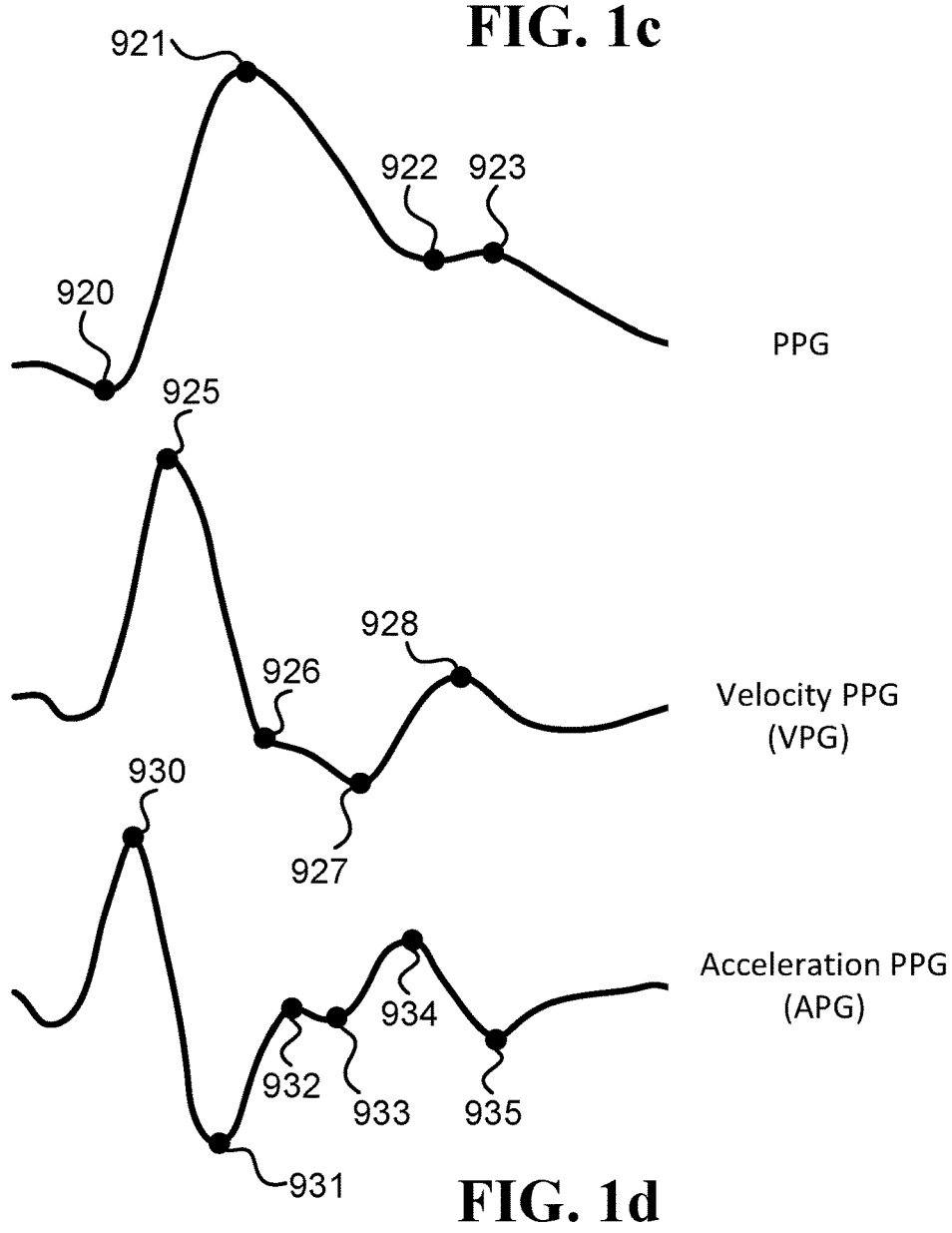
FIG. 1d is a schematic illustration of some of the various PPG fiducial points often used in the art.

Imaging photoplethysmogram signals (iPPG signals), which are extracted from the images 485, can provide indications of the extent of blood flow at the second region. In some embodiments, the computer 490 extracts iPPG signals from the images 485, and calculates the blood glucose level 492 based on differences between values (such as amplitudes and/or slopes) of the iPPG signals during the times of systolic notches and values of the iPPG signals during the times of systolic peaks. It is noted that the term "based on", as used in the previous sentence, is an open statement that may include additional differences relative to additional iPPG signals recognizable in images taken during times other than the systolic peaks and notches, such as other fiducial points that are illustrated in FIG. 1d. Additionally or alternatively, the differences may be indicative of different associations between iPPG signals recognizable in the different color channels in the images, which are related to different blood glucose levels.

Identifying the systolic peaks and notches may be done using one or more of the techniques known in the art, and/or described herein, that may be used to identify landmarks in a cardiac waveform (e.g., systolic peaks, diastolic peaks), and/or extract various types of known values that may be derived from the cardiac waveform.

In some embodiments, the camera 483 is sensitive to at least three noncoinciding wavelength intervals, such that the images include at least three channels. Optionally, the computer 490 generates at least some of the feature values based on the images 485 by extracting separate iPPG signals from each of the at least three channels in the images 485. Optionally, the feature values described herein as being generated based on iPPG signals may include separate feature values generated from iPPG signals extracted from different channels. Optionally, the computer 490 utilizes correlations between the PPG signal 481 and the separate iPPG signals in order to calculate the blood glucose level 492.

Blood flow in the face can cause certain facial coloration due to concentration of hemoglobin in various vessels such as arterioles, capillaries, and venules. In some embodiments described herein, coloration at a certain facial region, and/or changes thereto (possibly due to varying volume of blood in the certain region at different stages of cardiac pulses), can represent a hemoglobin concentration pattern at the certain region. This pattern can change because of various factors that can affect blood flow and/or vascular dilation, such as the external temperature, core body temperature, the emotional state, consumption of vascular dilating substances, and more. Hemoglobin concentration patterns may also provide a signal from which, in some embodiments, the computer 490 may calculate the blood glucose level 492. In one embodiment, the computer 490 calculates a first hemoglobin concentration pattern based on the first subset of the images 485, calculates a second hemoglobin concentration pattern based on the second subset of the images 485, and calculates the blood glucose level 492 based on differences between the first and second hemoglobin concentration patterns. It is noted that the term "based on", as used in the previous sentence, is an open statement that may include additional differences relative to additional hemoglobin concentration pattern recognizable in additional images taken during times other than the systolic peaks and notches. Additionally or alternatively, the differences may be indicative of different associations between the different hemoglobin concentration pattern associated with the different color channels in the images, which are related to different blood glucose levels.

In some embodiments, a hemoglobin concentration pattern calculated from images refers to a color mapping of various portions of an area captured in the images (e.g., the mapping provides the colors of different pixels in the images). In one example, the color mapping provides values that are average intensities of one or more colors of the pixels over a period of time during which the images were taken (e.g., values from one or more channels in the images). In another example, the color mapping provides values that are maximum intensities of one or more colors of the pixels over a period of time during which the images were taken (e.g., values of the maximum of one or more channels in the images). In yet another example, a hemoglobin concentration pattern may be a function of one or more colors (channels) of the pixels over a period of time during which the images were taken.

In yet other embodiments, a hemoglobin concentration pattern may refer to a contour map, representing the extent to which pixels at a certain wavelength (e.g., corresponding to the color red) have at least a certain value. Since the extent of hemoglobin concentration is correlated with an increase in intensity of certain colors (e.g., red), a hemoglobin concentration pattern for more dilated blood vessels will have different contour map than the contour map observed in a hemoglobin concentration pattern for that blood vessels when it is more contracted.

A hemoglobin concentration pattern, such as one of the examples described above, may be calculated, in some embodiments, from images by a computer, such as computer 490. Optionally, the hemoglobin concentration pattern may be utilized to generate one or more feature values that are used in a machine learning-based approach by the computer 490.

Additional information regarding calculation of hemoglobin concentration patterns from images and creating feature values therefrom may be found in U.S. Pat. No. 10,791,938, titled "Smartglasses for detecting congestive heart failure".

Facial flushing patterns may also provide a signal from which, in some embodiments, the computer 490 may calculate the blood glucose level 492. In one embodiment, the computer 490 extracts a first set of facial flushing patterns based on the first subset of the images 485, extracts a second set of facial flushing patterns based on the second subset of the images 485, and calculates the blood glucose level 492 based on differences between the first and second facial flushing patterns. It is noted that the term "based on", as used in the previous sentence, is an open statement that may include additional differences relative to additional images taken during times other than the systolic peaks and notches. Additionally or alternatively, the differences may be indicative of different associations between the different facial flushing patterns recognizable in the different color channels in the images, which are related to different blood glucose levels.

Pulse transit times are another type of value that may provide a signal, from which, in some embodiments, the computer 490 may calculate the blood glucose level 492. In one embodiment, the first and second regions are fed by different arteries, which cause a time difference between the times of systolic peaks in the PPG signal 481 and times of systolic peaks in iPPG signals recognizable the images 485. In this embodiment, the computer 490 calculates the aforementioned time difference, and utilizes the time difference to calculate the blood glucose level 492. For example, one or more of the feature values generated by the computer 490 and used to calculate the blood glucose level 492 may reflect the differences in the times of appearances of the systolic peaks at the first and second regions. Optionally, the computer 490 may also calculate a second time difference between the times of systolic notches in the PPG signal 481 and times of systolic notches in iPPG recognizable the images 485, and also utilize the second time difference to calculate the blood glucose level 492. For example, one or more of the feature values generated by the computer 490 and used to calculate the blood glucose level 492 may reflect the differences in the times of appearances of the systolic notches at the first and second regions.

The associations between the amplitudes of the different color channels in the images, as a function of the pulse transit times, are another type of value that may provide a signal, from which, in some embodiments, the computer 490 may calculate the blood glucose level 492. For example, when there is a change between the pulse transit times of two sub-regions in the second region, there may also be a change between the relative amplitudes of the different color channels in these two sub-regions, and this change in the relative amplitudes may be correlated with the blood glucose level.

Herein, sentences of the form "an iPPG signal recognizable in the images" refer to a signal indicative effects of blood volume changes due to pulse waves that may be extracted from one or more of the images. These changes may be identified and/or utilized by a computer, but need not necessarily be recognizable to the naked eye (e.g., because of their subtlety, the short duration in which they occur, or involvement of light outside of the visible spectrum). Additionally, it is to be noted that stating that a computer performs a calculation based on a certain value that is recognizable in certain data does not necessarily imply that the computer explicitly extracts the value from the data. For example, the computer may perform its calculation without explicitly extracting the iPPG signal. Rather, data that reflects the iPPG signal may be provided as input utilized by a machine learning algorithm. Many machine learning algorithms (e.g., neural networks) can utilize such an input without the need to explicitly calculate the value that is "recognizable".

In some embodiments, determining the aforementioned differences in occurrence of systolic peaks may involve calculation of pulse arrival times (PATs) at different regions. Optionally, a PAT calculated from a PPG signal (or iPPG signal) represents a time at which the value representing blood volume (in the waveform represented in the PPG) begins to rise (signaling the arrival of the pulse). Alternatively, the PAT may be calculated as a different time, with respect to the pulse waveform, such as the time at which a value representing blood volume reaches a maximum or a certain threshold, or the PAT may be the average of the time the blood volume is above a certain threshold. Another approach that may be utilized to calculate a PAT from an iPPG signal is described in Sola et al. "Parametric estimation of pulse arrival time: a robust approach to pulse wave velocity", Physiological measurement 30.7 (2009): 603, which describe a family of PAT estimators based on the parametric modeling of the anacrotic phase of a pressure pulse.

In some embodiments, at least some feature values utilized by the computer 490 to calculate the blood glucose level 492 may describe properties of the cardiac waveform in iPPG signals derived from subsets of the images 485. To this end, the computer 490 may employ various approaches known in the art to identify landmarks in a cardiac waveform (e.g., systolic peaks, diastolic peaks), and/or extract various types of known values that may be derived from the cardiac waveform, as described in the following examples. In one embodiment, at least some of the feature values generated based on an iPPG signal may be indicative of waveform properties that include: systolic-upstroke time, diastolic time, and the time delay between the systolic and diastolic peaks, as described in Samria, Rohan, et al. "Noninvasive cuffless estimation of blood pressure using Photoplethysmography without electrocardiograph measurement." 2014 IEEE REGION 10 SYMPOSIUM. IEEE, 2014. In another embodiment, at least some of the feature values generated based on an iPPG signal may be derived from another analysis approach to PPG waveforms, as described in US Patent Application US20180206733, entitled "Device, method and system for monitoring and management of changes in hemodynamic parameters". In still another embodiment, the computer 490 may utilize the various approaches described in Elgendi, M. (2012), "On the analysis of fingertip photoplethysmogram signals", Current cardiology reviews, 8(1), 14-25, in order to generate at least some of the feature values bases on the iPPG signal. This reference surveys several preprocessing approaches for PPG signals as well as a variety of feature values that may be utilized.

In some embodiments, one or more of the feature values utilized by the computer 490 to calculate the blood glucose level 492 may be generated based on additional inputs from sources other than the PPG device 480 and the camera 483.

Stress is a factor that can influence the diameter of the arteries, and thus influence the blood flow. In one embodiment, the computer 490 is further configured to: receive a value indicative of a stress level of the user, and generate at least one of the feature values based on the received value. Optionally, the value indicative of the stress level is obtained using a thermal camera. In one example, the system may include an inward-facing head-mounted thermal camera configured to take measurements of a periorbital region of the user, where the measurements of a periorbital region of the user are indicative of the stress level of the user. In another example, the system includes an inward-facing head-mounted thermal camera configured to take measurements of a region on the forehead of the user, where the measurements of the region on the forehead of the user are indicative of the stress level of the user. In still another example, the system includes an inward-facing head-mounted thermal camera configured to take measurements of a region on the nose of the user, where the measurements of the region on the nose of the user are indicative of the stress level of the user.

Hydration is a factor that affects blood viscosity, which can affect the speed at which blood flows in the body, and consequently may affect blood flow patterns recognizable in the images 485. In one embodiment, the computer 490 is further configured to: receive a value indicative of a hydration level of the user, and generate at least one of the feature values based on the received value. Optionally, the system includes an additional camera configured to detect intensity of radiation that is reflected from a region of exposed skin of the user, where the radiation is in spectral wavelengths chosen to be preferentially absorbed by tissue water. In one example, said wavelengths are chosen from three primary bands of wavelengths of approximately 1100-1350 nm, approximately 1500-1800 nm, and approximately 2000-2300 nm. Optionally, measurements of the additional camera are utilized by the computer 490 as values indicative of the hydration level of the user.

The user's skin temperature may affect blood viscosity, thus it may influence facial blood flow patterns that are recognizable in images taken by the camera 483. Some embodiments may include the skin temperature sensor 494, such as a head-mounted temperature sensor that measures skin temperature ($T_{skin}$) at a third region on a user's head. In one embodiments, the computer 490 is configured to utilize $T_{skin}$ to compensate for effects of skin temperature on facial blood flow. For example, the computer 490 may generate one or more feature values based on $T_{skin}$, such as feature values indicating average skin temperature or a difference from baseline skin temperature, and utilize these one or more feature values in the calculation of the blood glucose level 492.

The temperature in the environment may also be a factor that is considered in some embodiments. The temperature in the environment can both impact the user's skin temperature and cause a physiologic response involved in regulating the user's body temperature that effects facial blood flow. Some embodiments may include the environment temperature sensor 496, which may optionally, be head-mounted. The environment temperature sensor 496 measures an environmental temperature ($T_{env}$). In one embodiment, the computer 490 is configured to utilize $T_{env}$ to compensate for effects of physiologic changes related to regulating the user's body temperature. For example, the computer 490 may generate one or more feature values based on $T_{env}$, such as feature values indicating average environment temperature, maximal environment temperature, or a difference from baseline environment temperature, and utilize these one or more feature values in the calculation of the blood glucose level 492.

In an embodiment, the system includes a head-mounted anemometer that measures a signal indicative of wind speed hitting the user's head (wind signal) and/or the head-mounted hygrometer 499 that measures a signal indicative of humidity (humidity signal). In this embodiment, the computer 490 is configured to utilize the wind signal and/or the humidity signal to compensate for effects of physiologic changes related to regulating the user's body temperature. For example, the computer 490 may generate one or more feature values based the wind signal (e.g., a feature value representing the average wind speed measured) and/or the humidity signal (e.g., a feature value representing the average humidity measured), and utilize these one or more feature values in the calculation of the blood glucose level 492.

Variations in the reflected ambient light may introduce artifacts into images collected with inward-facing head-mounted cameras, such as the camera 483, which can add noise to these images and make detections and/or calculations based on these images less accurate. In some embodiments, the system includes at least one head-mounted outward-facing camera 498 for taking images of the environment. Optionally, the outward-facing camera 498 is located less than 10 cm from the user's face and weighs below 5 g. Optionally, the outward-facing camera 498 may include optics that provide it with a wide field of view. In one embodiment, the computer 490 generates, based on the images of the environment, one or more feature values indicative of ambient illumination levels during the times at which the images 485 were taken with the camera 483, and utilizes the one or more feature values indicative of the ambient illumination levels to improve the accuracy of the calculation of the blood glucose level 492, based on the images 485, the PPG signal 481, and optionally other data sources described herein.

In one example, the outward-facing head-mounted camera 498 may be a thermal camera for taking thermal measurements of the environment. Heat from the environment may affect the surface blood flow. By taking the thermal measurements of the environment into account, the computer 490 may be able to detect, and maybe even compensate, for temperature interferences from the environment. Examples of outward-facing head-mounted thermal cameras include thermopile-based and/or microbolometer-based cameras having one or more pixels.

In another example, the outward-facing head-mounted camera 498 may be a camera sensitive to wavelengths below 1050 nanometer (such as a CMOS camera sensor), and/or light intensity sensors (such as photodiodes, photoresistors, and/or phototransistor). Illumination from the environment may affect the surface blood flow (especially when heating the skin), and/or interfere with the photoplethysmogram signals and/or color changes to be measured by the system. By taking the illumination from the environment into account, the computer may be able to detect, and maybe even compensate, for the interferences from the environment.

The following are examples of embodiments that utilize additional inputs to generate feature values used calculate the blood glucose level 492. In one embodiment, the computer 490 receives a value indicative of a temperature of the user's body, and generates at least one of the feature values based on the received value. In another embodiment, the computer 490 receives a value indicative of a movement of the user's body, and generates at least one of the feature values based on the received value. For example, the computer 490 may receive the input form a head-mounted Inertial Measurement Unit (IMU) that includes a combination of accelerometers, gyroscopes, and optionally magnetometers, in a mobile device carried by the user. In yet another embodiment, the computer 490 receives a value indicative of an orientation of the user's head, and generates at least one of the feature values based on the received value. For example, the computer 490 may receive the values indicative of the head's orientation from the outward-facing head-mounted camera 498, and/or from a nearby non-wearable video camera. In still another embodiment, the computer 490 receives a value indicative of consumption of a substance by the user, and generates at least one of the feature values based on the received value. Optionally, the substance comprises a vasodilator and/or a vasoconstrictor.

In some embodiments, the computer 490 calculates the blood glucose level utilizing previously taken PPG signals of the user (taken with the PPG device 480) and/or previously taken images (taken with the camera 483) in which previous iPPG signals are recognizable Additionally, the computer 490 receives an indication of a measured blood glucose level corresponding to when the previous PPG signals and/or previous images were taken (e.g., obtained using an invasive blood test).

Having such previous values can assist the computer 490 to detect changes to in the PPG signal 841 and/or iPPG signals recognizable in the images 485, that may be indicative of the value of the blood glucose level 492. In some embodiments, previously taken PPG signals and/or images are used to generate baseline values representing baseline properties of the user's blood flow at a known blood glucose level. Optionally, calculating the baseline values may be done based on previously taken PPG signals and/or images that were measured at least an hour before taking the PPG signal 481 and/or the images 485. Optionally, calculating the baseline values may be done based on previously taken PPG signals and/or images that were measured at least a day before the PPG signal 481 and/or the images 485. Some examples of baseline values may include typical values of fiducial points (e.g., magnitudes of systolic peaks) and/or typical relationships between different fiducial points (e.g., typical distance between systolic peaks and dicrotic notches, and the like).

A baseline value may be calculated in various ways. In a first example, the baseline is a function of the average measurements of the user (which include previously taken PPG signals and/or iPPG signals recognizable in previously taken images described above). In a second example, the baseline value may be a function of the situation the user is in, such that previous measurements taken during similar situations are weighted higher than previous measurements taken during less similar situations. A PPG signal may show different characteristics in different situations because of the different mental and/or physiological states of the user in the different situations. As a result, a situation-dependent baseline can improve the accuracy of detecting the physiological response. In a third example, the baseline value may be a function of an intake of some substances (such as food, beverage, medications, and/or drugs), such that previous measurements taken after consuming similar substances are weighted higher than previous measurements taken after not consuming the similar substances, and/or after consuming less similar substances. A PPG signal may show different characteristics after the user consumes different substances because of the different mental and/or physiological states the user may enter after consuming the substances, especially when the substances include things such as medications, drugs, alcohol, and/or certain types of food. As a result, a substance-dependent baseline can improve the accuracy of detecting the physiological response.

The following are examples of some types of feature values that may be utilized in some embodiments to calculate the blood glucose level 492.

In some embodiments, at least some of the feature values may include values indicative of correlations between the PPG signal 481 and iPPG signals extracted from the images 485. In one example, the feature values may include values indicative of offsets between when certain fiducial points appear in the PPG signal 481, and when they appear in each of the iPPG signals. In another example, the feature values may include values indicative of offsets at which the correlation (e.g., as calculated by a dot-product) between the PPG signal 481 and the iPPG signals is maximized. In still another example, the feature values may include values indicative of maximal value of correlation (e.g., as calculated by a dot-product) between the PPG signal 481 and the iPPG signals (when using different offsets).

In some embodiments, at least some of the feature values may be "raw" or minimally processed measurements of the PPG device 481 and/or the camera 483. Optionally, at least some of the feature values may be pixel values obtained by the camera 483. Optionally, the pixel values may be provided as input to functions in order to generate the feature values that are low-level image-based features. Some examples of low-level features, which may be derived from images, include feature generated using Gabor filters, local binary patterns (LBP) and their derivatives, algorithms such as SIFT and/or SURF (and their derivatives), image keypoints, histograms of oriented gradients (HOG) descriptors, and products of statistical procedures such independent component analysis (ICA), principal component analysis (PCA), or linear discriminant analysis (LDA). Optionally, one or more of the feature values may be derived from multiple images taken at different times, such as volume local binary patterns (VLBP), cuboids, and/or optical strain-based features. In one example, one or more of the feature values may represent a difference between values of pixels at one time t and values of other pixels at a different region at some other time t+x (which, for example, can help detect different arrival times of a pulse wave).

In one non-limiting example, feature values generated by the computer 490 include: pixel values from the images 485 and magnitude values of the PPG signal 841. In another non-limiting example, feature values generated by the computer 490 include intensities of fiducial points (systolic peaks and systolic notches) identified in iPPG signals extracted from the images 485, at times corresponding to appearances of those fiducial points, as detected in the PPG signal 481.

Utilizing the model 491 to calculate the blood glucose level 492 may involve the computer 490 performing various operations, depending on the type of parameters in the model 491. The following are some examples of various possibilities for the model 491 and the type of calculations that may be accordingly performed by the computer 490, in some embodiments, in order to calculate a certain value indicative of the blood glucose level 492: (a) the model 491 comprises parameters of a decision tree. Optionally, the computer 490 simulates a traversal along a path in the decision tree, determining which branches to take based on the feature values. The certain value may be obtained at the leaf node and/or based on calculations involving values on nodes and/or edges along the path; (b) the model 491 comprises parameters of a regression model (e.g., regression coefficients in a linear regression model or a logistic regression model). Optionally, the computer 490 multiplies the feature values (which may be considered a regressor) with the parameters of the regression model in order to obtain the certain value; and/or (c) the model 491 comprises parameters of a neural network. For example, the parameters may include values defining at least the following: (i) an interconnection pattern between different layers of neurons, (ii) weights of the interconnections, and (iii) activation functions that convert each neuron's weighted input to its output activation. Optionally, the computer 490 provides the feature values as inputs to the neural network, computes the values of the various activation functions and propagates values between layers, and obtains an output from the network, which is the certain value In some embodiments, a machine learning approach that may be applied to calculating a value indicative of the blood glucose level 492 may be characterized as "deep learning". In one embodiment, the model 491 may include parameters describing multiple hidden layers of a neural network. Optionally, the model 491 may include a convolution neural network (CNN). In one example, the CNN may be utilized to identify certain patterns in the images 485, such as the patterns of corresponding to blood volume effects and ballistocardiographic effects of the cardiac pulse. Due to the fact that calculating the value indicative of blood glucose level may be based on multiple, possibly successive, images that display a certain pattern of change over time (i.e., across multiple frames), these calculations may involve retaining state information that is based on previous images. Optionally, the model 491 may include parameters that describe an architecture that supports such a capability. In one example, the model 491 may include parameters of a recurrent neural network (RNN), which is a connectionist model that captures the dynamics of sequences of samples via cycles in the network's nodes. This enables RNNs to retain a state that can represent information from an arbitrarily long context window. In one example, the RNN may be implemented using a long short-term memory (LSTM) architecture. In another example, the RNN may be implemented using a bidirectional recurrent neural network architecture (BRNN).

In one embodiment, a system configured to estimate blood glucose level a first head-mounted temperature sensor configured to measure skin temperature ($T_{skin}$) at a first region on a user's head, and a second head-mounted temperature sensor configured to measure temperature of the environment ($T_{env}$). The system also includes a first inward-facing head-mounted camera configured to capture a first set of images of a first skin region above the user's eye level, and a second inward-facing head-mounted camera configured to capture a second set of images of a second skin region below the user's eye level. The system also includes a computer that calculates, based on the first and second sets of images, patterns of hemoglobin concentrations at the first and second regions, respectively. Optionally, the computer calculates, based on previous first and second sets of the images captured while the user did not have hypoglycemia, a baseline pattern that includes first and second baseline hemoglobin concentrations at the first and second regions. Additionally, the computer calculates based on current first and second sets of the images, captured after the previous first and second sets, a current pattern that includes first and second current hemoglobin concentrations at the first and second regions, respectively. The computer then estimates the blood glucose level based on a deviation of the current pattern from the baseline pattern.

The following method for calculating blood glucose level may be used by systems modeled according to FIG. 1a. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps: In Step 1, receiving, from a head-mounted contact photoplethysmography device, a signal indicative of a photoplethysmogram signal (PPG signal) at a first region comprising skin on a user's head. In Step 2, receiving, from a head-mounted camera, images of a second region comprising skin on the user's head. In Step 3, identifying, based on the PPG signal, times of systolic notches and times of systolic peaks. And in Step 4, calculating the blood glucose level based on differences between a first subset of the images taken during the times of systolic notches and a second subset of the images taken during the times of systolic peaks.

In one embodiment, the method optionally includes the following steps: extracting imaging photoplethysmogram signals (iPPG signals) from the images, and calculating the blood glucose level based on differences between amplitudes of the iPPG signals during the times of systolic notches and the iPPG signals during the times of systolic peaks.

In another embodiment, the method optionally includes the following steps: calculating a first hemoglobin concentration pattern based on the first subset of the images, calculating a second hemoglobin concentration pattern based on the second subset of the images, and calculating the blood glucose level based on differences between the first and second hemoglobin concentration patterns.

In yet another embodiment, the method optionally includes the following steps: extracting a first set of facial flushing patterns based on the first subset of the images, extracting a second set of facial flushing patterns based on the second subset of the images, and calculating the blood glucose level based on differences between the first and second facial flushing patterns.

In one embodiment, the method optionally involves a step of utilizing a machine learning-based model to calculate, based on feature values generated from the first and second subsets of the images, a value indicative of the blood glucose level. Optionally, the machine learning-based model was trained based on data comprising: $3^{rd}$ and $4^{th}$ subsets of the images, taken during the times of systolic notches and systolic peaks, respectively, while the user had blood glucose level that was between 70 and 100; $5^{th}$ and $6^{th}$ subsets of the images, taken during the times of systolic notches and systolic peaks, respectively, while the user had blood glucose level that was between 100 and 125; 7th and $8^{th}$ subsets of the images, taken during the times of systolic notches and systolic peaks, respectively, while the user had blood glucose level that was between 120 and 150; and $9^{th}$ and $10^{th}$ subsets of the images, taken during the times of systolic notches and systolic peaks, respectively, while the user had blood glucose level that was between 150 and 180.

In one embodiment, the method optionally includes the following steps: receiving, from a head-mounted temperature sensor, skin temperature measurements ($T_{skin}$) at a third region on a user's head; generating feature values based on: the PPG signal, the images, and $T_{skin}$; and performing the calculating of the blood glucose level in Step 4 utilizing a machine learning-based model that is fed with the feature values.

In another embodiment, the method optionally includes the following steps: receiving images of the environment from an outward-facing head-mounted camera; generating feature values based on: the PPG signal, the images, and the images of the environment; and performing the calculating of the blood glucose level in Step 4 utilizing a machine learning-based model that is fed with the feature values.

The following is a description of embodiments of systems that utilize wearable ambulatory systems that include various sensors that are utilized to monitor a user's respiratory activity and/or coughing, as well as other parameters, for various health-related applications. In some embodiments, a wearable ambulatory system includes smartglasses, or a smart-helmet, with various sensors coupled thereto. For example, in some embodiments, one or more acoustic sensors coupled to smartglasses are used to take audio recordings comprising breathing and/or coughing sounds of a user wearing the smartglasses. Systems described herein also include computers that are used to analyze measurements obtained utilizing the sensors.

Figure 2A:
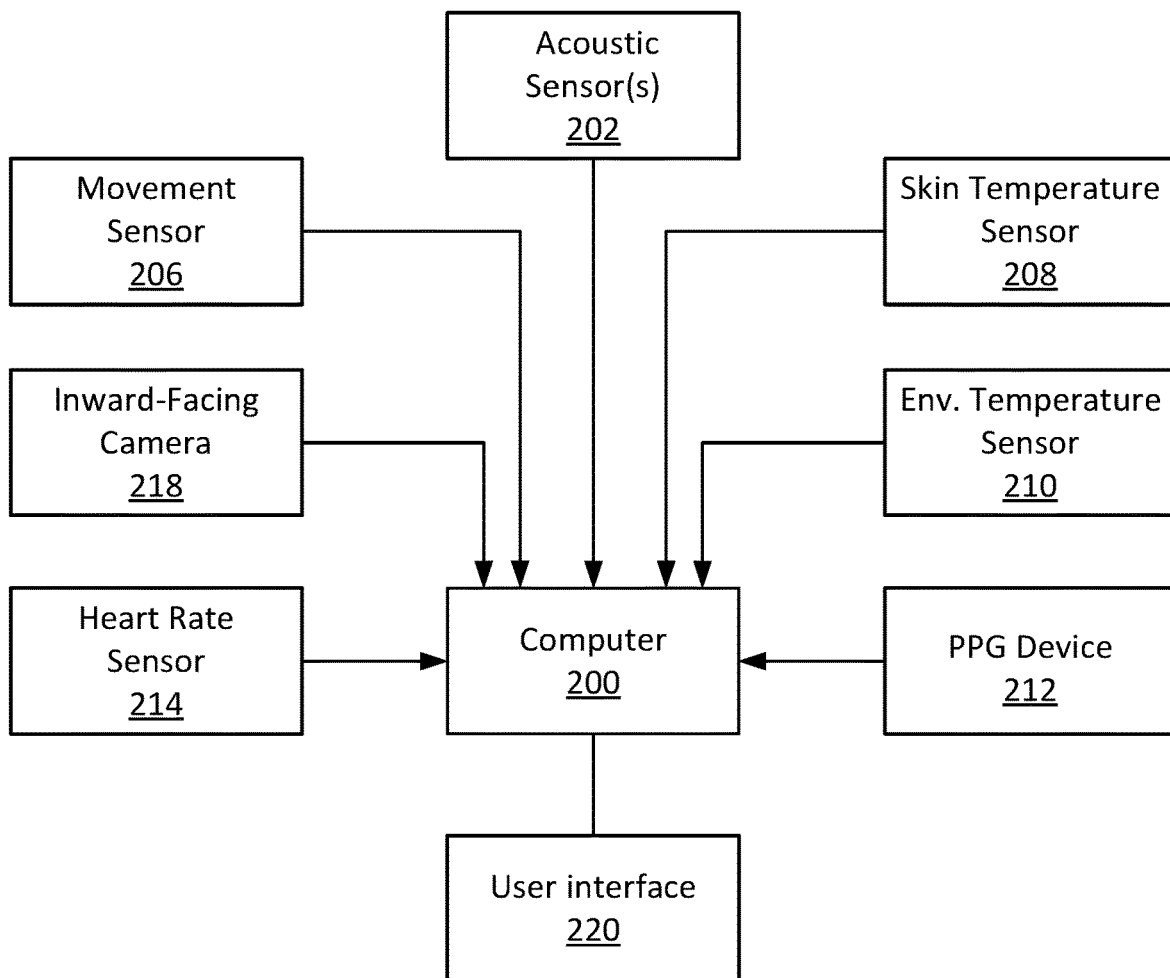
FIG. 2a is a schematic illustration of components of a system that utilizes an ambulatory wearable system to monitor a user's respiration and/or coughing.

FIG. 2a is a schematic illustration of components of a system that utilizes an ambulatory wearable system, such as smartglasses or a smart-helmet, to monitor a user's respiration and/or coughing, which may be used along with other data, for a variety of medical applications. The ambulatory wearable system includes one or more acoustic sensors 202, mounted to fixed positions relative to the head of the user wearing the ambulatory wearable system. The ambulatory wearable system may include additional sensors such as a movement sensor 206, a skin temperature sensor 208, an environment temperature sensor 210, a photoplethysmography (PPG) device 212, a heart rate sensor 214, and an inward-facing camera 218. The system also includes computer 200, which may perform at least some of the calculations involved in analysis of measurements taken with the various sensors described above, as well provide results of these calculations and/or interact with a user via user interface 220.

Figure 2B:
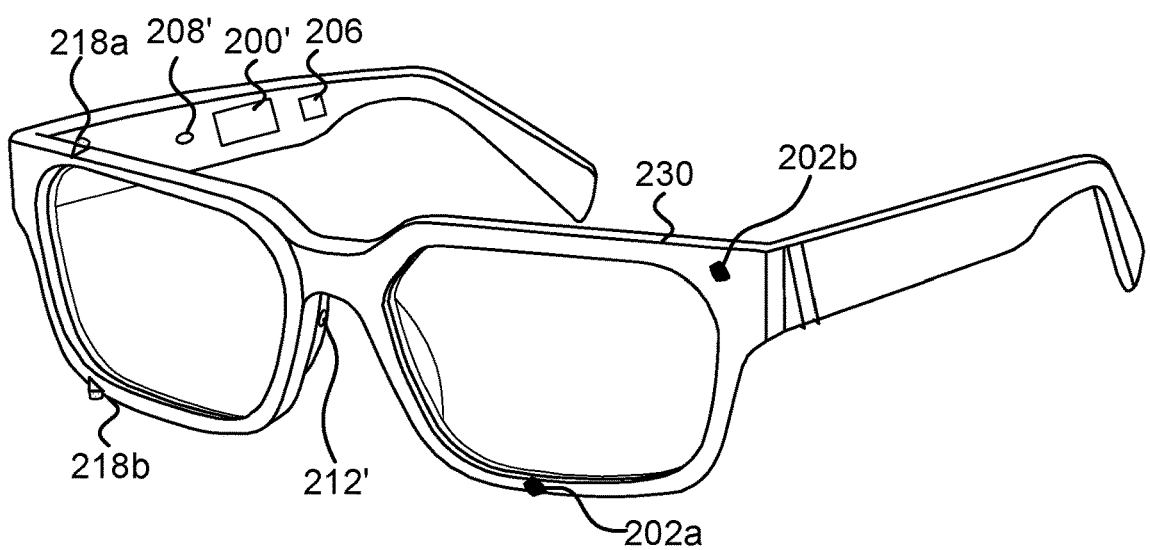
FIG. 2b illustrates an example of smartglasses that are a wearable ambulatory system utilized in some embodiments.

FIG. 2b illustrates an example of smartglasses that may be considered the wearable ambulatory system utilized in some embodiments described herein. FIG. 2b illustrates just one possible embodiment of a combination of some of the components described in FIG. 2a. The smartglasses include at least a frame 230, which is configured to be worn on a user's head, and several sensors configured to measure the user and/or the environment. Acoustic sensors 202a and 202b, which may be used to take audio recordings of the user, are mounted at fixed positions on the frame 230 (below and above the left lens, respectively). Contact PPG device 212' is located in the nose piece, and may be utilized to generate a PPG signal of the user, from which the heart rate of the user may be derived, as well as other blood flow-related parameters. Inward-facing cameras 218a and 218b are attached to the frame 230 at locations that are above and below the right lens, respectively. The inward-facing camera 218a is pointed upwards and configured to capture images of a region above the user's eyes (e.g., a portion of the forehead). The inward-facing camera 218b is pointed downwards and configured to capture images of a region below the user's eyes (e.g., a portion of a cheek). A non-contact thermal sensor 208' is coupled to a temple of the smart-glasses, which is part of the frame 230, and is configured to measure temperature at a region on the user's face. Additional thermal sensors may be coupled to the frame 230 and be used to measure temperatures at different regions. The environment temperature sensor 210, which may also be a non-contact thermal sensor, may be coupled to the frame 230 such that it is pointed away from the user's face in order to measure the temperature of the environment. Movement sensor 206 is also coupled to the frame 230 such that it measures the motion of the user's head. The computer 200' is coupled to the frame 230 and may perform at least some, and in some embodiments, all, of the operations attributed to computers in this disclosure, such as the computer 200, the computer 200', or computer 265 that are mentioned herein.

Figure 41A:
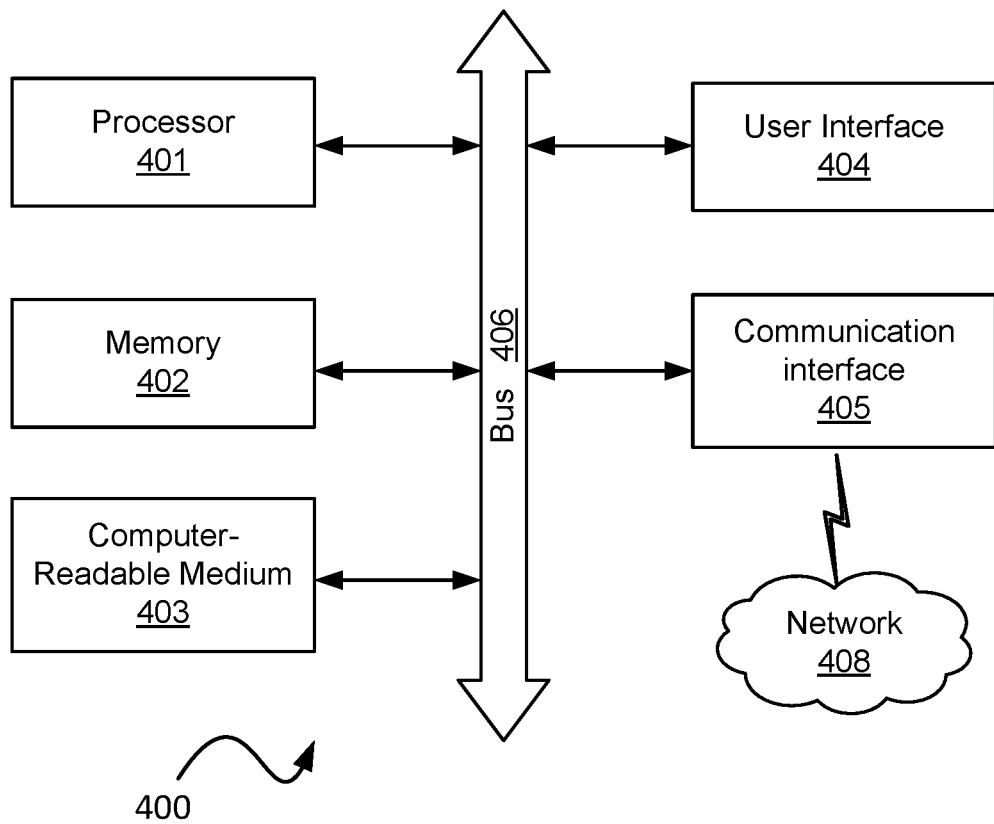
FIG. 41a and FIG. 41b are schematic illustrations of possible embodiments for computers.
Figure 41B:
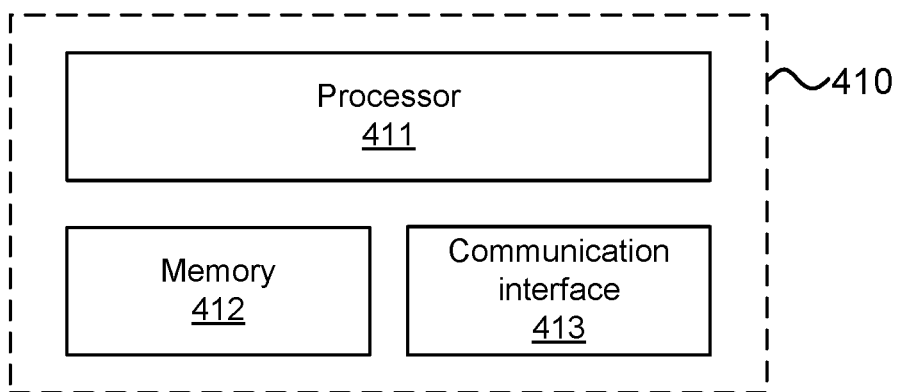

Further discussion regarding types computers that may be used in realization of embodiments described herein (i.e., perform at least some, if not all, of the functionality attributed to herein to computers such the computer 200, the computer 200', and the computer 265) may be found in the discussion regarding computer 400 or computer 410 illustrated in FIG. 41a and FIG. 41b, respectively.

Figure 3:
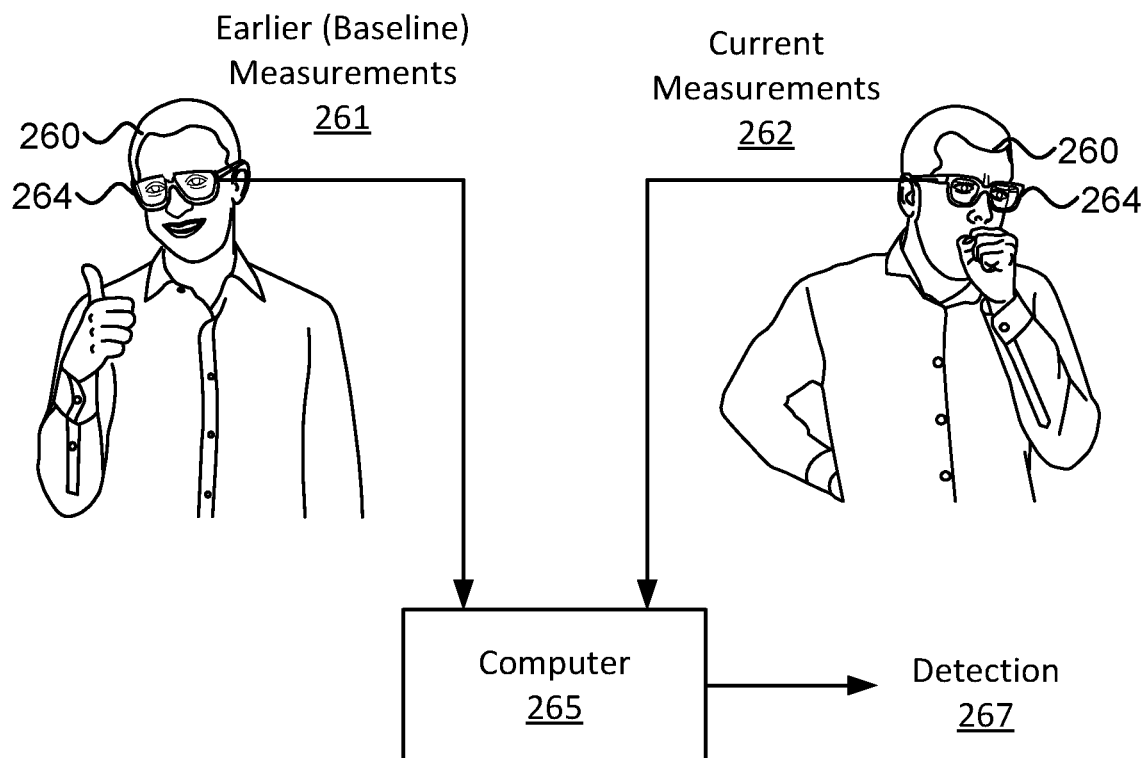
FIG. 3 illustrates a system configured to detect change to extent of a respiratory tract infection (RTI) based on monitoring coughing.

FIG. 3 illustrates an embodiment of a system illustrated in FIG. 2a, which may be utilized to make detections regarding a change to the extent of an RTI relative to a known extent of the RTI and/or whether a user exhibits early signs of an RTI. The system illustrated in FIG. 3 includes a wearable ambulatory system 264, which are smartglasses in the illustrated embodiment, that may be similar to the smartglasses illustrated in FIG. 2b. The wearable ambulatory system 264 includes various sensors that may be head-mounted (e.g., coupled to the illustrated smartglasses), or attached in some other way to the user 260, such as be neck-mounted, or coupled to some non-head-mounted device carried by the user 260 or attached to the user 260 (e.g., a sensor in a smartwatch).

The wearable ambulatory system 264 takes measurements of the user 260. Optionally, these measurements include values measured during different periods of time. Recently taken measurements, e.g., measurements taken during the preceding minutes or hours, may be considered "current measurements" (denoted as current measurements 262 in FIG. 3). Previously taken measurements, such as measurements taken at least 4 hours before the current measurements 262, or on preceding days, are considered "earlier measurements" or "baseline measurements" (denoted earlier measurements 261 in FIG. 3).

It is to be noted that when it is stated that sensors are used to take measurements (of a user and/or the environment) during a period, it does not imply that they are used continuously throughout the period. Rather, that they are used to take measurements, possibly sporadically or intermittently, at various times during the period.

The computer 265 analyzes data obtained by the wearable ambulatory system 264, such as the current measurements 262 and/or the earlier measurements 261, in order to detect various medical conditions. In one example, the computer 265 may detect early signs of an RTI and/or detect a change relative to a known extent of the RTI (corresponding to some previous time during which the user was monitored).

The wearable ambulatory system 264 includes the one or more acoustic sensors 202, which are configured to be mounted at a fixed position relative to the head of a user 260, and to take audio recordings of the user 260. Optionally, the one or more acoustic sensors 202 include two or more acoustic sensors. For example, FIG. 2b illustrates acoustic sensors 202a and 202b that are mounted at fixed positions relative to the head (when the frame 230 is worn). The audio recordings of the user 260 may include recordings of sounds produced by the user 260, such as sounds of respiration, coughing, speech, and the like.

Figure 5:
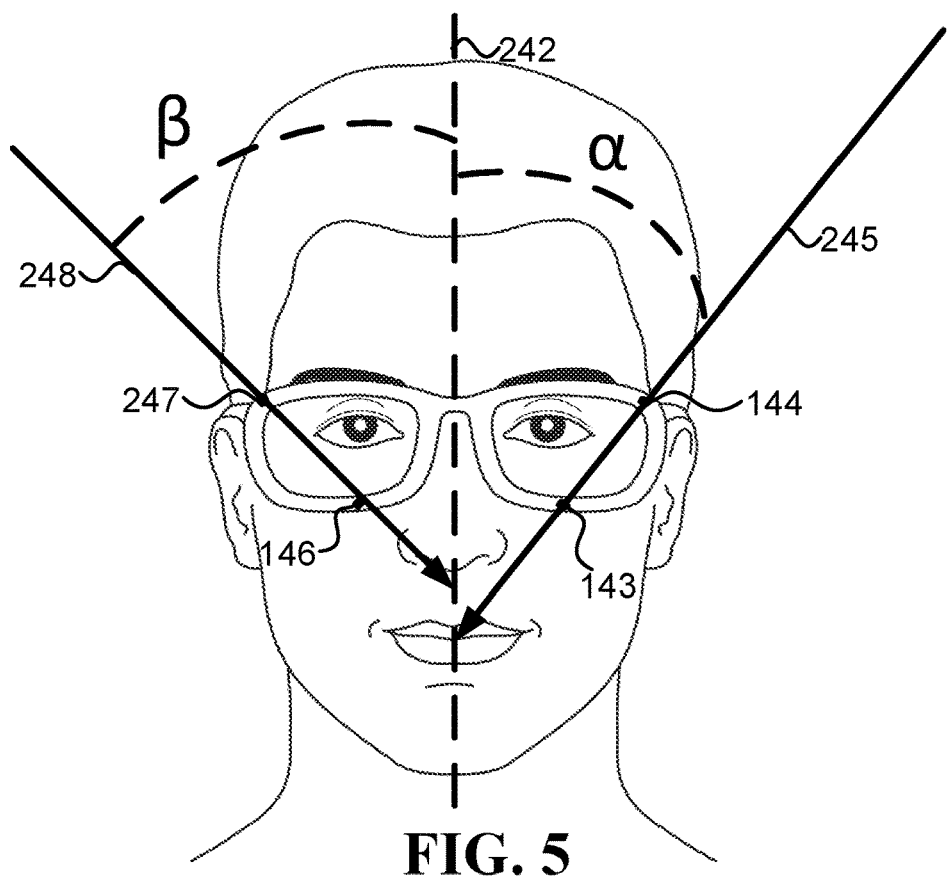
FIG. 5 and FIG. 6 illustrate different configurations in which multiple acoustic sensors may be utilized to obtain multiple audio recordings from which an enhanced signal can be extracted.
Figure 6:
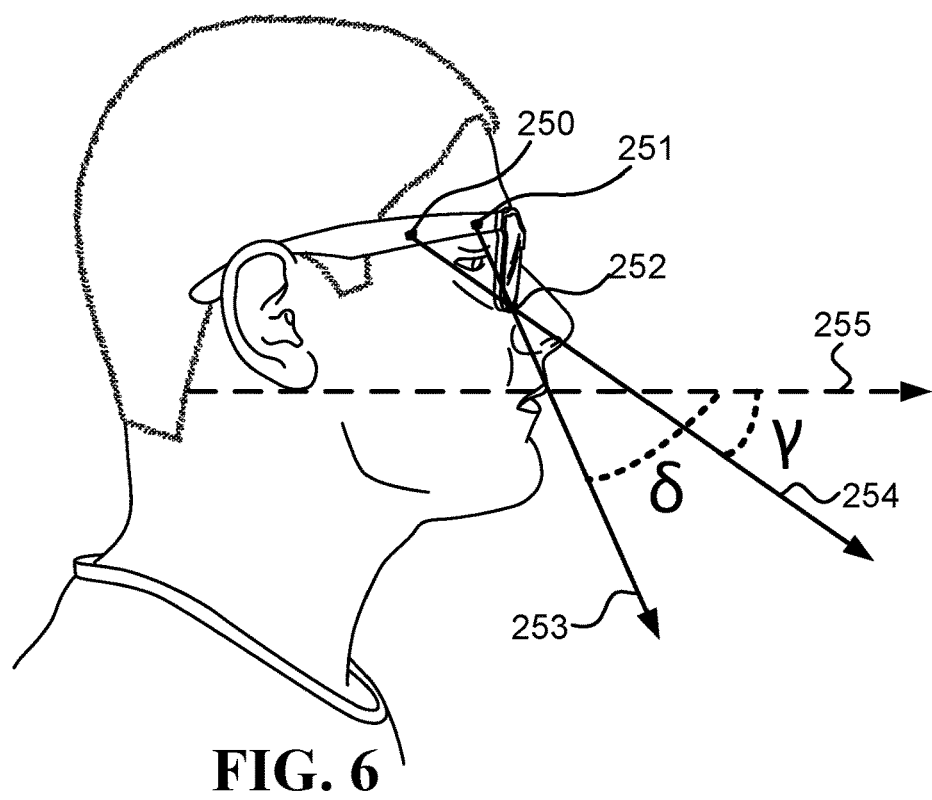

When multiple audio recordings are obtained with multiple acoustic sensors (as illustrated in FIG. 2b, FIG. 5, and FIG. 6), the multiple audio recordings may be provided to the computer 265 for analysis as multiple audio channels. Additionally or alternatively, the multiple audio recordings may be combined and/or used to enhance a signal in the audio recordings using various techniques known in the art, such as beamforming, which is discussed further below. Thus, in some embodiments, the computer 265 may receive an audio channel that is generated by combining multiple audio channels and/or the computer 265 may receive a certain channel that is enhanced based on audio appearing in other channels (e.g., the certain channel may have noise removed and/or have various modulations performed to it based on the other channels).

In one embodiment, the wearable ambulatory system 264 includes at least first and second head-mounted acoustic sensors, each configured to be mounted at a fixed position relative to the user's head. The first and second acoustic sensors are configured to take first and second audio recordings of the user 260. Optionally, the distance between the first and second head-mounted acoustic sensors is greater than 1 cm. Optionally, the computer 265 applies a beamforming technique to the first and second audio recordings in order to enhance a signal in which coughing sounds of the user are recognizable.

Herein, stating to the effect that coughing sounds are "recognizable" in an audio recording refers to portions of the audio that can be classified as including coughing when algorithms known in the art are utilized to detect coughing from the audio signal.

It is to be noted that having an acoustic sensor mounted to an ambulatory wearable system such as smartglasses means that the acoustic sensor is physically coupled to the wearable (e.g., attached or embedded in the frame of a pair of smartglasses), such that it does not move when the wearable is worn, in typical use, by the user. In some embodiments, acoustic sensors may be repositioned, e.g., by using a mechanism that enables the acoustic sensors to move along a track when sufficient pressure is applied or a locking latch is moved, etc. Such acoustic sensors may also be considered to be mounted in fixed positions because moving the acoustic sensors requires taking specific actions that are not taken during usual use, and the acoustic sensors are not designed to change their position without these certain actions taking place.

In one embodiment, the wearable ambulatory system 264 includes the head-mounted movement sensor 206, which may be, for example, an inertial measurements unit (IMU). Optionally, the movement sensor 206 measures a signal indicative of one or more of the following: movements of the head of user 260, an orientation of the head of the user 260 with respect to the earth's gravity (i.e., an angle between the head's orientation and the direction in which gravity acts). It is to be noted that various patterns of movements of the user's head may be detected using approaches known in that art to detect activities (e.g., walking or running), as well as whether the user is coughing, talking, or breathing, as explained below.

In another embodiment, the wearable ambulatory system 264 includes the skin temperature sensor 208, which is configured to measure temperature of a region of skin on the head of the user 260 (herein, the temperature of the region of skin on the head is denoted $T_{skin}$). Optionally, the skin temperature sensor 208 is head-mounted. In one example, the region of skin includes a portion of a temple of the user 260. In another example, the region of skin may include a portion of the forehead of the user 260. In yet another example, the region of skin may include a portion of a cheek of the user 260.

In some embodiments, the wearable ambulatory system 264 may include one or more additional head-mounted temperature sensors, such that measurements of multiple regions on the user's head may be provided to the computer 265 to perform its detections.

In some embodiments, $T_{skin}$ and optionally additional measurements of temperature at other regions on the head may be used as an input to calculate a value representing the core body temperature of the user 260. For example, the values of $T_{skin}$ may be offset by a predetermined value or according to a predetermined formula in order to obtain the value of the core body temperature. In another example, $T_{skin}$ and optionally additional measurements of temperature at other regions on the head may be used as input to a regression formula and/or used as feature values used to calculate core body temperature with a machine learning-trained model. In some embodiments, parameters used to convert $T_{skin}$ and the optional additional measurements of temperature to a core body temperature, such as the aforementioned offset, formula, regression formula, or model, are generated based on data of multiple users. Additionally or alternatively, these parameters may be set and/or adjusted based on calibration values of the user 260, obtained with an additional thermometer that provides a value of the core body temperature.

The computer 265 receives measurements taken with the sensors of the wearable ambulatory system 264 and utilizes them to detect various medical conditions. Optionally, these medical conditions are detected based on analysis of an extent of the user's coughing which is reflected in the measurements (e.g., coughing sounds identified in audio recordings or movements that characterize coughing measured by a movement sensor), as well as other signals. In one example, the computer 265 detects based on received measurements whether the user 260 user exhibits early signs of an RTI. In another example, the computer 265 detects a change to the extent of the RTI the user suffers from, relative to a previous known extent of the RTI, based on the current measurements that are compared to earlier measurements (when the user had the known extent of the RTI). In different embodiments, measurements utilized to make detections by the computer 265 may have different characteristics and/or collected under different circumstances, as the following examples demonstrate.

In one embodiment, the computer 265 receives the current measurements 262 of the user 260, taken with sensors that include at least the one or more acoustic sensors 202 and the movement sensor 206. The computer 265 also receives the earlier measurements 261 of the user 260, taken with the same sensors at least four hours before the current measurements 262 were taken. In this embodiment, the earlier measurements 261 were taken while the user 260 had a known extent of the RTI and the computer 265 calculates a change relative to the known extent of the RTI based on a difference between the earlier measurements 261 and the current measurements 262. Optionally, the known extent of the RTI corresponds to the user 260 not suffering from an RTI (thus the earlier measurements 261 may serve as baseline, corresponding to a healthy or non-RTI state measurements). Optionally, the earlier measurements 261 and/or the current measurements 262 include portions of audio recordings taken while a signal indicative of movements of the head of the user 260 (also referred to as the "head movement signal" or simply "movement signal") was indicative of head movements that characterize coughing. Additional discussion regarding the advantage of having another signal (in addition to audio) indicate coughing, as well as what are movements that characterize coughing, is given below.

In another embodiment, the earlier measurements 261 received by the computer 265 were taken during a previous period, for which the computer 265 received an indication that the user 260 did not exhibit early signs of an RTI. Thus, the earlier measurements 261 may serve as baseline measurements for a healthy state (or a non-RTI state) of the user 260. In this embodiment, the current measurements 262 of the user 260, as well as the earlier measurements 261, are taken with sensors that include at least the one or more acoustic sensors 202 and the skin temperature sensor 208. Optionally, while the earlier measurements 261 were taken, $T_{skin}$ was below a predetermined threshold. Optionally, having $T_{skin}$ be below the predetermined threshold corresponds to a state of normal, non-fever body temperature. Optionally, the previous period during which the earlier measurements 261 were taken occurred at least four hours before a period during which the current measurements 262 were taken. The computer 265 may determine that the user 260 is exhibiting early signs of the RTI based on differences between the earlier measurements 261 and the current measurements 262. Optionally, these difference involve at least an increase in $T_{skin}$ to above the predetermined threshold and an increase in coughing sounds recognizable in the audio recordings. For example, the extent of coughing recognizable in audio recordings belonging to the current measurements 262 is above a certain threshold, while the extent of coughing recognizable in audio recordings belonging to the earlier measurements 261 is not above the certain threshold.

There are various ways in which the predetermined threshold may be selected. In one embodiment, the predetermined threshold is set to be below 36.5° C. In another embodiment, the predetermined threshold is set to an average value of $T_{skin}$ measured for a plurality of people, whose core body temperature at the time was a certain value between 36.5° C. to 37.5° C. In yet another embodiment, the predetermined threshold is set to an average value of $T_{skin}$ measured for the user 260, while the core body temperature of the user 260 was a certain value between 36.5° C. to 37.5° C. (as determined by a thermometer that is not the skin temperature sensor 208).

In yet another embodiment, the computer 265 may detect the early signs of an RTI based on the current measurements 262, obtained by the wearable ambulatory system 264, which in this embodiment includes at least the following head-mounted or neck-mounted sensors: the one or more acoustic sensors 202, and the movement sensor 206. Optionally, the audio recordings in the current measurements 262 include sounds of breathing and/or coughing of the user 260. Optionally, the movement sensor 206 provides a signal indicative of an orientation of the user's head relative to gravity (this signal is denoted $H_{ori}$ signal). Optionally, the current measurements 262 used in this embodiment were obtained while $H_{ori}$ signal indicated that the head of the user 260 was upright. Optionally, the computer 265 also receives an indication of a previous period, which occurred at least four hours before the current measurements 262 were taken, during which the user did not exhibit any signs of an RTI. The computer 265 also receives the earlier measurements 261, which in this embodiment were obtained by the same head-mounted or neck-mounted sensors, while the $H_{ori}$ signal indicated that the user's head was upright. Optionally, detection of the early signs of the RTI is done based on differences between audio recordings belonging to current measurements 262 and audio recordings belonging to the earlier measurements 261.

When a person is not upright, in some cases, this may influence respiration sounds and/or increase the extent of coughing (e.g., because of movement of fluids in the lungs which cover more surface area). Thus, it can be important to receive an indication of the angle of the head and perform calculations when the person is in a consistent state, such as being upright.

Determining that the head of the user 260 is upright based on the $H_{ori}$ signal can be done based on the angle measured by the movement sensor 206. Assuming that when a person is completely upright and the person's gaze is parallel with the horizon the angle is 0°, then being upright means that the measured angle when wearing the wearable ambulatory system 264 is within a certain range near 0° (that is the angle of the gaze with the horizon falls within the certain range. In one example, the certain range is [−5°,+5°]. In another example, the certain range is [−10°,+10°]. And in still another example, the certain range is [−15°,+15°].

The computer 265 may be utilized, in some embodiments, to detect whether the user 260 exhibits early signs of an RTI, to what extent the user exhibits signs of an RTI, and/or a severity of the RTI. Optionally, the computer 265 utilizes a comparison with earlier measurements to report a change in the extent of the RTI compared to a known extent corresponding to when the earlier measurements were taken. Optionally, the user 260 may be considered to exhibit early signs of an RTI, when the extent of the RTI, as calculated by the computer 265, reaches a certain threshold. Herein, an extent of an RTI may be expressed in various ways. In some embodiments, the extent may be a binary value (either the user 260 exhibits signs of an RTI or not). In other embodiments, the extent of an RTI may be a value on a numerical scale or a probability indicative of the need for hospitalization or probability of death because of the RTI.

A known extent of RTI, which corresponds measurements of the user at a certain time, may be a value provided by an external source and/or by the computer 265 (e.g., based on a confident detection using algorithmic approaches described below).

In one embodiment, the known extent of the RTI is provided by a medical professional who examines a patient and determines the extent of various signs of an RTI (e.g., sneezing, coughing, sore throat, etc.) Optionally, the extent may also be determined based on various physiological measurements (e.g., to determine whether there is an elevated breathing rate) and/or biochemical measurements, such as determining whether there is an elevated level of C-reactive protein (CRP).

In another embodiment, the known extent of the RTI may be provided based on a report of the user and or caregiver after being prompted to do so. For example, the computer 265 may query the user 260, e.g., via the user interface 220 which may be a display of a smartphone or augmented reality glasses, bout whether the user 260 detects various early signs of an RTI, and then use this response to determine whether, at the time, the user 260 had the RTI or not. Optionally, the querying of the user 260 is done in response to analysis of measurements in which there are borderline signs (e.g., an increase in coughing to a certain level).

To calculate a value indicative of an extent of RTI (and/or change to the extent compared to a pervious state with a known extent of RTI), the computer 265 may utilize a machine learning-based approach. In some embodiments, calculating an extent of the RTI or change relative to a known extent of the RTI, involves the computer 265 generating feature values based on data that includes the current measurements 262 and the earlier measurements 261. The computer 265 then utilizes a machine learning-trained model to calculate, based on the feature values, a value indicative of the change relative to the known extent of the RTI.

The machine learning-trained model used to calculate the value indicative of the change relative to the known extent of the RTI may be generated, in some embodiments, based on training data of multiple users. This training data includes measurements of the multiple users taken with wearable ambulatory systems similar to the wearable ambulatory system 264 (e.g., the same model of smartglasses or smartglasses with the same types of sensors located at the same locations). The data collected from the multiple users includes measurements from different times, when the multiple users had different extents of the RTI (e.g., as reported by a physician, self-reported by the multiple users, medical records, etc.). Thus, for each certain user, from among the multiple users, the training data included certain first and second measurements taken while the certain user had certain first and second known extents of the RTI, respectively. Thus, the training data reflects measurements in which there is a known change in the extent of the RTI for the multiple users. In some embodiments, the model may be trained on training data of the user 260, and include first and second measurements taken with the sensors while the user had first and second known extents of the RTI, respectively.

The training data described above is used to create samples, where each sample includes feature values generated based on measurements of a certain user and a label which is indicative of the extent of RTI and/or change relative to a known extent of the RTI the certain user had. Optionally, the samples may be generated based on measurements collected in diverse conditions (on different times of day, different locations, different environmental conditions, etc.)

Various computational approaches may be utilized to train the model based on the samples described above. In one example, training the model may involve selecting a threshold based on the samples. Optionally, if a certain feature value reaches the threshold (e.g., an extent of coughing) then a certain extent of RTI is detected. Optionally, the model includes a value describing the threshold. In another example, a machine learning-based training algorithm known in the art may be utilized to train the model based on the samples. Optionally, the model includes parameters of at least one of the following types of models: a regression model, a neural network, a nearest neighbor model, a support vector machine, a support vector machine for regression, a naïve Bayes model, a Bayes network, and a decision tree.

The computer 265 may generate various types of features based on measurements it receives, such as the current measurements 262, the earlier measurements 261, and/or measurements utilized to generate the machine learning-trained model described above. Additionally, the feature values may be generated based on the additional sources of data described this disclosure.

In some embodiments, at least some of the feature values are generated based on audio recordings recorded utilizing the one or more acoustic sensors 202. Optionally, these include feature values resulting from analysis of the audio recording such as feature values indicating the extent of coughing (e.g., a frequency and/or intensity of coughing episodes), the type of coughing observed (e.g., wet, dry, barking, brassy, coarse crackles, or hoarse sounds of coughs) Additionally or alternatively, the at least some of the feature values may include feature values described below as being utilized to detect coughs from audio recordings (e.g., spectral property features).

Another type of audio based features that may be used in some embodiments are related to respiration. In one embodiment, one or more of the features may be indicative of a respiratory parameter (e.g., the respiratory rate), which is determined based on audio recordings.

In some embodiments, at least some of the feature values are generated based on measurements from the movement sensor 206 and include values indicative of the extent of movement of the head (e.g., average acceleration in different directions, variance of acceleration, average/total acceleration over various periods of time, and/or number of times the acceleration during a certain short period reaches a certain threshold). Additionally or alternatively, at least some of the feature values may be indicative of the orientation of the head relative to the direction in which gravity acts.

Feature values generated from measurements of the movement sensor 206 may also include values of a respiration parameter (e.g., the respiration rate) derived from movement data, or feature values known in the art that may be used to determine respiration from movement data. Some examples of approaches known in the art that may be utilized for this purpose are provided in Röddiger, Tobias, et al. "Towards Respiration Rate Monitoring Using an In-Ear Headphone Inertial Measurement Unit." *Proceedings of the 1st International Workshop on Earable Computing.* 2019, and by Hernandez, Javier, et al. "Cardiac and respiratory parameter estimation using head-mounted motion-sensitive sensors." *EAI Endorsed Transactions on Pervasive Health and Technology* 1.1 (2015).

The following are some examples of additional sensors that may be utilized to generate at least some of the feature values utilized to calculate a value indicative of the extent of the RTI and/or a change relative to a known extent of the RTI.

In one embodiment, the computer 265 generates one or more of the feature values based on first and second values of $T_{skin}$ measured while the earlier measurements 261 and the current measurements 262 were taken, respectively. For example, one of the feature values may be indicative of the $T_{skin}$ while the earlier measurements 261 were taken and another one of the feature values may be indicative of the $T_{skin}$ while the current measurements 262 were taken.

In another embodiment, the computer 265 may generate one or more of the feature values based on measurements of the environment temperature sensor 210. Optionally, the computer 265 generates one or more of the feature values based on first and second values of the environment temperature measured while the earlier measurements 261 and the current measurements 262 were taken, respectively.

In yet another embodiment, the computer 265 may generate one or more of the feature values based on measurements of the heart rate of the user 260, e.g., as taken by the heart rate sensor 214, which may be a PPG device (e.g., the PPG device 212) or some external sensor, such as a sensor embedded in a smartwatch. Optionally, the computer 265 generates one or more of the feature values based on first and second values of the user's heart rate measured while the earlier measurements 261 and the current measurements 262 were taken, respectively.

In yet another embodiment, the computer 265 may generate one or more of the feature values based on measurements of the PPG device 212, which measures a signal indicative of an oxygen saturation level of the user's blood ($SpO_2$). Optionally, the computer 265 generates one or more of the feature values based on first and second values of $SpO_2$ measured while the earlier measurements 261 and the current measurements 262 were taken, respectively.

It is to be noted that feature values may be indicative of a change between values of a certain parameter (as based on the current measurements 262 and the earlier measurements 261) in different ways. In one embodiment, the feature values may include two or more values derived from either the earlier measurements 261 or the current measurements 262. For example, the feature values may include a first feature value representing an average heart rate during an early period (determined based on some of the early measurements 261) and a second feature value an average heart rate during a later period (determined based on some of the current measurements 262). Thus, information about the difference between the two values is conveyed by the first and second feature values. In another embodiment, the feature values may include a certain feature value derived from both the earlier measurements 261 and the current measurements 262. For example, the feature values may include a single feature value representing the change in the average heart between the early period and the later period.

In some embodiments, the computer 265 may utilize values from sensors (e.g., the one or more acoustic sensors 202 and/or the movement sensor 206) to select portions of the current measurements 262 and/or the earlier measurements 261. Optionally, the selection is performed to identify times when the sensor measurements may be less noisy (e.g., when the user is not very active) and/or in order to identify periods in which the user was in similar situations (e.g., similar levels of activity and/or similar posture), which can help make a comparison between values derive from the current measurements 262 and the earlier measurements 261, more informative regarding the change relative to the known extent of the RTI.

In one embodiment, the computer 265 may utilize the head movement signal to select first and second portions of the audio recordings belonging to the earlier measurements 261 and the current measurements 262, respectively. Optionally, the first and second portions are selected to correspond to periods in which the head movement signal did not indicate head movements that are characteristic of coughing (e.g., they did not include patterns of accelerations typically observed when a person coughs) In one example, the computer 265 calculates based on the first and second portions, first and second respective respiration rates of the user, and generates, based on the first and second respiration rates, one or more of the feature values, which are utilized to calculate the value indicative of the change relative to the known extent of the RTI.

In another embodiment, the computer identifies, based on the $H_{ori}$ signal (the orientation of the user's head with respect to the direction in which earth's gravity acts), which is obtained from measurements of the movement sensor 206, first and second portions of the audio recordings in the earlier measurements 261 and the current measurements 262, respectively. Both the first and second portions are selected such that they were recorded when the user's head was upright. The computer 265 calculates first and second extents of coughing based on these first and second portions, and generates, based on the first and second extents of coughing, one or more of the feature values, which are utilized to calculate the value indicative of the change relative to the known extent of the RTI.

In yet another embodiment, values obtained by the movement sensor 206 may be indicative of movements of the user's body and provide information indicative of whether the user was stationary or active (e.g., walking, running, etc.). Optionally, the computer 265 utilizes these values to identify first and second portions of the audio recordings in the earlier measurements 261 and the current measurements 262, respectively, which were recorded after the user was stationary for at least a certain period, which is greater than one minute. The computer 265 calculates first and second extents of coughing based on these first and second portions, and generates, based on the first and second extents of coughing, one or more of the feature values, which are utilized to calculate the value indicative of the change relative to the known extent of the RTI.

In one embodiment, the feature values generated based on the current measurements 262 and the earlier measurements 261 include feature values indicative of the following: an average breathing rate during the earlier period (in which the earlier measurements 261 were taken), an average breathing rate during the current period (in which the current measurements 262 were taken), and average number of coughs per hour during the earlier period, and an average number of coughs per hour during the current period. The feature values also include a value representing the known extent of the RTI the user 260 had during the previous period. Optionally, the feature values may also include the average skin temperatures (as measured by the skin temperature sensor 208) during the previous period and the current period, and the average environment temperatures (as measured by the environment temperature sensor 210) during the previous period and the current period.

Various embodiments described herein rely on detecting the extent of coughing of the user 260 in portions of audio recordings obtained using the one or more acoustic sensors 202. Optionally, detection is performed after enhancing a signal that includes the sounds of coughing using a beamforming approach described herein. In order to identify extent of coughing, the computer 265 may utilize one or more various approaches known in the art that may be characterized as being machine learning-based approaches. This involves generating certain feature values based on audio recordings and/or additional data (e.g., movement data) and using a certain machine learning-trained model (which is not the same model as the one above used to detect the extent of the RTI or change relative to the known extent of the RTI).

In one embodiment, the computer 265 generates the certain feature values based on data that includes the earlier measurements 261 and the current measurements 262 (e.g., audio based and/or movement based features described above), and utilizes the certain machine learning-trained model to calculate, based on the certain feature values, one or more values indicative of a difference between first and second extents of coughing recognizable in the earlier measurements 261 and the current measurements 262, respectively. Optionally, the computer 265 then calculates the change relative to the known extent of the RTI based on a difference between the first and second extents of coughing (e.g., the first and second extents may be used as feature values, as described above). In some embodiments, the certain machine learning-trained model used to identify extents of coughing was trained on training data of multiple users, with training data of each certain user, from among the multiple users, comprising certain first measurements taken while the certain user was coughing, and certain second measurements taken while the certain user was not coughing.

The certain feature values according to which the extent of coughing is calculated may be generated from different sources of data, in different embodiments. Optionally, the different sources of data may be different sensors, which are described herein as belonging, in some embodiments, to the wearable ambulatory system 264.

In one embodiment, the computer 265 generates one or more of the certain feature values based on a portion of the audio recordings belonging to the current measurements 262 and at least one of the certain feature values based on a portion of the head movement signal (measured by the movement sensor 206) belonging to the current measurements 262. Thus, identification of coughing may utilize correlations between the sounds and the characteristic head jerking involved in coughing.

In another embodiment, the computer 265 may utilize a signal indicative of an orientation of the user's head relative to the earth's gravity (obtained with the movement sensor 206). Optionally, the computer 265 generates, based on a portion of the movements signal belonging to the current measurements 262, a feature value, from among the certain feature values, which is indicative of the head's orientation.

In yet another embodiment, the computer 265 generates one or more of the certain feature values based on images that include at least a portion of the user's mouth, which are captured by inward-facing camera 218. Thus, identification of coughing may utilize visual indications such as an open mouth and/or a hand or first in the proximity of the mouth.

Figure 4:
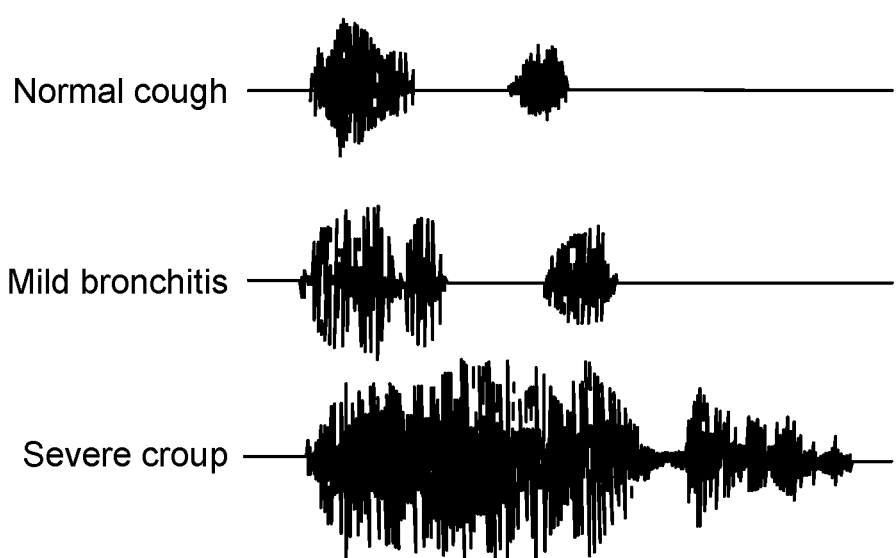
FIG. 4 illustrates different spectral properties of different types of coughs.

Coughing generates a distinctive auditory signal. This enables not only identification of coughing events, but also identification of different types of coughs due to their different spectral properties. Examples of different spectral properties of different types of coughs are illustrated in FIG. 4. There has been extensive work in the area of identifying and/or characterizing coughs from audio data. The following are some examples of machine learning-based approaches, including data processing and feature generation techniques, which may be used in different embodiments described herein (e.g., in order to generate at least some of the certain feature values described above, which are used to identify coughing and/or calculate extent of coughing).

In one embodiment, the computer 265 generates one or more of the time series features and/or one or more of the frequency features described in table 3 in Abaza, Ayman A., et al. "Classification of voluntary cough sound and airflow patterns for detecting abnormal pulmonary function." *Cough* 5.1 (2009): 8.

In another embodiment, the computer 265 may generate one or more of the features described in Rudraraju, Gowrisree, et al. "Cough sound analysis and objective correlation with spirometry and clinical diagnosis." *Informatics in Medicine Unlocked* (2020): 100319. Optionally, the generated feature values include one or more primary features which are extracted from audio recordings using standard signal processing techniques in both time and frequency domain Some examples of the primary features include Energy, Zero-crossing rate (ZCR), Mel Frequency Cepstral Coefficients and Spectral features (spectral centroid, spectral bandwidth, spectral roll-off), also discussed in Piirila, et al "Differences in acoustic and dynamic characteristics of spontaneous cough in pulmonary diseases", Chest, 96 (1989), pp. 46-53. Optionally, the generated feature values include one or more secondary/domain features, which include the type of cough sequence, number of bouts in a sequence, number of occurrences of cough sequence in a 2-min interval, and duration of cough sequences.

In yet another embodiment, the computer 265 generates one or more of the features described in Barry, Samantha J., et al. "The automatic recognition and counting of cough." *Cough* 2.1 (2006): 8, which include various features that are used to detect coughing events with the Hull Automatic Cough Counter (HACC) method. Optionally, the computer 265 may utilize one or more of the data processing techniques described therein to identify coughs.

In still another embodiment, the computer 265 generates one or more Mel-frequency cepstral coefficients (MFCC), from audio recordings as described in Vhaduri, Sudip, et al. "Nocturnal Cough and Snore Detection in Noisy Environments Using Smartphone-Microphones." 2019 *IEEE International Conference on Healthcare Informatics (ICHI)*. IEEE, 2019.

Since the extent of coughing is a strong indicator of an occurrence of an RTI, a change in the extent of the RTI is often directly correlated with the extents of coughing in the audio recordings. In one embodiment, the computer 265 calculates a first extent of coughing of the user 260, which is recognizable in the earlier measurements 261, and calculates a second extent of coughing of the user 260 recognizable in the current measurements 262, and then calculates the change relative to the known extent of the RTI based on a difference between the first and second extents.

As discussed above, coughing may be associated with characteristic movement patterns (e.g., jerking of the head). Such movement patterns may be used to identify coughing event in the head movement signal, measured by the movement sensor 206. In one embodiment, the computer 265 may be used to generate feature values based on the head movement signal obtained during a certain period (e.g., one second or several seconds). These feature values may include values indicative of the extent of head movement, number of times the head changed direction, average changes in acceleration during the period, and other values used to characterize head movement as described above in the references of Röddiger et al. and Hernandez et al., which describe movement-based features in the context of detection of respiration (which are readily available to be used for the more accentuated movements involved in coughing). A machine learning-based model can then be utilized to calculate, based on these movement-based feature values, a value indicative of whether the user coughed and/or how intensive the cough was. Optionally, the machine learning-based model is trained based on label movement data for which there are indications provided regarding when the recorded person coughed.

Herein, movements that characterize coughing refer to movements of the head that are typically observed when people cough (e.g., shaking and/or jerking of the head). Optionally, determining whether a certain sequence of movements is characteristic of coughing may be done using a machine learning-based approach, as described above. For example, if an extent of coughing calculated based on feature values, which are generated from a certain portion of a signal indicative of head movements, reaches a threshold, the certain portion of the signal is considered to be characteristic of coughing. Optionally, a certain sequence of movements of the user 260 is characteristic of coughing if it was observed previously when there was an indication that the user 260 coughed (e.g., identification of coughs in audio recorded at the same time).

In addition to detecting a change relative to the known extent of an RTI the computer 265 may also detect changes in extents of other respiratory conditions that may be identified via characteristic sounds. In one embodiment, the computer 265 may generate feature values based on data comprising the current measurements 262 and the earlier measurements 261, and utilize a machine learning-trained model to calculate, based on these feature values, a value indicative of a change to a certain type of respiratory condition the user has. Optionally, the certain type of respiratory condition involves one or more of the following: a widened airway, a narrowed airway, fluid filled air sacs, and stiff lungs. Optionally, the model was trained on training data of multiple users, with training data of each certain user, from among the multiple users, comprising certain first and second measurements taken with the sensors while the certain user had certain first and second known extents of the certain type of the respiratory condition, respectively. Optionally, generating feature values and training a model in this embodiment uses the same approaches described above with respect to generating feature values and training a model for detection of the change relative to the known extent of the RTI.

In some embodiments, the earlier measurements 261 may be selected in such a way such that user 260 was in a condition (while the earlier measurements 261 were taken) that is similar to the condition the user 260 was in when the current measurements 262 were taken. Being in "a similar condition" may mean different things in different embodiments.

In one embodiment, the computer 265 calculates a current heart rate based on measurements of the heart rate sensor 214 taken while the current measurements 262 were taken, and selects the earlier measurements 261 such that a corresponding heart rate measured with the heart rate sensor 214 while the earlier measurements 261 were taken, is within a predetermined distance from the current heart rate. Optionally, the predetermined distance is less than 10 beats per minute.

In another embodiment, the computer 265 selects the earlier measurements 261 such that a difference between the temperature in the environment, measured while the earlier measurements 261 were taken with environment temperature sensor 210, and a temperature in the environment, measured while the current measurements 262 were taken, is below a predetermined threshold. Optionally, the predetermined threshold is below 7° C.

In yet another embodiment, the computer 265 calculates, based on measurements of the movement sensor 206 belonging to the current measurements 262, a current level of physical activity that belongs to a set comprising: being stationary, and walking. The computer 265 select the earlier measurements 261 that were taken while the user's movements were indicative of a similar level of physical activity.

Having the one or more acoustic sensors 202 mounted to fixed positions relative to the head of the user wearing the ambulatory wearable system may confer several advantages when it comes to reproducing consistent audio recordings of the user. In particular, having the fixed positions makes it possible to know the exact distances of the sound sources (e.g., the mouth and nostrils) from the microphones. As discussed below, this information can be utilized to enhance the signals in audio recordings obtained with the one or more acoustic sensors utilizing computational approaches such as beamforming.

Beamforming is a class of algorithms for multichannel signal processing. The term Beamforming refers to the design of a spatio-temporal filter which operates on the outputs of a microphone array. Beamforming is achieved by filtering the microphone signals and combining the outputs to extract (by constructive combining) the desired signal and reject (by destructive combining) interfering signals according to their spatial location.

There are various beamforming techniques known in the art which may be utilized by the computer 265 to enhance audio recordings obtained when the one or more acoustic sensors 202 include two or more acoustic sensors as illustrated in FIG. 2, FIG. 5, and FIG. 6.

In one embodiment, the computer 265 may utilize techniques described in Hoshuyama, et al. "A robust adaptive beamformer for microphone arrays with a blocking matrix using constrained adaptive filters" IEEE Transactions on signal processing 47.10 (1999): 2677-2684, which describes a robust adaptive beamformer applicable to microphone arrays (involving two or more microphones). The beamformer described in this reference is a generalized sidelobe canceller (GSC) with an adaptive blocking matrix using coefficient-constrained adaptive filters (CCAF's) and a multiple-input canceller with norm-constrained adaptive filters (NCAF's).

In another embodiment, the computer 265 may utilize techniques described in Yousefian, et al. "A Dual-Microphone Speech Enhancement Algorithm Based on the Coherence Function." *IEEE TRANSACTIONS ON AUDIO, SPEECH, AND LANGUAGE PROCESSING* 20.2 (2012): 599, which describes an approach that utilizes the coherence between the target and noise signals as a criterion for noise reduction and can be generally applied to arrays with closely spaced microphones, where noise captured by the sensors is highly correlated.

In yet another embodiment, the computer 265 may utilize techniques described in Park, et al. "Two-Microphone Generalized Sidelobe Canceller with Post-Filter Based Speech Enhancement in Composite Noise." ETRI Journal 38.2 (2016): 366-375, which describes suppression of composite noise in a two-microphone speech enhancement system.

FIG. 5 and FIG. 6 illustrate some configurations in which multiple acoustic sensors may be utilized to obtain multiple audio recordings from which an enhanced signal can be extracted, in some embodiments, in order to better identify coughing and/or respiration activity.

FIG. 5 illustrates smartglasses with four acoustic sensors: acoustic sensors 244 and 243 on one side of the smartglasses, and acoustic sensors 247 and 246 on the other side. The direction of the two pairs of the acoustic sensors, vectors 245 and 248 are also illustrated with respect to the symmetry plane 242 that divides the face in to two sides. The figure shows how the pairs are oriented slightly differently, such that the vector 248 is oriented towards the nostrils, while the vector 245 is oriented lower, more in the direction of the mouth.

FIG. 6 illustrates smartglasses with three acoustic sensors on one side of the frame. The figure illustrates how the three acoustic sensors 250, 251, and 252 may be used to generate two different microphone arrays, oriented in different directions (vectors 253 and 254), with respect to the horizon 255.

Figure 7A:
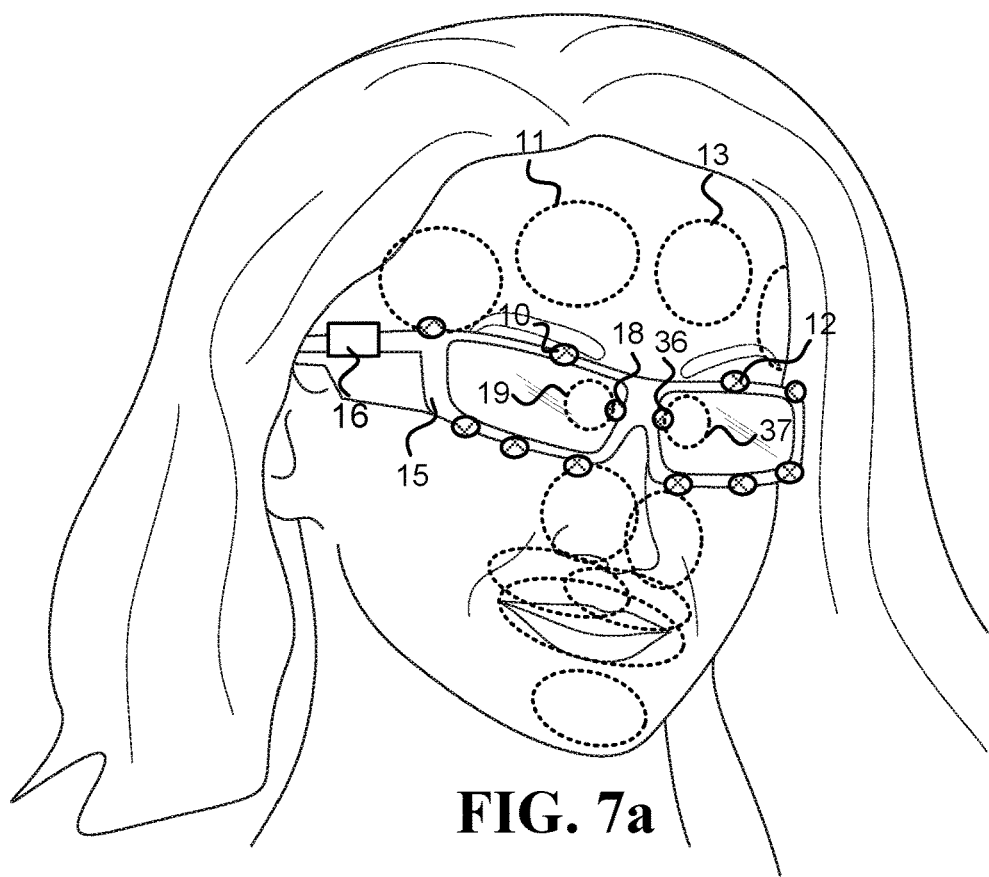
FIG. 7a and FIG. 7b illustrate various inward-facing head-mounted cameras coupled to an eyeglasses frame.

The following is a discussion of various aspects of embodiments involving utilization of head-mounted cameras for various applications. In some embodiments, a device, such as a camera, may be positioned such that it occludes an ROI on the user's face, while in other embodiments, the device may be positioned such that it does not occlude the ROI. Sentences in the form of "the system/camera does not occlude the ROI" indicate that the ROI can be observed by a third person located in front of the user and looking at the ROI, such as illustrated by all the ROIs in FIG. 13 and FIG. 17. Sentences in the form of "the system/camera occludes the ROI" indicate that some of the ROIs cannot be observed directly by that third person, such as ROIs 19 and 37 that are occluded by the lenses in FIG. 7a, and ROIs 97 and 102 that are occluded by cameras 91 and 96, respectively, in FIG. 15.

Although some of the disclosed embodiments can use occluding cameras successfully, in certain scenarios, such as when using a head-mounted system (HMS) on a daily basis and/or in a normal day-to-day setting, using cameras that do not occlude their ROIs on the face may provide one or more advantages to the user, to the HMS, and/or to the cameras, which may relate to one or more of the following: esthetics, better ventilation of the face, reduced weight, simplicity to wear, ability to operate without active illumination, and reduced likelihood to being tarnished.

In various embodiments, cameras are located close to a user's face, such as at most 2 cm, 5 cm, 10 cm, 15 cm, or 20 cm from the face (herein "cm" denotes to centimeters). The distance from the face/head in sentences such as "a camera located less than 10 cm from the face/head" refers to the shortest possible distance between the camera and the face/head. The head-mounted cameras used in various embodiments may be lightweight, such that each camera weighs below 10 g, 5 g, 1 g, and/or 0.5 g (herein "g" denotes to grams).

Figure 7B:
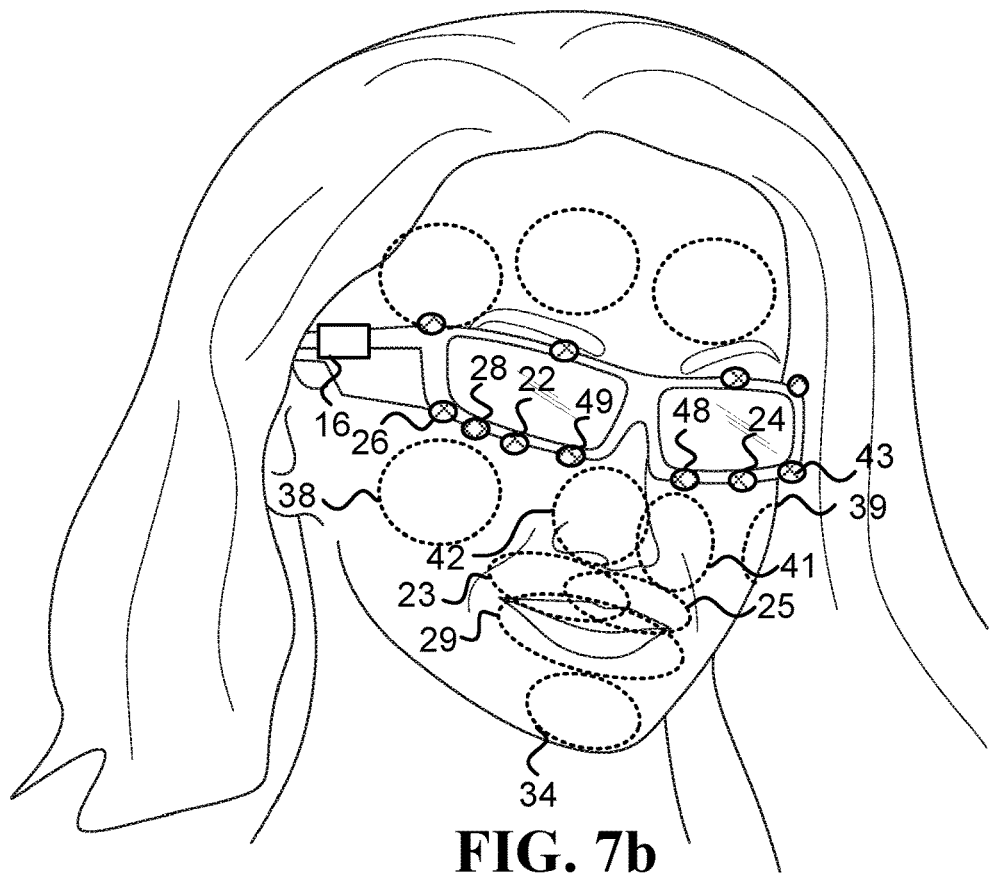

The following figures show various examples of HMSs equipped with head-mounted cameras. FIG. 1a illustrates various inward-facing head-mounted cameras coupled to an eyeglasses frame 15. Cameras 10 and 12 measure regions 11 and 13 on the forehead, respectively. Cameras 18 and 36 measure regions on the periorbital areas 19 and 37, respectively. The HMS further includes an optional computer 16, which may include a processor, memory, a battery and/or a communication module. FIG. 7b illustrates a similar HMS in which inward-facing head-mounted cameras 48 and 49 measure regions 41 and 41, respectively. Cameras 22 and 24 measure regions 23 and 25, respectively. Camera 28 measures region 29. And cameras 26 and 43 measure regions 38 and 39, respectively.

Figure 8:
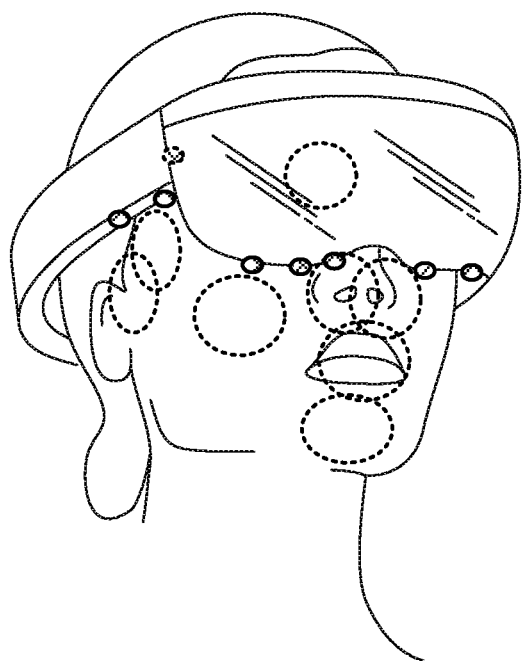
FIG. 8 illustrates inward-facing head-mounted cameras coupled to an augmented reality device.
Figure 9:
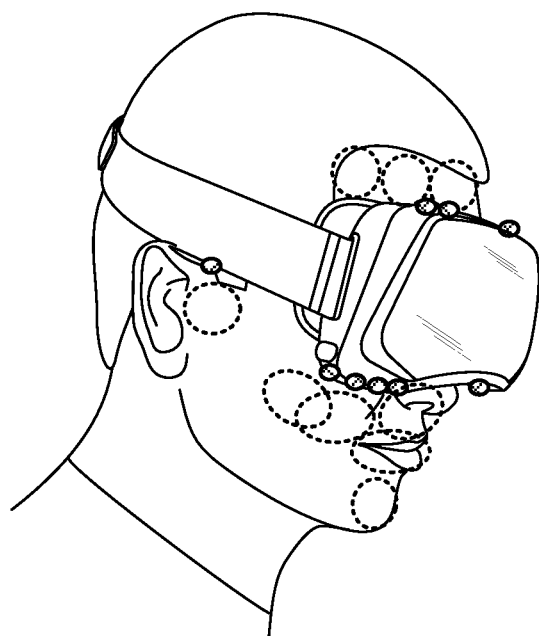
FIG. 9 illustrates head-mounted cameras coupled to a virtual reality device.
Figure 10:
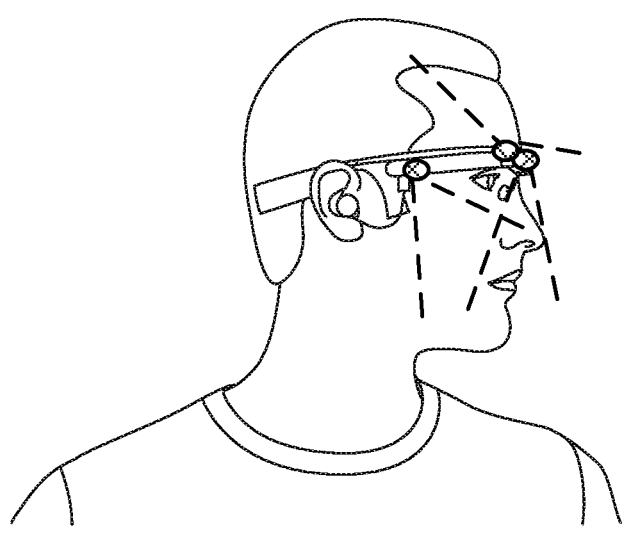
FIG. 10 illustrates a side view of head-mounted cameras coupled to an augmented reality device.
Figure 11:
FIG. 11 illustrates a side view of head-mounted cameras coupled to a sunglasses frame.

FIG. 8 illustrates inward-facing head-mounted cameras coupled to an augmented reality device such as Microsoft HoloLens™. FIG. 9 illustrates head-mounted cameras coupled to a virtual reality device such as Facebook's Oculus Rift™. FIG. 10 is a side view illustration of head-mounted cameras coupled to an augmented reality device such as Google Glass™. FIG. 11 is another side view illustration of head-mounted cameras coupled to a sunglasses frame.

FIG. 12 to FIG. 15 illustrate HMSs configured to measure various ROIs relevant to some of the embodiments describes herein. FIG. 12 illustrates a frame 35 that mounts inward-facing head-mounted cameras 30 and 31 that measure regions 32 and 33 on the forehead, respectively. FIG. 13 illustrates a frame 75 that mounts inward-facing head-mounted cameras 70 and 71 that measure regions 72 and 73 on the forehead, respectively, and inward-facing head-mounted cameras 76 and 77 that measure regions 78 and 79 on the upper lip, respectively. FIG. 14 illustrates a frame 84 that mounts inward-facing head-mounted cameras 80 and 81 that measure regions 82 and 83 on the sides of the nose, respectively. And FIG. 15 illustrates a frame 90 that includes (i) inward-facing head-mounted cameras 91 and 92 that are mounted to protruding arms and measure regions 97 and 98 on the forehead, respectively, (ii) inward-facing head-mounted cameras 95 and 96, which are also mounted to protruding arms, which measure regions 101 and 102 on the lower part of the face, respectively, and (iii) head-mounted cameras 93 and 94 that measure regions on the periorbital areas 99 and 100, respectively.

Figure 16:
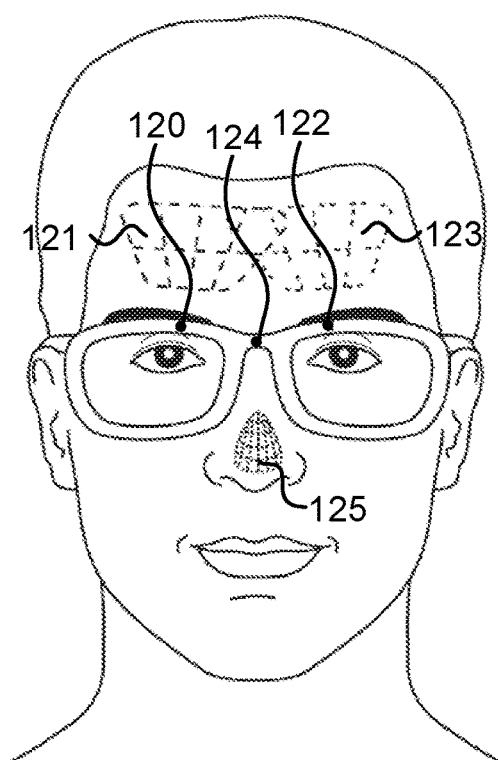
FIG. 16, FIG. 17, FIG. 18 and FIG. 19 illustrate various embodiments of systems that include inward-facing head-mounted cameras having multi-pixel sensors (FPA sensors)
Figure 17:
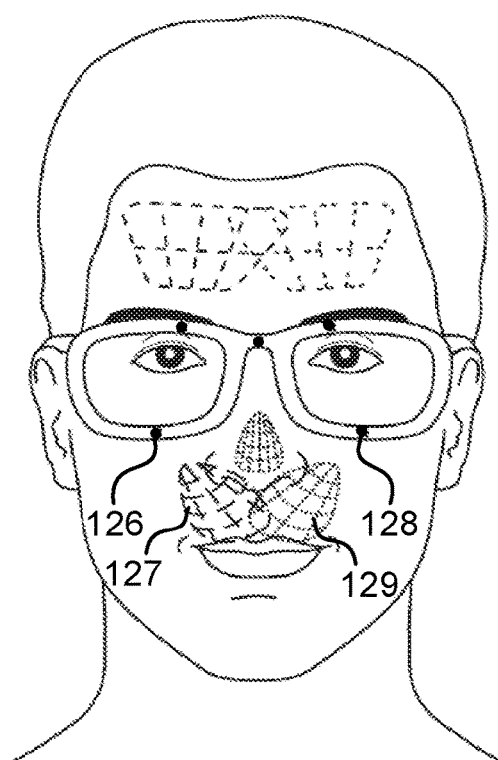
Figure 18:
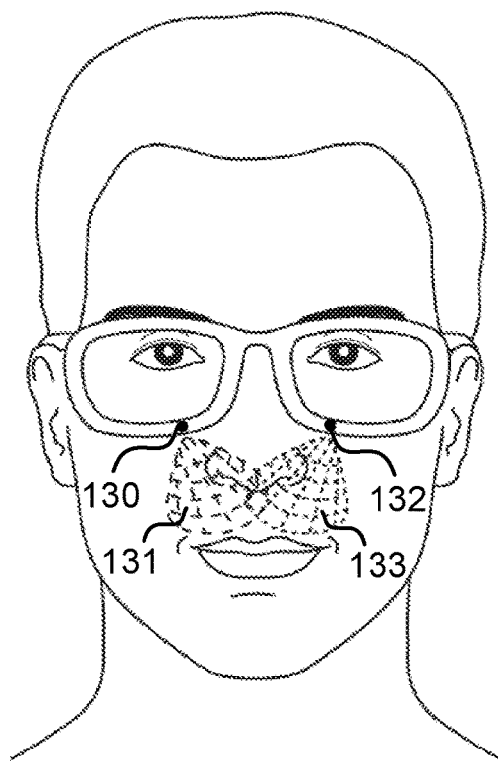
Figure 19:
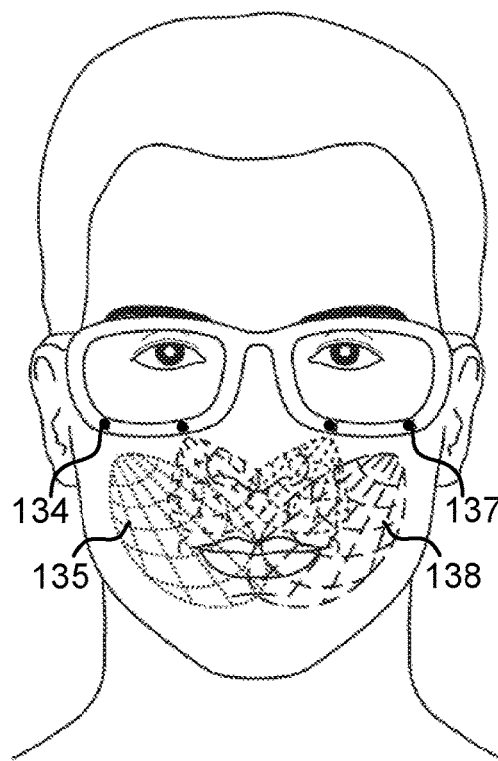

FIG. 16 to FIG. 19 illustrate various inward-facing head-mounted cameras having multi-pixel sensors (FPA sensors), configured to measure various ROIs relevant to some of the embodiments describes herein. FIG. 16 illustrates head-mounted cameras 120 and 122 that measure regions 121 and 123 on the forehead, respectively, and mounts head-mounted camera 124 that measure region 125 on the nose. FIG. 17 illustrates head-mounted cameras 126 and 128 that measure regions 127 and 129 on the upper lip, respectively, in addition to the head-mounted cameras already described in FIG. 16. FIG. 18 illustrates head-mounted cameras 130 and 132 that measure larger regions 131 and 133 on the upper lip and the sides of the nose, respectively. And FIG. 19 illustrates head-mounted cameras 134 and 137 that measure regions 135 and 138 on the right and left cheeks and right and left sides of the mouth, respectively, in addition to the head-mounted cameras already described in FIG. 18.

Figure 24:
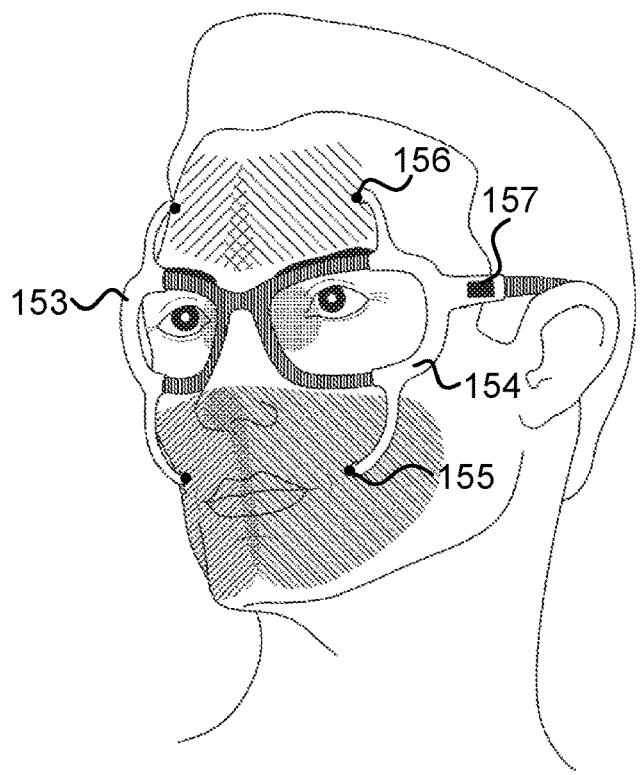
FIG. 24 illustrates embodiments of right and left clip-on devices, which are configured to be attached/detached from an eyeglasses frame, and have protruding arms to hold inward-facing head-mounted cameras.

In some embodiments, the head-mounted cameras may be physically coupled to the frame using a clip-on device configured to be attached/detached from a pair of eyeglasses in order to secure/release the device to/from the eyeglasses, multiple times. The clip-on device holds at least an inward-facing camera, a processor, a battery, and a wireless communication module. Most of the clip-on device may be located in front of the frame (as illustrated in FIG. 20b, FIG. 21b, and FIG. 24), or alternatively, most of the clip-on device may be located behind the frame, as illustrated in FIG. 23b and FIG. 22b.

FIG. 20a, FIG. 20b, and FIG. 20c illustrate two right and left clip-on devices 141 and 142, respectively, configured to attached/detached from an eyeglasses frame 140. The clip-on device 142 includes an inward-facing head-mounted camera 143 pointed at a region on the lower part of the face (such as the upper lip, mouth, nose, and/or cheek), an inward-facing head-mounted camera 144 pointed at the forehead, and other electronics 145 (such as a processor, a battery, and/or a wireless communication module). The clip-on devices 141 and 142 may include additional cameras illustrated in the drawings as black circles.

FIG. 21a and FIG. 21b illustrate a clip-on device 147 that includes an inward-facing head-mounted camera 148 pointed at a region on the lower part of the face (such as the nose), and an inward-facing head-mounted camera 149 pointed at the forehead. The other electronics (such as a processor, a battery, and/or a wireless communication module) is located inside the box 150, which also holds the cameras 148 and 149.

FIG. 23a and FIG. 23b illustrate two right and left clip-on devices 160 and 161, respectively, configured to be attached behind an eyeglasses frame 165. The clip-on device 160 includes an inward-facing head-mounted camera 162 pointed at a region on the lower part of the face (such as the upper lip, mouth, nose, and/or cheek), an inward-facing head-mounted camera 163 pointed at the forehead, and other electronics 164 (such as a processor, a battery, and/or a wireless communication module). The clip-on devices 160 and 161 may include additional cameras illustrated in the drawings as black circles.

FIG. 22a and FIG. 22b illustrate a single-unit clip-on device 170, configured to be attached behind an eyeglasses frame 176. The single-unit clip-on device 170 includes inward-facing head-mounted cameras 171 and 172 pointed at regions on the lower part of the face (such as the upper lip, mouth, nose, and/or cheek), inward-facing head-mounted cameras 173 and 174 pointed at the forehead, a spring 175 configured to apply force that holds the clip-on device 170 to the frame 176, and other electronics 177 (such as a processor, a battery, and/or a wireless communication module). The clip-on device 170 may include additional cameras illustrated in the drawings as black circles.

FIG. 24 illustrates two right and left clip-on devices 153 and 154, respectively, configured to attached/detached from an eyeglasses frame, and having protruding arms to hold the inward-facing head-mounted cameras. Head-mounted camera 155 measures a region on the lower part of the face, head-mounted camera 156 measures regions on the forehead, and the left clip-on device 154 further includes other electronics 157 (such as a processor, a battery, and/or a wireless communication module). The clip-on devices 153 and 154 may include additional cameras illustrated in the drawings as black circles.

It is noted that the elliptic and other shapes of the ROIs in some of the drawings are just for illustration purposes, and the actual shapes of the ROIs are usually not as illustrated. It is possible to calculate the accurate shape of an ROI using various methods, such as a computerized simulation using a 3D model of the face and a model of a head-mounted system (HMS) to which a camera is physically coupled, or by placing a LED instead of the sensor, while maintaining the same field of view (FOV) and observing the illumination pattern on the face. Furthermore, illustrations and discussions of a camera represent one or more cameras, where each camera may have the same FOV and/or different FOVs. Unless indicated to the contrary, the cameras may include one or more sensing elements (pixels), even when multiple sensing elements do not explicitly appear in the figures; when a camera includes multiple sensing elements then the illustrated ROI usually refers to the total ROI captured by the camera, which is made of multiple regions that are respectively captured by the different sensing elements. The positions of the cameras in the figures are just for illustration, and the cameras may be placed at other positions on the HMS.

Sentences in the form of an "ROI on an area", such as ROI on the forehead or an ROI on the nose, refer to at least a portion of the area. Depending on the context, and especially when using a camera having a small number of pixels, the ROI may cover another area (in addition to the area). For example, a sentence in the form of an "ROI on the nose" may refer to either: 100% of the ROI is on the nose, or some of the ROI is on the nose and some of the ROI is on the upper lip.

Figure 26:
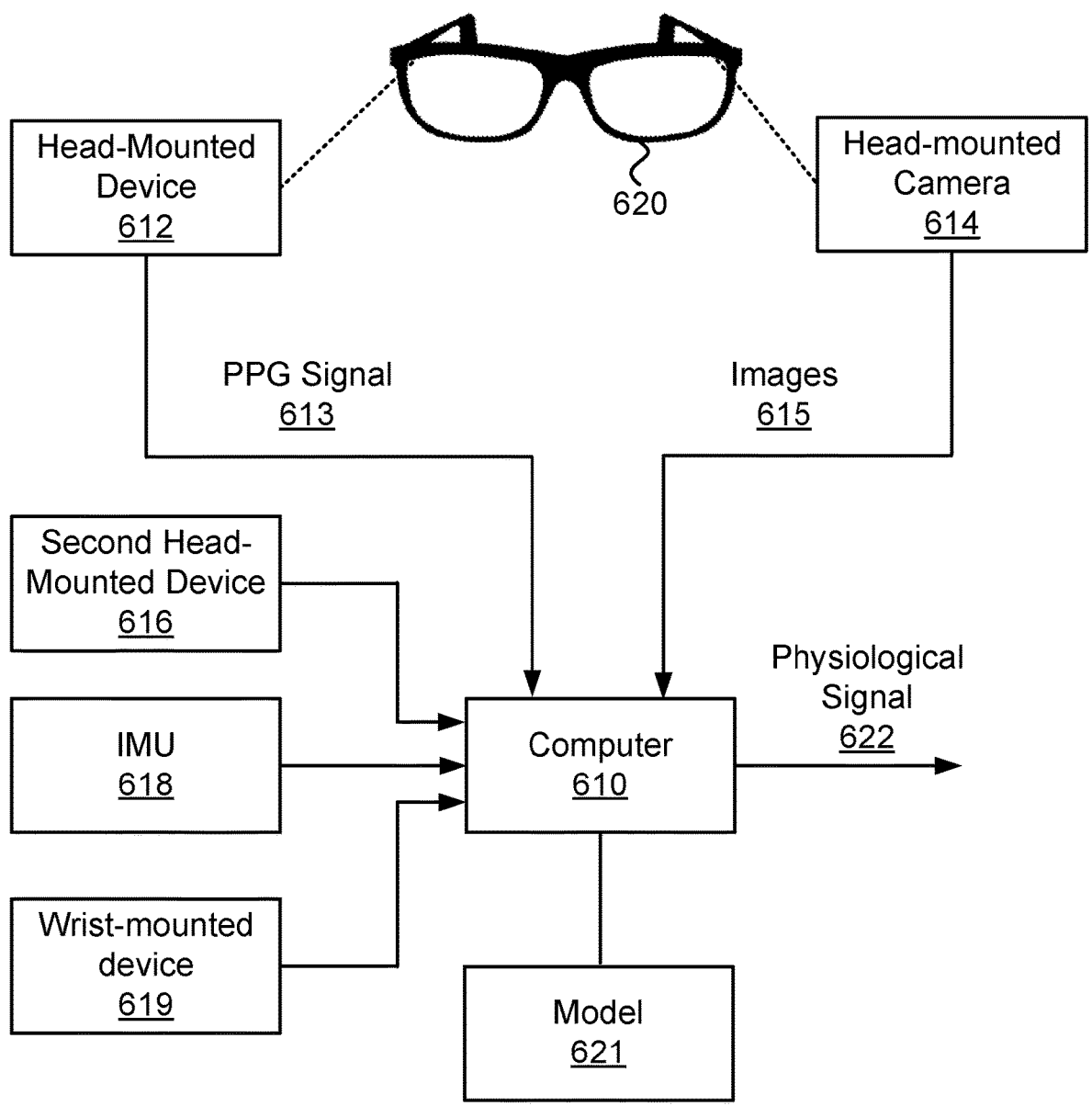
FIG. 26 illustrates an embodiment of a system configured to calculate a physiological signal.

FIG. 26 illustrates a system for calculating a physiological signal of a user. In one embodiment, the system includes at least a head-mounted device 612, a head-mounted camera 614, and a computer 610. Optionally, the system may include additional elements, such as a frame 620, a second head-mounted device 616, and/or an inertial measurement unit (IMU) 618.

The head-mounted device 612 measures photoplethysmographic signal (PPG signal) 613 at a region on the user's head. Some examples of regions at which measurements of the PPG signal 613 may be taken include a temple, the forehead, a cheek, the nose, and behind an ear. Optionally, the PPG signal 613 represents changes in the concentration levels of hemoglobin and blood oxygenation due to the dynamics of the user's blood flow. Various techniques may be utilized in order to quantify these changes, in order to produce the PPG signal.

In one embodiment, the head-mounted device 612 is a photoplethysmographic device (PPG device). In one example, the PPG device includes a light source and a photodetector. Optionally, the light source emits light to the region on the face, and the photodetector measures the reflected light from the tissue. Optionally, the reflected light is proportional to blood volume variations. In some embodiments, the PPG device utilizes light having a single wavelength (e.g., green light with a wavelength of ~530 nm). In another example, the PPG device utilizes light having multiple wavelengths, which may be emitted by multiple LEDs.

In another embodiment, the head-mounted device 612 is a second camera located more than 10 mm away from the region on the user's head, and the PPG signal 613 is recognizable from color changes in a region in images taken by the second camera. Thus, the second camera may be considered an inward-facing camera. Optionally, the second camera weighs less than 10 g (grams). Optionally, the second camera does not occlude the region on the user's head.

Known imaging photoplethysmographic techniques may be used to calculate the PPG signal 613 from the color changes that are recognizable in the region in the images taken by the second camera. Herein, sentences of the form "the PPG signal is recognizable from color changes in a region in the images" refer to effects of color changes due to variations in blood flow that may be identified and/or utilized by the computer 610, which are usually not recognized by the naked eye. Herein, "color changes" includes changes to amplitudes of one or more of the color channels in the images, and/or changes to ratios between amplitudes of two or more color channels in the images. There are various signal processing and/or analytical techniques known in the art that may be utilized by the computer 610 to extract the PPG signal 613 from the images taken by the second camera.

In some embodiments, the computer 610 may employ one or more of the following preprocessing techniques in order to obtain the PPG signal 613 from images taken by the second camera: normalization of pixel intensities (e.g., to obtain a zero-mean unit variance time series signal), and conditioning a time series signal by constructing a square wave, a sine wave, or a user defined shape, such as that obtained from an ECG signal or a PPG signal as described in U.S. Pat. No. 8,617,081. Various preprocessing techniques known in the art that may assist in extracting the PPG signal 613 from the images 615 are discussed in Zaunseder et al. (2018), "Cardiovascular assessment by imaging photoplethysmography—a review", Biomedical Engineering 63(5), 617-634. Additional examples of processing known in the art, which may be utilized by the computer 610, are given below.

In one example, U.S. Pat. No. 8,768,438, titled "Determining cardiac arrhythmia from a video of a subject being monitored for cardiac function", describes how to obtain a PPG signal from video of the user. In this example, a time series signal is generated from video images of a subject's exposed skin, and a reference signal is used to perform a constrained source separation (which is a variant of ICA) on the time series signals to obtain the PPG signal. Peak-to-peak pulse points are detected in the PPG signal, which may be analyzed to determine parameters such as heart rate, heart rate variability, and/or to obtain peak-to-peak pulse dynamics that can be indicative of conditions such as cardiac arrhythmia.

In another example, U.S. Pat. No. 8,977,347, titled "Video-based estimation of heart rate variability", describes how a times-series signal similar to the one described above may be subjected to a different type of analysis to detect the heart rate variability. In this example, the time series data are de-trended to remove slow non-stationary trends from the signal and filtered (e.g., using bandpass filtering). Following that, low frequency and high frequency components of the integrated power spectrum within the time series signal are extracted using Fast Fourier Transform (FFT). A ratio of the low and high frequency of the integrated power spectrum within these components is computed. And analysis of the dynamics of this ratio over time is used to estimate heart rate variability.

In yet another example, U.S. Pat. No. 9,020,185, titled "Systems and methods for non-contact heart rate sensing", describes how to obtain a PPG signal from video of a user, which can be filtered and processed to separate an underlying pulsing signal by, for example, using an ICA algorithm.

The separated pulsing signal from the algorithm can be transformed into frequency spacing data using FFT, in which the heart rate can be extracted or estimated.

Due to the proximity of the second camera to the face, in some embodiments, there may be an acute angle between the optical axis of second camera and the region on the face (e.g., when the region includes a portion on the forehead). In order to improve the sharpness of the images taken by the second camera, the second camera may be configured to operate in a way that takes advantage of the Scheimpflug principle. In one embodiment, the second camera includes a sensor and a lens; the sensor plane is tilted by a fixed angle greater than 2° relative to the lens plane according to the Scheimpflug principle in order to capture a sharper image when the second camera is worn by the user (where the lens plane refers to a plane that is perpendicular to the optical axis of the lens, which may include one or more lenses). Optionally, camera does not occlude the region on the user's face. In another embodiment, the second camera includes a sensor, a lens, and a motor; the motor tilts the lens relative to the sensor according to the Scheimpflug principle. The tilt improves the sharpness of images when the second camera is worn by the user. Additional details regarding utilization of the Scheimpflug principle are provided further below.

The head-mounted camera 614 captures images 615 indicative of posture of the user. For example, the head-mounted camera 614 is configured such that its field of view (FOV) includes portions of the user's body (e.g., feet or a shoulder) when the user stands upright and looks ahead (thus, the head-mounted camera 614 may be considered a down-pointing camera). In another embodiment, the head-mounted camera 614 has a FOV that is similar to the user's, e.g., it is oriented such that it has a frontal view when the user stands upright and looks ahead. Optionally, in this embodiment, the FOV of the head-mounted camera 614 does not include the feet and/or shoulders of the user when the user stands upright and looks ahead. Optionally, the head-mounted camera 614 is an outward-facing camera that is utilized by an extended reality device, such as an augmented reality device, a virtual reality device, or a mixed reality device. Optionally, the outward-facing camera is utilized by the extended reality device to capture images of the user's surroundings.

In one embodiment, the head-mounted camera 614 is a visible light camera and/or a near-IR camera. Optionally, the head-mounted camera 614 features an extended depth of field such as: (i) a camera that operates according to Scheimpflug principle, (ii) a light field camera, and/or (iii) a camera that utilizes at least one of the following techniques to achieve an extended depth of field: wavefront coding, diffusion coding, coded aperture, multiple apertures, and/or a lens array.

It is to be noted that some embodiments may involve utilization of multiple head-mounted cameras to generate images indicative of the user's posture. Some examples of head mounted cameras and their locations and/or orientations that may be utilized by embodiments of the system illustrated in FIG. 26 are illustrated herein in FIG. 30 to FIG. 40.

Various elements of the system illustrated in FIG. 26 may be coupled to the frame 620, which is configured to be worn on the user's head. In some embodiments, the head-mounted device 612 and/or the head-mounted camera 614 may be physically coupled to the frame 620. Optionally, the frame 620 may be an eyeglasses frame, or a frame of smartglasses or an extended reality device.

In one embodiment, the system illustrated in FIG. 26 includes an IMU 618, which provides a signal indicative of the movement and/or orientation of the user. Optionally, IMU 618 is physically coupled to the frame 620 and/or attached to the user's head in some other fashion. Thus, IMU 618 may provide a signal indicative of the movement and/or orientation of the user's head.

The computer 610 calculates a physiological signal 622 based on data that includes the PPG signal 613 and the user's posture (which is identifiable from the images 615). Optionally, the computer 610 may utilize additional sources of data, such as signals from the IMU 618, additional head-mounted cameras, additional PPG devices, and/or other sources of data. In order to calculate the physiological signal 622, the computer 610 may utilize various approaches describe below.

In some embodiments, the physiological signal 622 may be blood pressure. Optionally, the user's blood pressure may include one or more of the following values: systolic blood pressure, diastolic blood pressure, and the mean arterial pressure (MAP).

In other embodiments, the physiological signal 622 may be cardiac output, which is indicative of the volume of blood pumped by the heart through the circulatory system per unit of time (e.g., liters per minute). In still other embodiments, the physiological signal 622 may be tissue perfusion, which is indicative of the perfusion index (PI), which is the ratio of the pulsatile blood flow to the nonpulsatile or static blood in peripheral tissue. The PI represents a noninvasive measure of peripheral perfusion that can be continuously and noninvasively obtained from the PPG signal.

In yet other embodiments, the physiological signal 622 may be skin coloration, which is indicative of the hue of the skin (e.g., average pixel values in images of the skin, as taken by the second camera mentioned above). Optionally, the hue of the skin may refer to values at certain times during the cardiac cycle (e.g., the hue during the systolic peak or diastolic trough). Optionally, the hue may be normalized with respect to external lighting conditions (e.g., as determined based on the images 615 or measurements of a sensor that measures ambient lighting).

The computer 610 may utilize values of the physiological signals it calculates based on the PPG signal 613 and the images 615 to detect additional medical conditions. In one embodiment, the computer 610 identifies whether the user has orthostatic hypotension based on a drop of systolic blood pressure below a first threshold, and/or drop of diastolic blood pressure below a second threshold, within a predetermined duration from a transition in posture from supine to sitting posture, or from sitting to standing posture. In one example, the first threshold refers to a drop of 20 mm Hg, and the second threshold refers to a drop of 10 mm Hg, and the predetermined duration refers to 3 minutes from transition from supine to sitting posture, or from sitting to standing posture. In another example, the first threshold refers to a drop of 10 mm Hg, and the second threshold refers to a drop of 5 mm Hg, and the predetermined duration refers to 2 minutes from transition from supine to sitting posture, or from sitting to standing posture.

In one embodiment, the computer 610 calculates the user's heart rate, optionally from the PPG signal 613, and identifies Postural-Orthostatic Tachycardia Syndrome based on detecting a very fast heart rate, known as tachycardia, within a predetermined duration (such as 10 minutes) from a transition in posture from supine or sitting posture to standing posture.

Prior to calculating the physiological signal, and/or as part of this process, the computer 610 may utilize various preprocessing approaches in order to assist in calculations involving images such as the images 615 and/or images taken by the second camera (in order to provide the PPG signal 613 from those images). Some examples of preprocessing that may be used include: normalization of pixel intensities (e.g., to obtain a zero-mean unit variance time series signal), color space transformation (e.g., transforming RGB images into a monochromatic color or images in a different color space), blind source separation using algorithms such as independent component analysis (ICA) or principal component analysis (PCA), and various filtering techniques, such as detrending, bandpass filtering, and/or continuous wavelet transform (CWT).

As mentioned above, the computer 610 utilizes data related to the posture of the user (e.g., the images 615 and optionally also signals from the IMU 618). By doing so, the computer 610 may perform a calculation that adjusts for noise and/or artifacts that may influence the value of the physiological signal 622, which are due to the user's pose and/or change to the pose, which if left unaccounted for, may introduce errors into the calculation process. For example, in order to obtain accurate blood pressure values, it is standard practice to have a person seated and not standing up specifically in order to reduce the effects of posture. Thus, in some embodiments, calculation of the physiological signal 622 that utilizes both the PPG signal 613 and the images 615 is more accurate than detections based on the PPG signal 613 alone, because of the ability to adjust for artifacts and/or noise introduced due to posture.

Furthermore, because the computer 610 adjusts the calculation of the physiological signal 622 based on the user's posture, when provided with the same PPG signal in different calculations, but with different sets of images indicative of different posture, the computer 610 may calculate different values for the physiological signals. Thus, in some examples, for the same PPG signal, the computer 610 calculates and outputs different values for the physiological signal for the following different postures: standing, sitting, and lying down. For example, the same PPG signal will produce a first value for the user's blood pressure when the computer 610 receives images indicating the user is lying down, and a second value for the user's blood pressure when the computer 610 receives images indicating the user is standing.

In some embodiments, the computer 610 may utilize the user's posture to determine when the user has a posture in which calculations of the physiological signal are less accurate (e.g., standing or hunched over), and disregards measurements taken during that time, or assign a lower weight to measurements such times, when calculating the physiological signal that over a long duration.

In other embodiments, the computer 610 may utilize posture-dependent scaling factors. For example, the value of the physiological signal may be multiplied by a scaling factor, which is dependent on the posture the user has at the time. Optionally, the scaling factor is set based on comparing values of the physiological signal calculated by the computer 610 with values of the physiological signal calculated by other means (e.g., a cuff-based blood pressure monitor). Optionally, the scaling factors may be determined based on data collected from multiple users. Thus, using the scaling factors can help correct consistent posture-related artifacts, such as incorrect values for blood pressure that are calculated because of changes in blood flow due to the user's standing instead of sitting.

In still other embodiments, the computer utilizes a machine learning-based approach in which it generates feature values based on data comprising the PPG signal 613 and the images 615, and utilizes a model 621 to calculate the physiological signal 622 based on the feature values. In these embodiments, one or more of the feature values are generated based on the images 615 and are indicative of the user's posture. Adjustment for posture in these embodiments may be achieved by including an indication about the posture in the feature values, and having the model 621 account for the posture by virtue of it being generated based on training data that represents different postures. This enables the model 621 to account for the effects of posture on the PPG signal, and consequently to calculate the physiological signal 622 more accurately than would be possible without taking into account the user's posture.

Generally, machine learning-based approaches utilized by embodiments described herein involve training the model 621 on samples, with each sample including: feature values generated based on measurements (PPG signals from the head-mounted device 612, images from the head-mounted camera 614, and optionally other data) taken during a certain period, and a label indicative of the physiological signal during the certain period. In some embodiments, the model 621 may be personalized for a user by training the model on samples that include: feature values generated based on measurements of the user, and corresponding labels indicative of the user's respective physiological signals. In some embodiments, the model 621 may be generated based on measurements of multiple users, in which case, the model 621 may be considered a general model. Optionally, a model generated based on measurements of multiple users may be personalized for a certain user by being retrained on samples generated based on measurements of the certain user.

Some of the feature values in a sample may be generated based on other sources of data, such as measurements of the user generated using thermal cameras, movement sensors (e.g., the IMU 618), and/or other physiological sensors, and/or measurements of the environment. Optionally, measurements of the user taken during an earlier period may serve as a baseline to which to compare current values (and thus indicate whether current values represent an increase or decrease from a baseline). Optionally, some of the feature values may include indications of confounding factors, which may affect values of the physiological signal. Some examples of confounding factors include touching the face, thermal radiation directed at the face, and consuming certain substances, such as a medication, alcohol, caffeine, or nicotine.

Training the model 621 may involve utilization of various training algorithms known in the art (e.g., algorithms for training neural networks, and/or other approaches described herein). After the model 621 is trained, feature values may be generated for a certain PPG signal and images of the user, for which the value of the corresponding label (physiological signal) is unknown, and the computer 610 can utilize the model 621 to calculate the physiological signal 622 based on these feature values.

There are various types of feature values that may be generated by the computer 610 based on the data it utilizes to calculate the physiological signal 622. Some examples of feature values include "raw" or minimally processed values based on the data (i.e., the features are the data itself or applying generic preprocessing functions to the data). Other examples of feature values include feature values that are based on higher-level processing, such a feature values determined based on domain-knowledge (e.g., feature values describing properties of pulse waveforms) and/or feature values that are based on high-level image-analysis.

In some embodiments, detection of the physiological signal 622 is based on at least some feature values that describe properties of the cardiac waveform in the PPG signal 613. To this end, the computer 610 may employ various approaches known in the art to identify landmarks in a cardiac waveform (e.g., systolic peaks, diastolic peaks), and/or extract various types of known values that may be derived from the cardiac waveform, as described in the following examples.

In one embodiment, at least some of the feature values generated based on PPG signal 613 may be indicative of waveform properties that include: systolic-upstroke time, diastolic time, and the time delay between the systolic and diastolic peaks, as described in Samria, Rohan, et al. "Noninvasive cuffless estimation of blood pressure using Photoplethysmography without electrocardiograph measurement." 2014 IEEE REGION 10 SYMPOSIUM. IEEE, 2014.

In another embodiment, at least some of the feature values generated based on the PPG signal 613 may be derived from another analysis approach to PPG waveforms, as described in US Patent Application US20180206733, entitled "Device, method and system for monitoring and management of changes in hemodynamic parameters", which was published on 26 Jul. 2018. This approach assumes the cardiac waveform has the following structure: a minimum/starting point (A), which increases to a systolic peak (B), which decreases to a dicrotic notch (C), which increases to a dicrotic wave (D), which decreases to the starting point of the next pulse wave (E). Various features that may be calculated by the computer 610, which are suggested in the aforementioned publication, include: value of A, value of B, value of C, value of D, value of E, systol area that is the area under ABCE, diastol area that is the area under CDE, and the ratio between BC and DC.

In still another embodiment, the computer 610 may utilize the various approaches described in Elgendi, M. (2012), "On the analysis of fingertip photoplethysmogram signals", Current cardiology reviews, 8(1), 14-25, in order to generate at least some of the feature values bases on the PPG signal 613. This reference surveys several preprocessing approaches for PPG signals as well as a variety of feature values that may be utilized. Some of the techniques described therein, which may be utilized by the computer 610, include calculating feature values based on first and second derivatives of PPG signals.

In some embodiments, at least some of the feature values may represent calibration values of a user, which are values of certain parameters such as waveform properties described above when the user had a known value of the physiological signal (as determined based on a reference measuring device such as a cuff-based blood pressure device). Optionally, the computer 610 generates one or more values that are indicative of: (i) a value of the physiological signal of the user that was measured during a certain previous period, and (ii) a value of a property of the pulse waveform (e.g., systolic-upstroke time or diastolic time) during the certain previous period.

Various embodiments described herein may utilize various image-based feature function to generate one or more of the feature values based on the images 615 and/or images taken by the head-mounted device 612 in order to represent the PPG signal 613 (e.g., when the head-mounted device 612 is a camera). In one embodiment, at least some of the feature values may be derived directly from values of pixels in images 615 and/or images taken by the head-mounted device 612. Optionally, at least some of the feature values are values of pixels from the images 615 and/or the images taken by the head-mounted device 612. Optionally, one or more of the feature values may be the values of the pixels themselves or some simple function of the pixels, such as the average of pixels at certain regions in each of the images. Optionally, one or more of the feature values may be various low-level features derived from images, such as features generated using Gabor filters, local binary patterns (LBP) and their derivatives, algorithms such as SIFT and/or SURF (and their derivatives), image keypoints, histograms of oriented gradients (HOG) descriptors, and products of statistical procedures such independent component analysis (ICA), principal component analysis (PCA), or linear discriminant analysis (LDA). Optionally, one or more of the feature values may be derived from multiple images taken at different times, such as volume local binary patterns (VLBP), cuboids, and/or optical strain-based features. In one example, one or more of the feature values may represent a difference between values of pixels at one time t at a certain co-ordinate in the images and values of pixels at a different certain co-ordinate at some other time t+x (which can help detect different arrival times of a pulse wave).

One or more of the feature values generated by the computer 610 based on the images 615 may be indicative of the user's posture. These one or more feature values may be indicative of various properties such as location of the user's limbs, orientation of the head, angle of the torso, etc. These properties may be determined by analysis of the images indicating what is detected in the images (e.g., identifying the location of the feet, arms, etc.) Optionally, determining the user's posture relies on information about the orientation of the head-mounted camera 614 when the images 615 were taken (e.g., based on values acquire from IMU 618). Optionally, Identifying portions of the user's body in the images may involve various image analysis approaches known in the art.

Identifying the user's posture based on the images 615 may involve various techniques known in the art. Optionally, these approaches rely on models of the user's body. The following are some examples of models that may be utilized by the computer 610 to generate one or more of the feature values that are indicative of the user's posture. One example of a model of the human body parameterized by pose is described in the reference Zuffi, S., Black, M. J. (2015), "The Stitched Puppet: A Graphical Model of 3D Human Shape and Pose", In IEEE Conf. on Computer Vision and Pattern Recognition (CVPR). One example of a model based on a loose-limbed body model that requires a specification of the probabilistic relationships between body parts at a given time instant and over time is described in the reference Sigal, L., Isard, M., Haussecker, H., Black, M. J. (2012), "Loose-limbed people: Estimating 3d human pose and motion using non-parametric belief propagation", International journal of computer vision, 98(1), 15-48. More example of part-based model are described in the reference Ghosh, S., Sudderth, E., Loper, M., Black, M. (2012), "From Deformations to Parts: Motion-based Segmentation of 3D Objects", In Advances in Neural Information Processing Systems 25 (NIPS), MIT Press, pages 2006-2014; and in the reference Hirshberg, D., Loper, M., Rachlin, E., Black, M. J. (2012) "Coregistration: Simultaneous alignment and modeling of articulated 3D shape", In European Conf. on Computer Vision (ECCV), Springer-Verlag, LNCS 7577, Part IV, pages 242-255. One example of a model for on estimating articulated body posture and motion from monocular video sequences is described in the reference Rosales, R., Sclaroff, S. (2000), "Inferring body pose without tracking body parts", In IEEE Computer Society conference on computer vision and pattern recognition (CVPR) (Vol. 2, pp. 721-727). One example of a model for predicting soft-tissue deformations is described in the reference Pons-Moll, G., Romero, J., Mahmood, N., Black, M. J. (2015), "Dyna: A Model of Dynamic Human Shape in Motion", ACM Transactions on Graphics, (Proc. SIGGRAPH).

In some embodiments, the feature values generated by the computer 610 include one or more feature values, generated based on the images 615, which are indicative of a posture of the user being upright, seated, or lying down. Optionally, the one or more feature values are generated based on a classifier that identifies posture of a human body in images (e.g., utilizing a machine learning model trained on images of various people in various known postures). Optionally, the one or more feature values may identify additional postures and/or activities the user may be partaking in, such as: sitting in a hunched C-posture, reclining, walking, running, cycling, rowing, climbing stairs, using elliptical machine or Nordic track, using a cane or a walker.

Some postures, such as leg crossing and squatting, increase the blood pressure measured by the head-mounted device. In one embodiment, the computer 610 identifies such postures from the images 615 and generates a feature value from among the feature values, which is indicative of whether the user's legs are crossed.

A posture-related property, which may affect accuracy of calculations of values of physiological signals based on the PPG signal 613, is the height of the head-mounted device 612 relative to the heart and/or certain arteries in the user's body. Optionally, the vertical distance between the head-mounted device and the user's heart influences the blood flow (e.g., due to gravitational effects), which affects pulse cardiac waveforms. Examples of situations where the vertical distance between the head-mounted device 612 and the heart may change include when the user: hunches forwards, leans forwards, leans back, and/or enters recumbent or a semi-recumbent position. In order to account for this vertical distance factor, in some embodiments, the computer 610 calculates a feature value, from among the feature values, based on the images 615, which is indicative of the vertical distance between the head-mounted device 612 and the user's heart. In another embodiment, the computer 610 calculates, based on the images 615, a feature value from among the feature values, which is indicative of the vertical distance between the head-mounted device and the brachial artery of the user.

Muscle tensing, such as tensing of legs and buttocks, may increase the blood pressure measured by the head-mounted device 612. In one embodiment, the system further includes an additional head-mounted camera for capturing images of a portion of the user's face, and the computer 610 detects such muscle tensing from facial expressions, and/or changes to facial blood flow identifiable in these images, and generates one or more feature values indicative of the muscle tensing.

Feature values related to pulse transit time (PTT), e.g., as determined based on the pulse arrival times (PATs) at various regions, may be utilized in some embodiments, instead of, or in addition to, feature values related to waveforms, in order to calculate the user's blood pressure. While the PPG signal 613 may be indicative of times at which pulse waves arrive at the region on the user's head, in order to calculate blood pressure based on PTTs, in some embodiments, the computer 610 receives an additional signal related to the pulse wave at another region. The computer 610 utilizes the additional signal in order to generate feature values that are indicative of PTTs, and/or differences in PATs at different regions.

In one embodiment, the computer 610 receives a second photoplethysmographic signal (second PPG signal) indicative of pulse wave arrival times at a second region on the user's body, which is at least 25 mm away from the region on the user's head. The computer 610 generates at least one of the feature values based on the second PPG signal, such the at least one of the feature values are indicative of a difference in cardiac pulse wave arrival times at the region and the second region. Optionally, the at least one of the feature values are indicative of arrival of pulse wave at the second region or a difference in time (phase shift) between arrival at the region and the second region. In one embodiment, the second region is located on the user's head. Optionally, the second PPG signal is generated by a second head-mounted device 616, which is optionally physically coupled to the frame 620. In another embodiment, the second region is located on a wrist of the user, and the system includes a wrist-mounted device 619 to measure the second PPG signal. For example the wrist-mounted device 619 may be a PPG device embedded in a smartwatch or a fitness bracelet.

In another embodiment, the second region is located on the user's head, at least 25 mm away from the region on the user's head, and the head-mounted device 612 is a certain camera located more than 10 mm away from the region on the user's head and more than 10 mm away from the second region on the user's head. Optionally, the PPG signal 613 is recognizable from color changes in a first area in images taken by the certain camera, and the second PPG signal is recognizable from color changes in a second area in the images taken by the certain camera. Optionally, the area of the overlap between the first and second areas is less than 50% of the smaller from among the first and second areas. Optionally, the computer generate, based on the first PPG signal and the second PPG signal, one or more of the feature values, and the one or more of the feature values are indicative of a difference between when a pulse wave arrives at the region on the user's head and the second region on the user's head. Optionally, at least one of the feature values is indicative of pulse arrival times at the two regions.

In yet another embodiment, the computer 610 receives a signal indicative of the user's heart's electrical activity (EA signal), and generates at least one of the feature values based on the signal indicative of the user's heart's electrical activity. Optionally, the EA signal is generated utilizing an electrocardiogram (ECG) device coupled to the user. Optionally, the EA signal is indicative of times at which one or more of the following cardiac activity phases occur: atrial systole, ventricular systole, ventricular repolarization, and the at least one of the feature values are indicative of a difference in time between when a certain cardiac activity phase of the user and when a corresponding pulse wave arrives at the region on the user's head.

Additional details regarding identifying PATs, calculating PTTs based on multiple PPG signals and/or EA signals, as well as feature values that may be generated based on PATs and PTTs in order to calculate blood pressure are described in more detail below in this disclosure in the discussion regarding embodiments illustrated in FIG. 27 and FIG. 28.

Generating the model 621 requires providing labels to samples. These labels represent "ground truth" physiological signal values, which optionally represent the values to which the computer 610 (along with the model 621) is optimized to predict. Labels for the samples may be obtained from various sources. In one embodiment, the labels may be obtained utilizing one or more sensors that are neither the head-mounted device 612 nor physically coupled to a frame worn on the user's head. In one example, a physiological signal related to the heart rate and/or heart rate variability may be measured using an ECG sensor. In another example, a physiological signal related to blood pressure may be measured using a cuff-based blood pressure monitoring device. In yet another example, a physiological signal related to skin coloration and/or tissue perfusion may be measured based on analysis of images acquired with an external visible light camera, an external NIR camera, and/or an external IR camera.

In order to achieve a robust model, which may be useful for detecting the physiological signal in various conditions and/or when the user is in various postures, in some embodiments, the samples used in the training of the model 621 may include samples based on measurement taken in different conditions, and include samples with various labels (e.g., different values of physiological signals). Optionally, the samples are generated based on measurements taken on different days.

In some embodiments, the model 621 is generated based on samples comprising: feature values generated from PPG signals of multiple users (taken by the head-mounted device 612) and images of the multiple users (taken by the head-mounted camera 614), and labels generated based on corresponding values of physiological signals of the multiple users. Optionally, this data includes various compositions of postures of the users. In one example, a first non-empty subset of the samples is generated based on PPG signals and images taken while at least some of the multiple users were sitting, and a second non-empty subset of the samples is generated based on PPG signals and images taken while at least some of the multiple users were standing. In another example, a first non-empty subset of the samples is generated based on PPG signals and images taken while at least some of the multiple users were sitting, and a second non-empty subset of the samples is generated based on PPG signals and images taken while at least some of the multiple users were lying down.

In some embodiments, the model 621 is generated based on samples comprising feature values generated from PPG signals of the user (taken by the head-mounted device 612) and images of the user (taken by the head-mounted camera 614), and labels generated based on corresponding values of the physiological signal, which are generated based on measurements of the user taken by an apparatus that does not comprise the head-mounted device 612 nor the head-mounted camera 614. Optionally, this data includes various compositions of postures of the user. In one example, a first non-empty subset of the samples is generated based on PPG signals and images taken while the user is sitting, and a second non-empty subset of the samples is generated based on PPG signals and images taken while the user is standing. In another example, a first non-empty subset of the samples is generated based on PPG signals and images taken while the user is lying supine, and a second non-empty subset of the samples is generated based on PPG signals and images taken while the user is standing. In still another example, a first non-empty subset of the samples is generated based on PPG signals and images taken while the user is sitting up straight, a second non-empty subset of the samples is generated based on PPG signals and images taken while the user is sitting in a hunched C-posture, and a third non-empty subset of the samples is generated based on PPG signals and images taken while the user is reclining.

Various machine learning training algorithms, which are known in the art, may be utilized to generate the model 621 based on a set of samples (examples of which are described above). Optionally, the model 621 may include parameters of at least one of the following models: a regression model, a model utilized by a neural network, a nearest neighbor model, a model for a support vector machine for regression, and a model of a decision tree.

Due to the nature of the physiological signals being calculated, and the type of data utilized in some embodiments (e.g., video images), a machine learning approach that may be applied in some embodiments is "deep learning". In one embodiment, the model 621 may include parameters describing multiple hidden layers of a neural network. Optionally, the model 621 may include a convolution neural network (CNN). In one example, the CNN may be utilized to identify certain patterns in the video images, such as the patterns of the color changes corresponding to cardiac pulse wave. Optionally, calculating the physiological signal may be done based on multiple, possibly successive, images that display a certain pattern of change over time (i.e., across multiple frames), which characterizes the physiological signal. Thus, detecting the physiological signal may involve retaining state information that is based on previous images. Optionally, the model 621 may include parameters that describe an architecture that supports such a capability. In one example, the model 621 may include parameters of a recurrent neural network (RNN), which is a connectionist model that captures the dynamics of sequences of samples via cycles in the network's nodes. This enables RNNs to retain a state that can represent information from an arbitrarily long context window. In one example, the RNN may be implemented using a long short-term memory (LSTM) architecture. In another example, the RNN may be implemented using a bidirectional recurrent neural network architecture (BRNN).

In one embodiment, a method for calculating a physiological signal includes steps that may be implemented by a system that is illustrated in FIG. 26. In some embodiments, instructions for implementing the method may be stored on a computer-readable medium, which may optionally be a non-transitory computer-readable medium. In response to execution by a computer system including a processor and memory (e.g., the computer 610 described above), the instructions cause the computer system to perform operations of the method. In one embodiment, the method for calculating a physiological signal of a user includes at least the following steps: In Step 1, measuring a photoplethysmographic signal (PPG signal) at a region on the user's head utilizing a head-mounted device (e.g., the head-mounted device 612). In Step 2, capturing images indicative of the user's posture utilizing a head-mounted camera (e.g., the head-mounted camera 614). And in Step 3, calculating, by a computer (e.g., the computer 610), the physiological signal based on the PPG signal and the user's posture. In one embodiment, the method may optionally include the following steps: generating feature values based on data comprising the PPG signal and the images, and utilizing a model to calculate the physiological signal based on the feature values. Optionally, the model was generated based on samples comprising: feature values generated from PPG signals of multiple users and images of the multiple users, and labels generated based on corresponding values of physiological signals of the multiple users. Optionally, a first non-empty subset of the samples are generated based on PPG signals and images taken while at least some of the multiple users were sitting, and a second non-empty subset of the samples are generated based on PPG signals and images taken while at least some of the multiple users were lying down.

Additional Systems for Calculating Blood Pressure

The following is a description of embodiments of systems for calculating blood pressure, involving head-mounted cameras, which may be inward-facing or outward-facing cameras. An inward-facing head-mounted camera is a camera that captures images containing portions of a user's own face, while typically, an outward-facing camera will capture images that mostly do not include portions of the face. Captured images may be indicative of PATs at different regions. The PATs can be different at different regions of the body, due to the different distances of arterial pathways used by the blood to flow to the different regions, and difference in blood vessel characteristics (different diameters, elasticity, etc.). The difference between PATs at the different regions is utilized, in some embodiments, to calculate blood pressure values of the user.

In some embodiments, a system configured to calculate blood pressure of a user includes at least first and second head-mounted cameras (HCAMs), each configured to capture images of a region of interest (ROI) on the user's body. Herein, images of an ROI are denoted $IM_{ROI}$ and images of multiple ROIs may be denoted $IM_{ROIs}$. Optionally, each of the HCAMs is physically coupled to a frame worn on the user's head, such as an eyeglasses frame, or a frame of smartglasses or an extended reality device (i.e., an augmented realty device, a virtual reality device, and/or mixed reality device). The system also includes a computer that calculates a blood pressure value for the user based on imaging photoplethysmography (iPPG) signals recognizable in $IM_{ROIs}$ captured by HCAMs.

Some embodiments described herein typically rely on detecting PATs at multiple ROIs in order to calculate the blood pressure, where at least two of the ROIs are typically at least 5 cm away from each other, and/or the ROIs are on different body parts. Because of the distance between the ROIs and the fact that they may receive blood via different pathways, the changes observed due to an arrival of a pulse at a first ROI ($ROI_1$) may occur at a different time than changes observed due to the arrival of the pulse at a second ROI ($ROI_2$).

In one embodiment, the system that calculates blood pressure of a user includes a first inward-facing HCAM to capture images of a first ROI located on the face below the eyes and above the lips of the user (e.g., a maxillary process or the nose), and a second inward-facing HCAM to capture images of a second ROI comprising a portion of a temple and/or the forehead of the user. Optionally, at least one of the first and second HCAMs does not occlude its respective ROI. Optionally, both the first and second HCAMs do not occlude their respective ROIs. In one example, the center of the first ROI is located more than 6 cm away from the center of the second ROI, and changes in images of the first ROI due to a cardiac pulse wave occur at least 10 ms before, or at least 10 ms after, changes in images of the second ROI occur (due to the same cardiac pulse wave).

In one example, the second ROI comprises a portion of the right temple and/or the right side of the forehead, and the system includes a third inward-facing HCAM that captures images of a third ROI comprising a portion of the left temple and/or the left side forehead of the user. Optionally, the computer extracts from images of the third ROI an iPPG signal, and utilizes it to calculate the blood pressure value of the user (in addition to iPPG signals extracted from images taken with the other cameras).

Figure 27:
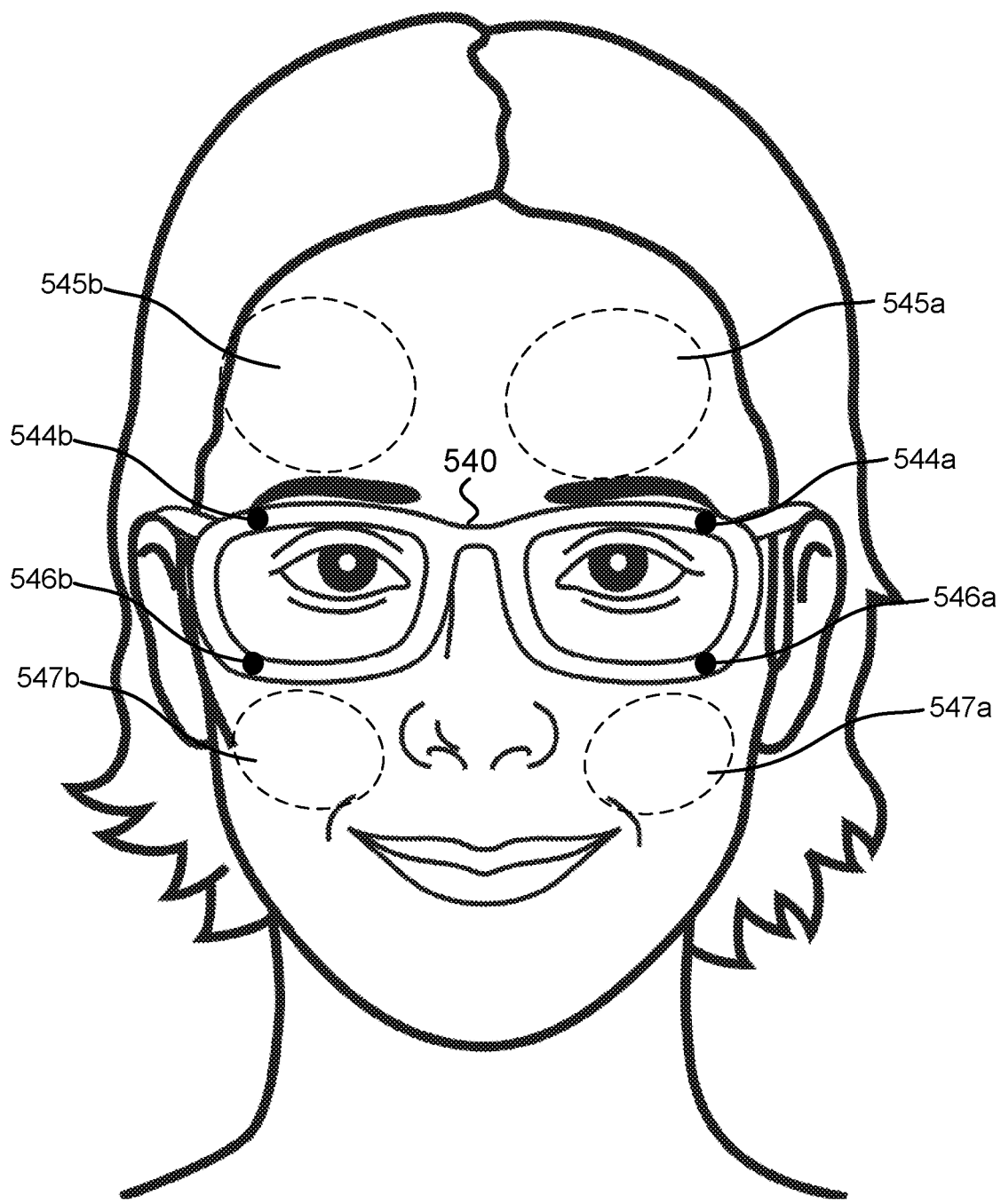
FIG. 27 illustrates an embodiment of a system configured to calculate blood pressure that includes at least two inward-facing HCAMs.

FIG. 27 illustrates one embodiment of a system configured to calculate blood pressure that includes at least two inward-facing HCAMs. The illustrated system includes frame 540, to which several HCAMs are coupled. These include inward-facing HCAMs 544a and 546a that are coupled to the left side of the frame 540 and are configured to capture images of ROIs 545a (portion left side of the forehead) and 547a (portion of left side maxillary process), respectively. Additionally, the illustrated system includes inward-facing HCAMs 544b and 546b that are coupled to the right side of the frame 540 and are configured to capture images of ROIs 545b (portion of right side of the forehead) and 547b (portion of right side maxillary process), respectively.

In another embodiment, the system that calculates blood pressure of a user includes an inward-facing HCAM to capture images of a first ROI that includes a portion of exposed skin of the user's face, and an outward-facing HCAM to capture images of a second ROI that includes exposed skin on a hand of the user (e.g., skin on the back of the hand, or skin on the palm of the hand). Optionally, the first ROI includes a portion of one or more of the following body parts of the user: a jaw, a cheek, a maxillary process, the nose, a skin around the eyes, a temple, and the forehead. Optionally, the second ROI comprises a portion of exposed skin located between the wrist and the fingertips. Optionally, at least one of the first and second HCAMs does not occlude its respective ROI. Optionally, both the first and second HCAMs do not occlude their respective ROIs.

In one example, the center of the first ROI is located more than 40 cm away from the center of the second ROI, when the hand is stretched to the side, and changes in images of the first ROI due to a cardiac pulse wave occur at least 20 ms before, or at least 20 ms after, changes in images of the second ROI occur (due to the same cardiac pulse wave).

Figure 28:
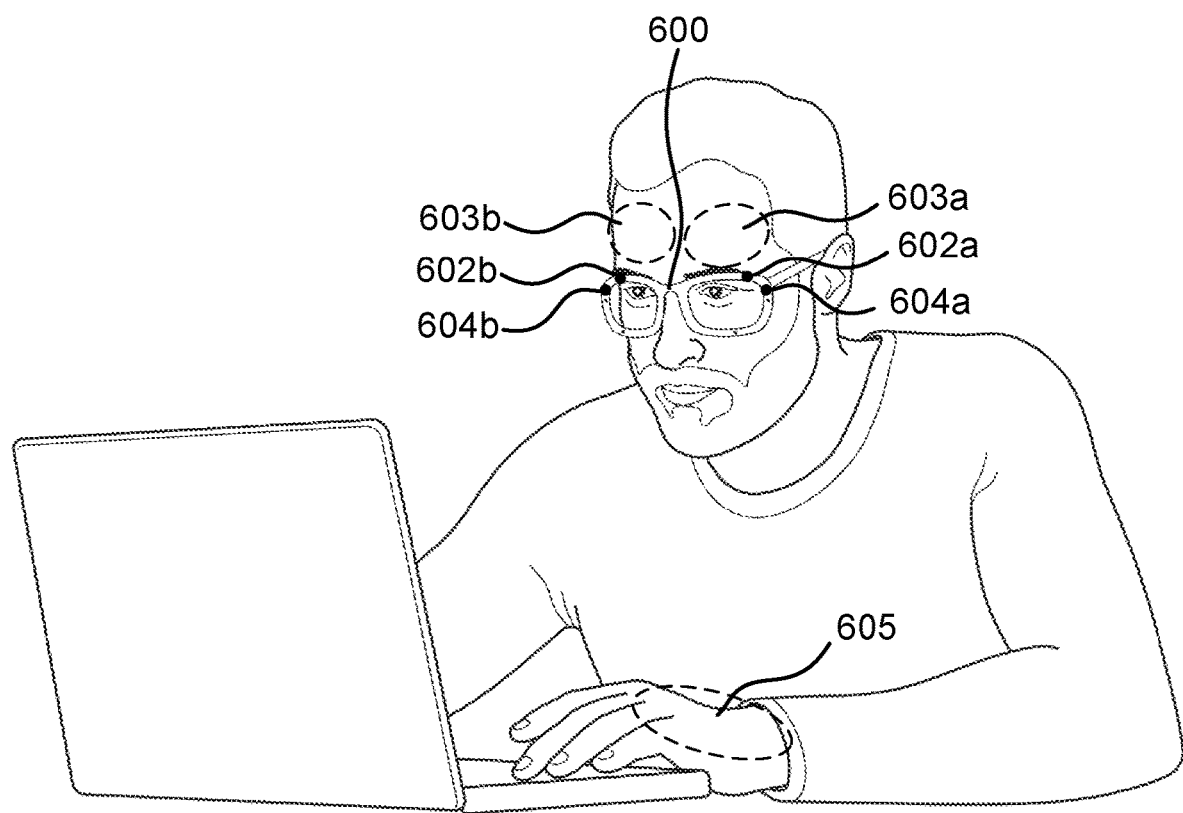
FIG. 28 illustrates one embodiment of a system configured to calculate blood pressure, which includes inward-facing HCAMs as well as outward-facing HCAMs.

FIG. 28 illustrates one embodiment of a system configured to calculate blood pressure, which includes inward-facing HCAMs as well as outward-facing HCAMs. The illustrated system includes frame 600, to which several HCAMs are coupled. These include inward-facing HCAMs 602a and 602b that are configured to capture images of ROIs 603a and 603b (portions of left and right sides of the forehead, respectively). Additionally, the illustrated system includes outward-facing HCAMs 604a and 604b. In the illustration, at least one of HCAMs 604a and 604b captures images that include the user's hand (ROI 605).

As opposed the ROIs on the face, which typically do not change their position with respect to an inward-facing HCAM, an ROI that includes a portion of the hand may change its position in $IM_{ROI}$ (due to movements of the head and/or hand), and may not appear in certain images at all. Thus, in some embodiments, to detect what portions of $IM_{ROI}$ include exposed skin located between the wrist and the fingertips (e.g., palm or back of hand), and/or whether an image includes portions of the user's hand, the computer may utilize various image detection algorithms known in the art. Some examples of algorithmic approaches that may be utilized are described in Kolsch et al., "Robust Hand Detection." FGR. 2004, which describe hand detection using a variant of the recognition method of Viola and Jones. Another approach to hand detection is given by Mittal et al., "Hand detection using multiple proposals", BMVC, 2011, which describe a two-stage method for detecting hands and their orientation in unconstrained images. Additional methods for detecting hands in images are reviewed in Erol et al., "Vision-based hand pose estimation: A review", Computer Vision and Image Understanding 108.1-2 (2007): 52-73.

It is to be noted that while the majority of algorithms for detecting hands in images are utilized with images from cameras that are not head-mounted, the described algorithmic approaches can work equally well for images from HCAMs, and/or be easily modified by one skilled in the art to detect hands in $IM_{ROI}$. For algorithms that utilize machine learning methods, adapting algorithms for detection of hands to handle data from HCAMs may simply involve collection of training data that includes $IM_{ROI}$ and annotations of the hands therein.

HCAMs utilized in embodiments described herein are typically small and lightweight. In some embodiments, an HCAM weighs below 10 g, or less than 2 g, and is physically coupled to a frame configured to be worn on the user's head (e.g., a frame of glasses or and augmented reality headset). The frame is configured to hold HCAM less than 10 cm from the user's head. HCAM may involve various types of sensors (sensing elements). In one example, HCAM is a video camera that includes multiple CMOS or CCD pixels. HCAMs may capture images at various rates. In one example, the images taken by HCAM are captured at a frame rate of at least 30 frames per second (fps). In another example, the images are captured at a frame rate of at least 100 fps. In still another example, the images are captured at a frame rate of at least 256 fps. In another embodiment, HCAM is an angle-sensitive pixel sensor camera, weighing less than 1 g. Some examples of angle-sensitive pixel sensor cameras are described in US Patent Applications 2017/0112376 and 2018/0031372, and in other publications by Dr. Albert Wang and Dr. Patrick Gill.

In some embodiments, HCAM may capture light in the near infrared spectrum (NIR). Optionally, HCAM may include optics and sensors that capture light rays in at least one of the following NIR spectrum intervals: 700-800 nm, 700-900 nm, or 700-1,000 nm. Optionally, the computer may utilize data obtained in a NIR spectrum interval to calculate the blood pressure (in addition to, or instead of, data obtained from the visible spectrum). Optionally, the sensors may be CCD sensors and/or CMOS sensors designed to be sensitive in the MR spectrum.

In some embodiments, the system may include an optical emitter configured to direct electromagnetic radiation at the ROI. Optionally, the optical emitter comprises one or more of the following: a laser diode (LD), a light-emitting diodes (LED), and an organic light-emitting diode (OLED).

It is to be noted that when embodiments described in this disclosure utilize optical emitters directed at a region of interest (ROI), the optical emitter may be positioned in various locations relative to the ROI. In some embodiments, the optical emitter may be positioned essentially directly above the ROI, such that electromagnetic radiation is emitted at an angle that is perpendicular (or within 10 degrees from being perpendicular) relative to the ROI. Optionally, a camera may be positioned near the optical emitter in order to capture the reflection of electromagnetic radiation from the ROI. In other embodiments, the optical emitter may be positioned such that it is not perpendicular to the ROI, and optionally does not occlude the ROI. In one example, the optical emitter may be located at the top of a frame of a pair of eyeglasses, and the ROI may include a portion of the forehead. In another example, the optical emitter may be located on an arm of a frame of a pair of eyeglasses, and the ROI may be located above or below the arm.

Due to the proximity of HCAM to the face, in some embodiments, there may be an acute angle between the optical axis of HCAM and the ROI (e.g., when the ROI includes a region on the forehead). In order to improve the sharpness of $IM_{ROI}$, HCAM may be configured to operate in a way that takes advantage of the Scheimpflug principle. In one embodiment, HCAM includes a sensor and a lens; the sensor plane is tilted by a fixed angle greater than 2° relative to the lens plane according to the Scheimpflug principle in order to capture a sharper image when HCAM is worn by the user (where the lens plane refers to a plane that is perpendicular to the optical axis of the lens, which may include one or more lenses). Optionally, HCAM does not occlude the ROI. In another embodiment, HCAM includes a sensor, a lens, and a motor; the motor tilts the lens relative to the sensor according to the Scheimpflug principle. The tilt improves the sharpness of $IM_{ROI}$ when HCAM is worn by the user. Additional details regarding the application of the Scheimpflug principle are discussed further below.

Variations in the reflected ambient light may introduce artifacts into images collected with HCAMs, which can add noise to an iPPG signal extracted from the images. In some embodiments, the system includes an outward-facing HCAM, which is worn on the user's head, and takes images of the environment ($IM_{EN_v}$). Optionally, this outward-facing HCAM is located less than 10 cm from the user's face and weighs below 10 g, or below 2 g. Optionally, the outward-facing HCAM may include optics that provide it with a wide field of view. Optionally, the computer calculates the blood pressure based on both $IM_{ROI}$ and $IM_{EN_v}$. In one example, given that $IM_{EN_v}$ is indicative of illumination towards the face and $IM_{ROI}$ is indicative of reflections from the face, utilizing $IM_{EN_v}$ can account, at least in part, for variations in ambient light that, when left unaccounted, may possibly lead, in some embodiments, to image artifacts that can lead to less accurate calculations.

The computer is configured, in some embodiments, to calculate a blood pressure value for the user based on iPPG signals recognizable in $IM_{ROIs}$ captured by HCAMs (e.g., the first and second HCAMs in one of the embodiments described above). Examples of computers that may be utilized to perform this calculation are computer 400 or computer 410 illustrated in FIG. 41*a* and FIG. 41*b*, respectively. Herein, sentences of the form "iPPG signal recognizable in $IM_{ROI}$" refer to effects of blood volume changes due to pulse waves that may be extracted from a series of images of an ROI. These changes may be identified and/or utilized by a computer (e.g., in order to generate a signal indicative of the blood volume at the ROI), but need not necessarily be recognizable to the naked eye (e.g., because of their subtlety, the short duration in which they occur, or involvement of light outside of the visible spectrum).

In some embodiments, the blood pressure calculated by the computer may refer to one or more of the following values: the systolic blood pressure of the user, the diastolic blood pressure of the user, and the mean arterial pressure (MAP) of the user. The computer may employ various approaches for calculating the blood pressure, as explained in further detail in embodiments described below.

The computer may utilize various preprocessing approaches to assist in calculations and/or in extraction of an iPPG signal from $IM_{ROI}$. Optionally, $IM_{ROI}$ may undergo various preprocessing steps prior to being used by the computer to detect the physiological response, and/or as part of the process of the detection of the physiological response. Some non-limiting examples of the preprocessing include: normalization of pixel intensities (e.g., to obtain a zero-mean unit variance time series signal), and conditioning a time series signal by constructing a square wave, a sine wave, or a user defined shape, such as that obtained from an ECG signal or a PPG signal as described in U.S. Pat. No.

8,617,081. Additionally or alternatively, images may undergo various preprocessing to improve the signal, such as color space transformation (e.g., transforming RGB images into a monochromatic color or images in a different color space), blind source separation using algorithms such as independent component analysis (ICA) or principal component analysis (PCA), and various filtering techniques, such as detrending, bandpass filtering, and/or continuous wavelet transform (CWT). Various preprocessing techniques known in the art that may assist in extracting an iPPG signal from $IM_{ROI}$ are discussed in Zaunseder et al. (2018), "Cardiovascular assessment by imaging photoplethysmography—a review", Biomedical Engineering 63(5), 617-634. An example of preprocessing that may be used in some embodiments is given in U.S. Pat. No. 9,020,185, titled "Systems and methods for non-contact heart rate sensing", which describes how a times-series signals obtained from video of a user can be filtered and processed to separate an underlying pulsing signal by, for example, using an ICA algorithm.

Calculating the blood pressure may be done in various approaches. In one example, iPPG signals are extracted from $IM_{ROIs}$ and utilized to directly calculate PATs at different ROIs. Optionally, a PAT calculated from an iPPG signal represents a time at which the value representing blood volume (in the waveform represented in the iPPG) begins to rise (signaling the arrival of the pulse). Alternatively, the PAT may be calculated as a different time, with respect to the waveform, such as the time at which a value representing blood volume reaches a maximum or a certain threshold, or the PAT may be the average of the time the blood volume is above a certain threshold. Another approach that may be utilized to calculate the PAT from an iPPG is described in Sola et al. "Parametric estimation of pulse arrival time: a robust approach to pulse wave velocity", Physiological measurement 30.7 (2009): 603, which describe a family of PAT estimators based on the parametric modeling of the anacrotic phase of a pressure pulse.

It is to be noted that while the prior art approaches involve analysis of video obtained from cameras that are not head-mounted, and are typically more distant from their ROI than the inward-facing HCAMs herein, and are possibly at different orientations relative to the ROI, the computational approaches described in the prior art used to detect pulse wave arrivals can be readily adapted by one skilled in the art to handle $IM_{ROI}$. In some cases, embodiments described herein may provide video in which a desired signal is more easily detectable compared to some of the prior art approaches. For example, given the typically short distance from an inward-facing HCAM to the ROI, the ROI is expected to cover a larger portion of the images in $IM_{ROI}$ compared to images obtained by video cameras in some of the prior art references. Additionally, due to the proximity of an inward-facing HCAM to the ROI, additional illumination that is required in some prior art approaches, such as illuminating the skin for a pulse oximeter to obtain a photoplethysmographic (PPG) signal, may not be needed. Furthermore, given an inward-facing HCAM's fixed location and orientation relative to the ROI (even when the user makes lateral and/or angular movements), many pre-processing steps that need to be implemented by the prior art approaches, such as image registration and/or face tracking, are extremely simplified in some of the embodiments described herein, or may be foregone altogether.

Calculating the blood pressure may be done in different ways, in different embodiments. In some embodiments, the blood pressure may be calculated based on a difference in PATs at different ROIs. In one example, first and second ROIs, denoted $ROI_1$ and $ROI_2$, are imaged using respective $HCAM_1$ and $HCAM_2$, to obtain $IM_{ROI1}$ and $IM_{ROI2}$, respectively. Using various processing approaches described above, the computer extracts two iPPG signals (denoted $iPPG_1$ and $iPPG_2$) from $IM_{ROI1}$ and $IM_{ROI2}$, respectively. The PATs are extracted from $iPPG_1$ and $iPPG_2$. The difference $\Delta t = t_1 - t_2$, between $t_1$ (a PAT at $ROI_1$) and $t_2$ (a PAT at $ROI_2$), can be utilized directly to calculate the blood pressure. The calculation of the blood pressure relies on the fact that the magnitude of $\Delta t$ is inversely proportional to the pulse wave velocity (that is directly correlated to the blood pressure). Thus, a smaller $\Delta t$ corresponds to a larger blood pressure value. In one example, the transformation from $\Delta t$ to a blood pressure value is a linear transformation of the form $BP = a/\Delta t + b$ (where a and b are fixed parameters). In other examples, a nonlinear transformation may be utilized to convert $\Delta t$ to a blood pressure value.

In some embodiments, due the each person's unique layout of the circulatory system, it might not be accurate to directly convert $\Delta t$ to blood pressure value with fixed, general parameters (e.g., use the same parameters for different users). Optionally, in order to improve accuracy of blood pressure calculations, the computer may utilize calibration values that can help account for a user's specific circulatory system characteristics. Optionally, calibration values include measurements of the user's blood pressure, taken by a different device (e.g., a cuff-based blood pressure monitoring system). These measurements, along with the $\Delta t$ values calculated from iPPG signals taken at the same time the blood pressure measurements were taken, can be used to calculate parameters, such as coefficients of linear or non-linear transformations between $\Delta t$ and blood pressure values. These parameters can then be used by the computer to calculate a blood pressure for a user, given $\Delta t$ calculated based on PATs detected in iPPG signals of the user (e.g., $iPPG_1$ and $iPPG_2$ mentioned above). Optionally, the parameters are calculated based on multiple calibration measurements that include PATs detected at different times, when the user's blood pressure had different values.

In another approach, the computer may utilize machine learning methods to calculate the blood pressure from $IM_{ROIs}$ captured by HCAMs. In some embodiments, the computer calculates feature values based on data comprising $IM_{ROIs}$ (e.g., $IM_{ROI1}$ and $IM_{ROI2}$ of one of the embodiments mentioned above) and utilizes a model to calculate, based on the feature values, the blood pressure value of the user. The following are some examples of the various types of feature values that may be generated based on $IM_{ROIs}$ by the computer.

In one embodiment, at least some of the feature values may be derived directly from values of pixels in $IM_{ROI}$. Optionally, at least some of the feature values are values of pixels from the $IM_{ROIs}$. Optionally, one or more of the feature values may be the values of the pixels themselves or some simple function of the pixels, such as the average of pixels at certain regions in each of the images. Optionally, one or more of the feature values may be various low-level features derived from images, such as features generated using Gabor filters, local binary patterns (LBP) and their derivatives, algorithms such as SIFT and/or SURF (and their derivatives), image keypoints, histograms of oriented gradients (HOG) descriptors, and products of statistical procedures such independent component analysis (ICA), principal component analysis (PCA), or linear discriminant analysis (LDA). Optionally, one or more of the feature values may derived from multiple images taken at different times, such as volume local binary patterns (VLBP), cuboids, and/or optical strain-based features. In one example, one or more of the feature values may represent a difference between values of pixels at one time t at a certain ROI and values of pixels at a different ROI at some other time t+x (which can help detect different arrival times of a pulse wave).

In some embodiments, at least some of the feature values are generated based on iPPG signals extracted from $IM_{ROIs}$. Optionally, the feature values indicate PATs at different ROIs, and/or a difference in PATs at different ROIs (e.g., a feature value may be indicative of $\Delta t$ described above). In one example, feature values are generated based on $iPPG_1$ and $iPPG_2$, which are indicative of PATs at $ROI_1$ and $ROI_2$, respectively. In this example, the computer generates a feature value, based on the PATs, which is indicative of the difference between when a pulse wave is manifested in $IM_{ROI1}$ and $IM_{ROI2}$. In another example, one or more of the feature values may be indicative of the shape and/or other characteristics of a pulse wave, as indicated in an iPPG signal extracted from $IM_{ROI}$. For example, feature values derived from an iPPG signal may indicate one or more of the following: magnitude of a systolic peak, magnitude of a diastolic peak, duration of the systolic phase, and duration of the diastolic phase.

In some embodiments, at least some of the feature values may represent calibration values of a user. For example, at least some of the feature values are indicative of a difference in PATs between different ROIs when certain blood pressure values were measured (e.g., using a different reference device such as a cuff-based blood pressure monitor). In one example, the computer extracts iPPG signals, denoted $iPPG_1$ and $iPPG_2$, from images of two ROIs, denoted $IM_{ROI1}$ and $IM_{ROI2}$, respectively. $iPPG_1$ and $iPPG_2$ are indicative of pulse arrival times at the first and second regions of interest, respectively. In this example, the computer generates one or more values that are indicative of: (i) a certain blood pressure value of the user that was measured during a certain previous period, and (ii) a difference between when pulse waves of the user, as manifested in $IM_{ROI1}$ and $IM_{ROI2}$ that were taken during the certain previous period. In another example, at least some of the feature values may represent measured blood pressure for various differences in PATs between ROIs.

In some embodiments, one or more of the feature values may be generated based on additional inputs from sources other than HCAMs. Optionally, these one or more feature values may assist in calculation of more accurate blood pressure values and/or with accounting for factors that can influence the user's blood pressure.

Stress is a factor that can influence the diameter of the arteries, and thus influence the value of the calculated blood pressure. In one embodiment, the computer is further configured to: receive a value indicative of a stress level of the user, and generate at least one of the feature values based on the received value. Optionally, the value indicative of the stress level is obtained using a thermal camera. In one example, the system may include an inward-facing head-mounted thermal camera configured to take measurements of a periorbital region of the user, where the measurements of a periorbital region of the user are indicative of the stress level of the user. In another example, the system includes an inward-facing head-mounted thermal camera configured to take measurements of a region on the forehead of the user, where the measurements of the region on the forehead of the user are indicative of the stress level of the user. In still another example, the system includes an inward-facing head-mounted thermal camera configured to take measurements of a region on the nose of the user, where the measurements of the region on the nose of the user are indicative of the stress level of the user.

Hydration is a factor that affects blood viscosity, which can affect the speed at which blood flows in the body, and consequently affect blood pressure calculated based on PATs. In one embodiment, the computer is further configured to: receive a value indicative of a hydration level of the user, and generate at least one of the feature values based on the received value. Optionally, the system includes an additional camera configured to detect intensity of radiation that is reflected from a region of exposed skin of the user, where the radiation is in spectral wavelengths chosen to be preferentially absorbed by tissue water. In one example, said wavelengths are chosen from three primary bands of wavelengths of approximately 1100-1350 nm, approximately 1500-1800 nm, and approximately 2000-2300 nm. Optionally, measurements of the additional camera are utilized by the computer as values indicative of the hydration level of the user.

The following are examples of embodiments that utilize additional inputs to generate feature values used to calculate blood pressure. In one embodiment, the computer is configured to: receive a value indicative of a temperature of the user's body, and generate at least one of the feature values based on the received value. In another embodiment, the computer is configured to: receive a value indicative of a movement of the user's body, and generate at least one of the feature values based on the received value. For example, the computer may receive the input form an accelerometer in a mobile device carried by the user. In yet another embodiment, the computer is configured to: receive a value indicative of an orientation of the user's head, and generate at least one of the feature values based on the received value. For example, the computer may receive the values indicative of the head's orientation from a gyroscope. In still another embodiment, the computer is configured to: receive a value indicative of consumption of a substance by the user, and generate at least one of the feature values based on the received value. Optionally, the substance comprises one or more of the following: a vasodilator, a vasoconstrictor.

The model utilized to calculate the blood pressure values of the user may be generated based on training data comprising: previous $IM_{ROIs}$ (e.g., $IM_{ROI1}$ and $IM_{ROI2}$ from one of the embodiments above) and blood pressure values corresponding to times at which the previous $IM_{ROIs}$ were taken. This data is used to generate samples, each sample including feature values generated based on some of the previously taken $IM_{ROI}$ that were taken during a certain period, and a label generated based on a blood pressure value, which corresponds to the certain period (e.g., it was taken during the certain period, and/or shortly before and/or after the certain period, such as within five minutes from the certain period).

The model may be generated based on data of the user and/or data of other users. In some embodiments, the previously taken $IM_{ROIs}$ comprise images of body parts of the user, and the blood pressure values corresponding to the previously taken $IM_{ROIs}$ are blood pressure values of the user measured using a device that does not utilize HCAMs (e.g., a cuff-based blood pressure monitor). In other embodiments, the previously taken $IM_{ROIs}$ comprise images of body parts of other users, and the blood pressure values corresponding to the previously taken $IM_{ROIs}$ are blood pressure values of the other users, measured using one or more devices that do not utilize HCAMs.

In order to achieve a robust model, which may be useful for calculating blood pressure of a user in various conditions, in some embodiments, the samples used in the training may include samples based on $IM_{ROIs}$ taken in different conditions. Optionally, the samples are generated based on $IM_{ROIs}$ taken on different days. In a first example, the system does not occlude the ROIs, and the model is trained on samples generated from a first set of $IM_{ROIs}$ taken while the user was indoors and not in direct sunlight, and is also trained on other samples generated from a second set of $IM_{ROIs}$ taken while the user was outdoors, in direct sunlight. In a second example, the model is trained on samples generated from a first set of $IM_{ROIs}$ taken during daytime, and is also trained on other samples generated from a second set of $IM_{ROIs}$ taken during nighttime. In a third example, the model is trained on samples generated from a first set of $IM_{ROIs}$ taken while the user was exercising and moving, and is also trained on other samples generated from a second set of $IM_{ROIs}$ taken while the user was sitting and not exercising. And a fourth example, the model is trained on samples generated from a first set of $IM_{ROIs}$ taken less than 30 minutes after the user had an alcoholic beverage, and is also trained on other samples generated from a second set of $IM_{ROIs}$ taken on a day in which the user did not have an alcoholic beverage.

Utilizing the model to calculate the blood pressure model may involve the computer performing various operations, depending on the type of model. The following are some examples of various possibilities for the model, and the type of calculations that may be accordingly performed by a computer, in some embodiments, in order to calculate the blood pressure: (a) the model comprises parameters of a decision tree. Optionally, the computer simulates a traversal along a path in the decision tree, determining which branches to take based on the feature values. A value indicative of the blood pressure may be obtained at the leaf node and/or based on calculations involving values on nodes and/or edges along the path; (b) the model comprises parameters of a regression model (e.g., regression coefficients in a linear regression model or a logistic regression model). Optionally, the computer multiplies the feature values (which may be considered a regressor) with the parameters of the regression model in order to obtain the value indicative of the blood pressure; and/or (c) the model comprises parameters of a neural network. For example, the parameters may include values defining at least the following: (i) an interconnection pattern between different layers of neurons, (ii) weights of the interconnections, and (iii) activation functions that convert each neuron's weighted input to its output activation. Optionally, the computer provides the feature values as inputs to the neural network, computes the values of the various activation functions and propagates values between layers, and obtains an output from the network, which is the value indicative of the blood pressure.

In some embodiments, a machine learning approach that may be applied to calculating the blood pressure based on $IM_{ROIs}$ may be characterized as "deep learning". In one embodiment, the model may include parameters describing multiple hidden layers of a neural network. Optionally, the model may include a convolution neural network (CNN). In one example, the CNN may be utilized to identify certain patterns in the video images, such as the patterns of corresponding to blood volume effects and ballistocardiographic effects of the cardiac pulse. Due to the fact that calculating the blood pressure may be based on multiple, possibly successive, images that display a certain pattern of change over time (i.e., across multiple frames), these calculations may involve retaining state information that is based on previous images. Optionally, the model may include parameters that describe an architecture that supports such a capability. In one example, the model may include parameters of a recurrent neural network (RNN), which is a connectionist model that captures the dynamics of sequences of samples via cycles in the network's nodes. This enables RNNs to retain a state that can represent information from an arbitrarily long context window. In one example, the RNN may be implemented using a long short-term memory (LSTM) architecture. In another example, the RNN may be implemented using a bidirectional recurrent neural network architecture (BRNN).

In order to improve the accuracy of blood pressure calculations, and in some cases in order to better account for interferences, in some embodiments, the computer may utilize $IM_{ROIs}$ captured by more than two HCAMs. Utilizing images from more than two ROIs may confer several advantages. First, calculating more than two PATs can give a larger number of differences between PATs (i.e., multiple Δt values), which can help to address issues involving noisy measurements (e.g., due to movement or environmental artifacts). However, having more than two PATs can also help account for different factors that may influence the speed at which a pulse wave travels.

The speed of blood propagating through the arteries, and therefore also the blood pressure calculated based on that value, is affected by multiple factors, such as the cardiac output, the vessel compliance, vessel diameter, vessel length, and blood viscosity. Some of these factors, such as cardiac output (at a given time) can change very quickly, while others, such as vessel length can change very slowly (over a course of years). Blood viscosity is a factor that can change throughout the day (e.g., due to hydration levels). Another factor mentioned above that can influence the velocity of the arterial blood flow is the diameter of the arteries. This value can change in certain circumstances, such as a result of stress (e.g., due to the release of stress hormones), or due to consumption of substances that cause arterial dilation. Thus, there is more than one varying factor that can influence blood pressure. Since different arteries at different locations have different properties (e.g., different thickness and elasticity), they may be affected differently by these factors; therefore, utilizing PATs at multiple ROIs can help better account for these factors and increase accuracy of blood pressure calculations.

Additional Head-Mounted Systems

In one embodiment, a head mounted system (HMS) configured to collect facial expressions of a user wearing the HMS, comprising: a frame configured to be worn on the user's head; first and second cameras coupled to the frame, at locations to the right and to the left of the symmetry axis that divides the face to the right and left sides, respectively, which are less than 15 cm away from the user's right and left pupils, respectively; the first and second cameras are oriented such that the user's right and left eyebrows are in the fields of view (FOVs) of the first and second cameras, respectively, and the user's left and right oral commissures are not in the FOVs of the first and second cameras, respectively; third and fourth cameras coupled to the frame, at locations to the right and to the left of the symmetry axis, respectively, and less than 15 cm away from the user's upper lip; the third and fourth cameras are oriented such that the right and left sides of the user's upper lip are in the FOVs of the third and fourth cameras, respectively, and the user's left and right eyebrows are not in the FOVs of the third and fourth cameras, respectively; and wherein the location and orientation of the first, second, third and fourth cameras relative to the user's head do not change even when the user's head performs wide angular movements.

Optionally, the facial expressions are microexpressions, and at least one of the cameras is configured to have at least a portion of the user's right cheek in its FOV, and that portion of the user's right cheek enables a microexpression analyzer to identify a raised right cheek. Optionally, at least one of the cameras is configured to have at least a portion of the user's left cheek in its FOV, and that portion of the user's left cheek enables a microexpression analyzer to identify a raised left cheek. Optionally, at least one of the cameras is configured to have at least a portion of the user's chin cheek in its FOV, and that portion of the user's chin enables a microexpression analyzer to identify a raised chin.

Optionally, the facial expressions are microexpressions, and further comprising a processor configured to extract vision-related features from data derived from images captured by the first and second cameras, and to utilize a machine learning trained classifier to identify a microexpression expressed by the user; wherein the machine learning trained classifier is trained to identify z microexpression that relates to the upper part of the face from vision-related features identified from images captured by the first and second cameras. Optionally, the data is derived from first and second video streams received from the first and second cameras; and wherein the vision-related features comprise temporal features. Optionally, the first and second cameras capture in high resolution and high frame rate. Optionally, the HMS further includes deriving vision-related features from locations of facial landmarks identified in the first and second images. Optionally, the HMS further includes a processor configured to extract vision-related features from data derived from images captured by the third and fourth cameras, and utilize a machine learning trained classifier to identify a microexpression expressed by the user; wherein the machine learning trained classifier is trained to identify a microexpression that relates to the lower part of the face from vision-related features identified from images captured by the third and fourth cameras. Optionally, the third and fourth cameras capture in high resolution and high frame rate. Optionally, comprising deriving vision-related features from locations of facial landmarks identified in the third and fourth images.

In some embodiments, facial cues refer to facial expressions and/or physiological signals that can be measured over certain parts of the face. In one embodiment, the cameras are coupled to the HMS, and at least one of the cameras does not have a line of sight to capture an image of the entire wearer's face, and in some cases the angle between the optical axis of at least one of the cameras and the Frankfort horizontal plane is greater than 20 degrees.

It is noted that all measurements, notations, planes, angles, distances, horizontal facial thirds, and/or elements of the user's face (such as eyes, nose, lips, eyebrows, hairline) herein refer to a normal, 20 years old, aesthetic human, such as described in Chapter 2, Facial Proportions, by Peter M. Prendergast, in the book "Advanced Surgical Facial Rejuvenation, Art and Clinical Practice", Editors: Erian, Anthony, Shiffman, Melvin A., Publisher: Springer-Verlag Berlin Heidelberg, 2012. It is further noted that the appearance of the face varies with facial movement, thus, the positions of the elements of the user's face (such as eyes, nose, lips, eyebrows, hairline) are assessed herein when the user has a relaxed (neutral) face: the eyes are open, the lips make gentle contact, and the teeth are slightly separated. The neck, jaw, and facial muscles are not stretched nor contracted, and the face is positioned using the Frankfort horizontal plane.

In one example, "a frame configured to be worn on the head of the user" is interpreted as a frame that loads more than 50% of its weight on the user's head. For example, the frame in Oculus Rift and HTC Vive is the foam placed on the user's face and the straps; the frame in Microsoft HoloLens is the adjustment wheel in the headband placed on the user's head.

Optionally, the HMS further includes a fifth camera coupled to the frame at a location that is less than 10 cm away from the user's right pupil; the fifth camera is oriented such that the lower orbital part of the user's orbicularis oculi muscle that surrounds the user's right eye is in the FOV of the fifth camera, and the user's left oral commissure is not in the FOV of the fifth camera; wherein the location and orientation of the fifth camera relative to the user's head does not change even when the user's head performs wide angular movements. In one example, the upper orbital part of the user's right side orbicularis oculi muscle is also in the FOV of the fifth camera. In another example, the distance between the fifth camera and the right lower orbital part is below 5 cm.

In one example, the HMS further includes a sixth camera coupled to the frame at a location that is less than 10 cm away from the user's left pupil; the sixth camera is oriented such that the lower orbital part of the user's orbicularis oculi muscle that surrounds the user's left eye is in the FOV of the sixth camera, and the user's right oral commissure is not in the FOV of the sixth camera; wherein the location and orientation of the sixth camera relative to the user's head does not change even when the user's head performs wide angular movements. Optionally, the image captured by the sixth camera further includes the upper orbital part of the user's left side orbicularis oculi muscle.

Common VR headsets are quite sealed to ambient light. Something there is light from the display, and something there is no. Moreover, the light from the display changes, which make it harder to capture facial expressions within the occluded area. Therefore, in one embodiment an IR light sources (e.g., IR LEDs) are add inside the headset, and the periorbital camera does not have an IR filer. Optionally, the periorbital camera captures only near IR waves so that visible light from the display does not interfere.

In one example, the frame is similar to extending side arms of eyeglasses. The frame may be positioned behind a user's ears to secure the HMS to the user. The frame may further secure the HMS to the user by extending around a rear portion of the user's head. Additionally or alternatively, the frame may connect to or be affixed within a head-mountable helmet structure.

The positions of the cameras on the figures are just for illustration. The cameras may be placed at other positions on the HMS. One of more of the cameras may be configured to capture images at various resolutions or at different frame rates. Many video cameras with a small form-factor, such as those used in cell phones or webcams, for example, may be incorporated into some of the embodiments.

Further, illustrations and discussions of a camera represent one of more cameras, where each camera may be configured to capture the same view, and/or to capture different views. In one embodiment, one of more of the cameras may include one or more elements, such as a gyroscope, an accelerometer, and/or a proximity sensor. Other sensing devices may be included within the camera, and/or in addition to the camera, and other sensing functions may be performed by one or more of the cameras.

In one embodiment, because facial structures generally differ from user to user, the HMS may calibrate the direction, position, algorithms, and/or characteristics of one or more of the cameras and/or light sources based on the facial structure of the user. In one example, the HMS calibrates the positioning of a camera in relation to a certain feature on the user's face. In another example, the HMS changes, mechanically and/or optically, the positioning of a camera in relation to the frame in order to adapt itself to a certain facial structure.

Optionally, the HMS further includes a display coupled to the frame and configured to present digital content to the user. Herein, phrases in the form of "a display coupled to the frame" are to be interpreted as one or more of the following: (i) the frame can be worn and/or take off together with the display such that when the user wears/takes off the helmet he/she also wears/takes off the display, (ii) the display is integrated with the frame, and optionally the display is sold together with the HMS, and/or (iii) the HMS and the display share at least one electronic element, such as a processor, a memory, a battery, an optical element, and/or a communication unit for communicating with a non-head mounted computer.

Optionally, the HMS further includes a helmet coupled to the frame and configured to protect the user's scalp; wherein the helmet is selected from the group of: a sport helmet, a motorcycle helmet, a bicycle helmet, and a combat helmet. Herein, phrases in the form of "a helmet coupled to the frame" are to be interpreted as one or more of the following: (i) the frame can be worn and/or take off together with the helmet such that when the user wears/takes off the helmet he/she also wears/takes off the HMS, (ii) the frame is integrated with the helmet and/or the helmet itself forms the frame, and optionally the HMS is sold together with the helmet, and/or (iii) the HMS and the helmet share at least one electronic element, such as an inertial measurement sensor, a processor, a memory, a battery, an image sensor, and/or a communication unit for communicating with a non-head mounted computer.

Optionally, the HMS further includes a brainwave headset coupled to the frame and configured to collect brainwave signals of the user. Herein, phrases in the form of "a brainwave headset coupled to the frame" are to be interpreted as one or more of the following: (i) the frame can be worn and/or take off together with the brainwave headset such that when the user wears/takes off the brainwave headset he/she also wears/takes off the HMS, (ii) the frame is integrated with the brainwave headset and/or the brainwave headset itself forms the frame, and optionally the HMS is sold together with the brainwave headset, and/or (iii) the HMS and the brainwave headset share at least one electronic element, such as an inertial measurement sensor, a processor, a memory, a battery, and/or a communication unit.

Optionally, at least one of the inward facing cameras is a depth camera that detects distances of items relative to the camera. Optionally, the depth camera is selected from the group comprising at least one of: a light field camera, a camera with active illumination, and a camera array. Optionally, the first camera features an extended depth of field that can capture in focus objects that are 2 to 5 cm from the first camera. Optionally, the first camera operates according to Scheimpflug principle in order to achieve an extended depth of field (DOF). Optionally, the first camera further comprises an autofocus mechanism configured to tilt and/or rotate the sensor and/or optics to obtain the extended DOF.

Optionally, the first camera is a light field camera. Optionally, the first camera utilizes at least one of the following techniques to achieve an extended depth of field: wavefront coding, diffusion coding, coded aperture, multiple apertures, and lens array.

Optionally, the HMS further includes a structured light pattern projector; wherein the first camera is configured to capture a distorted pattern of the reflected structured light. Optionally, the structured light pattern projector transmits in wavelength longer than 700 nm. Optionally, the HMS further includes a processor configured to calculate at least one of depth and movement from the captured distorted pattern in order to identify the facial cues.

Optionally, the HMS further includes an eye tracker configured to track gaze of the user in order to enable identification of an object the user is looking at; and further comprising a communication module configured to send an indication of the object and a facial cue derived from at least one of the first and second cameras; wherein the indication and the facial cue enable association of the object with an affective response of the user. Optionally, the HMS further includes a display coupled to the frame and configured to present digital content to the user, and the object is presented by the display. Optionally, the HMS further includes an optical-see-through display coupled to the frame and configured to present digital content to the user, and the object is a real world object.

Optionally, the HMS further includes an eye tracker and a processor; the eye tracker is configured to track gaze of the user in order to identify an object the user is looking at; the processor is configured to decode a facial expression of the user based on data received from at least one of the first and second cameras, and to associate the decoded facial expression with the object. Optionally, the HMS further includes a display coupled to the frame and configured to present digital content to the user, and the object is presented by the display. Optionally, the HMS further includes an optical-see-through display coupled to the frame and configured to present digital content to the user, and the object is a real world object.

Optionally, one or more of the cameras comprise a sensor configured to detect radiation in the visible spectrum. Optionally, the facial cues comprise facial expressions.

Optionally, one or more of the cameras comprise a sensor configured to detect radiation in the infrared spectrum. Optionally, the facial cues comprise changes to the temperature over time of a region of interest on the face.

Optionally, the HMS further includes a facial expression decoder configured to decode a facial expression of the user based on data received from at least one of the first and second cameras. Optionally, the received data is detailed and frequent enough to enable the facial expression decoder to decode a microexpression.

Optionally, the HMS further includes a wireless transceiver configured to connect the HNS with a computer that is not carried by the user; and further comprising a facial expression compressor configured to receive the pictures from the first and second cameras, extract points of interest that represent movements of the eyebrows, wherein storing the points of interest requires less than 10% of the storage required to store the pictures from the first and second cameras, and transmitting the points of interest to the computer.

Optionally, the HMS further includes a display and a controller; the display is coupled to the frame and configured to present digital content to the user; wherein the controller is configures to command the first and second cameras to capture images at a higher rate when the display presents an object that is expected to cause the user to have a noticeable emotional response, compared to the rate of capturing images by the first and second cameras when the display presents an object that is not expected to cause the user to have a noticeable emotional response.

In one example, one or more of the cameras includes a field splitter, which is a camera lens configured as a prism. A field splitter delivers multiple fields of view in a single camera lens such that a stereo vision can be achieved without multiple cameras. A field splitter may be useful for one of more of the following: machine vision applications, splitting the captured rays into two images to get a stereo view from a single camera, adjusting over a range of motion without changing the optical path length, allowing a single camera to view multiple fields at once, viewing the same field from multiple directions, and/or reducing the number of head mounted cameras as fewer cameras may be used to achieve the same number of views.

In one embodiment, a method for identifying facial expressions of a user wearing a head mounted system (HMS), includes the following steps: receiving first and second video streams from first and second cameras, respectively; the cameras are pointed at the user and are coupled to the HMS at locations that do not change relative to the user's head even when the user's head performs wide angular movements; wherein the user's right and left eyebrows are in the fields of view (FOVs) of the first and second cameras, respectively, and the user's left and right oral commissures are not in the FOVs of the first and second cameras, respectively; and identifying facial expressions related to the upper part of the user's face based on a model for extracting facial expressions from data comprising the first and second video streams.

Optionally, the method further includes receiving third and fourth video streams from third and fourth cameras pointed at the user and are coupled to the HMS at locations that do not change relative to the user's head even when the user's head performs wide angular movements; wherein the right and left sides of the user's upper lip are in the FOVs of the third and fourth cameras, and the user's left and right eyebrows are not in the FOVs of the third and fourth cameras; and identifying facial expressions related to the lower part of the user's face based on a model for extracting facial expressions from data comprising the third and fourth video streams.

Optionally, the facial expressions are microexpressions, and the model for extracting facial expressions is a model for extracting microexpressions. Optionally, the method further includes the step of calculating a global head motion based on data received from at least one of the following: inertial measurement unit of the HMS, and an external device configured to track the HMS.

Optionally, the HMS is a first HMD; and further comprising calculating a facial and/or body avatar for the user, sending the avatar to a second HMD, and presenting the avatar of the user on the second HMD; wherein the first and second HMDs comprise similar hardware and functionality, and the first HMD is configured to present the avatar of the second user on the first HMD. Optionally, the HMS is a first mixed reality HMD (MR-HMD); and further comprising calculating a non-complete facial avatar for the user, which covers at least some of the facial area occluded by the MR-HMD, sending the non-complete facial avatar to a second MR-HMD, and presenting the non-complete facial avatar of the user on the second MR-HMD, such that the user of the second MR-HMD sees simultaneously a combination of the user's real face and the non-complete facial avatar. In one example, the integrated operation of two or more HMDs with inward facing cameras, which can exchange posture and/or facial data in real time, enables the users to make large angle movements and move aside, essentially without affecting the exchanged posture/facial data.

In one embodiment, an emotion awareness head mounted display (HMD) configured to identify facial expressions to which the user may not be aware, and provide a feedback to the user to develop awareness on how the user feels and/or understand the trigger to the emotion driving the facial expressions. The HMD includes: a frame configured to be worn on the user's head; a display coupled to the frame; a first camera coupled to the frame at a location that is less than 15 cm away from the user's right pupil, and oriented such that the user's right eyebrow is in the FOV of the first camera and the user's left oral commissure is not in the FOV of the first camera; a second camera coupled to the frame at a location that is less than 15 cm away from the user's upper lip, and oriented such that the user's right upper lip is in the FOV of the second camera and the user's left eyebrow is not in the FOV of the second camera; wherein the location and orientation of the first, second, third and fourth cameras relative to the user's head do not change even when the user's head performs wide angular movements; and a processor configured to receive images from the first and second cameras, utilize a machine learning trained classifier to identify a facial expression expressed by the user, and present on the display a feedback related to the identified facial expression.

Optionally, the facial expressions are microexpressions, and the machine learning trained classifier identifies microexpressions expressed by the user. Optionally, the angle between the optical axis of at least one of the first and second cameras and the Frankfort horizontal plane is greater than 20 degrees. Optionally, the entire left eyebrow of the user is not in the FOV of the first camera. Optionally, the locations of the first and second cameras are less than 10 cm away from the user's face. Optionally, the locations of the first and second cameras are less than 5 cm away from the user's face.

Optionally, the optical axes of at least one of the first and second cameras is at least 20 degrees away from the Frankfort horizontal plane. Optionally, the optical axes of at least one of the first and second cameras is at least 30 degrees away from the Frankfort horizontal plane. Optionally, the optical axes of at least one of the first and second cameras is at least 45 degrees away from the Frankfort horizontal plane. Optionally, the optical axes of at least one of the first and second cameras is at least 60 degrees away the Frankfort horizontal plane.

Optionally, the HMS further includes a third camera coupled to the frame at a location that is less than 10 cm away from the user's right pupil; the third camera is oriented such that the lower orbital part of the user's orbicularis oculi muscle that surrounds the user's right eye is in the FOV of the fifth camera, and the user's left oral commissure is not in the FOV of the third camera; wherein the location and orientation of the third camera relative to the user's head does not change even when the user's head performs wide angular movements. In one example, the upper orbital part of the user's right side orbicularis oculi muscle is also in the FOV of the third camera. In another example, the distance between the third camera and the right lower orbital part is below 5 cm.

In one example, the HMS further includes a fourth camera coupled to the frame at a location that is less than 10 cm away from the user's left pupil; the fourth camera is oriented such that the lower orbital part of the user's orbicularis oculi muscle that surrounds the user's left eye is in the FOV of the fourth camera, and the user's right oral commissure is not in the FOV of the fourth camera; wherein the location and orientation of the fourth camera relative to the user's head does not change even when the user's head performs wide angular movements. Optionally, the image captured by the fourth camera further includes the upper orbital part of the user's left side orbicularis oculi muscle.

In one embodiment, a method for identifying facial expressions of a user wearing a head mounted system (HMS), includes the following steps: receiving first and second video streams from first and second cameras, respectively; the cameras are pointed at the user and are coupled to the HMS at locations that do not change relative to the user's head even when the user's head performs wide angular movements; wherein the user's right upper lip and left upper lip are in the fields of view (FOVs) of the first and second cameras, respectively, the middles of the user's right and left eyebrows are not in the FOVs of the first and second cameras, respectively, and the optical axes of the first and second cameras point at least 20 degrees below the Frankfort horizontal plane; and identifying the facial expressions of the user based on a model for extracting facial expressions from data comprising the first and second video streams.

In one embodiment, a head mounted system (HMS) configured to collect brainwaves and facial expressions of a user wearing the HMS, includes the following elements: a frame configured to be worn on the user's head; brainwave electrodes coupled to the frame; and a first camera coupled to the frame at a location that is less than 20 cm away from the user's right upper lip; the first camera is oriented such that the user's right upper lip is in the field of view (FOV) of the first camera, and the optical axis of the first camera points at least 20 degrees below the Frankfort horizontal plane; wherein the locations of the brainwave electrodes and the first camera, relative to the user's head, do not change even when the user's head performs wide angular movements.

Figure 29:
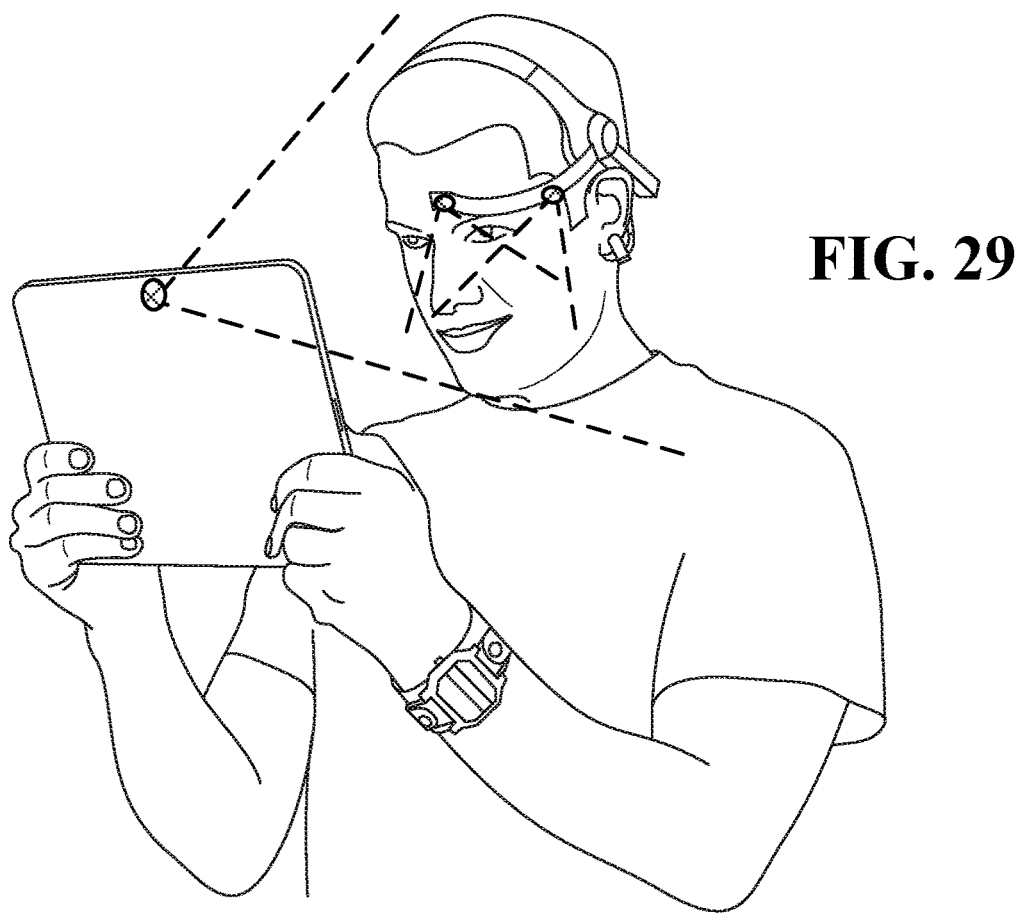
FIG. 29 and FIG. 30 illustrate brainwave headsets having at least two inward facing cameras that capture the user's facial expressions.
Figure 30:
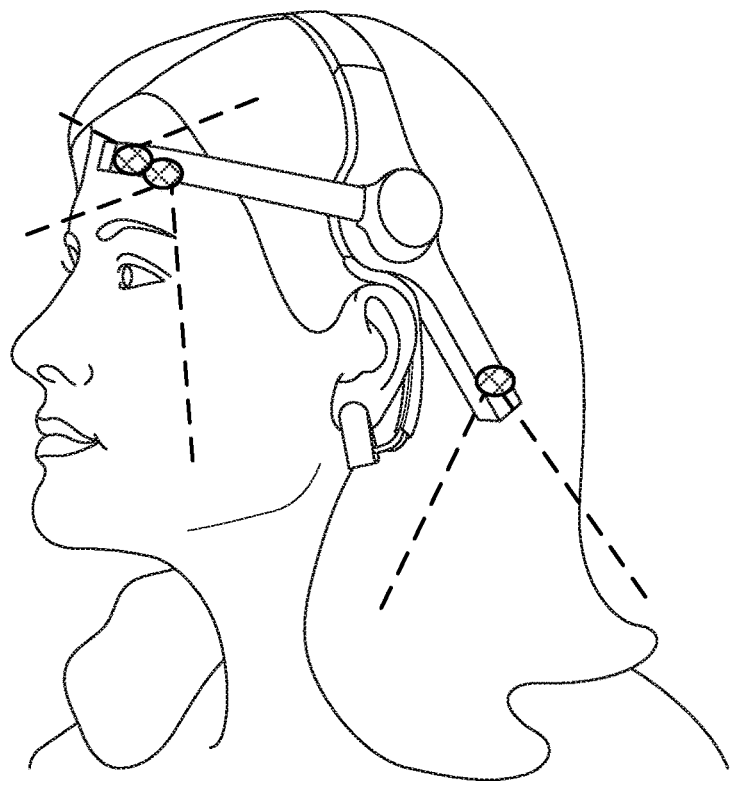
Figure 31:
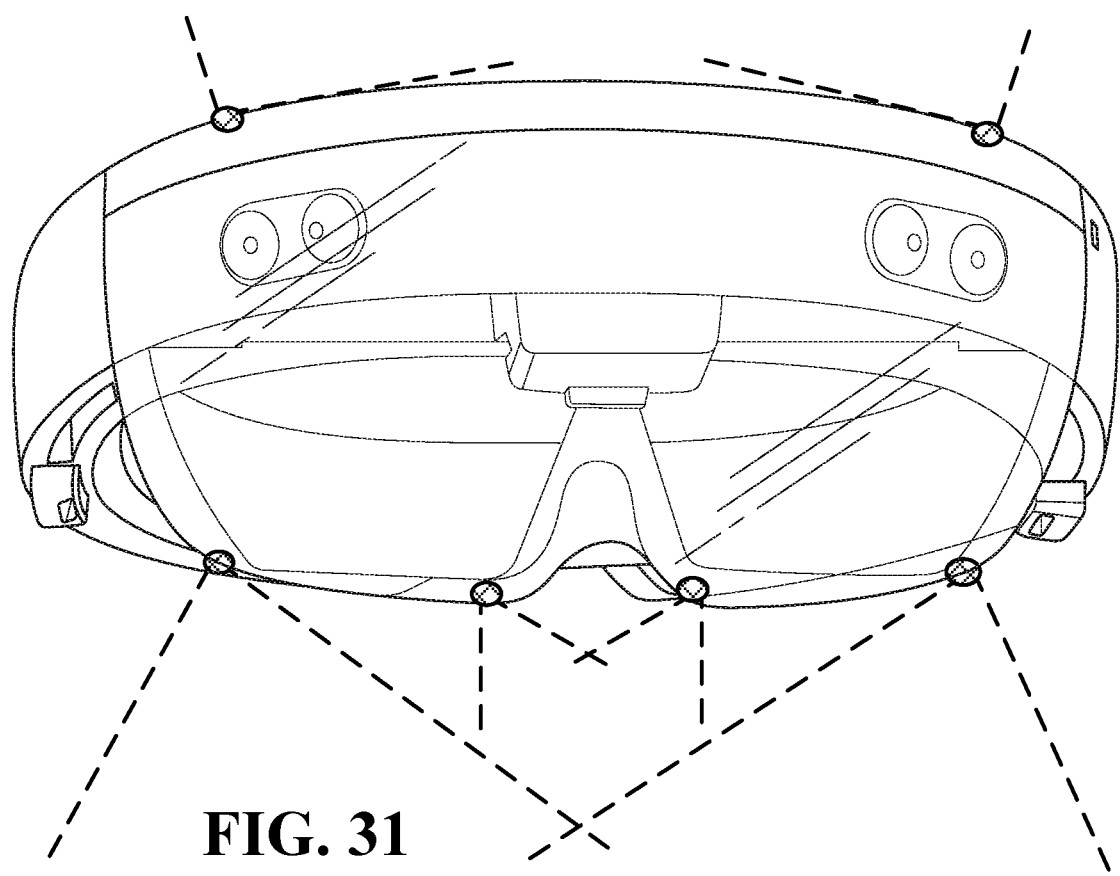
FIG. 31 illustrates an HMD having head mounted cameras able to capture both the user's face and the user's back.

Optionally, the HMS further includes a computer configured to calculate affective response of the user based on data received from the brainwave electrodes and the first camera. Optionally, the middles of the user's left eyebrow is not in the FOVs of the first camera. Optionally, the HMS further includes a second camera coupled to the frame, at a location that is less than 15 cm away from the user's left eyebrow; wherein the second camera is oriented such that the user's left eyebrow is in the field of view (FOV) of the second camera. Optionally, the HMS further includes a processor configured to extract vision-related features from data derived from images captured by the first and second cameras, and to utilize a machine learning trained classifier to identify a microexpression expressed by the user. Optionally, the data is derived from first and second video streams received from the first and second cameras; and wherein the vision-related features comprise temporal features. FIG. 29 and FIG. 30 illustrate brainwave headsets having at least two inward facing cameras that capture the user's facial expressions.

In one embodiment, a method for identifying affective response of a user wearing a head mounted system (HMS), includes the following steps: receiving brainwave signals from electrodes coupled to the HMS; receiving video streams from first and second cameras coupled to the HMS at locations that are less than 15 cm away from the user's face, and pointed at the user; the first camera is oriented such that more than 30% of the user's right cheek is in the FOV of the first camera, and the optical axis of the first camera points at least 20 degrees below the Frankfort horizontal plane; the second camera is oriented such that the more than 50% of the user's left eyebrow and less than 30% of the user's right cheek are in the FOV of the second camera; wherein the locations of the first and second cameras, relative to the user's head, do not change even when the user's head performs wide angular movements; and identifying facial expressions and/or microexpressions based on images captured by the first and second cameras; and calculating affective response of the user based on the brainwave signals and the identified facial expressions and/or microexpressions.

In one embodiment, the HMD is configured to identify brow contraction and/or Pursed lips using one or more cameras pointed at the brows and/or lips. When there is a contraction longer that a predetermined threshold (for example greater than 2, 5, or 10 seconds), the HMD alerts the user to release the contraction using visual and/or auditory notification. Optionally, when the user gets angry the system waits with the alert at least 30 second so that the notification does not make the user angrier. Optionally, the HMD shows a visual effect, such as red background or a degrading graph, when the user contracts the muscle at the Ajna chakra. As the user continues with the contraction, the visual effect gets more significant. As the user reduces the contraction, the visual effect gets less significant until it disappears.

In some cases, the system needs very limited face tracking and registration because the head mounted cameras are fixed to the user's face. The system needs limited tracking and registration also for estimating posture because the angle of view is limited by the possible movements of the body model. For example, the user cannot make any arbitrary movement with the head, thus the search space of head mounted cameras is limited in relation to the search space of an external camera that is not mounted on the user (such as Microsoft Kinect camera placed on a television display).

In one embodiment, a system configured to generate an avatar of a user's face from wearable cameras, includes: a frame configured to be worn on the user's head; first, second, and third cameras coupled to the frame, at locations that are less than 15 cm away from the user's head, respectively; the locations of the first, second and third cameras relative to the user's head do not change even when the user's head performs wide angular movements; the first, second, and third cameras are oriented such that at least 50% of: the right upper horizontal facial third, the left middle horizontal facial third, and the right lower-middle horizontal facial third are in the fields of view (FOVs) of the first, second, and third cameras, respectively; the FOVs of the first, second, and third cameras do not cover the at least 25% of: the left lower horizontal facial third, the right upper horizontal facial third, and the left upper horizontal facial third, respectively; and a training module configured to train a model based on data received from the first, second, and third cameras, and from an external camera; wherein the external camera captures in its FOV at least 80% of the user's upper, middle, and lower horizontal facial thirds, and is not worn on the user's head; wherein the model is configured to calculate information for rendering a facial avatar, which represents at least 80% of the user's face, without receiving from the external camera a stream comprising images of at least 80% of the user's upper, middle, and lower horizontal facial thirds.

Optionally, the model is configured to fill in missing data, based on the training, in order to calculate information for rendering the facial avatar, including a part of the user's face that is not directly available from data received from the first, second, and third cameras. Optionally, the model comprises correlations between data received from the first, second, and third cameras, and the missing data. Optionally, the model comprises a machine learning algorithm that receives, as input, data derived from the first, second, and third cameras, and outputs a model of the face of the user. Optionally, the HMS further includes a helmet coupled to the frame and configured to protect the user's scalp; wherein the helmet is selected from the group of: a sport helmet, a motorcycle helmet, a bicycle helmet, and a combat helmet.

In one embodiment, a HMS configured to collect facial expressions of the user wearing it, includes: a frame configured to be worn on the head of the user; a first camera, coupled to the frame, configured to picture the user above the right eye; a second camera, coupled to the frame, configured to picture the right eye of the user; a third camera, coupled to the frame, configured to picture the right upper lip of the user; wherein the first, second and third cameras do not have a direct line of sight to a part of the lips of the user; a processor, carried by the user, configured to receive images from the first camera, the second camera, and the third camera, and to extract data required by a model configured to render the face of the user, including the part of the lower lip; and a communication unit configured to send the data required by the model to a computer that is not fixed to the frame; wherein the entropy of the data required by the model is less than 10% of the entropy of the images from the first camera, the second camera, and the third camera.

Optionally, the processor is fixed to the frame. Optionally, the processor is located in a mobile phone associated with the user. Optionally, the processor is located in a wearable computer associated with the user. Optionally, the model is configured to render the face of the user as seen with the HMS. Optionally, the model is configured to render the face of the user as seen without the HMS.

FIG. 26 illustrates one embodiment of a HMD with cameras useful for estimating the posture of a user wearing the HMD. One of more of the cameras used to capture the user's body may feature an extended DOF, such as: (i) a camera that operates according to Scheimpflug principle, (ii) a light field camera, and/or (iii) a camera that utilizes at least one of the following techniques to achieve an extended depth of field: wavefront coding, diffusion coding, coded aperture, multiple apertures, and/or lens array.

Figure 34:
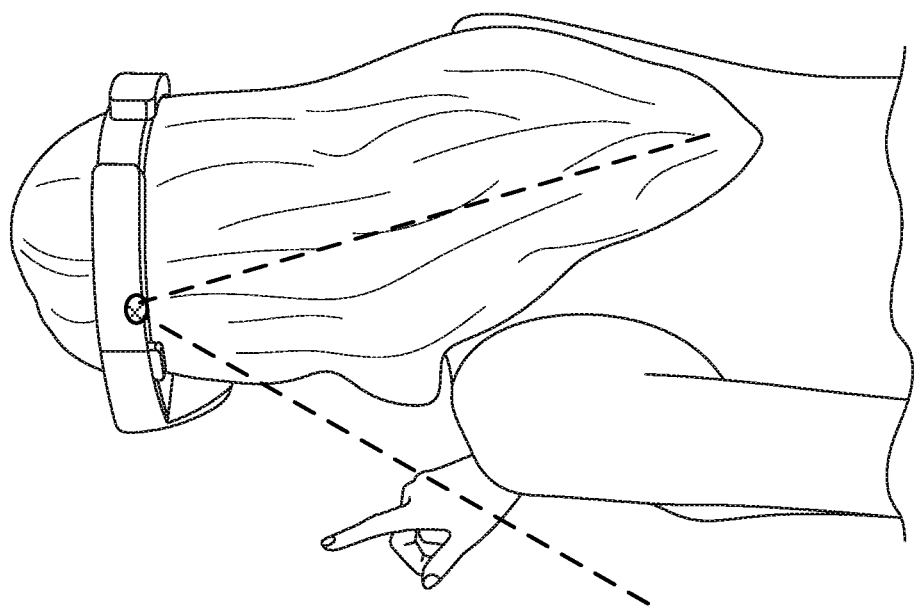
FIG. 34 illustrates a HMD having head mounted a camera able to capture the user's shoulder.
Figure 33:
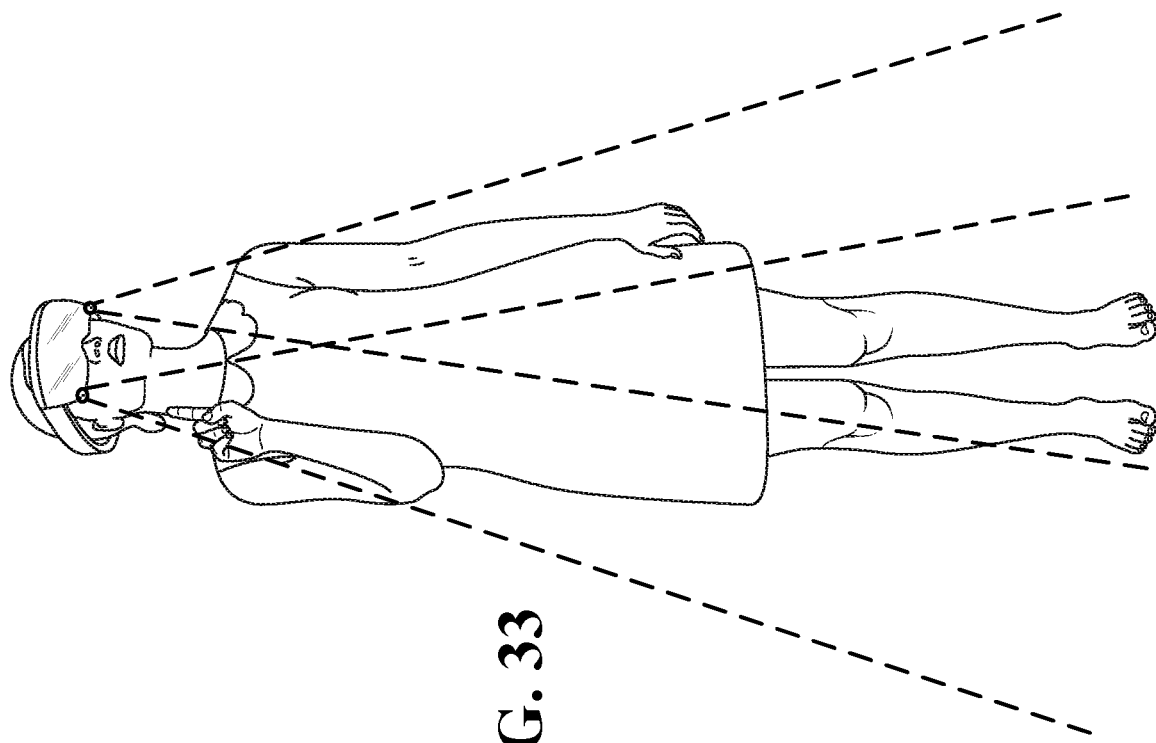
FIG. 33 illustrates a HMD having head mounted cameras able to capture portions of the user's torso, hands, and legs.

FIG. 34 illustrates one embodiment of a HMD with a side camera useful for estimating the posture of a user wearing the HMD. In normal standing the user's shoulder is in the FOV of the side camera.

In one embodiment, a head mounted system (HMS) configured to estimate posture of a user wearing the HMS, includes: a frame configured to be worn on the head of the user; first and second cameras, coupled to the frame at locations that are to the right and to the left of the symmetry axis that divides the face to the right and left sides, respectively, and less than 15 cm away from the user's head; wherein the first and second cameras are oriented downward such that portions of the user's torso are in the fields of view (FOVs) of the first and second cameras when the user stands up straight; and a training module configured to train a model for estimating posture of the user based on data received from the first and second cameras; wherein the training assumes that the locations of the first and second cameras, relative to the user's head, do not change even when the user's head performs wide angular and lateral movements.

Optionally, at least one of the first and second cameras is a depth camera. Optionally, the first and second cameras point at least 20 degrees to the right and to the left of the anterior facial plane, respectively. Optionally, the first camera is located behind the user's right ear.

In some embodiments, assuming that the locations of the first and second cameras, relative to the user's head, do not change even when the user's head performs wide angular and lateral movements, simplifies at least one of the training module and the model for estimating user's posture, compared to equivalent cases where it impossible to assume that the cameras have fixed positioning relative to the user's head. The assumption of fixed positioning relative to the user's head may also improve the performance of the model and reduce the required computations load compared to equivalent cases where it is impossible to make such assumption.

Optionally, the HMS further includes a third camera, coupled to the frame at a location behind the user's ear; wherein the third camera is oriented downwards such that a portion of the user's torso is in the FOV of the third camera when the user stands up straight; and wherein the training module is further configured to train the model based on data received from the third camera while assuming that the location of the third camera, relative to the user's head, does not change even when the user's head performs wide angular and lateral movements.

Optionally, the HMS further includes an inertial measurement unit (IMU) coupled to the frame and configured to measure orientation of the frame; wherein the training module is further configured to utilize the orientation for training the model. Optionally, the model is configured to estimate the angle between the head and the torso of the user based on the data received from the first and second cameras and the orientation measured by the IMU.

Optionally, the HMS further includes an external camera, which is not mechanically coupled to the frame, configured to have a direct line of sight to the front side of user's torso; wherein the training module is further configured to utilize data from the external camera in order to train the model.

Optionally, the HMS is coupled to a head mounted display comprising a display configured to present digital content to the user. Optionally, the HMS is coupled to at least one of a helmet and a hat; wherein the helmet is selected from the group of: sport helmet, motorcycle helmet, bicycle helmet, and combat helmet. Optionally, the HMS is coupled to a brainwave headset configured to collect brainwave signals of the user.

Figure 35:
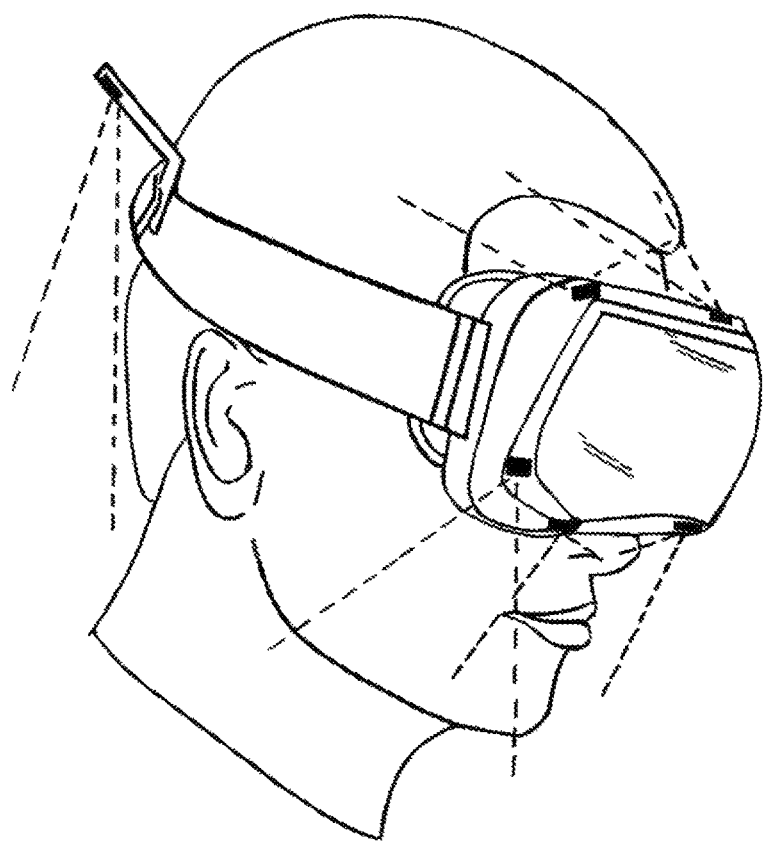
FIG. 35, FIG. 36, FIG. 37, and FIG. 38 illustrate HMDs having head mounted cameras able to capture both the user's face and the user's back.
Figure 36:
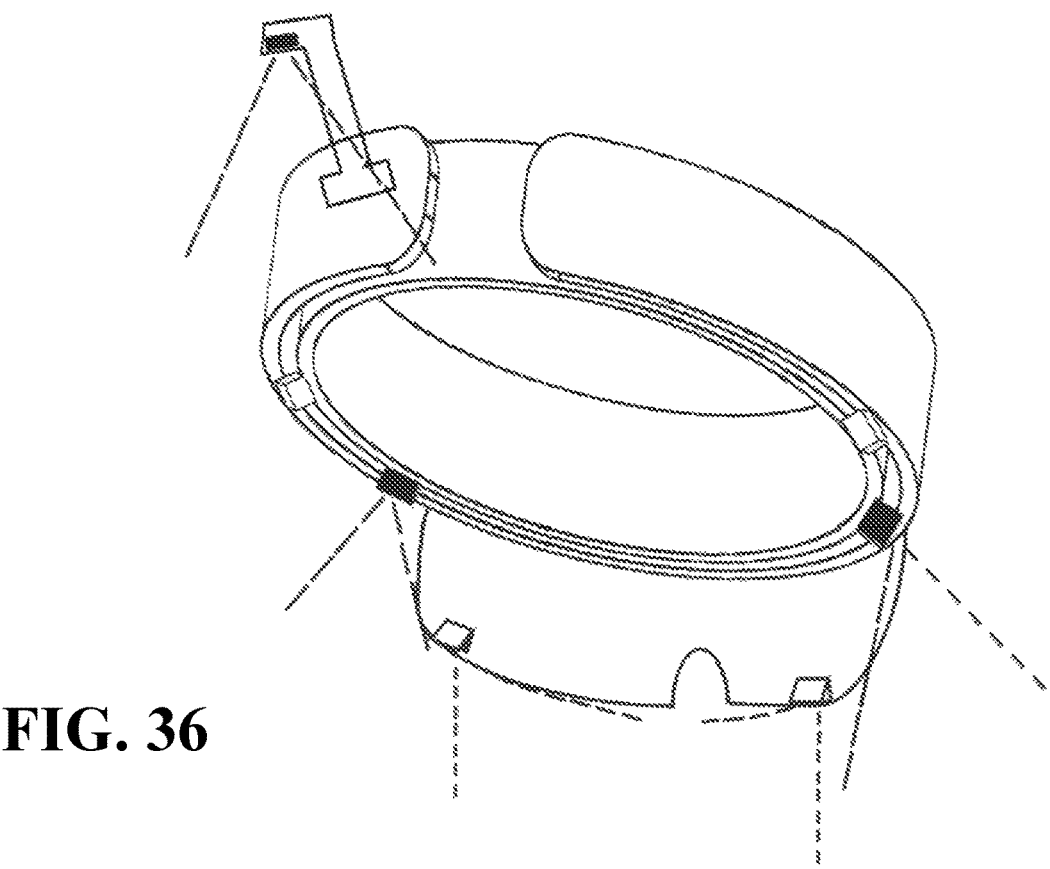
Figure 37:
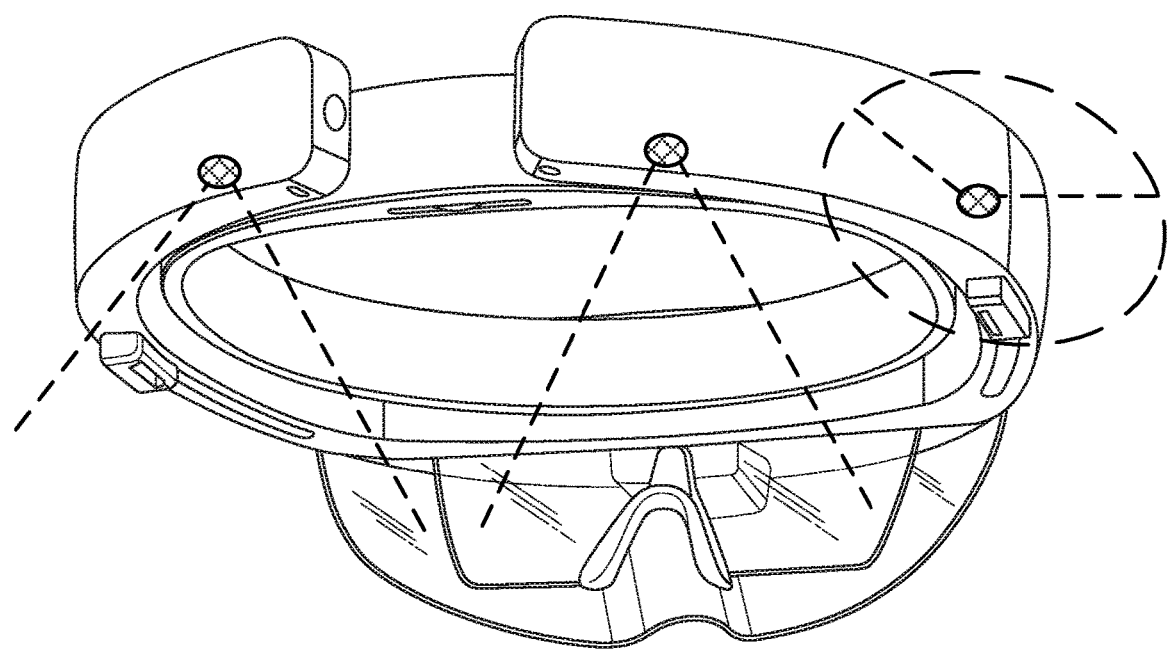
Figure 38:
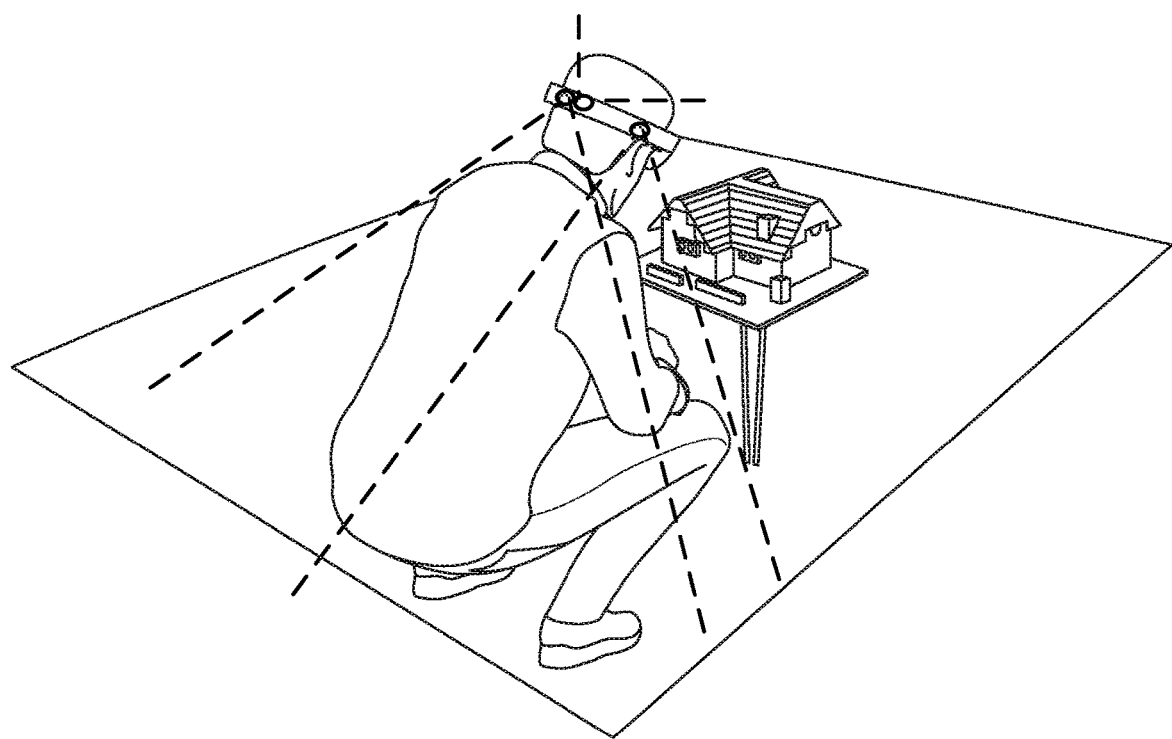

FIG. 35 illustrates one embodiment where the camera is coupled to an extender that is coupled to the head band of the HMD. FIG. 36 illustrates one embodiment where the camera is coupled to an extender that is coupled to the frame of the HMD. The extender may be an element on which the camera may adjust angles, optionally manually and/or using one or more motors. The extender may help to prevent concealment and may improve the field of view captured by the camera. The type of extender is not limited to the type illustrated in FIG. 35 and FIG. 36. The extender may have any shape that extends the camera away from the head, and/or may be formed as an integral part of the frame and/or any other part of the HMS. The extender may be coupled to the front, side, or rear portion of the HMD.

In one embodiment, a head mounted system (HMS) configured to identify posture and facial expression of a user wearing the HMS, includes: a frame configured to be worn on the user's head; an inertial measurement unit (IMU) coupled to the frame and configured to measure orientation of the frame; first and second cameras coupled to the frame, at locations that are before and after the ears, respectively, and less than 15 cm away from the user's head; the first and second cameras are oriented such that at least a portion of one of the user's eyebrow and at least a portion of one of the user's shoulder blades are in the fields of view (FOVs) of the first and second cameras, respectively; wherein the locations of the first and second cameras, relative to the user's head, do not change even when the user's head performs wide angular movements; and a computer configured to estimate the user's posture and facial expression based on: a model of the human body parameterized by pose, a model of the human face parameterized by expression, measurements of the IMU, and data extracted from images captured by the first and second cameras.

One example of a model of the human body parameterized by pose is described in the reference Zuffi, S., Black, M. J. (2015), "The Stitched Puppet: A Graphical Model of 3D Human Shape and Pose", In IEEE Conf. on Computer Vision and Pattern Recognition (CVPR).

One example of a model based on a loose-limbed body model that requires a specification of the probabilistic relationships between body parts at a given time instant and over time is described in the reference Sigal, L., Isard, M., Haussecker, H., Black, M. J. (2012), "Loose-limbed people: Estimating 3d human pose and motion using non-parametric belief propagation", International journal of computer vision, 98(1), 15-48.

More examples of a part-based model are described in the reference Ghosh, S., Sudderth, E., Loper, M., Black, M. (2012), "From Deformations to Parts: Motion-based Segmentation of 3D Objects", In Advances in Neural Information Processing Systems 25 (NIPS), MIT Press, pages 2006-2014; and in the reference Hirshberg, D., Loper, M., Rachlin, E., Black, M. J. (2012) "Coregistration: Simultaneous alignment and modeling of articulated 3D shape", In European Conf. on Computer Vision (ECCV), Springer-Verlag, LNCS 7577, Part IV, pages 242-255.

One example of a model for estimating articulated body posture and motion from monocular video sequences is described in the reference Rosales, R., Sclaroff, S. (2000), "Inferring body pose without tracking body parts", In IEEE Computer Society conference on computer vision and pattern recognition (CVPR) (Vol. 2, pp. 721-727). One example of a model for predicting soft-tissue deformations is described in the reference Pons-Moll, G., Romero, J., Mahmood, N., Black, M. J. (2015), "Dyna: A Model of Dynamic Human Shape in Motion", ACM Transactions on Graphics, (Proc. SIGGRAPH).

Figure 32:
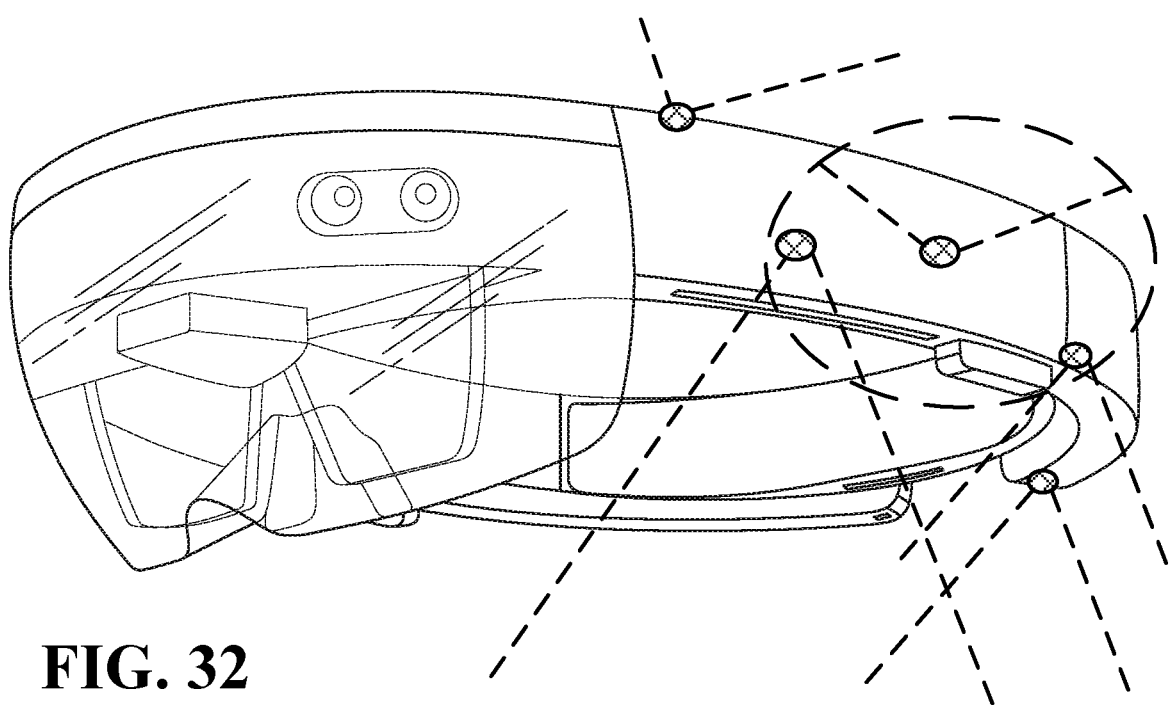
FIG. 32 illustrates a HMD having head mounted cameras around the head.
Figure 39:
FIG. 39 and FIG. 40 illustrate HMDs having head mounted cameras able to capture both the user's facial expressions and hand gestures with the same camera.
Figure 40:

FIG. 32 illustrates a HMD having head mounted cameras around the head, such that the head mounted cameras are able to capture the user's hands when stretched to the sides. In other words, the mead mounted cameras may be able to measure the user's hand almost in any direction they are stretched. FIG. 26 illustrates a HMD having head mounted cameras able to capture portions of the user's torso, hands, and legs. FIG. 34 illustrates a HMD having head mounted a camera able to capture the user's shoulder. FIG. 31, FIG. 35, FIG. 36, FIG. 37, and FIG. 38 illustrate HMDs having head mounted cameras able to capture both the user's face and the user's back. FIG. 39 and FIG. 40 illustrate HMDs having head mounted cameras able to capture both the user's facial expressions and hand gestures with the same camera.

In one embodiment, a portal effect that enables the user himself passes through a portal includes the following steps: the HMD measures the user's posture; the portal has a physical location in the real world; when the user passes the portal, the user sees a change in the environment. Optionally, the user and/or other users actually see the transient, i.e., how part of the user's body is in the new location and another part in the previous location; when the user passes the portal he may have a different avatar. Optionally, the user and/or other users may have the effect of seeing how the user's avatar changes as the user passes the portal. Optionally, other users can also see the transient effect of the user passing the portal, and they see the change of the environment. This is especially useful for portals that connect between different worlds.

In one embodiment, a head mounted display (HMD) systems configured to cooperate, includes: first and second head mounted display (HMD) systems, worn on first and second users, respectively; each HMD includes: a frame, a display, an inertial measurement unit (IMU), first and second cameras, a communication module, and a computer; the frame is configured to be worn on its user's head; the IMU is coupled to the frame and configured to measure orientation of the frame; the first and second cameras are coupled to the frame, at locations that are less than 15 cm away from its user's head; the first and second cameras are oriented downwards such that at least a portion of its user's front torso and at least a portion of one of its user's shoulder blades are in the fields of view (FOVs) of the first and second cameras, respectively; wherein the locations of the first and second cameras, relative to its user's head, do not change even when its user's head performs wide angular movements; and the computer is configured to calculate its user's posture based on: a model of the human body, measurements of the IMU, and data extracted from images captured by the first and second cameras; the communication module of the first HMD is configured to send the calculated posture of its user to the communication module of the second HMD, and vice versa; the computer of the first HMD is configured to render an avatar of the second user, based on the received posture of the second user, and vice versa; and the display of the first HMD is configured to present the avatar of the second user to the first user, and vice versa.

Optionally, the communication modules are further configured to exchange the measurements of the IMUs, and the computers utilize the measurements of the IMUs in the processed of determining where to render the avatars. Optionally, the distance between the first and second users is more than 10 meter. Optionally, there is no line of sight between the first and second users. Optionally, the HMDs are mixed reality HMDs, the rendered avatar of the second user (as presented to the first user) covers at least 10% of the physical body of the second user as seen by the first user, and vice versa. Optionally, the HMDs are virtual reality HMDs, the rendered avatar of the second user (as presented to the first user) is located at a relative angle to the first user which essentially corresponds to their relative angle in the real world, and vice versa. Optionally, "essentially corresponds" is interpreted as less than 15% inaccuracy in the angle when comparing the real and virtual angles to the second user as seen by the first user. Optionally, the virtual distance between the users is exaggerated in order to create an effect of fast movement along the Cartesian axes. Optionally, the HMDs are virtual reality HMDs, the rendered avatar of the second user (as presented to the first user) is located at a relative position to the first user which essentially corresponds to their relative position in the real world, and vice versa. Optionally, "essentially corresponds" is interpreted as less than 15% inaccuracy in angle and distance when comparing the real and virtual angles and distances to the second user as seen by the first user. Optionally, the HMDs system runs a game. Optionally, the HMDs system runs a video conference.

The embodiments described in this document may be utilized to implement one or more of the following multiplayer game embodiments:

In one embodiment, a user controls his/her model that is sent to other users, instead of the case where the other users control the user's model. This is useful for effects the user wants to apply on his avatar. Examples of scenarios having a need to enable to the user to control his/her avatar include multiplayer game, video conference, multiplayer events, when the user wants to look differently to different people who see the user simultaneously, when the user owns a unique model and does not want to share it with others, or when the user won a special "force" in a game.

In one embodiment, when user B can measure user A, then user B sends the measurements to user A, and these measurements are used to improve the model of user A (obtained from the HMD of user A). Optionally, the improved model of user A (based on measurements from both user A and user B) is sent to user C who cannot measure user A directly, but still enjoys from the improved model.

In one embodiment, a HMD of User A measures user B in order to render an avatar over user B for user A. HMD of user B sends the self-measured avatar of user B to the HMD of user A, which uses the received model to improve the accuracy of its rendering of the avatar over user B.

In one embodiment, players who are not present in the same room may see each other in the same room by replacing the models.

In one embodiment, the perceived size of a room is increased by hiding the walls, and playing with another user that his model appeared to be presented beyond the wall.

In one embodiment, user A is provided with an effect of seeing through a physical wall by receiving a self-measured avatar from user B who stands beyond the wall.

In one embodiment, a user can also send with a model (generated based on this HMD) objects he touches/holds, such as: a sword, a book, and a flower. For example, a user can give his girlfriend a flower by sending his model plus a model of the flower (which can be virtual, but both sides see it), and the girlfriend sees the flower as if she stands in front of the user (when they are physically located in places without a direct line of sight). Usually, the system accesses/prepares a model of the object in advanced, so that it can render the model in real time according to the user's actions.

In one embodiment, the user can have the feeling of living/working/traveling/learning/playing with a real human when each is in his own home. This is kind of a virtual-real partner because the parties are real, but each party is physically located in a different place, and they see each other through the exchanged avatars.

In one embodiment, the system supports changing perspective in a multiplayer game. Assume the user plays outside and wants to have an effect of becoming taller or shorter, or effect of flying. Because others users send the user their models, and the user has the model of the world, then the user's HMD can change the user's perspective on the situation while continuing to receive the real movements of the real people.

In one embodiment, a user can see himself from the side. Might be interesting when the user wants to understand how he/she looks to others. In one embodiment, the system creates an effect that the user is in someone else's body. User B sends his model to user A, who sees what user B, sees and also can see user's B body. This embodiment requires user A to be able to measure the body of user B. Optionally, the system renders a point of view as if user A follows user B (as if user A looks behind/goes after user B).

In one embodiment, the user's HMD measures the user's posture and generates an avatar of the user; the avatar is duplicated as one or more avatars around the user, where the duplicated avatars do what the user does (based on the user's model, as measured by the HMD). The user's duplications can be rendered as facing the same direction the user faces, as a mirror image (optionally in front of the user), and/or as playing with the user by imitating the user. Examples of games based on this technology include: the user is walking in parade with a thousand replications doing exactly what the user does, a ballet dancer can see many ballet dancers doing the same movements as he/she does (and optionally in a perfect synchronization), the user can see himself participating in a dance ball, line dances, Zumba—where everyone is doing exactly whatever the user does, or doing something that matches the movements the user does (in this example, the HMD measures the user's movements, and then the behavior of the replications is set based on the behavior of the user's movements). Optionally, the duplications are rendered in the real world, essentially everywhere, from any required angles, outdoors, and/or without an external tracking system to track the user's posture.

In one embodiment, a method for saving calculation power in a multiplayer game environment includes the following steps: Each user measures himself and the environment, and sends his measurements to a centralized computer and/or shares his measurements/models with the other users in the same physical room. The computer uses the measurements/models received from user to calculate the model of the room and the users, and sends the model of the environment to the users for rendering. This especially saves power in multiplayer games where each user cannot measure all the people around him because there are too many of them. But a centralized computer can track all the models and build a unified model based on the models it receives.

In one embodiment, user A and user B are involved in a multi-player game, where user A sees user B as an avatar that covers user B such that the avatar is bigger than user B. When user B is occluded by an object (which may be stationary such as a wall or a furniture, or non-stationary such as another user), part of the avatar of user B may still be visible to user A. In order to enable user A to render correctly the avatar of user B, the HMD of user B sends data describing the posture of user B, and the HMD of user A renders user's B avatar correctly based on the received data.

In one embodiment, a head mounted system (HMS) configured to collect facial cues of a user wearing the HMS, includes at least a frame and first and second cameras coupled to the frame. The frame is worn by the user and is situated on the user's head. In one example, the frame of the HMS may be the frame of eyeglasses, goggles (e.g., used for skiing, motor sports, skydiving, or diving), or any other device which houses lenses through which a user may peer at the physical world. In another example, the frame of the HMS includes the frames in the previous example, but possibly lacking one or more lenses. In still another example, the frame may belong to a head mounted display (HMD) that presents to the user digital content. For example, the HMD may be an augmented reality display, a virtual reality display, and/or a mixed reality display.

In one embodiment, the first and second cameras are coupled the frame at locations that are to the right and to the left of the symmetry axis that divides the face to the right and left sides, respectively. In one example, the locations at which the first and second cameras are couple to the frame are such that each location is less than 15 cm away from the closest pupil of the user. That is, the first camera is coupled to the frame at a location that is at most 15 cm away from the user's right pupil, and the second camera is coupled to the frame at a location that is at most 15 cm away from the user's left pupil.

The first and second cameras are oriented such that the middles of the user's right and left eyebrows are in the fields of view (FOVs) of the first and second cameras, respectively. Additionally, the orientation of the first and second cameras is such that the user's left and right oral commissures are not in the FOVs of the first and second cameras, respectively.

In some examples, the first and second cameras are coupled to the frame in such a way that the locations of the first and second cameras relative to the user's head do not change even when the user's head performs wide angular movements. In one example, the first and second cameras are coupled to the frame by being attached to the frame in a rigid manner such that their orientation and/or position relative to the frame do not change when the user moves his/her head while wearing the HMS. In another example, the first and second cameras are coupled to the frame by being attached to the frame in an essentially rigid manner Optionally, when attached in an essentially rigid manner, the orientation and/or position of the first and second cameras relative to the frame do not change by more than 5° when the user's head performs angular motion that exceeds 30°. Additionally or alternatively, when attached in an essentially rigid manner and the user's head performs angular motion that exceeds 30°, the orientations of the first and second cameras relative to the frame revert to within one second to within 5° of the respective orientations relative to the frame, at which the first and second camera were oriented prior to the angular motion being performed.

In some embodiments, the first and second cameras produce first and second video streams. The first and second cameras may be various types of cameras in different embodiments. In one example, the first and second cameras are visible and/or thermal video cameras, and the first and second video streams may include visible and/or thermal images at rates of at least 1 Hz. Optionally, the first and second video streams comprise images that include portions of the face of the user who wears the HMS to whose frame the first and second cameras are coupled. In one example, images belonging to the first stream comprise a portion of the user's face that has limited overlap with the portion of the user's face comprised in images belonging to the second stream. Optionally, by "limited overlap" it is meant that at least 20% of the area of the user's face that appears in images belonging to the first stream does not appear in images belonging to the second stream, and vice versa. Optionally, by "limited overlap" it is meant that most of the area of the user's face that appears in images belonging to the first stream does not appear in images belonging to the second stream, and vice versa.

In some embodiments, one or more video streams generated utilizing one or more respective video cameras may be used for various applications such as generating an avatar of a user and/or determining emotional response of a user. Each of the one or more video cameras is coupled to a frame of an HMS worn by a user.

In one embodiment, each of the one or more video streams comprises images of at least a portion of the face of the user. Optionally, none of the one or more video streams comprises an image that includes a full frontal view of the user's face. Herein an image that comprises a full frontal view of a person's face is an image in which all of the following features of the person are visible: both ears, both eyes, both eyebrows, the nose, and the chin.

In one embodiment, at least one of the one or more video cameras is oriented towards the face of the user. Optionally, the angle between the optical axis of each of the at least one of the one or more video cameras and the Frankfort horizontal plane of the user is greater than 20 degrees. Optionally, the angle between the optical axis of each of the at least one of the one or more video cameras and the Frankfort horizontal plane of the user is greater than 30 degrees. Optionally, the angle between the optical axis of each of the at least one of the one or more video cameras and the Frankfort horizontal plane of the user is greater than 45 degrees.

In one embodiment, none of the one or more video streams are a video stream that may be characterized as follows: (1) the video stream is generated by a camera coupled to a frame of an HMS worn by a user, (2) the stream includes an image comprising a full frontal view of the user's face, and (3) the camera is pointed towards the user's face and the angle between the optical axis of the camera and the user's Frankfort horizontal plane is less than 20 degrees.

Each camera from among the one or more cameras may be a certain type of camera. In one example, a camera from among the one or more cameras may be a visible light camera (e.g., RGB camera). In another example, a camera from among the one or more cameras may be a thermal imaging camera (IR camera). In still another example, a camera from among the one or more cameras may be a light field camera. In some embodiments, the frame of the HMS may have different types of cameras coupled to it. For example, the frame may have four cameras couple to it; two cameras may be IR cameras and another two may be visible light cameras. In other example, all the cameras coupled to the frame of the HMS are of the same type. For example, the frame has four cameras coupled to it, all of which are IR cameras, each pointed at different regions of interest (ROIs). In some embodiments, two cameras of different types, which are couple to the frame, may both be pointed at the same ROI. For example, the two cameras may be an IR camera and a visible light camera, situated next to each other and both pointed to the same area of the user's nose.

Each camera from among the one or more cameras may be coupled to the frame at a different location on the frame and/or may be oriented at a certain orientation relative to the frame. Optionally, each of the one or more cameras is coupled to the frame in such a way that the location and orientation of the camera relative to the user's head does not change even when the user's head performs wide angular movements. Following are some examples of locations and/or orientations cameras may possess in different embodiments.

In one embodiment, a camera from among the one or more cameras is coupled to the frame at a location that is to the right of the symmetry axis that divides the face to the right and left sides, and is less than 15 cm away from the middle of the user's right eyebrow. Additionally, the camera is oriented such that the middle of the user's right eyebrow is in the FOV of the camera, and the user's left oral commissure is not in the FOV of the camera. Optionally, the angle between the optical axis of the camera and the Frankfort horizontal plane is greater than 20 degrees. Optionally, the angle between the optical axis of the camera and the Frankfort horizontal plane is greater than 30 degrees. Optionally, the angle between the optical axis of the camera and the Frankfort horizontal plane is greater than 45 degrees. Additionally or alternatively, a similar configuration may be applied to a camera from among the one or more cameras that is coupled to the frame at a location that is to the left of the symmetry axis, and is less than 15 cm away from the middle of the user's left eyebrow.

In one embodiment, a camera from among the one or more cameras is coupled to the frame at a location that is to the right of the symmetry axis and less than 10 cm away from the user's right upper lip. Additionally, the camera is oriented such that the user's right upper lip is in the FOV of the camera, and the middle of the user's left eyebrow is not in the FOV of the camera. Optionally, the angle between the optical axis of the camera and the Frankfort horizontal plane is greater than 20 degrees. Optionally, the angle between the optical axis of the camera and the Frankfort horizontal plane is greater than 30 degrees. Optionally, the angle between the optical axis of the camera and the Frankfort horizontal plane is greater than 45 degrees. Additionally or alternatively, a similar configuration may be applied to a camera that is coupled to the frame at a location that is to the left of the symmetry axis and less than 10 cm away from the user's left upper lip.

In one embodiment, a camera from among the one or more cameras is coupled to the frame at a location that is less than 10 cm away from the user's right pupil. Additionally, the camera is oriented such that the skin around the user's right eye is in the FOV of the camera, and the user's left oral commissure is not in the FOV of the camera ("the skin around the eye" may refer to the periorbital area). In one example, the distance between the camera and the right eye is below 5 cm. Additionally or alternatively, a similar configuration may be applied to a camera that is coupled to the frame at a location that is less than 10 cm away from the left eye of the user.

In one embodiment, when the HMS is an occluded virtual reality HMD, the skin around the eyes may be measure using several small cameras placed within the hood of the HDM, and looking at the skin around the eyes. In one example, infrared LEDs are used to light the skin and infrared-only cameras are user to record the reflections.

The resolution of images from a video stream generated by a camera may vary, possibly significantly between embodiments described herein, and may depend on various factors such as the type of camera and/or a purpose for the which the images are to be used. In one embodiment, the camera may capture images that consist of a single pixel. For example, the camera may be a thermal imaging camera in close proximity to the face of the user (e.g., less than 2 cm from the surface of the face). In other embodiments, the camera may capture images comprising multiple pixels. The resolution of the images with multiple pixels may vary. Examples include 2 pixels, 2×2 pixels, 4×4 pixels, 16×9 pixels, 48×36 pixels, 64×64 pixels, and 256×56 pixels. Additional example include one of the following standard resolutions: CGA, VGA, PAL, XVGA, SD, 720p, 1080p, 2K, 4K, or 8K. Optionally, the ratio between the horizontal resolution and vertical resolution of the images is one of the following: 5:4, 4:3, 3:2, 16:10, 5:3, 16:9, 17:9, or 21:9. Alternatively, the ratio between the vertical resolution and horizontal resolution of the images is one of the following: 5:4, 4:3, 3:2, 16:10, 5:3, 16:9, 17:9, or 21:9. Optionally, the images may generate utilizing other resolutions known in the art or a custom sensor with resolutions or pixel counts that are not standardly used in the art.

The one or more video streams may include images generated at different rates (frequencies) depending on the embodiments. Herein a frequency and/or rate of a video stream may refer to the average number of images generated by the stream in a second and may be referred to as a number followed by Hz (Hertz) or as a number of frames per second (fps). Optionally, each of the one or more video streams operates at a rate of at least 1 Hz (i.e., on average its camera generates at least one image a second). Optionally, the rate of the video stream may be higher than 1 Hz, such as 10 Hz, 30 Hz, 60 Hz, 100 Hz, 200 Hz, a value between 1 Hz and 200 Hz, or a value higher than 200 Hz.

In some embodiments, the one or more video streams include multiple video streams, each including images generated at the same frequency. Alternatively, the one or more video streams involve a first video stream that includes images generated at a first rate and second video stream that includes images generated at a second rate that is higher than the first.

In some embodiments, at least some of the one or more video streams are synchronized. Optionally, synchronizing between video streams involves determining, for at least some images from a first stream, their corresponding images in a second stream. Optionally, when referring to corresponding images from different video streams, the relationship between two or more corresponding images is a temporal one, such that the corresponding images were taken essentially at the same time, or at a known offset from each other. In one example, a first image from the first stream corresponds to a second image in the second stream if it is taken at the same time as the second image in the second stream. In another example, two images from different video streams may be considered corresponding if they are taken within a certain time of each other. Optionally, the certain time may be a duration that is less than 0.01 seconds, less than 0.04 seconds, less than 0.1 seconds, or less than 1 second.

In some embodiments, different video streams may include images that were not taken exactly at the same time by their respective cameras (e.g., due to the cameras capturing images at different rates and/or starting capturing images at slightly different times). In such cases, it may be required to find corresponding images by determining which images from different video streams were captured essentially at the same time. In one example, a first image from a first stream and a second image from a second stream are considered corresponding images if the second image is taken before the first image is taken, but no other image in the second stream is taken at a time that is after the time the second image is taken and before the time the first image is taken. In another example, a first image from a first stream and a second image from a second stream are considered corresponding images if the second image is taken after the first image is taken, but no other image in the second stream is taken at a time that is before the time the second image is taken and after the time the first image is taken. In still another, a first image from a first stream and a second image from a second stream are considered corresponding images if the second image is an image from among the images in the second stream for which the difference between the time it was taken and the time the first image was taken is the smallest.

In one embodiment, an image from a first video stream that corresponds to an image from a second video stream may in fact represent multiple images from the first stream.

For example, this may occur if the first stream includes images generated at a higher frequency than the second stream. In such a case, there may be multiple images from the first stream that fall into a window during which the image from the second stream was taken. Optionally, the multiple images are represented by a single image (e.g., an average of the multiple images), which may in fact not be an image actually captured by the camera that generates the first stream.

When referring to images belonging to multiple video streams, a set of corresponding images is a set of images, each coming from a different video stream, which were taken essentially at the same time. Optionally, each pair of images in the set of corresponding images is considered to correspond to each other according to at least one of the examples for conditions for correspondence of images given above.

Embodiments described hereinbelow may involve representing images with feature values. The process of converting one or more images to feature values may be referred to hereinbelow as "feature generation" and/or "feature extraction". Optionally, the feature values may be represented as one or more vectors of feature values. Stating that feature values may be represented as a vector does not imply that they necessary need to be stored in a data structure that is a vector. Rather, that the features may be referred to logically as being in a vector such that each different feature corresponds to a different position (dimension) in the vector.

The terms "feature" and "feature value" may often be used interchangeably in this disclosure when the context of their use is clear. However, a "feature" typically refers to a certain type of value, and represents a property determined from one or more images. A "feature value" is the value of the property determined from the value of the one or more images. For example, a feature may be "distance between the edge of the left nostril and the edge of the left side of the lip". A feature value for that feature may be 3 cm. Optionally, when referring to feature values as vectors of feature values, each position in the vector (each dimension) represents a feature; the content of each position in the vector is a feature value (of the feature that corresponds to the position).

In some embodiments, data that represents images obtained from one or more video streams is converted into feature values. There are various ways to represent the data obtained from the one or more video streams as vectors of feature values, as explained in further detail below.

In one embodiment, each image belonging to a video stream is converted into a vector of feature values by extracting various feature values from the image. Optionally, multiple images (e.g., images belonging to a set of corresponding images), may be represented as a vector of feature values by combining feature values from vectors representing individual images. Optionally, some of the feature values in the vector representing the multiple images may be feature values taken from the vectors representing the individual images. For example, the vector representing the multiple images may include some, or even all, of the feature values of each vector representing an individual image. Optionally, some of the feature values in the vector representing the multiple images may be the results of functions of feature values from vectors representing individual images. For example, the vector representing the multiple images may include a feature value that is an average of feature values from different vectors representing individual images, or a difference between feature values from different vectors representing individual images.

In one embodiment, multiple images from one or more video streams may be converted into a vector of feature values by extracting various feature values from the images. For example, the multiple images may be stitched together (e.g., to create a single image representing a face) or represented as a single logical unit (e.g., a single image or file). Thus, extracting features from the multiple images may be done by accessing a single source (e.g., a single stitched image). Optionally, stitching the image may involve performing various image processing functions on individual images and/or the multiple images such as rotating, rescaling, and/or other transformations on the images.

Some methods for stitching multiple images of a face of user may involve mapping portions of the images to a 3D model of the face of the user. Thus, a 2D image of the user may be generated from the multiple images, even if the images are taken from different perspectives, may capture different portions of the face, and/or or may overlap, as may be the case in some of the embodiments described herein that involve images of one or more cameras coupled to a frame of an HMS worn by the user. In one example, combining the images of the one or more cameras into a single image from which features may be extracted may be done based on the teachings of Bradley, et al., "High resolution passive facial performance capture", in ACM Transactions on Graphics (TOG) 29.4 (2010): 41. Bradley et al. describe a method for constructing a 2D image that utilizes a 3D mesh model of the face. The domain of the combined image is given by the 2D parameterization of the mesh, such that every vertex of the 3D mesh has unique 2D coordinates in the parameter domain, yielding a one-to-one mapping between 2D and 3D mesh triangles. Each triangle of the 3D model that is covered by an image taken by one or more of the cameras is projected onto the image of the camera that observes it best, e.g., as determined by the dot product between the triangle normal and the camera direction. The camera pixels corresponding to the projection are then copied to the corresponding 2D triangle in the combined image. Optionally, to account for variations in brightness of images captured by different cameras various processing techniques may be applied such as Poisson image editing. For example, the process of Poisson editing can involve starting with the largest image patch and iteratively adding adjacent patches until the combined image is complete. For each new patch that is added, x- and y-gradients are computed inside the patch and used to solve a Poisson equation to find a new patch that matches the gradients as closely as possible, while also obeying the boundary conditions set by other completed patches. Optionally, in order to maintain continuity between images taken at different times (e.g., in order to avoid artifacts involving too extreme differences between consecutive combined images), previous images may be used to form per-pixel soft constraints when solving the Poisson equation involved in a certain combined image.

In some embodiments, data representing multiple images coming from a video stream of a camera is converted into feature values. Optionally, the feature values are represented as a vector of feature values. Optionally, the multiple images have a temporal relationship between them. For example, the images are successive images in the stream (i.e., they were generated one after the other) and/or the multiple images were all taken by the camera during a certain period. For example, the multiple images were all taken within a period lasting less than 0.1 seconds, less than 0.5 seconds, less than 3 seconds, or more than 3 seconds. Optionally, some of the feature values may be a function of multiple images (e.g., they may compare feature extracted from multiple images taken at different times).

In some embodiments, feature values are generated from multiple images. The multiple images include images belonging to multiple video streams (i.e., they are generated by multiple cameras). Additionally, the multiple images include images taken at different times (e.g., successive images from the same stream). Optionally, the multiple images include successive sets of corresponding images, which includes sets that may be ordered according to the time the images in each set were taken. Optionally, the feature values are represented as a vector of feature values. Optionally, some of the feature values include feature values that are a function of corresponding images from among the multiple images. Optionally, some of the feature values include feature values that are a function of successive images from among the multiple images.

Cameras coupled to a frame of an HMS worn by a user that are pointed to the user's face are typically very close to the user's face, with the distances between the camera to the face ranging from less than 1 cm to usually no more than 15 cm. Thus, portions of the user's face typically occupy a large portion of the images captured by the cameras, and even at times portions of the user's face can occupy the entire images. This is in contrast with other scenarios in which images of the users face are captured by a front facing camera (e.g., a webcam, a camera embedded in a TV, etc.) in which the face may occupy a smaller portion of the image. Additionally, due to the coupling the orientation and position of the cameras relative to the face does not significantly change (or change at all) event when the user's head performs angular motions or other movements in space. This means that images captured by a camera capture the same facial region of the user over long periods. This is different from many scenarios in which frontal cameras that are farther from the user capture images of the user. In such cases, the position and orientation of the face in images may change significantly as the user moves.

Some approaches routinely used in the art for acquiring feature values from images of faces involve additional elements that aim to ease the process of acquiring accurate feature values. In one example, markers are added to the face of a user, e.g., by paint (fluorescent or other), makeup, stickers, etc. Such markers on the face can be easily detected by image processing algorithms due to their different texture and/or color compared to the surrounding regions on the face. In another example, patterns may be painted on the face of a user and/or special makeup may be used in order to be able to better identify facial features and/or movements on the face (e.g., facial expressions). In another example, the face may be lighted in certain patterns (structured light) in order to assist in capturing facial features. For example, a projector may project a structured light pattern onto the face in order to provide dense surface texture, and/or the projector may project phase-shifted color-fringe patterns onto the face.

In some embodiments, none of the techniques mentioned above are utilized by systems and/or methods that involve acquiring facial feature values describing the face of a user and/or learning a model of the face of the user. That is, some embodiments described herein do not include a step or mechanism that involves placing markers on the face of the user (e.g., by applying paint or stickers), applying makeup in patterns designed to ease image processing tasks, or projecting structured light for (i.e., projecting certain patterns on the face). In other embodiments, some of the above techniques may be applied while others are not. For example, in one embodiment, no markers are place on the face, such as by applying black paint dots or stickers to the face. In another embodiment, makeup and/or paint is not applied to the face of the user in such a way that may assist in identifying facial features (e.g., contours of the face). In still another embodiment, the face of the user is not illuminated by structured light that projects certain patterns on the face of the user that may assist in extracting facial features from images of the face.

Registration is an initial step for many image processing tasks. When images include faces, the registration may also be referred to as facial registration. Facial registration typically involves identifying a face in an image and/or prominent facial features such as the corner of an eye, the tip of the nose, the edge of an eyebrow, the mouth, etc. Once facial registration is performed, the identified prominent features may be used to identify other points on the face. Additionally or alternatively, the identified features may be used to preprocess the image (e.g., move, rotate, and/or rescale) in order for the head and/or certain key points (e.g., the pupil) to be positioned in a certain place such that is shared by multiple images being processed. For example, to ease feature extraction from frontal images of a face, after facial registration each image is transformed such that nose appears in the middle of the image and the height of the face is a certain number of pixels (e.g., occupying 90% of the height of the image). While in may scenarios known in the art, facial registration may be a difficult task, due to the unique characteristics of the coupling of the cameras to the frame which enable a stationary position and orientation relative to the face, in some embodiments, facial registration is a relatively simple step to perform, while in other embodiments, this step might not even be performed at all.

In some embodiments, registration involves identifying a certain facial landmark and/or facial feature in an image. In one example, registration with images generated by an upward facing camera that is attached to a frame of an HMS may involve identifying the position of an eyebrow in the images (e.g., identifying the position of one or more edges of the eyebrow). In another example, registration with a downward facing camera attached to a frame of an HMS may involve identifying the position of an edge of the lip in the images. In still another example, registration with a camera attached to a frame of an HMS and oriented towards an eye may involve identifying the position of a pupil and/or an edge of an eye in the images. For the purpose of registration, various algorithms known in the art for identification of facial features can be used; examples of such algorithms are given below.

Some embodiments involve collecting a set of images of users taken while the users express various emotional responses. Optionally, the set includes images of one or more cameras that are not mounted to a frame of an HMS worn by users. For example, the images may include images captured by cameras that are at least 20 cm away from the face of the user, such as a Kinect and/or RGB camera in front of the user. Additionally or alternatively, the set may include images taken by one or more cameras coupled to a frame of an HMS worn by the users, were the cameras may be coupled to the frame at different locations and/or have different orientations, as discussed above. Optionally, the set of images is collected for training various predictors such as emotional response predictors (ERPs) discussed in this disclosure. Additionally or alternatively, the set of images is collected for training various facial feature identification modules mentioned in this disclosure, such as modules that identify action units, facial landmark locations, blendshape weights, and/or microexpressions. There may be various protocols for acquiring such data, which may involve verifying the data, extracting features from the data, and/or rewarding users for providing the data. Examples of such protocols are given in United States Patent Application 20150186912, titled "Analysis in response to mental state expression requests" filed on Mar. 16, 2015.

Identifying the facial features in the examples given above may be done in various ways known in the art. In particular, in some embodiments, machine-learning based algorithms may be used to identify the facial features in the images (e.g., an eye, an edge of the lip, edge of the nostril, location of an eyebrow, etc.) Such algorithms may use train a model utilizing annotated training data in which the facial features are identified. In one example, facial features may be identified using methods similar to the ones described in Milborrow, S., and Nicolls, F. (2008), "Locating facial features with an extended active shape model", in Computer Vision—ECCV, pp. 504-513. Active shape models typically deal with frontal views of faces, but these algorithms will work well for portions of faces and/or non-frontal perspectives, given appropriate training data (i.e., images corresponding to the specific position and/or orientation of the camera and with appropriately labeled landmarks) In another example, geometrical face models may be used to identify facial features, such as the models described in Jeng et al. "Facial feature detection using geometrical face model: an efficient approach." Pattern recognition 31.3 (1998): 273-282. Note that this reference describes models for frontal features in whole-face frontal views, but the same principles may be easily adapted by one skilled in the art to identify facial features in images of a camera that captures a portion of the face and/or does not necessarily provide a frontal view of the face. In another example, methods for identifying specific facial features may be utilized, such as the adaptations of the method for identifying eyes described in Lam, et al., "Locating and extracting the eye in human face images." Pattern recognition 29.5 (1996): 771-779.

It is to be noted, that due to the characteristics of the images generated by cameras so closely situation to the face, facial features in the images will tend to be significantly larger and more prominent than is typically encountered in the art. Thus, it becomes trivial for one skilled in the art to identify prominent features (e.g., an eyebrow that occupies half of an image) using various algorithms for object recognition that are known in the art.

In some embodiments, a facial feature recognition model may be trained using images of multiple users that include the facial feature. Optionally, the images are taken by cameras located at a similar position on a frame of an HMS worn by the users and/or the cameras have a similar orientation with respect to the users' faces. Optionally, such a model is considered a general facial feature identification model. Optionally, various general models may be created for users having certain characteristics involving one or more of the following: gender, ethnicity, skin color, facial hair, age, and/or facial augmentations. For example, a general model may be created for white males between the age of 21 and 40. In another example, a general model may be made for Asian female teenagers with braces. In yet another example, a general model may be made for bald bearded men.

In other embodiments, a facial feature recognition model may be trained using images of a certain user that include the facial feature. Optionally, the images are taken by a camera in a certain position on a frame of an HMS worn by the certain user and/or in a certain orientation with respect to the user's face. Optionally, such a model is considered a personal facial feature identification model.

In some embodiments, a personal facial feature identification model for a user may be initialized from general facial feature identification model appropriate for the user. For example, a model appropriate for the gender of the user or a combination of other characteristics mentioned above. Additional training samples for the user may be created by taking images and labeling them with facial features identified by the user's model. These training samples may be used to retrain the models to make them perform better when identifying facial features of the user.

In some embodiments, facial registration and/or preprocessing of images obtained utilizing a camera may involve various transformations such shifting scaling and/or rotating with respect to an identified facial feature (e.g., such that the facial feature may be located in a certain relative position, have a certain size, and/or certain orientation). In other embodiments, images may be preprocessed in order to adjust certain image properties such as brightness and/or improve image sharpness, contrast, etc.

In some embodiments, prior to feature extraction from images from a video stream, the images may undergo transformations such as rotation and/or scaling in order to produce an image that represents a (portion of a) frontal view of the face of the user.

Various types of feature may be derived from images from video streams and utilized in embodiments described herein for various purposes such as detecting affective response of a user and/or recreating facial expressions on an avatar. Generally, the feature values may be divided in two types: low-level features, and high-level facial-related features. The low-level features are features that are typically used in image processing and vision-related applications; they do not necessarily involve human faces, and are typically used for various applications such as general object and/or motion recognition. The high-level features are typically facial features that capture some aspect of faces or facial motion. Optionally, deriving high-level features utilizes domain knowledge of the face. High-level features may correspond to various aspects of the face. For example, they may correspond location of certain facial features (e.g., facial landmarks), certain movement patterns of facial muscles (e.g., action units and microexpressions), and/or a certain composition of a facial expression (e.g., blendshapes). While the high-level features in the literature are typically derived from whole images of the face (referred to herein as full frontal images), as explained below, these features can also be used with the type of images generated by cameras coupled to a frame of an HMS worn by a user.

It is to be noted that the categorization of features to high-level and low-level features is done purely to assist in distinguishing between groups of features. This is not a strict classification; various features that may be considered low-level in one embodiment may be considered high-level in another embodiment, and vice versa. In addition generating some low-level features may be done utilizing facial domain knowledge, and as such, in some cases, they may be considered high-level features.

Following are examples of various types of features and feature generation approaches that may be employed. This is not a comprehensive description; some embodiments may utilize other types of features that are not described below.

In some embodiments, feature values derived from images from video streams include various types of low-level features that are known in the art, which have been proven useful for various computer vision-related applications, but are not necessarily restricted to applications involving images that include the faces or body. Optionally, these features may be considered low-level features that do not require specific domain knowledge of the face to be generated. Nonetheless, many of the examples of features given below have been proven to work well with tasks involving human faces.

It is to be noted, that in typical applications that involve processing images of faces, the images being processed are full-face frontal images. However, the feature extraction techniques, and/or machine learning techniques they utilize (e.g., for identifying expressions), are agnostic to the fact that the source images are of a specific type (e.g., full-face frontal images). Thus, these techniques may be adapted easily by one skilled in the art, or even used as described in the references of the examples below, to generate feature values from multiple images, where not all the images may capture the same portions of the face, e.g., due to a different location and/or orientation of the camera.

In one example, applying one or more of the exemplary feature extraction techniques described below to inputs comprising images from multiple cameras may be done by creating a single image file from the multiple images concatenating the data representing the images, stitching the images one after the other, or placing them in a certain two dimensional arrangement. Optionally, multiple images may be combined by constructing a 2D image using mapping a mapping of the multiple images to a 3D mesh model of the face, as described above. Following this step, the single image may be provided to the algorithms described below instead of an image of a full face.

In another example, applying one or more of the exemplary feature extraction techniques described below to inputs comprising images from multiple cameras may be done by first applying the feature extraction techniques to each image to create a feature vector for the image. Following that, the feature vectors of the individual images may be combined (e.g., by concatenating them or in some other mode of combination) in order to produce a vector that represents the multiple images. This vector can then be used for various applications such as identification of facial expressions, determining emotional response, and/or mapping a facial expression to an avatar.

In some embodiments, features described below are extracted at certain positions that may be described as relative co-ordinates. In one embodiment, for at least some of the features, the co-ordinates are relative to image boundaries, and thus represent an absolute position in the image. For example, an absolute position may be if a feature is extracted from a pixel at location (120,100) in an image. In one embodiment, for at least some of the features, the co-ordinates are relative to the location of identified facial features and/or landmarks. For example, a feature may be extracted from a pixel in an image identified as being at the base of the right nostril.

It is to be noted that referring to a feature as being extracted from a pixel at a certain location does not limit the feature to being based on values related solely to that pixel. In various embodiments, features may be based on values of multiple pixels such a square patch (e.g., 3×3 pixels) covering a certain portion of the image or pixels that are within a certain distance from a certain pixel. When a feature is derived from multiple pixels and reference is given to a single location of a pixel, which typically indicates a reference point for the location of the multiple pixels (e.g., the center of a circular patch, or the center or corner of a square patch of pixels).

Following are some examples of feature extraction techniques known in the art that may be used in various embodiments described herein. Some of these techniques are considered to generate local features (i.e., they describe properties that are influenced by a relatively small region of an image). Other techniques generate features that describe properties of the whole images.

Gabor filters, which are utilized in some embodiments for feature extraction, are linear filters used for edge detection. Frequency and orientation representations of Gabor filters are similar to those of the human visual system, and they have been found to be particularly appropriate for texture representation and discrimination Gabor filters have been used extensively for various image analysis applications. In particular, they have been found to useful in many applications concerning facial recognition and/or expression identification. Following are some examples of some of the ways Gabor filters may be used for feature extraction in some embodiments. In one example, Lyons et al. "Coding facial expressions with Gabor wavelets." Automatic Face and Gesture Recognition, 1998. Proceedings. Third IEEE International Conference on. IEEE, 1998, construct a facial expression coding for images using a multi-orientation multi-resolution set of Gabor filters which are topographically ordered and aligned with facial features. In another example, Bartlett et al. "Recognizing facial expression: machine learning and application to spontaneous behavior", Computer Vision and Pattern Recognition (CVPR), 2005, investigate various feature selection techniques and machine learning methods that may be applied to Gabor filter-based representations of images in order to successfully identify facial expression. And in yet another example, Gu et al. "Facial expression recognition using radial encoding of local Gabor features and classifier synthesis", Pattern Recognition 45.1 (2012): 80-91, describe multi-scale Gabor-filter operations performed on images. The resulting Gabor decompositions are encoded using radial grids. The codes are fed to local classifiers to produce global features, representing facial expressions. Experimental results show successful results of such image representation for facial expression identification using a hierarchical classifier.

Local Binary Patterns, which are utilized in some embodiments for feature extraction, are feature values used extensively in image processing applications, and specifically, have been used successfully for various facial recognition related applications. In one example, Ahonen et al. "Face description with local binary patterns: Application to face recognition" Pattern Analysis and Machine Intelligence, IEEE Transactions on 28.12 (2006): 2037-2041, describe efficient facial image representation based on local binary pattern (LBP) texture features. The images are divided into several regions from which the LBP feature distributions are extracted and concatenated into an enhanced feature vector to be used as a face descriptor. In another example, Shan, et al. "Facial expression recognition based on local binary patterns: A comprehensive study" Image and Vision Computing 27.6 (2009): 803-816, formulate Boosted-LBP to extract the most discriminant LBP features. The extracted features are used successfully for facial expression recognition using Support Vector Machine classifiers with Boosted-LBP features.

Various extensions and variations to LBP that may be used in embodiments described herein for feature extraction. In one example, Islam, M. "Local Gray Code Pattern (LGCP): A Robust Feature Descriptor for Facial Expression Recognition", in International Journal of Science and Research (IJSR) (2013), describes an extension of LBP called Local Gray Code Pattern (LGCP). LGCP characterizes both the texture and contrast information of facial components. The LGCP descriptor is obtained using local gray color intensity differences from a local 3×3 pixels area weighted by their corresponding TF (term frequency).

In one embodiment, the SIFT algorithm is used to extract local features from images. This algorithm is descried in further detail in U.S. Pat. No. 6,711,293, "Method and apparatus for identifying scale invariant features in an image and use of same for locating an object in an image". In another embodiment, the SURF algorithm may be used to extract features corresponding to points of interest in images, as described in further detail in US 20090238460, "Robust interest point detector and descriptor". In other embodiments, various extensions and/or modifications of these techniques may also be employed such as BRIEF described in Calonder et al., "Brief: Binary robust independent elementary features", in European Conference on Computer Vision, 2010, or ORB described in Rublee et al., "ORB: an efficient alternative to SIFT or SURF", IEEE International Conference on Computer Vision (ICCV), 2011.

In one embodiment, at least some of the feature values derived from an image of a portion of a face taken by a certain camera, which is mounted on a frame of an HMS in at certain position and/or in a certain orientation, are derived from positions of a set of keypoints identified in the image. For example, the set of keypoints may include a predetermined number of keypoints, such as 1, 2, 5, 10, 25, or some other value greater than 1. Optionally, the set of keypoints includes keypoints for which a certain objective function reaches a certain threshold (and as such, the number of keypoints may vary between images). Optionally, the keypoints are automatically selected according to a certain criterion (e.g., indicative in difference in shades of adjacent pixels), so they may not necessarily correspond to a certain predefined facial feature (e.g., an edge of the lip or an edge of the eye). Thus, keypoints may represent locations where shape variation is high in 3D faces, without the need to define what facial features are expected to be at those locations. There various methods for automatic selection of keypoints known in the art, which may be used in some embodiments. For example, Mian et al., "Keypoint detection and local feature matching for textured 3D face recognition", International Journal of Computer Vision 79.1 (2008): 1-12, describe an algorithm that automatically selects keypoints in an image utilizing and extracts descriptive 3D features from those images.

In one embodiment, at least some of the feature values derived from an image of a portion of a face taken by a certain camera, which is mounted on a frame of an HMS in at certain position and/or in a certain orientation, are Histograms of Oriented Gradients (HOG) descriptors. HOG descriptors are image descriptors invariant to 2D rotation that have been used in many different problems in computer vision. Hog descriptions are often extracted at salient regions such as locations of facial landmarks Examples of methods for extracting HOG features that may be used in some embodiments are given in Déniz et al. "Face recognition using histograms of oriented gradients", in Pattern Recognition Letters 32.12 (2011): 1598-1603, and in the references cited therein.

In some embodiments, holistic methods developed for whole face applications can be used for portions of faces and/or oriented images of portions of faces too. One example of such an approach involves the feature extraction techniques used for Eigenfaces, which uses Principal Component Analysis (PCA). Another example of such an approach are the feature extraction techniques used for Fisherfaces, which are built on Linear Discriminant Analysis (LDA). Additional discussion about these techniques and their extension to be used with kernel-based method can be found in Ming-Hsuan, Y. "Kernel eigenfaces vs. kernel fisherfaces: Face recognition using kernel methods", in FGR '02 Proceedings of the Fifth IEEE International Conference on Automatic Face and Gesture Recognition, Page 215, 2002.

The dynamic nature of facial expressions involves phenomena that may be detected over periods of time (based on multiple images taken at different times) and which under certain conditions be less apparent when detected based on single frames. Thus, in some embodiments, a feature value may be derived from multiple images comprising sequential images taken during a certain period. For example, in some embodiments, the certain period may span a duration of 0.1 seconds, 0.25 seconds, 0.5 seconds, or 1 second. In other embodiments, the multiple images may include a certain number of consecutive video frames. It is to be noted that the term "sequential images" refers to images that were captured at sequential times, i.e., occurring one after the other, but not necessarily directly one after the other. Some examples of features having a temporal aspect are given in the references given above that discussed identifying landmarks and/or action units from multiple images. Some additional approaches that may be used for temporal features that are derived from sequential images are given below.

In one embodiment, at least some of the feature values derived from sequential images are generated using dynamic texture recognition. Dynamic texture is an extension of texture to the temporal domain One example of dynamic texture recognition is given by Zhao and Pietikainen, "Dynamic texture recognition using local binary patterns with an application to facial expressions" in Pattern Analysis and Machine Intelligence, IEEE Transactions on 29.6 (2007): 915-928. In this reference, Zhao and Pietikainen describe a method for generating features by having textures modeled with volume local binary patterns (VLBP), which are an extension of the LBP operator widely used in ordinary image-texture analysis, combining motion and appearance. To make the approach computationally simple and easy to extend, only the co-occurrences on three orthogonal planes (LBP-TOP) are then considered. A block-based method is also proposed to deal with specific dynamic events, such as facial expressions, in which local information and its spatial locations should also be taken into account. A somewhat similar approach involving spatio-temporal features is described in Bihan, et al., "Action unit detection using sparse appearance descriptors in space-time video volumes", in IEEE International Conference on Automatic Face & Gesture Recognition and Workshops (FG 2011), 2011, which is discussed above in this disclosure.

In another embodiment, at least some of the feature values derived from sequential images are spatio-temporal features similar to the cuboids described in Dollar et al. "Behavior recognition via sparse spatio-temporal features", in 2nd Joint IEEE International Workshop on Visual Surveillance and Performance Evaluation of Tracking and Surveillance, 2005. Dollar et al. demonstrate methods for behavior recognition (including identifying facial expressions) by characterizing behavior in terms of spatiotemporal features called cuboids, which are local regions of interest in space and time (cuboids) which serve as the substrate for behavior recognition.

In yet another embodiment, at least some of the feature values derived from sequential images are optical strain-based features similar to the spatio-temporal strain values described in Shreve et al. "Macro- and micro-expression spotting in long videos using spatio-temporal strain", in IEEE International Conference on Automatic Face & Gesture Recognition and Workshops, 2011. The strain magnitude is calculated using the central difference method over the robust and dense optical flow field observed in facial regions a user's face.

In some embodiments, feature values derived from images from video streams are higher-level features. Optionally, the high-level features are derived with some domain knowledge involving the face. That is, computing the feature values is done while accounting for the fact that the images involve portions of a human face (e.g., utilizing knowledge of expected positions of certain features and/or the type of facial features to expect in certain images).

In computer vision research, facial landmarks are usually defined as the most salient facial points. Various sets of facial landmarks may be used to annotate images of faces. Example of facial landmarks used to annotate images are described in Köstinger et al., "Annotated facial landmarks in the wild: A large-scale, real-world database for facial landmark localization", in Computer Vision Workshops (ICCV Workshops), 2011. Other sets of landmarks, that include fewer or more landmarks than this example, may be used in various embodiments.

Some embodiments described herein involve images taken by cameras situated in various locations and/or orientations relative to the face. Thus, images from a first camera may be significantly different from images taken with a second camera. In some embodiments, this difference manifests itself with different corresponding sets of landmarks that are visible in images (i.e., in the FOVs of the cameras that took the images). In another embodiment, a second camera coupled to the frame near the bridge of the nose of the user and pointed at the left eye of the user may have landmarks 7, 8, and 9 in its FOV, but none of the other landmarks from the other side of the face, or those above the eye-line or below the tip of the nose (including it). In yet another embodiment, a third camera coupled to the frame at a location that is below the eye-line, left of the nose, and oriented downward may have certain lower-face landmarks in its FOV, such as 14, 15, 18, 19, and/or 21.

Identification of landmarks is an important step in many computer vision-related algorithms, such as face detection and/or alignment. Facial landmarks are also used in many applications as features that are utilized for identifying facial expressions and/or emotional response, and for mapping facial expressions to avatars. As such, identification of facial landmarks has received much attention in research community and there are various approaches to this task known in the art, including successful algorithms for identifying landmarks from images taken in various uncontrolled conditions ("in the wild"), involving images with possibly varying scale, orientation, focus, and/or brightness. Additionally, some algorithms are trained to identify locations of occluded landmarks (e g, that may be occluded by hair or objects obstructing the line-of-sight to the camera).

A common approach used in many landmark identification algorithms involves the training of machine learning-based models using a training set of annotated images, which are images for which the location of at least some of the landmarks are marked. After training such a model, new images may be provided to a detector that utilizes the model in order for it to identify landmarks in the new images. The fact that the images and landmarks involve faces is typically accounted for by the nature for the training set of images and annotations that is provided. For example, typically the algorithms do not need additional information about physiology of faces encoded in them, beyond the images and landmarks that are given in the training set. Therefore, in some embodiments, the algorithms known in the art may be utilized "as is", or utilized after slight modifications that would be apparent to one skilled in the art, in order to identify facial landmarks in images obtained by cameras that are coupled to a frame of an HMS worn by a user. This being despite the fact that the images obtained by the cameras may be only of a portion of the face of the user and/or taken from perspectives that do not provide a frontal view of the face.

In some embodiments, a landmark identifier is a module that receives an image taken by a camera coupled to a frame of an HMS worn by a user and identifies the location of facial landmarks. The landmark identifier utilizes a machine learning-based algorithm that is trained to identify landmarks in the images taken by the camera. Optionally, the camera is one of the cameras described above in this disclosure, which generates one of the one or more video streams mentioned above. For example, the camera may be coupled to the frame at a location that is to the right of the symmetry axis that divides the face to the right and left sides, and is less than 15 cm away from the middle of the user's right eyebrow. In another example, the camera may be coupled to the frame at a location that is to the right of the symmetry axis and less than 10 cm away from the user's right upper lip. In a similar manner to these examples, the camera may be coupled to locations on the left side of the face as well.

Various approaches and machine learning algorithms may be used to train the landmark detector. Examples of algorithms used with full face and/or frontal images of faces, which may be utilized (possibly after adaptation by one skilled in the art), are given below. One thing that is often needed to train the landmark detector is a labeled training set. The labeled training set contains images taken by the camera coupled to the frame of the HMS, and identification of landmarks on those images. Optionally, images in a training set may contain images of multiple users, in multiple conditions (e.g., different lighting conditions) and/or while making different facial expressions (e.g., expressing different emotions). Having a diverse set of images included the training set of a landmark detector can help improve its generalizability, making it more likely to accurately identify landmarks in unseen images that were not included in the training set. Alternatively, images in a training set used to train the landmark identifier may mostly contain images of a certain user in order to train a landmark identifier that works well with images of the certain user.

It is to be noted that while in some embodiments, the landmarks that are used may come from the set of landmarks that is typically used for face analysis applications. In other embodiments, due to the camera perspective that may involve various locations on the frame and/or orientations of various angles, the set of landmarks used may differ from landmarks typically used with full frontal views of faces. For example, in some embodiments, certain landmarks that are typically used may be inappropriate, e.g., due to their lack of distinguishing features in images taken at certain angles. In other examples, the perspective of the camera may cause certain points that are typically not considered landmarks to be easily identifiable in multiple images (and thus they may be considered good candidates for landmarks).

In one embodiment, a separate machine learning-based model is trained for each specific location and/or orientation a camera coupled to the frame of an HMS may be in. Optionally, each model is trained with a training set that includes images taken by a camera in the specific location and/or orientation.

Obtaining images for a training set for training the landmark identifier is typically straightforward and involves acquiring images of a user's face from cameras coupled to a frame of an HMS while the user wears the frame. Optionally, the images may be converted to feature values. The feature values may include of various types described below, such as low-level features derived using Gabor filters, local binary patterns and their derivatives, features derived using algorithms such as SIFT, SURF, and/or ORB, image keypoints, HOG descriptors and features derived using PCA or LDA. Other examples of features may include features derived from sequences of images taken at different times, such as volume local binary patterns (VLBP), cuboids, and/or optical strain-based features that are mentioned in this disclosure. In addition to deriving feature values from images, for training, the images need to be assigned with labels describing the locations of the facial landmarks on the images. Labels may be provided in different embodiments in various ways. Some examples are given below.

In one embodiment, labels are marked by an expert. For example, the expert may be a human that views images taken by a camera coupled to a frame of an HMS at a certain location and/or orientation and indicates the positions of one or more landmarks on the images. Optionally, the expert may mark the positions on the images (e.g., on a touchscreen), and/or record coordinates of the landmarks in a file.

In other embodiments, an automatic labeling method may be employed to mark facial landmarks on images taken by a camera coupled to a frame of and HMS in a certain location and/or orientation. One example of an automatic landmark labeling system for such images involves an additional camera that takes a frontal image of the user. The camera that takes a frontal image may be any camera that takes an image of the face of the user from an optical distance of at least 20 cm from the face. For example, the camera that takes the frontal images may be embedded in a smartphone held by the user, a webcam, and/or a camera belonging to an entertainment system (e.g., Microsoft's Kinect or a camera embedded in a TV). In another example, the camera that takes the frontal image may be a camera of another user (e.g., mounted to the other user). In still another example, the camera may be mounted to the user, such as a camera that gives an image corresponding to the line of the sight of the user, but in this case, in order to get a frontal image of the user, the user stands in front of a mirror. The frontal images of the user may be used to identify facial landmarks using algorithms known in the art. Examples of such algorithms are given below.

In order to obtain less obstructed frontal images of the user, in some embodiments, certain elements such as lenses and/or displays may be removed from the HMS when frontal images of the user are acquired. In one embodiment, in a virtual reality display, the frontal panel containing the display may be removed while training images are acquired. For example, the frontal panel of an HMS built on Oculus Rift system may be removed. In another example, images may be acquired with a HMS that involves a smartphone while the user only wears the HMS without the smartphone (e.g., a system built upon Samsung Gear without a smartphone inserted in the HMS). In another example, lenses involved in a holographic augmented reality display, such as one built on Microsoft's HoloLens may be removed while the frontal images are taken. In other embodiments, for training, a user may wear a special frame with cameras coupled to it in locations and/or orientations similar to their locations and/or orientations on an HMS, but without additional elements of the HMS that may obstruct a frontal view of the user. Optionally, corresponding images taken by cameras couples to the frame may be modified (e.g., cropped) in mimic obstructions that the views of the cameras coupled to the frame of the HMS may have, but which are not present in images acquired when the cameras are coupled to the special frame.

The frontal images of the user may be used, in some embodiments, to identify facial landmarks using one or more of the automated methods known in the art, of which some examples are given below. In one example, the location of a landmark identified in the frontal image may be mapped to a location in an image taken at the same time the frontal image was taken (e.g., within 50 milliseconds of that time), by a camera coupled to a frame of an HMS worn by the user, where the camera has a specific location on the frame and/or a specific orientation towards the user. The mapping of the locations from the frontal image to the image of the camera coupled to the frame may be done by performing a transformation (e.g., which includes a rotation and scaling) that corresponds to the specific location and/or the specific orientation.

In some embodiments, a projected grid is utilized in order to assist with the mapping of facial landmarks identified on a frontal image to locations on images taken by cameras coupled to a frame of an HMS. Optionally, the projected grid may be similar to the grids used by various depth perception systems such as ones included in Microsoft's Kinect or Intel's RealSense. In one example, the projected grid is a lattice projected in IR, such that the grid may be detected, both by a camera in a frontal position and by cameras coupled to the frame of the HMS worn by the user. After observing the location on the grid of a landmark identified in the frontal image, it is possible to identify the corresponding location on the grid on an image taken by a camera that has a different FOV (e.g., due to its close proximity and sharp angle relative to the user's face). Optionally, the camera mounted to the frame may capture an additional image that does not include the grid (e.g., taken a millisecond after the projection of the grid is performed), in order to provide an image that does not include the grid, which can be used for training the landmark detector.

Following are some examples of approaches for landmark detection known in the art, which may be used to detect landmarks in frontal images of the user. These approaches can also be adapted by one skilled in the art, or even used without any adaptation, to identify landmarks in images of a user captured by cameras coupled, at various locations and/or orientations, to a frame of an HMS worn by the user.

In some embodiments, landmarks may be identified utilizing a separate detector for each landmark (e.g., a detector for the right pupil, a detector for the left nostril, etc.) For example, the AdaBoost based detectors and its modifications have been frequently used for this task, as described in Viola and Jones, "Robust real-time face detection" in Int. Journal of Computational Vision 57(2), 151-173 (2004). Examples of various detectors for individual landmarks are given in Castrillón et al. "A comparison of face and facial feature detectors based on the Viola-Jones general object detection framework" in Machine Vision and Applications 22.3 (2011): 481-494.

In other embodiments, when identifying locations of landmarks, a detector takes into account the relationship between multiple landmarks, such as pairwise distances between multiple landmarks. In one example, a variant of the Active Appearance Models (AAM), described in Cootes, et al. "Active appearance models", IEEE Transactions on Pattern Analysis & Machine Intelligence 6 (2001): 681-685, may be used for identifying landmarks An AAM uses a joint statistical model of appearance and shape. Detectors that utilize AAM can identify a dense set of facial features, allowing extraction of whole contours of facial parts like eyes, etc. In another example, detecting landmarks in images depicting portions of a face may be done utilizing a detector of facial landmarks based on the Deformable Part Models, as described in Uřičář et al., "Detector of facial landmarks learned by the structured output SVM", VISAPP 12 (2012): 547-556. Uřičář et al. treat the task of landmark detection as an instance of the structured output classification problem and learn the parameters of the detector from data by the Structured Output Support Vector Machines algorithm (that receives labeled images as a training set). In yet another example, a detector for facial landmarks may utilize a graph matching approach, such as the one described in Zhou et al. "Exemplar-based Graph Matching for Robust Facial Landmark Localization", in IEEE International Conference on Computer Vision (ICCV), 2013.

After landmarks are detected on images from video streams of one or more cameras coupled to a frame of an HMS, these landmarks can be used to devise various feature values. In one example, the absolute location of a certain landmarks may be converted into a feature value. For example, the location of a pixel representing the center of a landmark (e.g., the edge of the mouth) may be used as a feature value. In another example, the difference between two or more landmarks may be converted into a feature value. For example, a feature value may correspond to the distance between the edge of the nostril and the edge of the lips (for a certain side of the face). In still another example, a set of landmark locations may be converted into feature values (e.g., by projecting the data according to eigenvectors found with PCA).

In some embodiments, feature values may involve landmarks in multiple corresponding images. For example, a feature value may correspond to the difference in height between the left and right eyebrows, when the landmark of each eyebrow appears in a different image (e.g., the landmarks for the left and right eyebrows appear in images taken by up-facing cameras couple to a frame to the left and right of the user's nose, respectively). Optionally, in order to derive features from landmarks in multiple images taken with different cameras, the images may be combined in various ways, and the features are derived from an image representing the combination of the multiple images. For example, the multiple images may be stitched one after the other, or arranged in a certain 2D arrangement, and distances between different landmarks may be determined according to their distance in the combined image. In another example, multiple partial images of a face may be combined into a single image by mapping the multiple images to a 3D mesh model, as described above in this disclosure.

In some embodiments, feature values may involve landmarks in sequential images, such as images taken at different times by the same camera. Such features can track how the location of certain landmarks changes with time, in order to help identify certain action units and/or facial expressions.

Determining emotional response and/or modelling facial expressions may involve feature values that rely on identification of certain types of facial movements that can change the appearance of the face, which are referred to as Action Units. Ekman and Friesen "The Facial Action Coding System: A Technique For The Measurement of Facial Movement", Consulting Psychologists Press, Inc., San Francisco, Calif., 1978, describe the Facial Action Coding System (FACS) for describing facial expressions by action units (AUs). Of 44 FACS AUs that they defined, 30 AUs are anatomically related to the contractions of specific facial muscles: 12 are for upper face, and 18 are for lower face. AUs can occur either singly or in combination. When AUs occur in combination they may be additive, in which the combination does not change the appearance of the constituent AUs, or non-additive, in which the appearance of the constituents does change. Although the number of atomic action units is relatively small, a large number of combinations of AUs may be observed. FACS provides descriptive power often needed to describe the details of facial expression. In some embodiments, other methods of taxonomizing human facial movement may be used, one of them being an updated version of FACS described in Ekman et al., "Facial Action Coding System: The Manual on CD ROM", *A Human Face*, Salt Lake City, 2002.

There are various methods known in the art that may be used to identify AUs from video streams. While the methods are typically utilized for full frontal views of faces, as discussed above with regards to facial landmarks, these methods can be used without change, or with slight modifications that would be known to one skilled in the art, in order to identify action units in images taken by cameras coupled to a frame of an HMS as described in this disclosure. The main difference between using these approaches for identifying AUs from images taken by cameras coupled to a frame of an HMS, and the way they are used in the examples below, would be the nature of the training set provided. For example, instead of involving video images of full frontal views of faces, the training images would typically include images from video streams generated by the cameras coupled to frame, which may be different in their nature (e.g., include portions of the face and/or displaying the face from perspectives that are significantly different from a frontal view). Nonetheless, even with the different type of images, the algorithmic steps described in the references below can be used with the different type of images.

Following are some examples of algorithmic approaches that may be used by an action unit identifier; other approaches, not mentioned below, may also be utilized in some embodiments described herein. The approaches below include both static modeling, which is typically posed as a discriminative classification problem in which each video frame is evaluated independently, and temporal modeling, in which frames are segmented into sequences and typically modeled together in order to identify AUs occurring over multiple frames.

In one example, identifying AUs may be done utilizing one or more of the methods described in Bartlett, et al., "Measuring facial expressions by computer image analysis", in Psychophysiology, 36:253-264, 1999. Bartlett et al. describe applications of computer image analysis to the problem of automatically detecting facial actions in sequences of images. They compare three approaches: holistic spatial analysis, explicit measurement of features such as wrinkles, and estimation of motion flow fields. The three methods were also combined in a hybrid system that classified six upper facial actions.

In another example, identifying AUs may be done utilizing one or more of the methods described Tian et al. "Recognizing Action Units for Facial Expression Analysis", in IEEE Transactions on Pattern Analysis and Machine Intelligence, 23.2 (2001): 97-115. Tian et al. describe an Automatic Face Analysis (AFA) system to analyze facial expressions based on both permanent facial features (brows, eyes, mouth) and transient facial features (deepening of facial furrows). The AFA system recognizes fine-grained changes in facial expression into action units (AUs) of the Facial Action Coding System (FACS), instead of a few prototypic expressions. Multi-state face and facial component models are proposed for tracking and modeling the various facial features, including lips, eyes, brows, cheeks, and furrows.

In still another example, identifying AUs may be done utilizing one or more of the methods described in Valstar and Pantic, "Fully automatic facial action unit detection and temporal analysis", in IEEE Conference on Computer Vision and Pattern Recognition Workshop, 2006. Valstar and Pantic describe methods in which AUs are identified using a set of spatio-temporal features calculated from tracking data for 20 facial landmarks points that are detected using a facial point localization method that uses individual feature GentleBoost templates built from Gabor wavelet features. Additionally, the facial landmarks are tracked using a particle filtering scheme that uses factorized likelihoods and a model that combines a rigid and a morphological model. The AUs displayed in the input video and their temporal segments are identified by Support Vector Machines trained on a subset of most informative spatio-temporal features selected by AdaBoost.

In still another example, identifying AUs may be done utilizing one or more of the methods described in Bihan, et al., "Action unit detection using sparse appearance descriptors in space-time video volumes", in IEEE International Conference on Automatic Face & Gesture Recognition and Workshops (FG 2011), 2011. Bihan et al. describe various methods for identifying AUs, which involve Local Binary Patterns (LBP) or Local Phase Quantization (LPQ). Since facial expressions (and the AUS they involve) are inherently dynamic processes, the method include temporal extensions of LBP and LPQ to account for the temporal dynamics.

As the examples above demonstrate, a common approach used in many action unit (AU) identification algorithms involves the training of machine learning-based models using a training set of annotated images, which are images for which the relevant AUs are identified. After training such a model, new images may be provided to a detector that utilizes the model in order for it to identify AUs. The fact that the images and AUs involve faces is typically accounted for by the nature for the training set of images and annotations that are provided. Therefore, in some embodiments, the algorithms known in the art may be utilized "as is", or utilized after slight modifications that would be apparent to one skilled in the art, in order to identify AUs in images obtained by cameras that are coupled to a frame of an HMS worn by a user. One example of a modification that may be done is to utilize different preprocessing steps. For example, instead of using a landmark identification algorithm designed for full frontal images of a face, an approach suitable for identifying landmarks in images taken with cameras coupled to the frame of the HMS may be used.

In some embodiments, an AU identifier is a module that receives a set of images comprising one or more images taken by one or more cameras coupled to a frame of an HMS worn by a user and identifies which AUs are expressed in the images. The AU identifier utilizes a machine learning-based algorithm that is trained to identify AU in the images taken by the camera. Optionally, the one or more camera are described above in this disclosure, and they generate the one or more video streams mentioned above. For example, a camera from among the one or more cameras may be coupled to the frame at a location that is to the right of the symmetry axis that divides the face to the right and left sides, and is less than 10 cm away from the middle of the user's right eyebrow. In another example, the camera may be coupled to the frame at a location that is to the right of the symmetry axis and less than 10 cm away from the user's right upper lip. In a similar manner to these examples, the camera may be coupled to locations on the left side of the face as well.

In one embodiment, AUs are identified from samples, with each sample being derived from a set of images taken from a single camera. For example, the set of images may include sequential images taken during a certain period (e.g., 0.5 seconds) from a certain camera coupled to a frame of an HMS worn by a user. It is to be noted, that due to the dynamic nature of AUs, at least some of the features may be derived from multiple temporally successive images, e.g., to reflect properties related to facial movements involved in AUs.

In another embodiment, AUs are identified from samples, with each sample being derived a set of images taken from multiple cameras. For example, the set of images may include sequential sets of corresponding images taken during a certain period (e.g., 0.5 seconds) from multiple cameras coupled to a frame of an HMS worn by a user. In this example, each camera is coupled to the frame at a certain location and/or has a certain orientation to the face, which is different from the location and/or orientation of the other cameras. When features are extracted in order to identify the action units, they may be extracted from each image independently and/or jointly from multiple images (in a similar fashion to the way described above in which features may be generated for landmark identification). Additionally or alternatively, as explained above, certain feature values may be extracted from multiple temporally successive images, e.g., to reflect properties related to facial movements involved in AUs.

In some embodiments, images in a training set used to train the AU identifier may contain images of multiple users, in multiple conditions (e.g., different lighting conditions) and/or while making different facial expressions (e.g., expressing different emotions). Having a diverse set of images included the training set of a landmark detector can help improve its generalizability, making it more likely to accurately identify landmarks in unseen images that were not included in the training set. In other embodiments, images in a training set used to train the AU identifier may mostly contain images of a certain user in order to train an AU identifier that works well with images of the certain user.

Obtaining images for a training set for training the AUs identifier is typically straightforward and involves acquiring images of a user's face from cameras coupled to a frame of an HMS while the user wears the frame. These images may be converted to samples comprising feature values. The feature values may include various types such as features derived from locations of landmarks in the images and/or low-level features described above, such as features derived using Gabor filters, local binary patterns and their derivatives, features derived using algorithms such as SIFT, SURF, and/or ORB, image keypoints, HOG descriptors, and features derived using PCA or LDA. Other examples of features may include features derived from multiple images taken at different times, such as volume local binary patterns (VLBP), cuboids, and/or optical strain-based features. In addition to deriving feature values from images, for training, samples derived from the images need to be assigned with the locations of the facial landmarks on the images. Labels may be provided in different embodiments in various ways. Some examples are given below.

In one embodiment, labels are marked by an expert. For example, the expert may be a human that views images taken by one or more camera coupled to a frame of an HMS at a certain location and/or orientation and indicates which AUs appear to have occurred in the images. For example, the expert may mark identify which AUs were expressed in images. Optionally, the human expert may view frontal images of the user taken at the same time as the images from the cameras coupled to the HMS were taken, and determine which AUs occurred based on those images. A human expert may be more capable of accurately determining AUs from the standard frontal images that are more frequently encountered in the art.

In one embodiment, some of the images provided for training may be premeditated. For example, a user may be asked to move certain facial muscle and/or make certain facial expressions while the images are taken by the one or more cameras coupled to the frame. In such a case, the labels (i.e., which AUs occurred) may be assumed to be the AUs the humans typically perform when moving the certain facial muscles and/or making the certain facial expressions.

In other embodiments, an automatic labeling method may be employed to identify AUs in a set of images comprising one or more images taken by one or more cameras coupled to a frame of an HMS worn by a user. One example of an automatic AU labeling system for such images involves an additional camera that takes frontals image of the user. The camera that takes frontal images may be any camera that takes images of the face of the user from an optical distance of at least 15 cm from the face. For example, the camera that takes the frontal images may be embedded in a smartphone held by the user, a webcam, and/or a camera belonging to an entertainment system (e.g., Microsoft's Kinect or a camera embedded in a TV). In another example, the camera that takes the frontal image may be a camera of another user (e.g., mounted to an HMS of the other user). In still another example, the camera may be mounted to the user, such as a camera that gives an image corresponding to the line of the sight of the user, but in this case, in order to get a frontal image of the user, the user stands in front of a mirror. The frontal images of the user may be used to identify AU using algorithms known in the art. Examples of such algorithms are given above. Optionally, in order to obtain less obstructed frontal images of the user, in some embodiments, certain elements such as lenses and/or displays may be removed from the HMS when frontal images of the user are acquired, as discussed above in the discussion related to obtaining frontal images for training a landmark identifier.

Given training samples and corresponding labels describing the AUs appearing in the images from which the samples are derived, various machine learning algorithms may be used to train the AU identifier, such as SVMS, multiple kernel learning, and/or other machine learning algorithms known in the art. The AU identifier may then be used to identify AUs in samples derived from images for which the label (AU) is unknown.

Determining emotional response and/or modelling (and rendering) facial expressions may involve feature values that express the extent different basic facial expressions are being expressed by the user. That is, every facial expression the user makes may be approximated by a combination (e.g., a linear combination) of the basic expressions. Optionally, each basic expression may represent a certain 3D model of a face expressing the basic expression. One family of models that are formulated according to this principle are blendshape models.

A blendshape model generates a facial pose as a linear combination of a number of facial expressions, the blendshape "targets". By varying the weights of the linear combination, a range of facial expressions can be expressed with little computation. The set of shapes can be extended as desired to refine the range of expressions that the character can produce. One advantage that some blendshapes models have is that blendshapes have asemantic parameterization: the weights have intuitive meaning corresponding to the strength or influence of the various facial expressions. Additionally, to some extent blendshapes force facial expressions to stay "on model", that is, arbitrary deformations to the face are not possible with these models. This helps to maintain facial character and avoid deformation artifacts that may occur while rendering an avatar to mimic a user's facial expressions. Blendshapes are discussed in further detail in Lewis et al., "Practice and Theory of Blendshape Facial Models", in EUROGRAPHICS 2014.

One example of a blenedshape model, which may be utilized in some embodiments, is given by Bouaziz et al., "Online modeling for real-time facial animation", in ACM Transactions on Graphics (TOG), 32.4 (2013): 40. The blendshape model of Bouaziz et al. includes a set of blendshape meshes $B=[b_0, \ldots, b_n]$, where $b_0$ is the neutral pose and the for i>0 define specific base expressions. All blendshapes have the same static mesh combinatorics and are represented by stacked coordinate vectors. A new facial expression is generated a weighted function $F(x)=b_0+\Delta Rx$, where $\Delta B=[b_1-b_0, \ldots, b_n-b_0]$, and $x=[x_1, \ldots, x_n]^T$ are blendshape weights bounded between 0 and 1. The blendshape representation may be well suited, in some embodiments, for real-time performance capture because it may reduce tracking to estimating the rigid head alignment and then blendshape weights for each frame. Optionally, the blendshapes $b_i$ can be chosen to match predefined semantics of common face animation controllers, e.g., mouth-open, smile, frown, etc., which may simplify certain processes as post-editing and animation retargeting.

In some embodiments, blendshape weights are derived from images generated by one or more video streams, with each video stream being generated by a camera coupled to a frame of an HMS worn by a user. From the blendshape weights one or more feature values are derived which represent the facial expression of the user. Optionally, the blendshape weights may serve as feature values. Additionally or alternatively, the feature values may be functions of the blendshape weights. As described in Bouaziz et al. above, and in other references mentioned in this disclosure, determining blendshape weights typically utilizes frontal facing cameras that may optionally have depth measuring capabilities (e.g., RGB-D cameras or systems that use IR grids, such as Microsoft's Kinect). Many of the embodiments described herein involve cameras that are coupled a frame of an HMS and are close to the face and/or are oriented at an angle that does not provide a frontal view of the face. When the input of images from video streams come from such cameras coupled to the frame, approaches known in the art for determining blendshape weights may not work well, or may not be applicable at all due to the different nature of the images (compared to the type of images the approaches were originally designed for). Therefore, in order to be able to assign blendshape weights that represent a facial expression of a user from images of the user taken with the one or more cameras coupled to the frame of an HMS worn by the user, in some embodiments, the blendshape weights are predicted utilizing a blendshape weight predictor.

In one embodiment, the blendshape weight predictor is a machine learning-based predictor that receives samples comprising feature values that are derived from images taken with the one or more cameras coupled to a frame of an HMS worn by a user. The blendshape weight predictor computes, based on the feature values, weights of one or more blendshapes that correspond to the facial expression depicted in the images taken with the one or more cameras. Optionally, the feature values may be various features described in this disclosure. Examples of the features include high-level facial-related feature values and their derivatives such as location and dimensions of facial features and/or landmarks, and/or identification of action units (AUs) or microexpressions in images. Other examples of features include various low-level features such as features derived using Gabor filters, local binary patterns (LBP) and their derivatives, HOG descriptors, features derived using algorithms such as SIFT, SURF, and/or ORB, image keypoints, and features derived using PCA or LDA. Additional examples of features may also include features derived from multiple images taken at different times, such as volume local binary patterns (VLBP), optical strain-based features, and/or cuboids that are described in this disclosure.

In one embodiment, training a blendshape weight predictor can be done according to the teachings of Romera-Paredes et al., "Facial expression tracking from head-mounted, partially observing cameras", in IEEE International Conference on Multimedia and Expo (ICME), 2014. Romera-Paredes et al. derive feature values from images of cameras coupled to an HMS to extract features (e.g., LBP described in this disclosure). Ground-truth values of blendshape weights are obtained using a Kinect camera. They also explore various machine learning algorithms that may be used to create the predictor of blendshape weights.

Facial microexpressions are rapid involuntary facial expressions that may reveal suppressed affect. These are typically very rapid (e.g., ¼ to 1/25 of a second) involuntary facial expressions which give a brief glimpse to feelings that people have, but may be trying not to express. In some embodiments, microexpressions are identified from images generated by one or more video streams, with each video stream being generated by a camera coupled to a frame of an HMS worn by a user. Optionally, the microexpressions are identified by a module called a microexpression identifier. Optionally, identified microexpressions may be utilized to derive feature values that may be utilized for various applications such as determining emotional response and/or rendering an avatar expressing facial expressions of a user. Thus, in some embodiments, microexpressions may serve as feature values in a similar capacity to facial landmarks, action units, and/or blendshape weights, which are mentioned above. Additionally or alternatively, the microexpressions themselves may be an end product of a system in some embodiments described herein. An example of such a system may be a system that is configured to identify certain microexpre ssions from video streams generated by a plurality of cameras coupled to a frame of an HMS worn by a user.

In one embodiment, the microexpression identifier is a machine learning-based predictor that receives samples comprising feature values that are derived from images taken with the one or more cameras coupled to a frame of an HMS worn by a user. The microexpression identifier determines, based on the feature values, which microexpressions were expressed in the images taken with the one or more cameras, where the feature values may be various high-level and low-level features described in this disclosure, or other types of features derived from images. Examples of high-level features include facial-related values and their derivatives such as location and dimensions of facial features and/or landmarks, and/or identification of action units (AUs) in images. Other examples of features include low-level features such as features derived using Gabor filters, local binary patterns and their derivatives, features derived using algorithms such as SIFT, SURF, and/or ORB, image keypoints, HOG descriptors, and features derived using PCA or LDA. Other examples of features include features derived from multiple images taken at different times, such as volume local binary patterns (VLBP), optical strain-based features, and/or cuboids that are described in this disclosure. Additional examples of types of features, and how they may be used for identification of microexpressions is given in the examples below describing methods known in the art for identifying microexpressions.

There are various methods known in the art that may be used to identify microexpressions from video streams. While the methods are typically utilized for full frontal views of faces, these methods may be adapted by one skilled in the art, in order to identify microexpressions in images taken by cameras coupled to a frame of an HMS as described in this disclosure. The main difference between the way these approaches are used in the examples below, and how they are used in embodiments herein, would be the nature of the training set provided. For example, instead of involving video images of full frontal views of faces, the training images would typically include images from video streams generated by the cameras coupled to frame, which may be different in their nature (e.g., include portions of the face and/or displaying the face from perspectives that are significantly different from a frontal view). Additionally, different types of features and/or feature extraction techniques may be utilized in order to provide feature values from images taken by cameras coupled to the frame of the HMS.

Following are some examples of algorithmic approaches that may be used by an action unit identifier; other approaches, not mentioned below, may also be utilized in some embodiments described herein.

In one example, identifying microexpressions may be done utilizing the teachings of Pfister et al. "Recognising spontaneous facial micro-expressions", in IEEE International Conference on Computer Vision (ICCV), 2011. Pfister et al. introduce a framework that involves temporal interpolation to counter short video lengths, spatiotemporal local texture descriptors (e.g., LBP-TOP mentioned further below) to handle dynamic features and various machine learning approaches, such as SVMS, multiple kernel learning and random forests to classify sets of images to microexpression categories. In addition, Pfister describe a protocol for collecting a training corpus of expressions that are involuntary, and introduce temporal interpolation using graph embedding to enable identification of microexpressions with images from a standard 25 fps camera.

In another example, identifying microexpressions may be done utilizing the teachings of Shreve et al., "Macro- and micro-expression spotting in long videos using spatio-temporal strain", in IEEE International Conference on Automatic Face & Gesture Recognition and Workshops, 2011.

Shreve et al. introduce features based on the strain impacted on the facial skin due to the nonrigid motion caused during facial expressions. The strain magnitude is calculated using the central difference method over the robust and dense optical flow field observed in facial regions a user's face.

In yet another example, identifying microexpressions may be done utilizing the teachings of Wang et al., "Face recognition and micro-expression recognition based on discriminant tensor subspace analysis plus extreme learning machine", in Neural processing letters 39.1 (2014): 25-43. Wang et al. describe a recognition technique for microexpressions that is based on Discriminant Tensor Subspace Analysis (DTSA) and Extreme Learning Machine (ELM). 2D face images are first dimensionally reduced using DTSA to generate discriminant features, then the reduced features are fed into the ELM classifier to analytically learn an optimal model for recognition.

In still another example, identifying microexpressions may be done utilizing the teachings of Lu et al., "A Delaunay-Based Temporal Coding Model for Micro-expression Recognition", in Computer Vision-ACCV 2014 Workshops. Lu et al. describe a Delaunay triangulation-based temporal coding model (DTCM), which is used to generate features that encode texture variations corresponding to muscle activities on face due to dynamical microexpressions.

As the examples above demonstrate, a common approach used in many microexpression identification algorithms involves the training of machine learning-based models using a training set of annotated sequences of images, which are sequences of images for which the relevant microexpressions are identified. After training such a model, new images may be provided to a microexpression detector that utilizes the model in order for it to identify microexpressions. The fact that the images and microexpression involve faces is typically accounted for by the nature for the training set of images and annotations that are provided. Therefore, in some embodiments, the algorithms known in the art may be utilized after modifications that would be apparent to one skilled in the art, in order to identify microexpressions in images obtained by cameras that are coupled to a frame of an HMS worn by a user. One example of a modification that may be done is to utilize various preprocessing steps, such as identifying landmarks, which are suitable for images taken with cameras coupled to the frame of the HMS, and are described above.

In some embodiments, a microexpression identifier is a module that receives a set of images comprising one or more images taken by one or more cameras coupled to a frame of an HMS worn by a user and identifies which microexpression (if any) was expressed in the set of images. The microexpression identifier may utilize a machine learning-based algorithm that is trained to identify microexpressions in a set of images taken by the camera. Typically, the set of images comprises images taken during a period of at least 0.05 seconds, and at most, 0.5 seconds. Optionally, the microexpression identifier may process images in a sliding window on a video stream (i.e., a temporal window of a certain length that spans a certain portion of the stream). Thus, a given video stream may be evaluated many times in order to identify microexpressions, when each time, a different portion (window) is evaluated.

In one embodiment, one or more cameras, as described above, generate one or more video streams as mentioned above. For example, a camera from among the one or more cameras may be coupled to the frame at a location that is to the right of the symmetry axis that divides the face to the right and left sides, and is less than 10 cm away from the middle of the user's right eyebrow. In another example, the camera may be coupled to the frame at a location that is to the right of the symmetry axis and less than 10 cm away from the user's right upper lip. In a similar manner to these examples, the camera may be coupled to locations on the left side of the face as well.

In one embodiment, microexpressions are identified from samples, with each sample derived from a set of images taken from a single camera. For example, the set of images may include sequential images taken during a certain period (e.g., 0.5 seconds) from a certain camera coupled to a frame of an HMS worn by a user. It is to be noted, that due to the dynamic nature of AUs, at least some of the features may be derived from multiple temporally successive images, e.g., to reflect properties related to facial movements involved in microexpressions.

In another embodiment, microexpressions are identified from samples, with each sample derived from a set of images taken from multiple cameras. For example, the set of images may include sequential sets of corresponding images taken during a certain period (e.g., 0.5 seconds) from multiple cameras coupled to a frame of an HMS worn by a user. In this example, each camera is coupled to the frame at a certain location and/or has a certain orientation to the face, which is different from the location and/or orientation of the other cameras. When features are extracted in order to identify the microexpressions, they may be extracted from each image independently and/or jointly (in a similar fashion to the way described above in which features may be generated for landmark identification). Additionally or alternatively, as explained above, certain feature values may be extracted from multiple temporally successive images, e.g., to reflect properties related to facial movements involved in microexpressions.

In some embodiments, images in a training set used to train the microexpression identifier may contain images of multiple users, in multiple conditions (e.g., different lighting conditions) and/or while making different facial expressions (e.g., expressing different emotions). Having a diverse set of images included the training set of a landmark detector can help improve its generalizability, making it more likely to accurately identify landmarks in unseen images that were not included in the training set. In other embodiments, images in a training set used to train the microexpression identifier may mostly contain images of a certain user in order to train a microexpression identifier that works well with images of the certain user.

Obtaining images for a training set for training the microexpression identifier is typically straightforward and involves acquiring images of a user's face from cameras coupled to a frame of an HMS while the user wears the frame. However, due to the involuntary nature of microexpressions, and their short durations, getting images from periods of times in which a user expresses a genuine microexpression may be challenging. Some of the approaches that may be used in some embodiments to collect microexpressions that may be used (possibly after adaptations to include cameras coupled to a frame of an HMS) are discussed in Li et al. "A spontaneous microexpression database: Inducement, collection and baseline", in the 10th IEEE International Conference and Workshops on Automatic Face and Gesture Recognition (FG), 2013, and the references mentioned therein.

Once training images are acquired, they may be converted to samples comprising feature values. The feature values may include various types such as features derived from locations of landmarks, identified action units, blendshape weights and/or low-level features described below, such as features derived using Gabor filters, local binary patterns and their derivatives, features derived using algorithms such as SIFT, SURF, and/or ORB, image keypoints, HOG descriptors, and features derived using PCA or LDA. Additional examples of features may also include features derived from multiple images taken at different times, such as volume local binary patterns (VLBP), optical strain-based features, and/or cuboids that are described in this disclosure. In addition to deriving feature values from images, for training, samples derived from the images need to be assigned with the locations of the facial landmarks on the images. Labels may be provided in different embodiments in various ways. Some examples are given below.

In one embodiment, labels are marked by an expert. For example, the expert may be a human that views images taken by one or more camera coupled to a frame of an HMS at a certain location and/or orientation and indicates which microexpressions were expressed. For example, the expert may mark identify which microexpressions were expressed in images. Optionally, the human expert may view frontal images of the user taken at the same time as the images from the cameras coupled to the HMS were taken, and determine which microexpressions were expressed in those images. A human expert may be more capable of accurately determining microexpressions from the standard frontal images that are more frequently encountered in the art.

In one embodiment, some of the images provided for training may be premeditated. For example, a user may be asked to move certain facial muscle and/or make certain facial expressions while the images are taken by the one or more cameras coupled to the frame.

In other embodiments, an automatic labeling method may be employed to identify microexpressions in a set of images comprising sequences of images taken by one or more cameras coupled to a frame of an HMS worn by a user. One example of an automatic microexpression labeling system for such images involves an additional camera that takes frontals image of the user. The camera that takes frontal images may be any camera that takes images of the face of the user from an optical distance of at least 15 cm from the face. For example, the camera that takes the frontal images may be embedded in a smartphone held by the user, a webcam, and/or a camera belonging to an entertainment system (e.g., Microsoft's Kinect or a camera embedded in a TV). In another example, the camera that takes the frontal image may be a camera of another user (e.g., mounted to an HMS of the other user). In still another example, the camera may be mounted to the user, such as a camera that gives an image corresponding to the line of the sight of the user, but in this case, in order to get a frontal image of the user, the user stands in front of a mirror. The frontal images of the user may be used to identify microexpressions using algorithms known in the art. Examples of such algorithms are given above. Optionally, in order to obtain less obstructed frontal images of the user, in some embodiments, certain elements such as lenses and/or displays may be removed from the HMS when frontal images of the user are acquired, as discussed above in the discussion related to obtaining frontal images for training a landmark identifier.

Given training samples and corresponding labels describing the microexpressions appearing in the images from which the samples are derived, various machine learning algorithms may be used to train the microexpression identifier, such as SVMS, multiple kernel learning, and/or other machine learning algorithms known in the art. The microexpression identifier may then be used to identify microexpressions in samples derived from images for which the label (microexpression) is unknown.

Some embodiments may involve use of a potentially large number of features to represent images and/or sets of images, as described in the examples above. In order to increase computational efficiency and/or improve performance, feature selection is utilized, in some embodiments, to reduce the number of features. Feature selection may also be referred to hereinbelow as "dimensionality reduction". Feature selection may involve techniques that create new features from other features (e.g., various projection methods or PCA described below). Additionally or alternatively, feature selection may involve selection of a subset of existing features that includes relevant features for the task at hand (e.g., recognizing facial expressions and/or emotions or mapping expressions to a facial model). Many feature dimensionality reduction techniques have been proposed in the literature. Among them, Principal Component Analysis (PCA) has been widely used for feature reduction in face recognition research for decades. Another example of a feature reduction technique known in the art that may be used in some embodiments is Fisher Linear Discriminant (FLD). FLD attempts to project the most discriminative features for class distinction. Other examples of approaches that involve selection of a subset of the possible features, which are known in the art and may be used in some embodiments include branch and bound, sequential selection, mutual information (MI), Minimum Redundancy Maximum Relevance (mRMR), or evolutionary approaches such as Particle Swarm Optimization (PSO). Additional discussion regarding features selection and/or generation techniques that may be used for vision-related application are described in Neoh et al., "Intelligent facial emotion recognition using a layered encoding cascade optimization model", Applied Soft Computing 34 (2015): 72-93. Bartlett et al. "Recognizing facial expression: machine learning and application to spontaneous behavior", in Computer Vision and Pattern Recognition, 2005 (CVPR 2005), IEEE Computer Society Conference on. Vol. 2, pp. 568-573, also describe various feature selection approaches that may be used in detection of facial expressions, such as selection using AdaBoost and/or reduction of dimensionality using principal component analysis (PCA).

Given feature values extracted from images of video streams, as described above, various machine learning models may be trained and utilized for identifying facial expressions in various ways. Some examples of machine learning-based approaches for identifying facial expressions were given in the references that discussed types of feature values (e.g., facial landmarks and action units). Following are some examples of approaches that may be utilized by one skilled in the art (possibly with slight modifications as described above) in embodiments described herein.

In one example, methods following the teachings of Bartlett, et al. "Recognizing facial expression: machine learning and application to spontaneous behavior", in Computer Vision and Pattern Recognition, 2005 (CVPR 2005), IEEE Computer Society Conference on. Vol. 2, pp. 568-573, may be used. Bartlett et al. describe experiments in which various approaches such as support vector machines (SVMs), linear discriminant analysis (LDA), and/or AdaBoost were used successfully for this task.

In another example, machine learning methods descried in Littlewort, et al. "Dynamics of facial expression extracted automatically from video", in Image and Vision Computing 24.6 (2006): 615-625, may be used to facial expressions. Littlewort et al. describe fully automatic recognition of facial expressions, using diverse machine learning approaches including AdaRoost, support vector machines, and linear discriminant analysis.

In still another example, methods adapted from the teachings of El Kaliouby and Robinson, "Real-time inference of complex mental states from facial expressions and head gestures", in Real-time vision for human-computer interaction, Springer US, 2005, pages 181-200, may be utilized for identifying facial expressions and/or emotional response. El Kaliouby and Robinson describe systems in which video input is abstract into different levels, each representing head and facial events at different granularities of spatial and temporal abstraction. Dynamic Bayesian Networks are used to model the unfolding of head and facial displays, and corresponding mental states over time. The system's recognition accuracy and real-time performance is described for six classes of complex mental states: agreeing, concentrating, disagreeing, being interested, thinking, and being unsure.

In yet another example, methods adapted from the teachings of Fanelli et al. "Hough forest-based facial expression recognition from video sequences", in Trends and Topics in Computer Vision, Springer Berlin Heidelberg (2012), pp: 195-206, may be used to identify facial expressions from image sequences. Fanelli et al. utilize a Hough transform voting method based on randomized forests in order to determine what facial expressions are displayed in a sequence of images.

Tasks involving determining facial expressions and/or emotional response may be considered, in some embodiments, to involve a predictor. In some embodiments, a module that receives a query that includes a sample (e.g., a vector of one or more feature values), and predicts a label for that sample (e.g., a class associated with the sample), is referred to as a "predictor". A sample provided to a predictor in order to receive a prediction for it may be referred to as a "query sample" or simply a "sample". A value returned by the predictor, which it computed from a sample given to it as input, may be referred to hereinbelow as a "label" and/or a "predicted value". A pair that includes a sample and a corresponding label may be referred to as a "labeled sample". A sample that is used for training a predictor may be referred to as a "training sample" or simply a "sample". Similarly, a sample that is used for testing a predictor may be referred to as a "testing sample" or simply a sample. In typical embodiments, samples used for various purposes (e.g., training, testing, and/or a query) are assumed to have a similar structure (e.g., similar dimensionality) and are assumed to be generated in a similar process (e.g., they all undergo the same type of preprocessing). Optionally, a sample for a predictor (e.g., a sample used as training data and/or a query sample) includes a description of one or more feature values. Optionally, at least some of the feature values are numerical values (e.g., integer and/or real values). Optionally, at least some of the feature values may be categorial values that may be represented as numerical values (e.g., via indexes for different categories). Optionally, feature values comprised in a sample may be represented as a vector of values.

Various preprocessing, processing, and/or feature extraction techniques known in the art may be used to generate the one or more feature values comprised in a sample. Additionally, in some embodiments, samples may contain noisy or missing values. There various methods known in the art that may be used to address such cases. It is to be noted that many of the examples given above of machine learning-based algorithms known in the art, such as algorithms for identifying landmarks, action units, and/or facial expressions involve predictors as the term is described above.

In some embodiments, a predictor receives a sample that includes feature values generated based on one or more images from one or more video streams of one or more cameras coupled to a frame of an HMS worn by a user. Optionally, based on an evaluation of the sample, the predictor returns a label indicating a facial expression the user expressed. Such a predictor may be referred to hereinbelow as a facial expression predictor. Optionally, based on an evaluation of the sample, the predictor returns a label indicating an emotional response of the user. Such a predictor may be referred to hereinbelow as emotional response predictor (ERP). Samples provided to such predictors may include feature values that include values of one or more of the high-level and/or low-level features described in this disclosure and/or in the references mentioned in this disclosure, and/or are derived from one or more of those feature values. Examples of the high-level features include facial-related values and their derivatives such as location and dimensions of facial features and/or landmarks, and/or identification of action units (AUs) in images. Additional examples of high-level features include blendshape weights and microexpressions. Examples of low level features that may be used include low-level features include features derived using Gabor filters, local binary patterns and their derivatives, features derived using algorithms such as SIFT, SURF, and/or ORB, image keypoints, HOG descriptors, and features derived using PCA or LDA. Similarly, the features may include features derived from multiple images taken at different times, such as volume local binary patterns (VLBP), optical strain-based features.

It is to be noted that since facial expressions typically indicate emotional response, in some embodiments, the terms "facial expression" and "emotional response" may be used interchangeably. Similarly, in those embodiments, the terms "facial expression predictor" and "emotional response predictor" may be used interchangeably. The main difference between the way the terms "facial expression" and "emotional response" are typically used hereinbelow is that emotional response may be something that in some embodiments is measured over a longer period of time (e.g., seconds, minutes, hours, days, or even longer). For example, emotional response may be based on multiple facial expressions identified over time. Additionally, in some embodiments, a sample for predictor of emotional response may include, in addition to feature values derived from images taken by cameras, other feature values generated based on data from other sources, as described below (though in some embodiments a sample fir facial expression predictor may also include feature values generated based on data from other sources).

In some embodiments, a label that may serve as prediction value for a query sample provided to a predictor, may take one or more types of values. For example, a label maybe include a discrete categorial value (e.g., a category describing an emotional response or one or more AUs), a numerical value (e.g., a real number describing the extent a certain emotion was expressed), and/or a multidimensional value (e.g., a point in multidimensional space, a database record, and/or another sample).

Emotional responses, such as labels returned by an emotional response predictor, may be represented by various types of values in embodiments described herein. In one embodiment, emotions are represented using discrete categories. For example, the categories may include three emotional states: negatively excited, positively excited, and neutral. In another example, the categories may include emotions such as happiness, surprise, anger, fear, disgust, and sadness. In still another example, the emotions may be selected from the following set that includes basic emotions, including a range of positive and negative emotions such as Amusement, Contempt, Contentment, Embarrassment, Excitement, Guilt, Pride in achievement, Relief, Satisfaction, Sensory pleasure, and Shame, as described by Ekman P (1999), "Basic Emotions", in Dalgleish Power, Handbook of Cognition and Emotion, Chichester, UK: Wiley.

In another embodiment, emotions are represented using a multidimensional representation, which typically characterizes the emotion in terms of a small number of dimensions. In one example, emotional states are represented as points in a two dimensional space of Arousal and Valence. Arousal describes the physical activation and valence the pleasantness or hedonic value. Each detectable experienced emotion is assumed to fall in a specified region in that two-dimensional space. Other dimensions that are typically used to represent emotions include potency/control (refers to the individual's sense of power or control over the eliciting event), expectation (the degree of anticipating or being taken unaware), and intensity (how far a person is away from a state of pure, cool rationality). The various dimensions used to represent emotions are often correlated. For example, the values of arousal and valence are often correlated, with very few emotional displays being recorded with high arousal and neutral valence. In one example, emotions are represented as points on a circle in a two dimensional space pleasure and arousal, such as the circumflex of emotions. In another example, emotions may be represented as points in a two dimensional space whose axes correspond to positive affect (PA) and negative affect (NA), as described by Watson et al. (1988), "Development and validation of brief measures of positive and negative affect: the PANAS scales", Journal of Personality and Social Psychology 54.6: 1063.

In yet another embodiment, emotions are represented using a numerical value that represents the intensity of the emotional state with respect to a specific emotion. For example, a numerical value stating how much the user is enthusiastic, interested, and/or happy. Optionally, the numeric value for the emotional state may be derived from a multidimensional space representation of emotion; for instance, by projecting the multidimensional representation of emotion to the nearest point on a line in the multidimensional space.

In some embodiments, a predictor may utilize a model in order to make predictions for a given query sample. A plethora of machine learning algorithms are available for training different types of models that can be used for this purpose. Many examples of machine learning models and approaches are given in the examples discussed above. In general, some of the algorithmic approaches that may be used for creating the predictor are classification, clustering, function prediction, and/or density estimation Those skilled in the art can select the appropriate type of model and/or algorithm depending on the characteristics of the training data (e.g., its dimensionality or the number of samples), and/or the type of value used as labels (e.g., discrete value, real value, or multidimensional).

In one example, classification methods like Support Vector Machines (SVMs), Naive Bayes, nearest neighbor, decision trees, logistic regression, and/or neural networks can be used to create a predictor that predicts a discrete class label. In another example, methods like SVMs for regression, neural networks, linear regression, and/or gradient boosted decision trees can be used to create a predictor for real-valued labels, and/or multidimensional labels. In yet another example, a predictor may utilize clustering of training samples in order to partition a sample space such that new query samples can be placed in clusters and assigned labels according to the clusters to which they belong. In a somewhat similar approach, a predictor may utilize a collection of labeled samples in order to perform nearest neighbor classification (in which a query sample is assigned a label according to one or more of the labeled samples that are nearest to them in some space).

In one embodiment, semi-supervised learning methods may be used to train a predictor's model, such as bootstrapping, mixture models and Expectation Maximization, and/or co-training. Semi-supervised learning methods are able to utilize as training data unlabeled samples in addition to the labeled samples.

In one embodiment, a predictor may return as a label other samples that are similar to a given query sample. For example, a nearest neighbor approach method may return one or more samples that are closest in the data space to the query sample (and thus in a sense are most similar to it.)

In another embodiment, a predictor may return a value representing a probability of a sample according to a model utilized by the predictor. For example, the value may represent a probability of the sample according to a probability density function, which is described and/or defined by the model, and assigns probability values to at least some of the samples in the space of all possible samples. For example, the predictor may be a single class support vector machine, a naïve Bayes classifier, a graphical model (e.g., Bayesian network), or a maximum entropy model.

In addition to a label predicted for a query sample, in some embodiments, a predictor may provide a value describing a level of confidence in its prediction of the label (e.g., confidence that the user had a certain emotional response or the confidence that the user expressed a certain facial expression). In some cases, the value describing the confidence level may be derived directly from the prediction process itself. For example, a predictor utilizing a classifier to select a label for a given query sample may provide a probability or score according to which the specific label was chosen (e.g., a naïve Bayes' posterior probability of the selected label or a probability derived from the distance of the sample from the hyperplane when using an SVM).

In one embodiment, a predictor making a prediction for a query sample returns a confidence interval as its prediction or in addition to a predicted label. A confidence interval is a range of values and an associated probability that represents the chance that the true value corresponding to the prediction falls within the range of values. For example, if a prediction is made according to an empirically determined Normal distribution with a mean m and standard deviation $\sigma$, the range $[m-2\sigma, m+2\sigma]$ corresponds approximately to a 95% confidence interval surrounding the mean value m.

Samples provided to a predictor and/or that are used for its training, may in some embodiments, be generated from data that may be received from various sources (in addition to cameras), and have various characteristics (e.g., the data may comprise numerical values, text, images, audio, video, and/or other types of data). Various dimensionality reduction techniques that may be used with respect to images were discussed above In some embodiments, a predictor may be described as including and/or utilizing a model. A model that is included in a predictor, and/or utilized by it, may include parameters used by the predictor to compute a prediction value. Non-limiting examples of such parameters include support vectors (e.g., used by an SVM), points in a multidimensional space (e.g., used by a Nearest-Neighbor predictor), regression coefficients, distribution parameters (e.g., used by a graphical model), topology and/or weight parameters (e.g., used by a neural network). When a model contains parameters that are used by the predictor to compute a prediction value, such as in the examples above, the terms "model" and "predictor" (and derivatives thereof) may at times be used interchangeably herein. Thus, for example, language reciting "a model that predicts" or "a model used for predicting" is acceptable. Similarly, when a discussion relates to parameters of a predictor, this may be interpreted as relating to parameters of a model used by the predictor.

The type and quantity of training data used to train a predictor's model can have a dramatic influence on the quality of the predictions made by the predictor. Generally speaking, the more data available for training a model, and the more the training samples are similar to the samples on which the predictor will be used (also referred to as test samples), the more accurate the predictions for the test samples are likely to be. Therefore, when training a model that will be used to make predictions regarding a specific user, it may be beneficial to collect training data from the user (e.g., data comprising measurements of the specific user). In such a case, the predictor may be referred to as a "personalized predictor".

Due to the wide variety in human heads and faces (e.g., various head shapes, hairlines, facial features, and pigmentation), in some embodiments, multiple predictors may be trained from data obtained from subsets of similar people. For example, there may be a separate predictor trained for bearded men, teenage Caucasian girls, or Asian men in the ages 20-40, etc. Optionally, subsets of similar users are selected according to their demographic characteristics and/or their appearance. Additionally or alternatively, users may be clustered according to images of their face and/or a model of their face, as described further below. Optionally, a model is trained for each cluster of similar users by collecting labeled images of the users belonging to each cluster or group of users, and providing the labeled images to an algorithm for training one or more of the machine learning-based predictors described herein.

In some embodiments, making predictions for a user from images of the user involves identifying one or more of the following from the images: landmarks, action units, facial expressions, and/or emotional response. Optionally, in order to make a prediction for the user, one or more suitable predictors are selected for the user from among the multiple predictors. In one example, a suitable model is selected for the user based on the user's demographic and/or appearance characteristics. For instance, if there is a predictor trained from images of males between ages 20-40, and the user is such a person, then that predictor is selected for the user. In another example, an image of the user and/or a model of the user's face may be used to find one or more clusters to which the user may belong (e.g., by applying the distance function that measures the similarity between the image and/or model of the user and representative images and/or models of clusters). Thus, in these embodiments, instead of using a predictor trained on images from a large pool of diverse people, the user may receive results of a predictor that is trained on images that are more similar to him or her, which may improve the accuracy of predictions made for the user.

Training a predictor and/or utilizing a predictor may be done utilizing various computer system architectures. In particular, some architectures may involve a single machine and/or single processor, while other architectures may be distributed, involving many processors (e.g., possibly thousands or more processors on various machines). For example, some predictors may be trained on distributed architectures such as Hadoop, utilizing distributed machine learning-based algorithms. In this example, it is possible that each processor will only have access to a portion of the training data. Another example of a distributed architecture that may be utilized in some embodiments is a privacy-preserving architecture in which users process their own data. In this example, a distributed machine learning training algorithm may allow a certain portion of the training procedure to be performed by users, each processing their own data and providing statistics computed from the data rather than the actual data itself. The distributed training procedure may then aggregate the statistics in order to generate a model for the predictor.

In some embodiments, a sample for a predictor, such as a facial expression predictor and/or an emotional response predictor, may include, in addition to feature values derived from images obtained by cameras coupled to a frame of an HMS, feature values derived from a measurement of affective response. Optionally, the measurement of affective response is obtained utilizing one or more sensors that measure a physiological signal and/or a behavioral cue of a user. Optionally, the one or more sensors used to obtain the measurement of affective response do not include a camera coupled to a frame of an HMS worn by a user.

Some examples of types of sensors that may be used to measure affective response and/or values that may be comprised in a measurement of affective response include the following: (i) Heart Rate (HR), Heart Rate Variability (HRV), and Blood-Volume Pulse (BVP), and/or other parameters relating to blood flow, which may be determined by various means such as electrocardiogram (ECG), photoplethysmogram (PPG), and/or impedance cardiography (ICG); (ii) Skin conductance (SC), which may be measured via sensors for Galvanic Skin Response (GSR), which may also be referred to as Electrodermal Activity (EDA); (iii) Skin Temperature (ST) may be measured, for example, with various types of thermometers; (iv) Brain activity based on Magnetoencephalography (MEG); (v) Muscle activity, which may be determine via electrical signals indicative of activity of muscles, e.g., measured with electromyography (EMG). In one example, surface electromyography (sEMG) may be used to measure muscle activity of frontalis and corrugator supercilii muscles, indicative of eyebrow movement, and from which emotional response may be recognized; (vi) Eye movement, e.g., measured with electrooculography (EOG); and (vii) Brain activity and/or brainwave patterns, which may be measured with electroencephalography (EEG), which is elaborated on below.

EEG is a common method for recording brain signals in humans because it is safe, affordable, and easy to use; it also has a high temporal resolution (of the order of milliseconds). EEG electrodes, placed on the scalp, can be either "passive" or "active". Passive electrodes, which are metallic, are connected to an amplifier, e.g., by a cable. Active electrodes may have an inbuilt preamplifier to make them less sensitive to environmental noise and cable movements. Some types of electrodes may need gel or saline liquid to operate, in order to reduce the skin-electrode contact impedance. While other types of EEG electrodes can operate without a gel or saline and are considered "dry electrodes". There are various brain activity patterns that may be measured by EEG. Some of the popular ones often used in affective computing include Event Related Desynchronization/Synchronization, Event Related Potentials (e.g., P300 wave and error potentials), and Steady State Evoked Potentials. Measurements of EEG electrodes are typically subjected to various feature extraction techniques that aim to represent raw or preprocessed EEG signals by an ideally small number of relevant values, which describe the task-relevant information contained in the signals. For example, these features may be the power of the EEG over selected channels, and specific frequency bands. Various feature extraction techniques are discussed in more detail in Bashashati, et al., "A survey of signal processing algorithms in brain-computer interfaces based on electrical brain signals", in Journal of Neural engineering, 4(2):R35, 57, 2007. Additional discussion about the using EEG in affective computing and brain computer interfaces (BCI) can be found in Lotte, et al., "Electroencephalography (EEG)-based Brain Computer Interfaces", in Wiley Encyclopedia of Electrical and Electronics Engineering, pp. 44, 2015, and the references cited therein.

In some embodiments, a measurement of affective response of a user comprises, and/or is based on, a behavioral cue of the user. A behavioral cue of the user is obtained by monitoring the user in order to detect things such as facial expressions of the user, gestures made by the user, tone of voice, and/or other movements of the user's body (e.g., fidgeting, twitching, or shaking). The behavioral cues may be measured utilizing various types of sensors. Some non-limiting examples include an image capturing device (e.g., a camera), a movement sensor, a microphone, an accelerometer, a magnetic sensor, and/or a pressure sensor. In one example, a behavioral cue may involve prosodic features of a user's speech such as pitch, volume, tempo, tone, and/or stress (e.g., stressing of certain syllables), which may be indicative of the emotional state of the user. In another example, a behavioral cue may be the frequency of movement of a body (e.g., due to shifting and changing posture when sitting, laying down, or standing). In this example, a sensor embedded in a device such as accelerometers in a smartphone or smartwatch may be used to take the measurement of the behavioral cue.

In some embodiments, samples provided to a predictor may include feature values from multiple types of sources (referred to as modalities). For examples, the samples may include feature values derived from images from video streams of cameras coupled to a frame of an HMS, and in addition, feature values generated using EEG, GSR, and/or EMG. Processing this type of data may optionally involve fusion of data from the multiple modalities. Different types of data fusion techniques may be employed, for example feature-level fusion, decision-level fusion, or model-level fusion, as discussed in Nicolaou et al. (2011), "Continuous Prediction of Spontaneous Affect from Multiple Cues and Modalities in Valence-Arousal Space", IEEE Transactions on Affective Computing. Another example of use of fusion-based predictors of emotional response may be found in Schels et al. (2013), "Multi-modal classifier-fusion for the recognition of emotions", Chapter 4 in Coverbal synchrony in Human-Machine Interaction. The benefits of multimodal fusion typically include more resistance to noise (e.g., noisy sensor measurements) and missing data, which can lead to better affect detection when compared to affect detection from a single modality. For example, in meta-analysis described in D'mello and Kory (2015) "A Review and Meta-Analysis of Multimodal Affect Detection Systems" in ACM Computing Surveys (CSUR) 47.3: 43, multimodal affect systems were found to be more accurate than their best unimodal counterparts in 85% for the systems surveyed.

In one embodiment, a predictor may receive as input, e.g., as one or more feature values comprised in a sample), a baseline affective response corresponding to the user. Optionally, the baseline affective response value may be derived from measurements of affective response of the user (e.g., earlier measurements) and/or it may be a predicted value (e.g., based on measurements of other users and/or a model for baseline affective response values). Accounting for the baseline affective response value (e.g., by normalizing the measurement of affective response according to the baseline), may enable the predictor, in some embodiments, to more accurately predict the emotional response a user is feeling.

In some embodiments, some of the feature values in a sample for a predictor may be derived from additional information not obtained from measuring the user. Optionally, the additional information is used to provide context with respect to the user and/or an experience the user is having. Knowing context may be helpful since depending on the sensors used, in some embodiments, it may be the case that in different conditions the same signal values may be correspond to different emotions (e.g., extreme excitement or high stress). Knowing the context (e.g., playing a difficult level in a game or hearing a noise when alone in a dark parking lot) can assist in deciding which emotion the user is having.

Context may be given by identifying a situation the user is in. Examples of situations may include a mood of the user, a health state of the user, the type of activity the user is partaking in (e.g., relaxing, exercising, working, and/or shopping), the location the user is (e.g., at home, in public, or at work), and/or the alertness level of the user. The additional situation information may be used by a predictor improve the prediction of the emotional response of the user and/or facial expression of the user. In one example, the predictor may normalize values according to the situation (e.g., according to situation-specific baselines). In another example, the predictor may select certain models to use based on the additional information. For example, separate models may be used by a predictor for different situations a user is in, such as being at home vs. outside, or for when the user is alone vs. in a group. In still another example, separate models may be used for different types of experiences. For example, a first model may be used for determining emotional response to experiences that are considered primarily physical activities (e.g., cycling or jogging), while a second model may be used for experiences that may be considered primarily mental activities (e.g., consuming digital content).

In one embodiment, additional information received by predictor may include information derived from semantic analysis of communications of a user. The choice of words a user uses to communicate (in addition to the way the user says the words), may be indicative of the emotion being expressed. For example, semantic analysis may help determine whether a user is very excited or very angry.

In another embodiment, additional information received by a predictor may include information derived from measurements of the environment the user is in. For example, the additional information may include values that are indicative of one or more of the following: the temperature, humidity, precipitation levels, noise level, air pollution level, allergen levels, time of day, and ambient illumination level.

Similar to the discussion regarding training of predictors such as landmark identifiers, action unit identifiers, and facial expression identifier, training a predictor of emotional response may require appropriate training samples. In particular, training a personalized model for a user, which involves collecting samples that involve the user (possibly in addition to samples derived from measurements of other users). These samples typically feature values (derived from images and optionally other signals) and labels corresponding to the samples, representing an emotional response the user had when the measurements were taken. Inferring what emotional response the user had at a certain time measurements (e.g., images) were taken can be done in various ways.

In one embodiment, determining emotional response labels for samples may be done utilizing additional feature values that are not included in the samples. For example, the sample may include feature values derived from images, and the additional feature values may include signals derived from EEG, GSR, heart rate, voice analysis, etc. The additional feature values may be used to determine emotional response using a different predictor than the one being trained (e.g., a predictor of emotional response from EEG signals). Then the obtained label may be used to train a certain predictor that is not the different predictor, such as predictor of emotional response from image-based features. In one example, times when a user is measured by additional sensors (e.g., EEG, GSR, and/or external cameras that provide full frontal view) may be utilized to collect labeled samples for training a suitable predictor for time when the additional sensors are not used.

It is to be noted that similar to some embodiments described above involving the identifying of landmarks, action units, and/or facial expressions. Emotional response labels may be obtained by utilizing an external camera that takes images that include a frontal view of the face of the user, at the same time images are taken by one or more cameras coupled to a frame of an HMS worn by the user. As described above, this process may involve removing portions of the HMS (e.g., removing a display or lenses) and/or using a frame that offers less obfuscation of the face than the HMS, but maintains the cameras in the same locations and/or orientations they have when coupled to the frame of the HMS.

In another embodiment, labels representing an emotional response may be self-reported by a user stating how the user feels at the time. For example, a user may declare how he or she is feeling, select an image representing the emotion, and/or provide another form of rating for his or her feelings. Optionally, the user describes his or her emotional response after being prompted to do so by the software agent.

In another embodiment, labels representing an emotional response may be derived from communications of the user. For example, semantic analysis may be used to determine the meaning of what the user says, writes, and/or communicates in other ways (e.g., via emojis and/or gestures). These emotions may be attributed to samples collected from measurement of the user at the time the communications were made.

One approach, which may be used in some embodiments, for addressing the task of obtaining labeled samples for training a personalized predictor is to use a form of bootstrapping. In one example, training a personalized predictor for a certain user may start by utilizing a general predictor trained on labeled samples obtained from data of multiple user. These labeled samples may be added to a pool of training samples used to train the personalized predictor. As the body of labeled samples increases in size, the predictor trained on them will begin to represent the particular characteristics of how the user expresses emotions. Eventually, after a sufficiently large body of training samples is generated (or some of the samples of multiple users are removed or have their weight decreased), it is likely that the personalized predictor will perform better than a general predictor on the task of identifying the emotional response of the user.

In some embodiments, images from one or more video streams generated by one or more cameras coupled to a frame of an HMS worn by a user are utilized to generate a representation of facial expressions and/or other body movements of the user. In some embodiments, the representation of facial expressions and/or other body movements of the user are done on a rendered avatar of the user. Thus, in real-time, it is possible for a user to re-target motions and detailed expressions to avatars, e.g., for gaming or video conferencing. In other embodiments, the representation of facial expressions and/or other body movements of the user are done via movements of physical robot.

In some embodiments, images captured by one or more cameras coupled to the frame of an HMS worn by a user are converted into feature values. Optionally, the feature values include values of one or more of the high-level and/or low-level features described above, and/or are derived from one or more of the high-level and/or low-level features described above.

The feature values may be utilized to update a real-time representation of the facial expressions of the user via parameters of a 3D model of the user. Optionally, a real-time representation involves updating the 3D model based on feature values derived from an image up to one second after the image was taken. Alternatively, "real-time" may refer to shorter periods between the time images are taken and the time a model is updated and/or an avatar representation is updated accordingly. For example, in different embodiments, real-time may refer to model updates and/or avatar rendering within 0.5 seconds of taking images, within 0.2 seconds, within 0.1 seconds, or even within periods of less than 0.05 seconds.

There are various ways to represent faces via 3D models known in the art. In some embodiments, the 3D models are generated utilizing one or more images captured by cameras. Optionally, algorithms are used to reconstruct the 3D models from color images. Additionally or alternatively, algorithms may be used reconstruct the 3D models by fitting a template mesh to a depth scan of the face. Various types of cameras may be used in different embodiments. In one example, the cameras may be regular RGB cameras. In another example, the cameras may include depth-measuring capabilities (e.g., cameras that utilize IR grids and/or IR sensors such as Microsoft's Kinect). In still another example, the cameras may be light field cameras. In other embodiments, the 3D images may be created de novo, utilizing various 3D modeling software. For example, such models may be created by animators, possibly without relying on similarity to a specific person or being of which an image is taken.

There are various ways known in the art to represent the shape, texture, and/or lighting of a 3D object with models. Many of these models have been used to represent 3D faces. Additionally, a model may include ways in which the representation of the face, such as when rendered on an avatar, may manipulated (deformed). As such, in some embodiments, a 3D model of a face includes the parameters involved in a "facial rigging", for example, as described in Orvalho, et al., "A facial rigging survey", in Proc. of the 33rd Annual Conference of the European Association for Computer Graphics-Eurographics, pp. 10-32. 2012. Following are some examples of elements that may be included in a 3D model of a face used in embodiments described herein.

In some embodiments, the 3D model of the user involves an anatomical physically-based model that approximates the mechanical properties of the face such as skin layers, muscles, fatty tissues, bones, etc. Sifakis et al. "Automatic determination of facial muscle activations from sparse motion capture marker data", in ACM Transactions on Graphics (TOG), 24:3, pp. 417-425, 2005, describe an example of such an anatomically accurate model of facial musculature, passive tissue and underlying skeletal structure using volumetric data. Siakis et al. teach a method for automatically determining muscle activations and bone kinematics that is done by tracking locations of facial landmarks. The resulting rendering of facial expressions on an avatar produces visually plausible, and anatomically correct, deformations with spatial and temporal coherence that provides robustness against outliers in the motion capture data.

In some embodiments, the 3D model of a user comprises a 3D mesh representing the face of the user (e.g., a polygonal mesh such as a triangular mesh). Various examples of ways to construct and/or manipulate 3D mesh models are described in Sheffer, et al., "Mesh parameterization methods and their applications", in Foundations and Trends in Computer Graphics and Vision 2.2 (2006): 105-171.

In some embodiments, the 3D model of the user may involve blendshape models to render an avatar with facial expressions of a user, as described by feature values derived from images captured by one or more cameras coupled to a frame of an HMS worn by the user. Blenshape models are discussed in further detail elsewhere in this disclosure.

Following are some examples of methods known in the art for creating a 3D model of a face and/or body that may be used to represent facial expressions and/or other forms of body movement of a user. These are non-restricting examples; other methods for generating such a model may be used in embodiments described herein.

In one embodiment, a method for generating a 3D model of a face of a user may be based on the teachings of Zollhöfer et al. "Automatic reconstruction of personalized avatars from 3D face scans", in Computer Animation and Virtual Worlds 22.2-3 (2011): 195-202. Zollhöfer et al. use a Kinect sensor, which combines a regular RGB camera and a 3D scanner that comprises an infrared (IR) projector and an IR camera, in order to acquire input data describing a face. This input data is used by their algorithm to reconstruct a high quality 3D face model with texture from an RGB image and a depth map by fitting a morphable face model to the input data. Morphable face models are discussed further in Blanz et al. "A morphable model for the synthesis of 3D faces", in Proceedings of the 26th annual conference on Computer graphics and interactive techniques, ACM Press/ Addison-Wesley Publishing Co., 1999, which describes how to match 3D mesh models to images and various options for manipulating models (e.g., changing characteristics of facial features).

In another embodiment, a method for generating a 3D model of a face of a user may be based on the teachings of Zhang, et al. "Spacetime faces: High-resolution capture for modeling and animation", in Data-Driven 3D Facial Animation, Springer London, 2008, pp: 248-276. Zhang et al. describe a system that employs synchronized video cameras and structured light projectors to record videos of a moving face from multiple viewpoints. A spacetime stereo algorithm is used to compute depth maps accurately. A template surface fitting and tracking procedure is used to combine the depth maps based on optical flow to create face models with vertex correspondence. Once acquired, this sequence of models can be interactively manipulated to create expressions using a data-driven inverse kinematics technique.

In yet another embodiment, a method for generating a 3D model of a face of a user may be based on the teachings of Bradley, et al. "High resolution passive facial performance capture", in ACM Transactions on Graphics (TOG) 29.4 (2010): 41. Bradley et al. describe a passive facial capture approach that uses an array of video cameras, and requires no template facial geometry, no special makeup or markers, and no active lighting. Initial facial geometry is obtained using multi-view stereo, which enables automatically tracking texture detail across frames. This approach can yield a high-resolution sequence of compatibly triangulated and parameterized meshes that may be used to model the face.

In still another embodiment, a method for generating a 3D model of a face of a user may be based on the teachings of Zollhöfer et al. "Real-time Non-rigid Reconstruction using an RGB-D Camera", in ACM Transactions on Graphics (TOG) 33.4 (2014): 156. In this reference, Zollhöfer et al. describe a combined hardware and software solution for marker-less real-time reconstruction of non-rigidly deforming physical objects (including bodies and/or detailed faces). Their system uses a single self-contained stereo camera unit built from off-the-shelf components and consumer graphics hardware to generate spatio-temporally coherent 3D models at 30 Hz. The general usage scenario comprises two phases: online template acquisition and real-time non-rigid reconstruction. The online template acquisition phase that takes approximately one minute to perform, and from it a triangle mesh model is automatically extracted. The mesh model is preprocessed to create a multi-resolution hierarchy to be used in the online phase, which involves real-time non-rigid reconstruction, which produces a deformed mesh at every time step.

It is to be noted that the hardware setup utilized to generate a 3D model of a user may be different from the hardware setup that is utilized when the model is used on a day-to-day basis, such as when it is used to transfer facial expressions of the user and/or body movements to an animated avatar. In some embodiments, generating a 3D model of the face and/or body of a user may utilize one or more cameras that are located more than 20 cm away from the user and/or generating the model may utilize one or more images of a camera that is not coupled to a frame of an HMS worn by the user. For example, a 3D face and/or body model of the user may be generated utilizing a depth camera system such as Microsoft Kinect mentioned below. However, after the model is generated, utilizing the model to animate an avatar with real-time facial expressions of a user may involve cameras coupled to a frame of an HMS worn by the user, without needing the user to be in front of a depth camera.

In some embodiments, feature values that represent a facial expression of the user are used to render an avatar based on a 3D model that describes a face. Optionally, the feature values are derived from images taken by one or more cameras coupled to a frame of an HMS worn by the user. Optionally, the 3D model is generated based on images of the face of the user taken by the one or more cameras. Additionally or alternatively, the 3D model may be generated based on images taken with a camera that is not one of the one or more cameras, e.g., a camera that is more than 20 cm away from the face of the user), as described above.

Depending on the type of 3D model used (e.g., the type of parameters), and/or the type of feature values that are extracted from the images taken by the one or more cameras captured to the frame, various approaches may be used to convert the feature values into a rendered avatar expressing a facial expression of the user. Following are some non-restricting examples of approaches known in the art that may be used in some embodiments. Other approaches, not described below may also be utilized in embodiments described in this disclosure for that task.

Additional examples of ways blendshapes can be utilized in some embodiments in this disclosure are given in the following references:
(i) Bouaziz, Sofien, Yangang Wang, and Mark Pauly. "Online modeling for realtime facial animation" ACM Transactions on Graphics (TOG) 32.4 (2013): 40. (ii) Ichim et al., "Dynamic 3D Avatar Creation from Hand-held Video Input", in ACM Transactions on Graphics (Proceedings of SIGGRAPH), 2015 (iii) Li with the oculus without the display. (example of blendshapes) (vi) US patent application 20140362091 (v) Kakarla, Mounika, Mohana Reddy, and G. Ram. "A real time facial emotion recognition using depth sensor and interfacing with Second Life based Virtual 3D avatar." Recent Advances and Innovations in Engineering (ICRAIE), 2014. IEEE, 2014. (vi) Liu, Caixia, et al. "Representing affective facial expressions for robots and embodied conversational agents by facial landmarks" International Journal of Social Robotics 5.4 (2013): 619-626. (vii) Mazzei, Daniele, et al. "Hefes: An hybrid engine for facial expressions synthesis to control human-like androids and avatars." Biomedical Robotics and Biomechatronics (BioRob), 2012 4th IEEE RAS & EMBS International Conference on. IEEE, 2012.

Face Transfer is a method for mapping video-recorded performances of one individual to facial animations of another. It extracts visemes (speech-related mouth articulations), expressions, and three-dimensional (3D) pose from monocular video or film footage. These parameters are then used to generate and drive a detailed 3D textured face mesh for a target identity, which can be seamlessly rendered back into target footage. The underlying face model automatically adjusts for how the target performs facial expressions and visemes. The performance data can be easily edited to change the visemes, expressions, pose, or even the identity of the target—the attributes are separably controllable. This supports a wide variety of video rewrite and puppetry applications.

Other face transfer methods that may be used in embodiments described herein are given in the following references: (i) Vlasic, Daniel, et al. "Face transfer with multilinear models." ACM Transactions on Graphics (TOG). Vol. 24. No. 3. ACM, 2005. (ii) Cao, Chen, et al. "3D shape regression for real-time facial animation" ACM Transactions on Graphics (TOG) 32.4 (2013): 41.

In one embodiment, generating a 3D model of a body of a user may be done according to the teachings of Tong et al. "Scanning 3d full human bodies using kinects", in IEEE Transactions on Visualization and Computer Graphics, 18.4 (2012): 643-650. The method of Tong et al. can handle non-rigid alignment with loop closure constraint and complex occlusions. They utilize a two-stage registration algorithm that performs pairwise deformation on the geometry field, followed by global alignment on the deformation field. Registration with a rough template, such as the skeleton model can be utilized in order to enable manipulation of the avatar to perform various movements. Such registration can involve manually segmenting the first frame, and then identifying and tracking the rigid components of each frame, while accumulating the geometric information. Additional information regarding registration of images of a body to a template skeleton may be found in Pekelny and Gotsman, "Articulated object reconstruction and markerless motion capture from depth video", in Computer Graphics Forum (EUROGRAPHICS 2008). Vol. 27. No. 2. Blackwell Publishing Ltd, 2008.

Examples of models of body and shape completion and/or animation of people that may be used in some embodiments are described in the following references: (i) Baak, Andreas, et al. "A data-driven approach for real-time full body pose reconstruction from a depth camera." Consumer Depth Cameras for Computer Vision. Springer London, 2013. 71-98. (ii) Anguelov, Dragomir, et al. "SCAPE: shape completion and animation of people." ACM Transactions on Graphics (TOG). Vol. 24. No. 3. ACM, 2005. (iii) U.S. Pat. No. 8,139,067 titled "Shape completion, animation and marker-less motion capture of people, animals or characters".

Examples of models for human actions that may be utilized in embodiments described herein are given in the following references: (i) Sheikh, Yaser, Mumtaz Sheikh, and Mubarak Shah. "Exploring the space of a human action." Computer Vision, 2005. ICCV 2005. Tenth IEEE International Conference on. Vol. 1. IEEE, 2005. (ii) Gall, Juergen, et al. "Motion capture using joint skeleton tracking and surface estimation" Computer Vision and Pattern Recognition, 2009. CVPR 2009. IEEE Conference on. IEEE, 2009. (iii) Poppe, Ronald. "A survey on vision-based human action recognition." Image and vision computing 28.6 (2010): 976-990. (iv) Wang, Jiang, et al. "Robust 3d action recognition with random occupancy patterns." Computer vision—ECCV 2012. Springer Berlin Heidelberg, 2012. 872-885. (v) Chaudhry, Rizwan, et al. "Bio-inspired dynamic 3d discriminative skeletal features for human action recognition." Computer Vision and Pattern Recognition Workshops (CVPRW), 2013 IEEE Conference on. IEEE, 2013. (vi) Tang, Danhang, Tsz-Ho Yu, and Tae-Kyun Kim. "Real-time articulated hand pose estimation using semi-supervised transductive regression forests." Computer Vision (ICCV), 2013 IEEE International Conference on. IEEE, 2013.

In one embodiment, a method for 3D face scan for customized VR headset frame includes the following steps: receiving a 3D model of a user's face; based on the model, selecting a shape for the frame of the head mounted display that best fits the user's face; and (i) printing the frame utilizing a 3D printer to specifically match the face; or (ii) selecting, from a set of predefined shapes, a shape for the frame of the head mounted display that best fits the user's face.

The method may further include the step of selecting at least one location for a sensor and/or identify locations that are not suitable for a sensor based on the face model. The regions may be unsuitable because various reason such as angle and/or size of forehead or ears (varies between humans) Facial hair (beard, mustache, sideburns) can also be problematic. Additionally, piercings and the like can also make some locations inappropriate for certain sensors.

This method selects the appropriate frame for the user based on one or more of the following constraints: to the user's facial dimensions, the sensors the user needs, the specific location of the user's arteries, and/or planned type of usage for the HMD. Optionally, the HMD is designed for quick replacement of frames so that different users having different personalized frames can share the same expensive electronic modules (such as display, processor, memory, thermal sensors, visible spectrum cameras, communication link, IMU).

In one embodiment, a grid of sensors is placed nearby one or more ROI, such as nearby the superficial temporal arteries, nostrils, periorbital regions, cheeks. The system is configured to find which one or more sensors provide the best measurements, and base its operation on the best positioned sensors. Additionally or alternatively, the system may turn off sensors that are not positioned well and thus do not provide adequate measurements of the ROI. Additionally or alternatively, when the measurement quality decreases below a threshold, the system turns on the sensors that were turned off, and repeats the process of finding the sensors providing the best measurements.

In one embodiment, the HMS includes a mechanical slider that can move the camera, either manually or electromechanically, to various positions in order to find the best position to measure the ROI. Optionally, the movement is performed by the HMS utilizing an electromechanical device, and the HMS is configured to move the camera until it finds the best position.

Normally, the lens plane and the sensor plane of a camera are parallel, and the plane of focus (PoF) is parallel to the lens and sensor planes. If a planar object is also parallel to the sensor plane, it can coincide with the PoF, and the entire object can be captured sharply. If the lens plane is tilted (not parallel) relative to the sensor plane, it will be in focus along a line where it intersects the PoF. The Scheimpflug principle is a known geometric rule that describes the orientation of the plane of focus of a camera when the lens plane is tilted relative to the sensor plane.

Figure 25A:
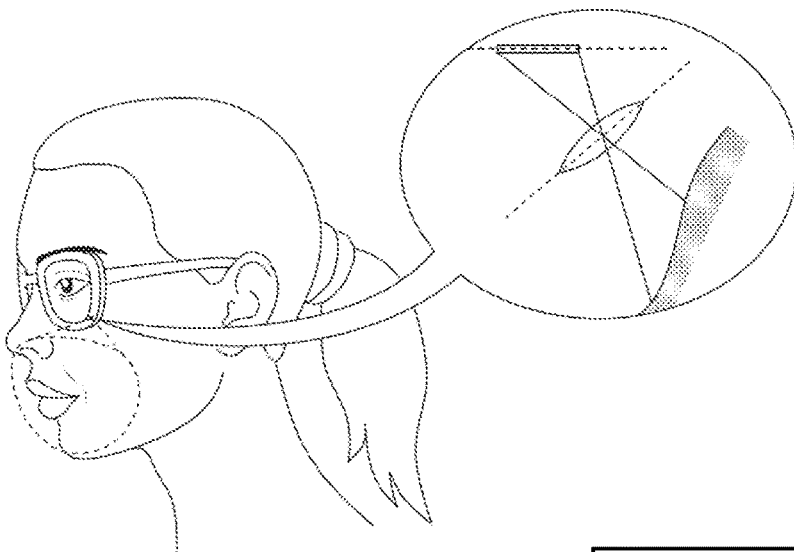
FIG. 25a is a schematic illustration of an inward-facing head-mounted camera embedded in an eyeglasses frame, which utilizes the Scheimpflug principle.

FIG. 25a is a schematic illustration of an inward-facing head-mounted camera 550 embedded in an eyeglasses frame 551, which utilizes the Scheimpflug principle to improve the sharpness of the image taken by the camera 550. The camera 550 includes a sensor 558 and a lens 555. The tilt of the lens 555 relative to sensor 558, which may also be considered as the angle between the lens plane 555 and the sensor plane 559, is determined according to the expected position of the camera 550 relative to the ROI 552 when the user wears the eyeglasses. For a refractive optical lens, the "lens plane" 556 refers to a plane that is perpendicular to the optical axis of the lens 555. Herein, the singular also includes the plural, and the term "lens" refers to one or more lenses. When "lens" refers to multiple lenses (which is usually the case in most modern cameras having a lens module with multiple lenses), then the "lens plane" refers to a plane that is perpendicular to the optical axis of the lens module.

Figure 25B:
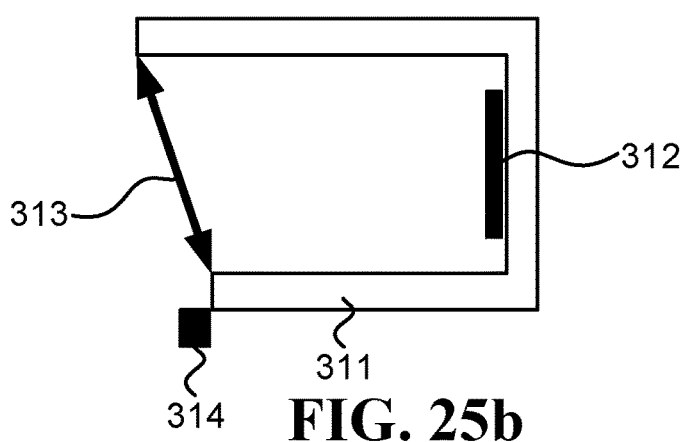
FIG. 25b is a schematic illustration of a camera that is able to change the relative tilt between its lens and sensor planes according to the Scheimpflug principle.

The Scheimpflug principle may be used for both thermal cameras (based on lenses and sensors for wavelengths longer than 2500 nm) and visible-light and/or near-IR cameras (based on lenses and sensors for wavelengths between 400-900 nm). FIG. 25b is a schematic illustration of a camera that is able to change the relative tilt between its lens and sensor planes according to the Scheimpflug principle. Housing 311 mounts a sensor 312 and lens 313. The lens 313 is tilted relative to the sensor 312. The tilt may be fixed according to the expected position of the camera relative to the ROI when the user wears the HMS, or may be adjusted using motor 314. The motor 314 may move the lens 313 and/or the sensor 312.

In one embodiment, an HMS device includes a frame configured to be worn on a user's head, and an inward-facing camera physically coupled to the frame. The inward-facing camera may assume one of two configurations: (i) the inward-facing camera is oriented such that the optical axis of the camera is above the Frankfort horizontal plane and pointed upward to capture an image of a region of interest (ROI) above the user's eyes, or (ii) the inward-facing camera is oriented such that the optical axis is below the Frankfort horizontal plane and pointed downward to capture an image of an ROI below the user's eyes. The inward-facing camera includes a sensor and a lens. The sensor plane is tilted by more than 2° relative to the lens plane according to the Scheimpflug principle in order to capture a sharper image.

In another embodiment, an HMS includes an inward-facing head-mounted camera that captures an image of an ROI on a user's face, when worn on the user's head. The ROI is on the user's forehead, nose, upper lip, cheek, and/or lips. The camera includes a sensor and a lens. And the sensor plane is tilted by more than 2° relative to the lens plane according to the Scheimpflug principle in order to capture a sharper image.

Because the face is not planar and the inward-facing head-mounted camera is located close to the face, an image captured by a camera having a wide field of view (FOV) and a low f-number may not be perfectly sharp, even after applying the Scheimpflug principle. Therefore, in some embodiments, the tilt between the lens plane and the sensor plane is selected such as to adjust the sharpness of the various areas covered in the ROI according to their importance for detecting the user's physiological signals. In one embodiment, the ROI covers first and second areas, where the first area includes finer details and/or is more important for detecting the physiological signals than the second area. Therefore, the tilt between the lens and sensor planes is adjusted such that the image of the first area is shaper than the image of the second area.

In one embodiment, the tilt between the lens plane and sensor plane is fixed. The fixed tilt is selected according to an expected orientation between the camera and the ROI when a user wears the frame. Having a fixed tilt between the lens and sensor planes may eliminate the need for an adjustable electromechanical tilting mechanism. As a result, a fixed tilt may reduce the weight and cost of the camera, while still providing a sharper image than an image that would be obtained from a similar camera in which the lens and sensor planes are parallel. The magnitude of the fixed tilt may be selected according to facial dimensions of an average user expected to wear the system, or according to a model of the specific user expected to wear the system in order to obtain the sharpest image.

In another embodiment, the system includes an adjustable electromechanical tilting mechanism configured to change the tilt between the lens and sensor planes according to the Scheimpflug principle based on the orientation between the camera and the ROI when the frame is worn by the user. The tilt may be achieved using at least one motor, such as a brushless DC motor, a stepper motor (without a feedback sensor), a brushed DC electric motor, a piezoelectric motor, and/or a micro-motion motor.

The adjustable electromechanical tilting mechanism configured to change the tilt between the lens and sensor planes may include one or more of the following mechanisms: (i) a mirror that changes its angle; (ii) a device that changes the angle of the lens relative to the sensor; and/or (iii) a device that changes the angle of the sensor relative to the lens. In one embodiment, the camera, including the adjustable electromechanical tilting mechanism, weighs less than 10 g, and the adjustable electromechanical tilting mechanism is able to change the tilt in a limited range below 30° between the two utmost orientations between the lens and sensor planes. Optionally, the adjustable electromechanical tilting mechanism is able to change the tilt in a limited range below 20° between the two utmost orientations between the lens and sensor planes. In another embodiment, the adjustable electromechanical tilting mechanism is able to change the tilt in a limited range below 10°. In some embodiments, being able to change the tilt in a limited range reduces at least one of the weight, cost, and size of the camera, which is advantageous for a wearable device. In one example, the camera is manufactured with a fixed predetermined tilt between the lens and sensor planes, which is in addition to the tilt provided by the adjustable electromechanical tilting mechanism. The fixed predetermined orientation may be determined according to the expected orientation between the camera and the ROI for an average user, such that the adjustable electromechanical tilting mechanism is used to fine-tune the tilt between the lens and sensor planes for the specific user who wears the frame and has facial dimensions that are different from the average user.

Various embodiments described herein involve an HMS that may be connected, using wires and/or wirelessly, with a device carried by the user and/or a non-wearable device. The HMS may include a battery, a computer, sensors, and a transceiver.

FIG. 41a and FIG. 41b are schematic illustrations of possible embodiments for computers (400, 410) that are able to realize one or more of the embodiments discussed herein that include a "computer". The computer (400, 410) may be implemented in various ways, such as, but not limited to, a microcontroller, a computer on a chip, a system-on-chip (SoC), a system-on-module (SoM), a processor with its required peripherals, a server computer, a client computer, a personal computer, a cloud computer, a network device, a handheld device (e.g., a smartphone), an head-mounted system (such as smartglasses, an augmented reality system, a virtual reality system, and/or a smart-helmet), a computing device embedded in a wearable device (e.g., a smartwatch or a computer embedded in clothing), a computing device implanted in the human body, and/or any other computer form capable of executing a set of computer instructions. Further, references to a computer or a processor include any collection of one or more computers and/or processors (which may be at different locations) that individually or jointly execute one or more sets of computer instructions. This means that the singular term "computer" is intended to imply one or more computers, which jointly perform the functions attributed to "the computer". In particular, some functions attributed to the computer may be performed by a computer on a wearable device (e.g., smartglasses) and/or a computer of the user (e.g., smartphone), while other functions may be performed on a remote computer, such as a cloud-based server.

The computer 400 includes one or more of the following components: processor 401, memory 402, computer readable medium 403, user interface 404, communication interface 405, and bus 406. The computer 410 includes one or more of the following components: processor 411, memory 412, and communication interface 413.

Functionality of various embodiments may be implemented in hardware, software, firmware, or any combination thereof. If implemented at least in part in software, implementing the functionality may involve a computer program that includes one or more instructions or code stored or transmitted on a computer-readable medium and executed by one or more processors. Computer-readable media may include computer-readable storage media, which corresponds to a tangible medium such as data storage media, and/or communication media including any medium that facilitates transfer of a computer program from one place to another. Computer-readable medium may be any media that can be accessed by one or more computers to retrieve instructions, code, data, and/or data structures for implementation of the described embodiments. A computer program product may include a computer-readable medium. In one example, the computer-readable medium 403 may include one or more of the following: RAM, ROM, EEPROM, optical storage, magnetic storage, biologic storage, flash memory, or any other medium that can store computer readable data.

A computer program (also known as a program, software, software application, script, program code, or code) can be written in any form of programming language, including compiled or interpreted languages, declarative or procedural languages. The program can be deployed in any form, including as a standalone program or as a module, component, subroutine, object, or another unit suitable for use in a computing environment. A computer program may correspond to a file in a file system, may be stored in a portion of a file that holds other programs or data, and/or may be stored in one or more files that may be dedicated to the program. A computer program may be deployed to be executed on one or more computers that are located at one or more sites that may be interconnected by a communication network.

Computer-readable medium may include a single medium and/or multiple media (e.g., a centralized or distributed database, and/or associated caches and servers) that store one or more sets of instructions. In various embodiments, a computer program, and/or portions of a computer program, may be stored on a non-transitory computer-readable medium, and may be updated and/or downloaded via a communication network, such as the Internet. Optionally, the computer program may be downloaded from a central repository, such as Apple App Store and/or Google Play. Optionally, the computer program may be downloaded from a repository, such as an open source and/or community run repository (e.g., GitHub).

As used herein, references to "one embodiment" (and its variations) mean that the feature being referred to may be included in at least one embodiment of the invention. Moreover, separate references to "one embodiment", "some embodiments", "another embodiment", "still another embodiment", etc., may refer to the same embodiment, may illustrate different aspects of an embodiment, and/or may refer to different embodiments.

Some embodiments may be described using the verb "indicating", the adjective "indicative", and/or using variations thereof. Herein, sentences in the form of "X is indicative of Y" mean that X includes information correlated with Y, up to the case where X equals Y. Stating that "X indicates Y" or "X indicating Y" may be interpreted as "X being indicative of Y". Additionally, sentences in the form of "provide/receive an indication indicating whether X happened" may refer herein to any indication method, including but not limited to: sending/receiving a signal when X happened and not sending/receiving a signal when X did not happen, not sending/receiving a signal when X happened and sending/receiving a signal when X did not happen, and/or sending/receiving a first signal when X happened and sending/receiving a second signal X did not happen.

Herein, "most" of something is defined as above 51% of the something (including 100% of the something). Both a "portion" of something and a "region" of something refer to a value between a fraction of the something and 100% of the something. For example, sentences in the form of a "portion of an area" may cover between 0.1% and 100% of the area. As another example, sentences in the form of a "region on the user's forehead" may cover between the smallest area captured by a single pixel (such as 0.1% or 5% of the forehead) and 100% of the forehead. The word "region" refers to an open-ended claim language, and a camera said to capture a specific region on the face may capture just a small part of the specific region, the entire specific region, and/or a portion of the specific region together with additional region(s).

The terms "comprises", "comprising", "includes", "including", "has", "having", or any other variation thereof, indicate an open-ended claim language that can include additional limitations. The "a" or "an" is employed to describe one or more, and the singular also includes the plural unless it is obvious that it is meant otherwise. For example, "a computer" refers to one or more computers, such as a combination of a wearable computer that operates together with a cloud computer.

The phrase "based on" indicates an open-ended claim language, and is to be interpreted as "based, at least in part, on". Additionally, stating that a value is calculated "based on X" and following that, in a certain embodiment, that the value is calculated "also based on Y", means that in the certain embodiment, the value is calculated based on X and Y. Variations of the terms "utilize" and "use" indicate an open-ended claim language, such that sentences in the form of "detecting X utilizing Y" are intended to mean "detecting X utilizing at least Y", and sentences in the form of "use X to calculate Y" are intended to mean "calculate Y based on X".

The terms "first", "second" and so forth are to be interpreted merely as ordinal designations, and shall not be limited in themselves. A predetermined value is a fixed value and/or a value determined any time before performing a calculation that compares a certain value with the predetermined value. A value is also considered to be a predetermined value when the logic, used to determine whether a threshold that utilizes the value is reached, is known before start performing computations to determine whether the threshold is reached.

The embodiments of the invention may include any variety of combinations and/or integrations of the features of the embodiments described herein. Although some embodiments may depict serial operations, the embodiments may perform certain operations in parallel and/or in different orders from those depicted. Moreover, the use of repeated reference numerals and/or letters in the text and/or drawings is for the purpose of simplicity and clarity and does not in itself dictate a relationship between the various embodiments and/or configurations discussed. The embodiments are not limited in their applications to the order of steps of the methods, or to details of implementation of the devices, set in the description, drawings, or examples. Moreover, individual blocks illustrated in the figures may be functional in nature and therefore may not necessarily correspond to discrete hardware elements.

Certain features of the embodiments, which may have been, for clarity, described in the context of separate embodiments, may also be provided in various combinations in a single embodiment. Conversely, various features of the embodiments, which may have been, for brevity, described in the context of a single embodiment, may also be provided separately or in any suitable sub-combination. Embodiments described in conjunction with specific examples are presented by way of example, and not limitation. Moreover, it is evident that many alternatives, modifications, and variations will be apparent to those skilled in the art. It is to be understood that other embodiments may be utilized and structural changes may be made without departing from the scope of the embodiments. Accordingly, this disclosure is intended to embrace all such alternatives, modifications, and variations that fall within the spirit and scope of the appended claims and their equivalents.

We claim:

1. A system configured to calculate blood glucose level, comprising:
    a head-mounted contact photoplethysmography device configured to measure a signal indicative of a photoplethysmogram signal (PPG signal) at a first region comprising skin on a user's head;
    a head-mounted camera configured to capture images of a second region comprising skin on the user's head; and
    a computer configured to:
    identify, based on the PPG signal, times of systolic notches and times of systolic peaks; and
    calculate the blood glucose level based on differences between a first subset of the images taken during the times of systolic notches and a second subset of the images taken during the times of systolic peaks.

2. The system of claim 1, wherein the systolic notch is a minimum of a pulse wave in the PPG signal and the systolic peak is the maximum of the pulse wave; and wherein the head-mounted camera is sensitive to at least three noncoinciding wavelength intervals, the head-mounted camera is located more than 5 mm away from the second region, and both the head-mounted camera and the head-mounted contact photoplethysmography device are physically coupled to smartglasses or to a smart-helmet, which is designed to measure the user in day-to-day activities, over a duration of weeks, months, and/or years.

3. The system of claim 1, wherein the computer is further configured to calculate a time difference between the times of systolic peaks in the PPG signal and times of systolic peaks in imaging photoplethysmogram signals recognizable the images, and to utilize the time difference in calculations of the blood glucose level, whereby the first and second regions are fed by different arteries, which cause said time difference between observance of systolic peaks at the first and second regions.

4. The system of claim 1, wherein the computer is further configured to extract imaging photoplethysmogram signals (iPPG signals) from the images, and to utilize, in calculations of the blood glucose level, differences between amplitudes of the iPPG signals during the times of systolic notches and amplitudes of the iPPG signals during the times of systolic peaks.

5. The system of claim 1, wherein the computer is further configured to: calculate a first hemoglobin concentration pattern based on the first subset of the images, calculate a second hemoglobin concentration pattern based on the second subset of the images, and to utilize in calculations of the blood glucose level, differences between the first and second hemoglobin concentration patterns.

6. The system of claim 1, wherein the computer is further configured to: extract a first set of facial flushing patterns based on the first subset of the images, extract a second set of facial flushing patterns based on the second subset of the images, and to utilize, in calculations of the blood glucose level, differences between the first and second sets of facial flushing patterns.

7. The system of claim 1, wherein calculation of the blood glucose level comprise performing the following by the computer: generating feature values from the first and second subsets of the images, and utilizing a machine learning-based model to calculate, based on the feature values, a value indicative of the blood glucose level; and wherein the machine learning-based model was generated using training data comprising: $3^{rd}$ and $4^{th}$ subsets of the images, taken during the times of systolic notches and systolic peaks, respectively, while the user had blood glucose level that was between 70 and 100; $5^{th}$ and $6^{th}$ subsets of the images, taken during the times of systolic notches and systolic peaks, respectively, while the user had blood glucose level that was between 100 and 125; $7^{th}$ and $8^{th}$ subsets of the images, taken during the times of systolic notches and systolic peaks, respectively, while the user had blood glucose level that was between 120 and 150; and $9^{th}$ and $10^{th}$ subsets of the images, taken during the times of systolic notches and systolic peaks, respectively, while the user had blood glucose level that was between 150 and 180.

8. The system of claim 1, further comprising a head-mounted temperature sensor configured to measure skin temperature ($T_{skin}$) at a third region on a user's head; and wherein calculation of the blood glucose level by the computer comprises: (i) generating feature values based on: the PPG signal, the images, and $T_{skin}$, and (ii) utilizing a machine learning-based model to calculate the blood glucose level based on the feature values.

9. The system of claim 1, further comprising an outward-facing head-mounted camera configured to take images of the environment; and wherein calculation of the blood glucose level by the computer comprises: (i) generating feature values based on: the PPG signal, the images, and the images of the environment, and (ii) utilizing a machine learning-based model to calculate the blood glucose level based on the feature values.

10. A method for calculating blood glucose level, comprising:
receiving, from a head-mounted contact photoplethysmography device, a signal indicative of a photoplethysmogram signal (PPG signal) at a first region comprising skin on a user's head;
receiving, from a head-mounted camera, images of a second region comprising skin on the user's head;
identifying, based on the PPG signal, times of systolic notches and times of systolic peaks; and
calculating the blood glucose level based on differences between a first subset of the images taken during the times of systolic notches and a second subset of the images taken during the times of systolic peaks.

11. The method of claim 10, further comprising: extracting imaging photoplethysmogram signals (iPPG signals) from the images, and utilizing, in calculations of the blood glucose level, differences between amplitudes of the iPPG signals during the times of systolic notches and amplitudes of the iPPG signals during the times of systolic peaks.

12. The method of claim 10, further comprising: calculating a first hemoglobin concentration pattern based on the first subset of the images, calculating a second hemoglobin concentration pattern based on the second subset of the images, and utilizing, in calculations of the blood glucose level, differences between the first and second hemoglobin concentration patterns.

13. The method of claim 10, further comprising extracting a first set of facial flushing patterns based on the first subset of the images, extracting a second set of facial flushing patterns based on the second subset of the images, and calculating the blood glucose level based on differences between the first and second sets of facial flushing patterns.

14. The method of claim 10, wherein calculating the blood glucose level based on the differences between the first subset of the images taken during the times of systolic notches and the second subset of the images taken during the times of systolic peaks comprises: generating feature values from the first and second subsets of the images, and utilizing a machine learning-based model to calculate, based on the feature values a value indicative of the blood glucose level; and wherein the machine learning-based model was generated using training data comprising: $3^{rd}$ and $4^{th}$ subsets of the images, taken during the times of systolic notches and systolic peaks, respectively, while the user had blood glucose level that was between 70 and 100; $5^{th}$ and $6^{th}$ subsets of the images, taken during the times of systolic notches and systolic peaks, respectively, while the user had blood glucose level that was between 100 and 125; $7^{th}$ and $8^{th}$ subsets of the images, taken during the times of systolic notches and systolic peaks, respectively, while the user had blood glucose level that was between 120 and 150; and $9^{th}$ and $10^{th}$ subsets of the images, taken during the times of systolic notches and systolic peaks, respectively, while the user had blood glucose level that was between 150 and 180.

15. The method of claim 10, further comprising: receiving, from a head-mounted temperature sensor, skin temperature measurements ($T_{skin}$) at a third region on a user's head; generating feature values based on the PPG signal, the images, and $T_{skin}$; and performing the calculating of the blood glucose level utilizing a machine learning-based model that is fed with the feature values.

16. The method of claim 10, further comprising: receiving images of the environment from an outward-facing head-mounted camera; generating feature values based on: the PPG signal, the images, and the images of the environment; and performing the calculating of the blood glucose level utilizing a machine learning-based model that is fed with the feature values.

17. A non-transitory computer readable medium storing one or more computer programs configured to cause a processor based system to execute steps comprising:
receiving, from a head-mounted contact photoplethysmography device, a signal indicative of a photoplethysmogram signal (PPG signal) at a first region comprising skin on a user's head;
receiving, from a head-mounted camera, images of a second region comprising skin on the user's head;
identifying, based on the PPG signal, times of systolic notches and times of systolic peaks; and
calculating a blood glucose level based on differences between a first subset of the images taken during the times of systolic notches and a second subset of the images taken during the times of systolic peaks.

18. The non-transitory computer readable medium of claim 17, further comprising instructions for execution of the following steps: extracting imaging photoplethysmogram signals (iPPG signals) from the images, and utilizing, in calculations of the blood glucose level, differences between amplitudes of the iPPG signals during the times of systolic notches and amplitudes of the iPPG signals during the times of systolic peaks.

19. The non-transitory computer readable medium of claim 17, further comprising instructions for execution of the following steps: calculating a first hemoglobin concentration pattern based on the first subset of the images, calculating a second hemoglobin concentration pattern based on the second subset of the images, and utilizing, in calculations of the blood glucose level, differences between the first and second hemoglobin concentration patterns.

20. The non-transitory computer readable medium of claim 17, further comprising instructions for execution of the following steps: extracting a first set of facial flushing patterns based on the first subset of the images, extracting a second set of facial flushing patterns based on the second subset of the images, and calculating the blood glucose level based on differences between the first and second sets of facial flushing patterns.

* * * * *